US007619005B2

(12) United States Patent
Epstein et al.

(10) Patent No.: US 7,619,005 B2
(45) Date of Patent: *Nov. 17, 2009

(54) METHODS FOR TREATING COGNITIVE IMPAIRMENT IN HUMANS WITH MULTIPLE SCLEROSIS

(75) Inventors: Mel H. Epstein, Bristol, RI (US); Kjesten A. Wiig, Providence, RI (US); Randall L. Carpenter, Waban, MA (US)

(73) Assignee: Cognition Pharmaceuticals LLC, New York, NY (US)

( * ) Notice: Subject to any disclaimer, the term of this patent is extended or adjusted under 35 U.S.C. 154(b) by 157 days.

This patent is subject to a terminal disclaimer.

(21) Appl. No.: 11/133,144

(22) Filed: May 19, 2005

(65) Prior Publication Data

US 2006/0111448 A1    May 25, 2006

Related U.S. Application Data

(63) Continuation-in-part of application No. PCT/US2004/015974, filed on May 21, 2004, which is a continuation-in-part of application No. 10/791,223, filed on Mar. 2, 2004, which is a continuation-in-part of application No. 10/444,970, filed on May 23, 2003, now abandoned, which is a continuation-in-part of application No. 10/139,606, filed on May 2, 2002, now abandoned, which is a continuation-in-part of application No. 10/003,740, filed on Oct. 31, 2001, now Pat. No. 6,828,351.

(60) Provisional application No. 60/245,323, filed on Nov. 1, 2000, provisional application No. 60/473,168, filed on May 23, 2003.

(51) Int. Cl.
   *A61K 31/135* (2006.01)
   *A61K 31/445* (2006.01)
(52) U.S. Cl. .................................. 514/654; 514/317
(58) Field of Classification Search ...................... None
   See application file for complete search history.

(56) References Cited

U.S. PATENT DOCUMENTS

| | | |
|---|---|---|
| 2,828,343 A | 3/1958 | Tindall |
| 3,728,445 A | 4/1973 | Bardani |
| 3,996,381 A | 12/1976 | Florvall et al. |
| 4,034,113 A | 7/1977 | Shulgin |
| 4,105,695 A | 8/1978 | Partyka et al. |
| 4,479,932 A | 10/1984 | Bodor |
| 4,598,094 A | 7/1986 | Wurtman et al. |
| 4,636,494 A | 1/1987 | Growdon et al. |
| 4,647,591 A | 3/1987 | Cherkin et al. |
| 5,019,594 A | 5/1991 | Wurtman et al. |
| 5,075,338 A | 12/1991 | Knoll et al. |
| 5,096,712 A | 3/1992 | Wurtman |
| 5,151,449 A | 9/1992 | Milgram |
| 5,220,068 A | 6/1993 | Knoll et al. |
| 5,225,446 A | 7/1993 | Milgram |
| 5,422,355 A | 6/1995 | White et al. |
| 5,684,018 A | 11/1997 | Alexander |
| 5,914,129 A | 6/1999 | Mauskop |
| 6,104,956 A | 8/2000 | Naritoku et al. |
| 6,204,245 B1 | 3/2001 | Siegel et al. |
| 6,228,875 B1 | 5/2001 | Tsai et al. |
| 6,251,938 B1 | 6/2001 | Chorev et al. |
| 6,284,760 B1 | 9/2001 | Marston et al. |
| 6,451,806 B2 | 9/2002 | Farrar |
| 6,492,427 B2 | 12/2002 | Shankar et al. |
| 6,635,675 B2 | 10/2003 | Kranzler et al. |
| 6,699,495 B2 | 3/2004 | Blume et al. |
| 6,828,351 B2 | 12/2004 | Epstein et al. |
| 7,244,769 B2 * | 7/2007 | Epstein et al. ............... 514/654 |
| 2002/0066457 A1 | 6/2002 | Landfield et al. |
| 2002/0115725 A1 | 8/2002 | Epstein et al. |
| 2007/0099999 A1 * | 5/2007 | Epstein et al. ............... 514/649 |
| 2007/0100000 A1 * | 5/2007 | Epstein et al. ............... 514/649 |
| 2007/0117869 A1 * | 5/2007 | Epstein et al. ............... 514/649 |

FOREIGN PATENT DOCUMENTS

| | | |
|---|---|---|
| EP | 1 743 641 A2 | 1/1707 |
| GB | 2 122 617 | 1/1984 |
| WO | WO 97/17067 A1 | 5/1997 |
| WO | WO 97/26871 A1 | 7/1997 |
| WO | WO 99/16746 A1 | 4/1999 |
| WO | WO 00/01379 A1 | 1/2000 |
| WO | WO 00/32556 A1 | 6/2000 |
| WO | WO 00/59479 A1 | 10/2000 |
| WO | WO 01/09897 A1 | 2/2001 |
| WO | WO 02/39998 A2 | 5/2002 |
| WO | WO 02/053104 A2 | 7/2002 |

OTHER PUBLICATIONS

Chertkow, H., "Mild Cognitive Impairment," *Curr. Opin. in Neurol.* 15:401-407 (2002).
Clarke, A., "A New Formulation of Selegiline: Improved Bioavailability and Selectivity for MAO-B Inhibition," *J. Neural. Transm.* 110:1241-1255 (2003).
Gauthier, S., et al., "Mild Cognitive Impairment," *The Lancet* 367:1262-1270 (2006).
Grundman, M., et al., "Mild Cognitive Impairment Can Be Distinguished From Alzheimer Disease and Normal Aging for Clinical Trials," *Arch. Neurol.* 61:59-66 (2004).
Halgren, E., et al., "Human Hippocampal Formation EEG Desynchronizes During Attentiveness and Movement," *Electroencephalography and Clinical Neurophysiology* 44:778-781 (1978).

(Continued)

*Primary Examiner*—Brian-Yong S Kwon
(74) *Attorney, Agent, or Firm*—Hamilton, Brook, Smith & Reynolds, P.C.

(57) ABSTRACT

Cognitive impairments in humans with multiple sclerosis are treated and cognition is improved with an amphetamine compound. In one embodiment, the method includes administering an l-amphetamine compound. In another embodiment, the method includes administering an l-methamphetamine compound.

8 Claims, 55 Drawing Sheets

OTHER PUBLICATIONS

Kwon, Y. S., et al., "Selegiline Potentiates the Effects of Egb 761 in Response to Ischemic Brain Injury," *Neurochemistry International* 45:157-170 (2004).

Lynch, G., et al., "The Nature and Causes of Hippocampal Long-term Potentiation," *Progress in Brain Research* 83:233-250 (1990).

Meeker, J.S. and Reynolds, P.C., "Postmortem Tissue Methamphetamine Concentrations Following Selegiline Administration," *J. of Analytical Toxicology* 14:330-331 (1990).

Mild Cognitive Impairment. Alzheimer's Society Information Sheet [online], Mar. 2005. Retrieved from the Internet <URL: http://www.alzheimers.org.uk>.

Mild Cognitive Impairment-Alzheimer's Disease Part XVI, [online] Nov. 2006 [retrieved on Jan. 24, 2007]. Retrieved from the Internet <URL:http://www.therubins.com>.

Nickel, B., et al., "Evaluation of Physical Dependence Liability of *l*-deprenyl (Selegiline) in Animals," *Clinical Pharmacology & Theraptutics*, 56(6):757-767 (1994).

Petersen, R.C., et al., "Current Concepts in Mild Cognitive Impairment," *Arch Neurol.* 58:1985-1992 (2001).

Semkova, I., et al., "Selegiline Enhances NGF Synbthesis and Protects Central Nervous System Neurons from Excitotoxic and Ischemic Damage," *European Journal of Pharmacology* 315:19-30 (1996).

Sivenius, J., et al., "Selegiline Treatment Facilitates Recovery After Stroke," *Neurorehabilitation and Neural Repair* 15:183-190 (2001).

Uchida, S., et al., "Cortical Oscillations in Human Medial Temporal Lobe During Wakefulness and All-night Sleep," *Brain Research* 891:7-19 (2001).

Yasar, S., et al., "Metabolic Transformation Plays a Primary Role in the Psychostimulant-Like Discriminative-Stimulus Effects of Selegiline [(R)-(—)-Deprenyl]," *The Journal of Pharmacology and Experimental Therapeutics* 317(1):387-394 (2006).

Peterson, D. W., and Sparber, S. B., "Differential Actions of d- and l-amphetamine on the Metabolism of 3H-norepinephrine in Rat Brain," *Pharmacol. Biochem. Behav.*, 4(5): Abstract (1976).

Alafuzoff, I., et al., "Selegiline Treatment and the Extent of Degenerative Changes in Brain Tissue of Patients with Alzheimer's Disease," *Eur. J. Clin. Pharmacol.*, 55:815-819 (2000).

Alles, G. A., "Comparative Physiological Actions of the Optically Isomeric Phenisopropylamines," *University of California Publications in Pharmacology*,129-150 (1939).

Angrist, B. M., et al., "Comparative Psychotomimetic Effects of Stereoisomers of Amphetamine," *Nature*, 234:152-153 (1971).

Anisman, H. and Waller, T. G., "Effects of Methamphetamine and Shock Duration During Inescapable Shock Exposure on Subsequent Active and Passive Avoidance," *J. Comp.Physiol. Psychol.*, 77(1):143-151 (1971).

Arakawa, O., "Effects of Methamphetamine and Methylphenidate on Single and Paired Rat Open-Field Behaviors," *Physiol. Behav.*, 55(3):441-446 (1994).

Arnold, L. E., "Levoamphetamine vs Dextroamphetamine in Minimal Brain Dysfunction ," *Arch. Gen. Psychiatry.*, 33:292-301 (1976).

Arnold, L. E., "Levoamphetamine and Dextroamphetamine: Comparative Efficacy in the Hyperkinetic Syndrome," *Arch. Gen. Psychiat.*, 27:816-822 (1972).

Axelrod, J., "Amphetamine: Metabolism, Physiological Disposition and It's Effects on Catecholamine Storage," *Amphetamines and Related Compounds*, 207-216 (1970).

Axelrod, J., "The Enzymatic Deamination of Amphetamine (Benzedrine)," *Laboratory of Chemical Pharmacology*, 753-763 (1954).

Balster, R. L., et al., "A Comparison of *d*-Amphetamine, *l*-Amphetamine, and Methamphetamine Self-administration in Rhesus Monkeys," *Pharm. Biochem. Behav.*, 1:67-71(1973).

Barch, D. M., et al., "The Effects of D-Amphetamine on Language Function in Schizophrenia," *Society for Neuroscience Abstracts* 23(1-2):p. 1952 (1997).

Bartus, R. T., "Drugs to Treat Age-Related Neurodegenerative Problems," *JAGS*, 38(6):680-695 (1990).

Bartzokis, G., et al., "Selegiline Effects on Cocaine-Induced Changes in Medial Temporal Lobe Metabolism and Subjective Ratings of Euphoria," *Neuropsychopharmacology*, 20(6): 582-590 (1999).

Bauer, R. and Evey, L., "Differential Effects of L-Amphetamine on Ontogeny of Active Avoidance, Intertitial Responses, and Locomotor Activity," *Psychopyharmacology* 75: 299-304 (1981).

Beckett, A. M., et al., "Metabolic Oxidation on Aliphatic Basic Nitrogen Atoms and Their α-carbon Atoms-Some Unifying Principles," *Letters to the Editor, J. Pharm. Pharmac.* 23:809-812 (1971).

Berlyne, D. E., "Arousal, Reward and Learning," *Ann. N. Y. Acad. Sci.*, 159(3):1059-1070 (1969).

Biel, J. H., "Structure-Activity Relationships of Amphetamine and Derivatives," *Amphetamines and Related Compounds*, 3-19 (1970).

Biel, J. H. and Bopp. B. A., "Amphetamines: Structure-Activity Relationships," in The Handbook of Psychopharmacology, vol. 11, stimulants, L. L. Iversen, S. D. Iverson. and S. H. Snyder. Eds.. Plenum Publishing Company, New York, 1978, pp. 1-39.

Birkmayer, W., "Long Term Treatment With L-Deprenyl," *J. Neural Transm.*, 43:239-244 (1978).

Bisagno, V., et al., "Short Toxic Methamphetamine Schedule Impairs Object Recognition Task in Male Rats," *Brain Res.*, 940:95-101 (2002).

Blaug, S. M. and Huang W.-T., "Interaction of Dextroamphetamine Sulfate with Spray-Dried Lactose," *J. Pharm. Sci.*,61(11):1770-1775 (1972).

Bodkin, J. A. and Amsterdam, J. D., "Transdermal Selegiline in Major Depression: A Double-Blind, Placebo-Controlled, Parallel-Group Study in Outpatients," *Am. J. Psychiatry*, 159(11):1869-1875 (2002).

Brandeis, R. et al., "Improvement of Cognitive Function by MAO-B Inhibitor L-Deprenyl in Aged Rats," *Pharmacol. Biochem. Behav.*, 39:297-304 (1991).

Bromage, P. R., "Comparison of Vasoactive Drugs in Man," *Bri. Med. J.*, 72-74 (Jul. 12, 1952).

Brown, G. L., "Plasma Levels of *d*-Amphetamine in Hyperactive Children," *Psychopharmacology*, 62:133-140 (1979).

Brown, R. W., et al., "D-amphetamine Facilitation of Morris Water Task Performance is Blocked by Eticlopride and Correlated with Increased Dopamine Synthesis in the Prefrontal Cortex," *Behav. Brain Res.*, 114:135-143 (2000).

Browne, R. G. and Segal, D. S., "Metabolic and Experiential Factors in the Behavioral Response to Repeated Amphetamine," *Pharmacol. Biochem. Behav.*, 6:545-552 (1977).

Burešová, O. and Bureš, J., "Radial Maze as a Tool for Assessing the Effect of Drugs on the Working Memory of Rats," *Psychopharmacology*, 77:268-271 (1982).

Caldwell, J., et al., "Metabolism of [$^{14}$C]Methamphetamine in Man, the Guinea Pig and the Rat," *Biochem. J.*, 129:11-22 (1972).

Cappon, G. D. and Vorhees, C. V., "Plasma and Brain Methamphetamine Concentrations in Neonatal Rats," *Neurotoxicol. Teratol.*, 23:81-88 (2001).

Carr, G. D. and White, N. M., "The Relationship Between Stereotypy and Memory Improvement Produced by Amphetamine," *Psychopharmacology* 82:203-209 (1984).

Chang, L., et al., "Perfusion MRI and Computerized Cognitive Test Abnormalities in Abstinent Methamphetamine Users," *Psychiatry Research Neuroimaging*, 114:65-79 (2002).

Chapman, D. E., et al., "Long-Term Changes in Basal Ganglia Function After a Neurotoxic Regimen of Methamphetamine," *J. Pharmacol.Exp. Ther.*, 296(2):520-527 (2001).

Cho, D., et al., "Behavioral Teratogenicity of Methamphetamine," Department of Toxicology, National Institute of Safety Research, Seoul, Korea., *Journal Toxicol. Sci.*, 16 (Supp. 1):37-49 (1991).

Chrisp, P., et al., "Selegiline: A Review of its Pharmacology, Symptomatic Benefits and Protective Potential in Parkinson's Disease," *Drugs & Aging*, 1(3):228-248 (1991).

Clement, B., et al., "Reduction of Amphetamine Hydroxylamine and Other Aliphatic Hydroxylamines by Benzamidoxime Reductase and Human Liver Microsomes," *Chem. Res. Toxicol.*, 13:1037-1045 (2000).

Cochran, J. C., et al., "Parsing Attentional Components During a Simple Reaction Time Task Using Sleep Deprivation and Amphetamine Intervention," *Precet. Mot. Skills*, 75:675-689 (1992).

Cochran, J. C., et al., "Decoupling Motor Memory Strategies: Effects of Sleep Deprivation and Amphetamine," *Intern. J. Neurosci.*, 74:45-54 (1994).

Cody, J. T. and Schwarzhoff, R., "Interpretation of Methamphetamine and Amphetamine Enantiomer Data," *J. Anal Toxicol.,*, 17:321-326 (Oct. 1993).

Cody, J. T., "Metabolic Precursors to Amphetamine and Methamphetamine," *Forensic Sci. Rev.*, 5(2):110-127 (1993).

Comer, S. D., et al., "Effects of Repeated Oral Methamphetamine Administration in Humans," *Psychopharmacology*, 155:397-404 (2001).

Cook, C. E., et al., Pharmacokinetics of Oral Methamphetamine and Effects of Repeated Daily Dosing in Humans, *Drug Metab. Dispos.*, 20(6):856-862 (1992).

Cook, C. E., et al., "Pharmacokinetics of Methamphetamine Self-Administered to Human Subjects by Smoking S-(+)-Methamphetamine Hydrochloride," *Drug Metab. Dispos.*, 21(4):717-723 (1993).

Cooke, B. J. A., "Chirality of Methamphetamine and Amphetamine From Workplace Urine Samples," *J. Anal Toxicol.*, 18:49-51 (1994).

Cookson, J. and Silverstone, T., "The Effects of Methamphetamine on Mood and Appetite in Depressed Patients: A Placebo-controlled Study," *Int. Clin. Psychopharmacol.*, 1:127-133 (1986).

Corsi-Cabrera, M., et al., "Gender Differences in the EEG During Cognitive Activity," *Intern. J. Neurosci.* 72:257-264 (1993).

Courtney, K. D. and Valerio, D.A., "Teratology in the *Macaca mulatta*," *Teratology*, 1:163-172 (1968).

Crabbe, J. C. and Alpern, H. P., "d-Amphetamine: Disruptive Effects on the Long-Term Store of Memory and Proactive Facilitatory Effects on Learning in Inbred Mice," *Pharmacol. Biochem. Behav.*, 3:647-652 (1975).

Croce, P. D., et al., "A Simple Procedure for N-Propenylation and N-Propynylation of Secondary Amines," *Gazzetta Chimica Italiana*, 126:107-109 (1996).

Csanda, E., et al., "Experiences With L-Deprenyl in Parkinsonism," *J. Neural Transm.*, 43:263-269 (1978).

Czub, M., et al., "Effects of Selegiline in a Retroviral Rat Model for Neurodegenerative Disease," *J. NeuroVirol.*, 5:458-464 (1999).

Davis, J. M., et al., "Effects of Urinary pH on Amphetamine Metabolism," *Ann. N.Y. Acad. Sci.*, 179:493-501 (1971).

DeLuca, J., "Cognitive Dysfunction After Aneurysm of the Anterior Communicating Artery," *J. Clin. Exp. Neuropsychol.*, 14(6):924-934 (1992).

Dixit, S. N., et al., "Effect of Selegiline on Cognitive Functions in Parkinson's Disease," *JAPI*, 47(8):784-786 (1999).

Donnan, P. T., et al., "Selegiline and Mortality in Subjects with Parkinson's Disease: a Longitudinal Community Study," (Reply from the authors), *Neurology*, 57(2): Correspondence (2001).

Dring, L. G., et al., "The Metabolic Fate of Amphetamine in Man and Other Species," *Biochem. J.*, 116:425-435 (1970).

Dring, L. G., et al., "The Fate of Amphetamine in Man and Other Mammals," *Letters to the Editor, J. Pharm. Pharmac.* 18:402-405 (1966).

Dringenberg, H. C., et al., "Increased Effectiveness of Tacrine by Deprenyl Co-treatment in Rats: EEG and Behavioral Evidence," *Neuropharmacology and Neurotoxicology*, 11(16):3513-3516 (2000).

Ebadi, M., et al., "Neuroprotective Actions of Selegiline," *J. Neurosc. Res.*, 67:285-289 (2002).

Ebert, U. and Kirch, W., "Scopolamine Model of Dementia: Electroencephalogram Findings and Cognitive Performance," *Eur. J. Clin. Invest.*, 28:944-949 (1998).

Elsworth, J. D., et al., "The Contribution of Amphetamine Metabolites of (-)-Deprenyl to Its Antiparkinsonian Properties," *J. Neural Transm.*, 54:105-110 (1982).

Ernst, M., et al., "Selegiline in ADHD Adults: Plasma Monoamines and Monoamine Metabolites," *Neuropsychopharmacology*, 16(4):276-284 (1997).

Ernst, M., et al., "Selegiline in Adults With Attention Deficit Hyperactivity Disorder: Clinical Efficacy and Safety," *Psychopharmacol. Bull.*, 32(3):327-334 (1996).

Falsaperla, A., et al., "Selegiline Versus Oxiracetam in Patients With Alzheimer-Type Dementia," *Clinical Therapeutics*, (12)5:376-384, (1990).

Fang, J. and Yu, P. H., "Effect of L-Deprenyl, its Structural Analogues and Some Monoamine Oxidase Inhibitors on Dopamine Uptake," *Neuropharmacology*, 33(6):763-768 (1994).

Ferrando, R. L., et al., "Bizarre Behavior Following the Ingestion of Levo-Desoxyephedrine," *Drug Intelligence and Clinical Pharmacy*, 22:214-216 (1988).

Filip, V. and Kolibas, E., "Selegiline in the Treatment of Alzheimer's Disease: a Long-Term Randomized Placebo-Controlled Trial," *J. Psychiatry Neurosci.*, 24(3):234-243 (1999).

Finali, G., et al., "L-Depreynl Therapy Improves Verbal Memory in Amnesic Alzheimer Patients," *Clin. Neuropharmacol.*, 14(6):523-536 (1991).

Finali, G., et al., "Alzheimer-type Dementia and Verbal Memory Performances: Influence of Selegiline Therapy," *Ital. J. Neurol. Sci.*, 13:141-148 (1992).

Finkelstein, J. E., et al., "Milacemide Treatment in Mice Enhances Acquisition of a Morris-Type Water Maze Task," *Pharmacol. Biochem. Behav.*, 49(3):707-710 (1994).

Fitzgerald, R. L., et al., "Resolution of Methamphetamine Stereoisomers in Urine Testing: Urinary Excretion of R(-)-Methamphetamine Following Use of Nasal Inhalers," *J. Anal Toxicol.*, 12:255-259 (Sep.-Oct. 1988).

Fleming, K., et al., "Neuropsychological Effects of Amphetamine May Correlate with Personality Characteristics," *Psychopharmacol. Bull.*, 31(2):357-362 (1995).

Foster, B. S. and Gilbert, D. D., "Enantiomeric Determination of Amphetamine and Methamphetamine in Urine by Precolumn Derivatization with Marfey's Reagent and HPLC," *J. Anal. Toxicol.*, 22:265-269 (1998).

Fowler, J. S., et al., "Evidence That L-deprenyl Treatment for One Week Does Not Inhibit MAO A or the Dopamine Transporter in the Human Brain," *Life Sci.*, 68:2759-2768 (2001).

Gelowitz, D. L., et al., "Chronic L-Deprenyl or L-Amphetamine: Equal Cognitive Enhancement, Unequal MAO Inhibition," *Pharmacol. Biochem. Behav.*, 47:41-45 (1994).

Gibbs, M. E., "Effects of Amphetamine on Short-Term, Protein-Independent, Memory in Day-Old Chickens," *Pharmacol. Biochem. Behav.*, 4:305-309 (1976).

Glennon, R. A., et al., "A Preliminary Behavioral Investigation of PMMA, the 4-Methoxy Analog of Methamphetamine," *Pharmacol. Biochem. Behav.*, 31:9-13 (1988).

Golbe, L. I., et al., "Selegiline and Parkinson's Disease: Protective and Symptomatic Considerations," *Drugs*, 39(5):646-651 (1990).

Gold, P. E., et al., "Modulation of Long-Term Potentiation by Peripherally Administered Amphetamine and Epinephrine," *Brain Res.*, 305:103-107 (1984).

Goldstein, L. B., "Effects of Amphetamines and Small Related Molecules on Recovery After Stroke in Animals and Man," *Neuropharmacology* 39:852-859 (2000).

Gordon, M. N., et al., "Oral Versus Transdermal Selegiline: Antidepressant-Like Activity in Rats," *Pharmacol. Biochem. Behav.*, 63(3):501-506 (1999).

Grasing, K., et al., "Biphasic Effects of Selegiline on Striatal Dopamine: Lack of Effect on Methamphetamine-Induced Dopamine Depletion," *Neurochem. Res.*, 26(1):65-74 (2001).

Gunaratna, C. and Kissinger, P. T., "Investigation of Stereoselective Metabolism of Amphetamine in Rat Liver Microsomes by Microdialysis and Liquid Chromatography with Precolumn Chiral Derivatization," *J. Chromatography A*, 828:95-103 (1998).

Gunne. L-M., "The Urinary Output of d- and l-Amphetamine in Man," *Biochem. Pharmacol.*, 16:863-869 (1967).

Gyarmati, Z. S., et al., "Behavioural Consequences of Methamphetamine-Induced Neurotoxicity in Rats," *Neurobiology*, 9(1):37-39 (2001).

Haley, T. J., "Desoxyephedrine—A Review of the Literature," *J. Am. Pharm. Assoc.*, 36(6):161-169 (1947).

Hardman, J.G., et al., "Goodman & Gilman's The Pharmacological Basis of Therapeutics," 9th Edition eds. (NY: McGraw-Hill), pp. 202 and 221 (1995).

Harris, H., et al., "Behavioral Properties of Amphetaminil Enantiomers," National Institute of Mental Health—42nd Annual NCDEU Meeting: Poster Session I [online], Jul. 2002 [retrieved on Mar. 11, 2003]. Retrieved from the Internet <URL: http://www.nimh.nih.gov/ncdeu/abstracts2002/ncdeu1025.cfm>.

Hart, C. L., et al., "Methamphetamine Self-administration by Humans," *Psychopharmacology*, 157:75-81 (2001).

Hartmann, E. and Cravens, J., "Sleep: Effects of *d*- and *l*-Amphetamine in Man and in Rat," *Psychopharmacology*, 50:171-175 (1976).

Haughey, H. M., et al., "Differential Effects of Methamphetamine on $NA^+/Cl^-$ Dependent Transporters," *Brain Res.*, 863:59-65 (2000).

Haycock, J. W., et al., "Effects on Retention of Posttraining Amphetamine Injections in Mice: Interaction with Pretraining Experience," *Psychopharmacology*, 54:21-24 (1977).

Heinonen, E. H., et al., "Pharmacokinetic Aspects of 1-deprenyl (Selegiline) and its Metabolites," *Clin. Pharmacol. Ther*+ 56(6), *part 2*, 742-749 (1994).

Heinonen, E. H., et al., "Pharmacokinetics and Metabolism of Selegiline," *Acta Nerol Scand.*, 126:93-99 (1989).

Herrell, J. M., et al., "A Multisite Study of the Effectiveness of Methamphetamine Treatment: An Initiative of the Center for Substance Abuse Treatment," *J. Psychoactive Drugs*, 32(2):143-147 (2000).

Hornbeck, C. L. and Czarney, R. J., "Retrospective Analysis of Some L-Methamphetamine/L-Amphetamine Urine Data," *J. Anal Toxicol.*, 17:23-25 (1993).

Hutchaleelaha, A., et al., "Disposition Kinetics of *d*- and *l*-Amphetamine Following Intravenous Administration of Racemic Amphetamine to Rats," *Drug Metab. Dispos.*, 22(3):406-411 (1994).

Itoh, J., et al., "Utility of an Elevated Plus-Maze for Dissociation of Amnesic and Behavioral Effects of Drugs in Mice," *Eur. J. Pharmacol.*, 194:71-76 (1991).

Jelic, V., et al., "Quantitative Electroencephalography in Mild Cognitive Impairment: Longitudinal Changes and Possible Prediction of Alzheimer's Disease," *Neurobiol. of Aging*, 21:533-540 (2000).

Jirovsky, D., et al., "Methamphetamine—Properties and Analytical Methods of Enantiometer Determination," *Forensic Sci. Int.*, 96:61-70 (1998).

Jirovsky, D., et al., "The Pilot Study of Methamphetamine Enantiometer Metabolism in Man by Capillary Electrophoresis," *Chemica*, 40:25-34 (2001).

Johnson, B. A., et al., "Effects of Isradipine, A Dihydropyridine-Class Calcium Channel Antagonist, on D-Methamphetamine-Induced Cognitive and Physiological Changes in Humans," *Neurophychopharmacology*, 22(5):504-512 (2000).

Jonason, K. R., et al., "Effects of Amphetamine Upon Relearning Pattern and Black-White Discriminations Following Neocortical Lesions in Rats," *J. Comp. Physiol. Psychol.*, 73(1):47-55 (1969).

Jori, A., et al., "Differences in the Availability of *d*- and *l*-Enantiomers after Administration of Racemic Amphetamine to Rats," *Xenobiotica*, 8(10):589-595 (1978).

Karch, S. B., et al., "Methamphetamine-Related Deaths in San Francisco: Demographic, Pathologic, and Toxicologic Profiles," *J. Forensic Sci.*, 44(2):359-368 (1999).

Karoum, F., et al., "Metabolism of (-) Deprenyl to Amphetamine and Methamphetamine May Be Responsible for Deprenyl's Therapeutic Benefit: a Biochemical Assessment," *Neurology (Ny)*, 32:503-509 (1982).

Kasirsky, G. and Tansy, M.F., "Teratogenic Effects of Methamphetamine in Mice and Rabbits," *Teratology*, 4:131-134 (1971).

Kieburtz, K., et al., "A Randomized, Double-Blind, Placebo-Controlled Trial of Deprenyl and Thioctic Acid in Human Immunodeficiency Virus-Associated Cognitive Impairment," *Neurology*, 50:645-651 (Mar. 1998).

Kikuchi, M., et al., "EEG Changes Following Scopolamine Administration in Healthy Subjects," *Neuropsychobiology* 39:219-226 (1999).

Kim, E. M., et al., "Determination of Enantiomeric Metabolites of L-deprenyl, d-methamphetamine, and Racemic Methamphetamine in Urine by Capillary Electrophoresis: Comparison of Deprenyl Use and Methamphetamine Use," *J. Anal Toxicol.*, 24(4):238-244 (2000).

Kirrane et al., "Effects of Amphetamine on Visuospatial Working Memory Performance in Schizophrenia Spectrum Personality Disorder," *Neuropsychopharmacology 2000* 22(1):14-18 (2000).

Knoefel, P., "The Influence of Phenisopropyl Amine and Phenisopropyl Methyl Amine on Work Output," *Society for Pharmacol. Exp. Ther.*, p. 83 (1943).

Knoll, J., "The Possible Mechanisms of Action of (-)Deprenyl in Parkinson's Disease," *J. Neural Transm.*, 43:177-198 (1978).

Knoll, J., "The Pharmacology of (-)Deprenyl," *J. Neural Transm.*, (*Suppl*), 22:75-89 (1986).

Kohl, R. L., et al., "Arousal and Stability: The Effects of five New Sympathomimetic Drugs Suggest a New Principle for the Prevention of Space Motion Sickness," *Aviat. Space, Environ. Med.*, 137-143 (1986).

Kopell, B. S., et al., "The Effects of Methamphetamine and Secobarbital on the Continent Negative Variation Amplitude," *Psychopharmacoligia (Berl.)*, 34:55-62 (1974).

Kopell, B. S. and Wittner, W. K., "The Effects of Chlorpromazine and Methamphetamine on Visual Signal-From-Noise Detection," *J. Nerv. Ment. Dis.*, 147(4):418-424 (1968).

Kraemer, T. and Maurer, H. H., "Toxicokinetics of Amphetamines: Metabolism and Toxicokinetic Data of Designer Drugs, Amphetamine, Methamphetamine, and Their N-Alkyl Derivatives," *Ther. Drug Monit.*, 24(2):277-289 (2002).

Kraemer, T. and Maurer, H. H., "Determination of Amphetamine, Methamphetamine and Amphetamine-derived Designer Drugs or Medicaments in Blood and Urine," *J. Chromatogr. B.*, 713:163-187 (1998).

Krivanek, J. A. and McGaugh, J. K., "Facilitation Effects of Pre- and Posttrial Amphetamine Administration on Discrimination Learning in Mice," *Agents and Actions*, 1:36-42 (1969).

Kuczenski, R., et al., "Hippocampus Norepinephrine, Caudate Dopamine and Serotonin, and Behavioral Responses to the Stereoisomers of Amphetamine and Methamphetamine," *J. Neurosci.*, 15(2):1308-1317 (1995).

Kuhn, D. M., and Geddes, T. J., "Molecular Footprints and Neurotoxic Amphetamine Action," *Ann. N. Y. Acad. Sci.*, 914:92-103 (2000).

Kulig, B. M., and Calhoun, W. H., "Enhancement of Successive Discrimination Reversal Learning by Methamphetamine," *Psychopharmacologia (Berl.)*, 27:233-240 (1972).

Kumar, V. and Banker, G. S., "Maillard Reaction and Drug Stability," *Maillard Reactions in Chemistry, Food, and Health*, 151:20-27 (1994).

Laine, K., et al., "Multiple-Dose Pharmacokinetics of Selegiline and Desmethylselegiline Suggest Saturable Tissue Binding," *Clin. Neuropharmacol.*, 23(1):22-27 (2000).

Lajtha, A., et al., "Mebabolism of (-)-Deprenyl and PF-(-)-Deprenyl in Brain After Central and Peripheral Administration," *Neurochem. Res.*, 21(10):1155-1160 (1996).

Larsen, J. P., et al., "Does Selegiline Modify the Progression of Early Parkinson's Disease? Results from a Five-year Study," *Eur. J. Neurol.*, 6:539-547 (1999).

Law, M. Y. L., "Selective Involvement of Cytochrome P450 2D Subfamily in In Vivo 4-Hydroxylation of Amphetamine in Rat," *Drug Metab.Dispos.*, 28(3):348-353 (2000).

Law. M. Y. L. and Moody, D. E., "Urinary Excretion of Amphetamine and 4'-Hydroxyamphetamine by Sprague Dawley and Dark Agouti Rats," *Life Sci.*, 54(15):1073-1079 (1994).

Lee, E. H. Y. and Ma, Y. L., "Amphetamine Enhances Memory Retention and Facilitates Norepinephrine Release from the Hippocampus in Rats," *Brain Res. Bull.*, 37(4):411-416 (1995).

Lehmann, H. E., et al., "The Effect of Psychostimulants on Psychometric Test Performance With Special Reference to Conflict Avoidance Behavior," *Curr. Ther. Res.*, 12(6):390-393 (1970).

Lin, L. Y., et al., "Cytochrome P4502D Isozymes Catalyze the 4-Hydroxylation of Methamphetamine Enantiomers," *Drug Metab. Dispos.*, 23(6):610-614 (1995).

Lokiec, F., et al., "A Comparison of the Kinetics of *d*- and *l*-Amphetamine in the Brain of Isolated and Aggregated Rats," *Psychopharmacology* 58:73-77 (1978).

M'Harzi, M., et al., "d-Amphetamine Enhances Memory Performance in Rats with Damage to the Fimbria," *Physiol. Behav.*, 42:575-579 (1988).

Magidson, O.Y., and Garkusha, G.A., "The Synthesis of 2-phenylisopropylamine (phenamine)," *Chemical Abstracts* 35, 5868 (1941).

Mangoni, A. "Effects of a MAO-B Inhibitor in the Treatment of Alzheimer Disease," *Eur Neurol.* 31: 100-107 (1991).

Mann, J. J., et al., "A Controlled Study of the Antidepressant Efficacy and Side Effects of(-)-Deprenyl," *Arch. Gen. Psychiatry*, 46:45-50 (1989).

Martin, W. R., et al., "Physiologic, Subjective, and Behavioral Effects of Amphetamine, Methamphetamine, Ephedrine, Phenmetrazine, and Methylphenidate in Man," *Clin. Pharmacol. Ther.*, 12(2):245-258 (1970).

Martinez, J. L., et al., "Central and Peripheral Actions of Amphetamine on Memory Storage," *Brain Research*, 182:157-166 (1980).

Maruyama, W. and Naoi, M., "Neuroprotection by (-)-deprenyl and Related Compounds," *Mech. Ageing Dev.*, 111:189-200 (1999).

Matsubara, K., et al., "L-Deprenyl Prevents the Cell Hypoxia Induced by Dopaminergic Neurotoxins, Mpp+ and β-carbolinium: a Microdialysis Study in Rats," *Neuroscience Lett.*, 302:65-68 (2001).

Matthews, C., "Overweight Relapse: Effects of Training and Methamphetamine with Pentobarbital," *Curr. Ther. Res.*, 12(1):34-39 (1970).

Mayfield, D. G., "The Effect of Intravenous Methamphetamine on Mood," *Int. J.Addict.*, 8(3):565-568 (1973).

McIntyre, H. B., "Computer Analyzed EEG in Amphetamine-Responsive Hyperactive Children," *Psychiatry Res.*, 4:189-197 (1981).

Melega, W. P., et al., "Pharmacokinetic and Pharmacodynamic Analysis of the Actions of D-Amphetamine and D-Methamphetamine on the Dopamine Terminal," *J. Pharmacol. Exp. Ther.*, 274(1): 90-96 (1995).

Melega, W. P., et al., "*l*-Methamphetamine Pharmacokinetics and Pharmacodynamics for Assessment of in vivo Deprenyl-Derived *l*-Methamphetamine," *J.Pharmacol. Exp. Ther.*, 288(2):752-758 (1999).

Metcalf, F. U., et al., "Methamphetamine Effects Upon Avoidance Behavior during Limbic Seizures in the Cat," *Psychopharmacologia (Berl.)*, 21:390-400 (1971).

Mewaldt, S. P., and Ghoneim, M. M., "The Effects and Interactions of Scopolamine, Physostigmine and Methamphetamine on Human Memory," *Pharmacol. Biochem. Behav.*, 10:205-210 (1979).

Milgram, N. W., et al., "The Effect of L-Deprenyl on Behavior, Cognitive Function, and Biogenic amines in the Dog," *Neurochem. Res.*,18(12):1211-1219 (1993).

Mills, D. and Ledger, R., "The Effects of Oral Selegiline Hydrochloride on Learning and Training in the Dog: A Psychobiological Interpretation," *Prog. Neuro-Psychopharmacol. & Biol. Psychiat.*, 25:1597-1613 (2001).

Miyamoto, K., "Conditioned Drug Effects of Pimozide, Haloperidol and Chlorpromazine on Methamphetamine-Induced Behavior," *Japanese J. Psychiat. Neurol.*, 44(3):629-636 (1990).

Mohs, R. C., et al., "Sensitivity of Some Human Cognitive Functions to Effects of Methamphetamine and Secobarbital," *Drug and Alcohol Depend.*, 5:145-150 (1980).

Mohs, R. C., et al., "Methamphetamine and Diphenhydramine Effects on the Rate of Cognitive Processing," *Psychopharmacology*, 59:13-19 (1978).

Monmaur, P., et al., "Involvement of Septal Muscarinic Receptors in Cholinergically Mediated Changes in Rat Rearing Activity," *Pharmacol. Biochem. Behav.*, 58(2):577-582 (1997).

Moretti, R., et al., "Effects of Selegiline on Fronto-temporal Dementia: a Neuropsychological Evaluation," *Int. J. Geriatr. Psychiatry*, 17:391-392 (2002).

Muller, H., et al., "Rey Auditory-Verbal Learning Test: Structure of a Modified German Version," *Jornal of Clinical Psychology*, 53(7):663-671 (1997).

Munzar, P., et al., "Potentiation of the Discriminative-stimulus Effects of Methamphetamine by the Histamine $H_3$ Receptor Antagonist Thioperamide in Rats," *Eur. J. Pharmacol.*, 363:93-101 (1998).

Musshoff, F., "Illegal or Legitimate Use? Precursor Compounds to Amphetamine and Methamphetamine," *Drug Metab. Rev.*, 32(1):15-44 (2000).

Myers, C.E., et al., "Impaired Delay Eyeblink Classical Conditioning in Individuals With Anterograde Amnesia Resulting From Anterior Communicating Artery Aneurysm Rupture," *Behav. Neurosci.*, 115(3):560-570 (2001).

Nickel, B., et al., "Effect of Enantiomers of Deprenyl (Selegiline) and Amphetamine on Physical Abuse Liability and Cortical Electrical Activity in Rats," *Neuropharmacology*, 29(11):983-992 (1990).

Nicolaus, B. J. R., "Symbiotic Approach to Drug Design," *Decision Making in Drug Research*, pp. 173-186 (1983).

Ogata, A., "Constitution of Ephedrine," *Chemical Abstracts 14*, 745 (1920).

Ong, Y. L., et al., "Suppression of Bulimic Symptoms with Methylamphetamine," *Brit. J. Psychiat.*, 143: 288-293 (1983).

Ozaki, T., et al., "The Adverse Effects of *l*-Methamphetamine on the Development of Explanted Rat Embryos," *Asia-Oceania Journal Obstet. Gynaecol. 18*(3):277-281 (1992).

Parkes, J. D., et al., "Amphetamines in the Treatment of Parkinson's Disease," *J. Neurol., Neurosurg., Psychiat.*, 38:232-237 (1975).

Parkes, J. D. and Fenton, G. W., "Levo(-) Amphetamine and Dextro(+) Amphetamine in the Treatment of Narcolepsy," *J. Neurol., Neurosurg., Psychiat.*, 36:1076-1081 (1973).

Parkinson Study Group, "Impact of Deprenyl and Tocopherol Treatment on Parkinson's Disease in DATATOP Subjects Not Requiring Levodopa," *Ann. Neurol.*, 39(1):29-36 (1996).

Penetar, D. M., et al., "Amphetamine Effects on Recovery Sleep Following Total Sleep Deprivation," *Human Psychopharmacology*, 6:319-323 (1991).

Pepeu, G., "Memory Disorders: Novel Treatments, Clinical Perspective," *Life Sci.*, 55(25-26):2189-2194 (1994).

Perez-Reyes, M., et al., "Clinical Effects of Methamphetamine Vapor Inhalation," *Life Sci.*, 49(13):953-959 (1991).

Perez-Reyes, M., "Differences in Sedative Susceptibility Between Types of Depression," *Arch. Gen. Psychiat.*, 19:64-71 (1968).

*Physician Desk Reference* 946, 1221 (1969).

Pitsikas, N., et al., "Effect of Org2766, an ACTH(4-9) Analogue, on Recovery After Bilateral Transection of the Fimbria Fornix in the Rat," *Pharmacol. Biochem. Behav.*, 38:931-934 (1991).

Pitsikas, N., et al., "DAU 6215, A Novel 5-HT3 Receptor Antagonist, Improves Performance in the Aged Rat in the Morris Water Maze Task," *Neurobiol. of Aging* 14:561-564 (1993).

Plasznik, A. and Kostowski, W., "Effects of p-Bromo-Methamphetamine (V-111) on Conditioned Avoidance Behavior in Rats with Lesioned *Raphe Nuclei*," *Fol. J. Pharmacol. Pharm.* 21, 193-198 (1997).

Platel, A. and Porsolt, R. D., "Habituation of Exploratory Activity in Mice: A Screening Test for Memory Enhancing Drugs," *Psychopharmacology*, 78:346-352 (1982).

Prinzmetal, M. and Alles, G. A., "The Central Nervous System Stimulant Effects of Dextro-Amphetamine Sulphate," 200(5):665-673 (1940).

Przuntek, H., et al., "SELEDO: a 5-year Long-term Trial on the Effect of Selegiline in Early Parkinsonian Patients Treated with Levodopa," *Eur. J. Neurology*, 6:141-150 (1999).

Quartermain, D., et al., "Amphetamine Enhances Retrieval Following Diverse Sources of Forgetting," *Physiol. Behav.*, 43:239-241 (1988).

Quartermain, D. and Altman, H .J., "Facilitation of Retrieval by d-Amphetamine Following Anisomycin-Induced Amnesia," *Physiol. Psychol.*, 10(3):283-292 (1982).

Quartermain, D. and Jung, H., "Persistence of Retrieval Enhancement by Amphetamine Following Scopolamine-Induced Amnesia," *Pharmacol. Biochem. Behav.*, 33:51-54 (1989).

Quartermain, D., et al., "Alleviation of Scopolamine Amnesia by Different Retrieval Enhancing Treatments," *Pharmacol. Biochem. Behav.* 30(4):1093-1096 (1988).

Ramos, J., et al., "EEG Activity During Cognitive Performance in Women," *Intern. J. Neurosci.*, 69:185-195 (1993).

Reus, V. I., et al., "d-Amphetamine: Effects on Memory in a Depressed Population," *Biol. Psychol.*, 14(2):345-356 (1979).

Reynolds, G. P., et al., "Deprenyl is Metabolized to Methamphetamine and Amphetamine in Man," *Br. J. Clin. Pharmac.*, 6:542-544 (1978).

Richards, J. B., et al., "Trained and Amphetamine-Induced Circling Behavior in Lesioned, Transplanted Rats," *J. Neural Transplantation & Plasticity*, 4(2):157-166 (1993).

Richter, D., "CCXXIX. Elimination of Amines in Man," *Biochem. J.*, 32:1763-1769 (1938).

Richter-Levin, G. and Yaniv, D., "Is LTP in the Hippocampus a Useful Model for Learning-Related Alterations in Gene Expression?," *Reviews in Neurosciences*, 12:289-296 (2001).

Riederer, P. and Przuntek, H. (eds.), "MAO-B-Inhibitor Selegiline (R-(-)-Deprenyl), A New Therapeutic Concept in the Treatment of Parkinson's Disease," *J.Neural Transm., Supp.* 25: (1987).

Riederer, P., et al., "On the Mode of Action of L-Deprenyl in the Human Central Nervous System," *J. Neural Transm.*, 43:217-226 (1978).

Riekkinen, Jr., P., et al., "Effects of Alzene and Tacrine on Water Maze Reference and Working Memory Function in Medial Septal-Lesioned Rats," *Brain Res.*, 714:118-124 (1996).

Riley, D. E., "Reversible Transvestic Fetishism in a Man With Parkinson's Disease Treated With Selegiline," *Clin. Neuropharmacol.*, 25(4):234-237 (2002).

Riviere, G. J., et al., "Disposition of Methamphetamine and Its Metabolite Amphetamine in Brain and Other Tissues in Rats after Intravenous Administration," *J. Pharmacol. Exp. Ther.*, 292(3):1042-1047 (2000).

Riviere, G. J., et al., "Spontaneous Locomotor Activity and Pharmacokinetics of Intravenous Methamphetamine and Its Metabolite Amphetamine in the Rat," *J. Pharmacol. Exp. Ther.*, 291(3):1220-1226 (1999).

Roth, L. W., et al., "A Comparison of the Analeptic, Circulatory and Other Properties of D- and L-Desoxyephedrine," *Arch. Int. Pharmacoyn.*, XCVII(3):362-368 (1954).

Sainsbury, R. S., "Hippocampal Theta: A Sensory-Inhibition Theory of Function," *Neurosc. Biobehav. Rev.*, 22(2):237-241 (1998).

Sano, M., et al., "A Controlled Trial of Selegiline, Alpha-Tocopherol, or Both as Treatment for Alzheimer's Disease," *NEJM*, 336(17):1216-1222 (1997).

Sansone, M., et al., "Interaction between Nootropic Drugs and Methamphetamine on Avoidance Acquisition but not on Locomotor Activity in Mice," *Arch. Int. Pharmacodyn.*, 278:229-235 (1985).

Sansone, M., et al., "Minaprine, but not Oxiracetam, Prevents Desipramine-Induced Impairment of Avoidance Learning in Mice," *Pol. J. Pharmacol.* 47:69-73 (1995).

Sara, S. J. and Deweer, B., "Memory Retrieval Enhanced by Amphetamine After a Long Retention Interval," *Behavioral and Neural Biology*, 36:146-160 (1982).

Sarter, M., "Behavioral Screening for Cognition Enhancers from Indiscriminate to Valid Testing: Part II" *Psychopharmacology*, 107:461-473 (1992).

Sarter, M., "Behavioral Screening for Cognition Enhancers: from Indescriminate to Valid Testing: Part I," *Psychopharmacology*, 107:144-158 (1992).

Satoh, M., et al., "A Pharmacological Profile of LTP in CA3 Region of Guinea-Pig Hippocampus In Vitro," *Biomedical Research*, 10(2):125-129, 1989.

Schachter, M., et al., "Deprenyl in the Management of Response Fluctuations in Patients with Parkinson's Disease on Levodopa," *J. Neurol., Neurosurg., Psychiatry*, 43:1016-1021 (1980).

Scheinin, H., et al., "CYP2D6 Polymorphism is Not Crucial for the Disposition of Selegiline," *Clin. Pharmacol. Ther.*, 64(4):402-411 (1998).

Shappell, S. A., et al., "Stimulated Sustained Flight Operations and Performance, Part 2: Effects of Dextro-Methamphetamine," *Military Psychology*, 4(4), 267-287 (2002).

Shimada, A., et al., "Neurochemical Analysis of the Psychotoxicity of Methamphetamine and Cocaine by Microdialysis in the Rat Brain," *Ann. N. Y. Acad. Sci*, 801(1):361-370 (1996).

Shimosato, K., "Urinary Excretion of *p*-Hydroxylated Methamphetamine Metabolites in Man. II Effect of Alcohol Intake on Methamphetamine Metabolism," *Pharmacol. Biochem. Behav.*, 29: 733-740 (1988).

Shutter, L. and Garell, D. C., "Obesity in Children and Adolescents: A Double-Blind Study with Cross-Over," *J. Sch. Health*, 273-275 (1966).

Sim, T., et al., "Cognitive Deficits Among Methamphetamine Users with Attention Deficit Hyperactivity Disorder Symptomatology," *J. Addict. Dis.*, 21(1):75-89 (2002).

Simpson, L. L., "Blood Pressure and Heart Rate Responses Evoked by *d*- and *l*-Amphetamine in the Pithed Rat Preparation," *J. Pharmacol. Exp. Ther.*, 193:149-159 (1975).

Simpson, L. L., "Evidence That Deprenyl, A Type B Monoamine Oxidase Inhibitor, Is an Indirectly Acting Sympathomimetic Amine," *Biochem. Pharmacol.*, 27:1591-1595 (1978).

Smith, R. C., et al., "Comparative Effects of *d*-Amphetamine, *l*-Amphetamine, and Methylphenidate on Mood in Man," *Psychopharmacology* 53:1-12 (1977).

Soetens, E., et al., "Effect of Amphetamine on Long-Term Retention of Verbal Material," *Psychopharmacology*, 119:155-162 (1995).

Soetens, E., et al., "Amphetamine Enhances Human-Memory Consolidation," *Neurosci. Lett. 161*:9-12 (1993).

Song, J. K., et al., "Neuroradiologic Diagnosis and Treatment of Vasospasm," *Cerebral Aneurysms*, 7(4):819-835 (1997).

Sprague, J. E. and Nichols, D. E., "The Monoamine Oxidase-B Inhibitor L-Deprenyl Protects Against 3,4-Methylenedioxymethamphetamine-Induced Lipid Peroxidation and Long-term Serotonergic Deficits," *J. Pharmacol. Exp. Ther.*, 273(2):667-673 (1995).

Squire, L. R., "Cerebral Protein Synthesis Inhibition and Discrimination Training: Effects of D-amphetamine," *Brain Res.*, 177:401-406 (1999).

Stein, L., et al., "Memory Enhancement by Central Administration of Norepinephrine," *Brain Res.* 84(1):329-335 (1975).

Strupp, B. J., et al., "Time-Dependent Effects of Post-Trial Amphetamine Treatment in Rats: Evidence for Enhanced Storage of Representational Memory," *Behav. Neural. Biol.*, 56:62-76 (1991).

Szende, B., et al., "Anti-apoptotic and Apoptotic Action of (-)-deprenyl and its Metabolites," *J. Neural. Transm.*, 108:25-33 (2001).

Szoko, E., et al., "Biotransformation of Deprenyl Enantiomers," *Eur. J. Drug Metab. Pharmacokinet.*, 24(4):315-319 (1999).

Tariot, P. N., et al., "Cognitive effects of L-deprenyl in Alzheimer's Disease," *Psychopharmacology*, 91:489-495 (1987).

Tariot, P. N., et al., "L-Deprenyl in Alzheimer's Disease," *Arch. Gen. Psychiatry*, 44:427-433 (1987).

Tatton, W. G., "Selegiline Can Mediate Neuronal Rescue Rather Than Neuronal Protection," *Movement Disorder Society*, 8(Supp. 1):S20-S30 (1993).

Teter, D. F., "Metabolism of Diet Pill to Amphetamine and Methamphetamine," (Letters to the Editor), *JOEM*, 41(3):139 (1999).

ThyagaRajan, S., et al., "Region-specific Alterations in the Concentrations of Catecholamines and Indoleamines in the Brains of Young and Old F344 Rats after L-deprenyl Treatment," *Brain Res. Bull.*, 48(5):513-520 (1999).

Van Rijzingen, I. M. S., "ACTH(4-9) Analog ORG2766 Treatment 7 Months Delayed Still Improves Morris Maze Performance of Fimbria-Lesioned Rats," *Pharmacol. Biochem. Behav.*, 53(1):163-169 (1996).

Van Alyea, O. E., and Donnelly, W. A., "Systemic Effects of Intranasal Medication," *Eye, Ear, Nose & Throat Monthly*, 31:476-480 (1952).

Van Kammen, D. P. and Murphy, D. L., "Attenuation of the Euphoriant and Activating Effects of *d*- and *l*-Amphetamine by Lithium Carbonate Treatment," *Psychopharmacologia (Berl.)*, 44:215-224 (1975).

Vidrio, H., "Cardiovascular Effects of Methamphetamine in Dogs Treated Chronically with the Amine," *J. Cardiovas. Pharmacol.*, 4(2):326-329 (1982).

Volkow, N. D., et al., "Loss of Dopamine Transporters in Methamphetamine Abusers Recovers with Protracted Abstinence," *J. Neurosci.*, 21(23):9414-9418 (2001).

Vorhees, C. V., et al., "Adult Learning Deficits After Neonatal Exposure to D-Methamphetamine: Selective Effects on Spatial Navigation and Memory," *J. Neurosc.*, 20(12):4732-4739 (2000).

Vree, T. B., and van Rossum, J. M., "Kinetics of Metabolism and Excretion of Amphetamines in Man," in *Amphetamines and Related Compounds*, Costa and Garattini, eds. (Rave Press, NY) pp. 165-190 (1970).

Walter-Batson, D., et al., "Amphetamine Paired with Physical Therapy Accelerates Motor Recovery After Stroke," *Stroke*, 26(12):2254-2259 (1995).

Wan, S. H., et al., "Kinetics, Salivary Excretion of Amphetamine Isomers, and Effect of Urinary pH," *Clin. Pharmacol. Ther.*, 23(5):585-590 (1978).

Wang, J. Q. and McGinty, J. F., "Dose-Dependent Alteration in zif/268 and Preprodynorphin mRNA Expression Induced by Amphetamine or Methamphetamine in Rat Forebrain," *J. Pharmacol. Exp. Ther.*, 273(2):909-917 (1995).

Wiegmann, D. A., et al., "Methamphetamine Effects on Cognitive Processing During Extended Wakefulness," *Int. J. Aviat. Psychol.*, 6(4):379-397 (1996).

Wilcock, G. K., et al., "The Effect of Selegiline in the Treatment of People with Alzheimer's Disease: a Meta-analysis of Published Trials," *Int. J. Geriatr. Psychiatry 17*:175-183 (2002).

Witkin, J. M. et al., "Behavioral, Toxic and Neurochemical Effects of Sydnocarb, a Novel Psychomotor Stimulant: Comparisons with Methamphetamine," *Pharmacol. Exp. Ther.*, 288(3):1298-1310 (1999).

Wolthuis, O. L., "Experiments With UCB 6215, A Drug Which Enhances Acquisition In Rats: Its Effects Compared With Those of Metamphetamine," *Eur. J. Pharmacol.*, 16:283-297 (1971).

Yamamoto, R., and Takasaki, K., "Involvement of Presynaptic $\alpha_2$-Adrenoreceptors in the Depressor Response Produced by Repeated Administration of Dextro-Methamphetamine," *J. Auton. Pharmac.*, 3:79-88 (1983).

Yamamura, T., et al., "Effects of Methamphetamine and Ethanol on Learning and Brain Neurotransmitters in Rats," *Pharmacol. Biochem. Behav.*, 42:389-400 (1992).

Yamamura, T., et al., "Effects of Daily Administration of Methamphetamine on Multiple Active/Passive Avoidance Performance in Rats," *Behav. Brain Res.*, 53:105-112 (1993).

Yanagisawa, Y., et al.,"Association Equilibrium of *d*-Methamphetamine and *l*-Methamphetamine With Serum Albumin," *Chirality 10*:742-746 (1998).

Yasar, S., et al., "Are Metabolites of I-deprenyl (Selegiline) Useful or Harmful? Indications From Preclinical Research," J. Neurol. Transmission [suppl 48], Springer Verlag, Wein, New York, pp. 61-73 (1996).

Yasar, S. and Bergman, J., "Amphetamine-like effect of *l*-deprenyl (selegiline) in Drug Discrimination Studies," *Clin. Pharmacol. Ther.*, 56(6):768-773 (1994).

Yasar, S. et al., "Evaluation of the Sterioisomers of Deprenyl for Amphetamine-Like Discriminative Stimulus Effects in Rats," *J. Pharmacol. Exp. Ther.*, 265(1):1-6 (1993).

Yasar, S., et al., "Preclinical Evaluation of *l*-Deprenyl: Lack of Amphetamine-Like Abuse Potential," *Inhibitors of Monoamine Oxidase B Pharmacology and Clinical Uses in Neurodegenerative Disorders*, I. Szelenyi, ed. (Switzerland: Birkhauser Verlag Basel), pp. 215-233 (1993).

Yi-Ping, H., "Effects of Modafinil and Amphetamine on Sleep-Wake Cycle After Sleep Deprivation in Cats," *Acta Pharmacol Sin*, 20(9):813-818 (1999).

Yokel, R. A. and Pickens, R., "Self-Administration of Optical Isomers of Amphetamine and Methylamphetamine by Rats," *J. Pharmacol. Exp. Ther.*, 187(1):27-33 (1973).

Yonkov, D. I., "Participation of Cholinergic Mechanics in The Memory Effects of CNS Stimulants," *Advanced In The Bioscience, Pergamon Press, GB.*, 59:347-350 (1986).

Yoshida, T., et al., "Metabolism of Deprenyl, a Selective Monoamine Oxidase (MAO) B Inhibitor in Rat: Relationship of Metabolism to MAO-$\beta$ Inhibitory Potency," *Xenobiotica*, 16(2):129-136 (1986).

Young, G. A., "Relationship Between Amphetamine-Induced Effects on EEG Power Spectra and Motor Activity in Rats," *Pharmacology Biochemistry & Behavior 30*:489-492 (1988).

Yui, K., et al., "Noradrenergic Activity and Spontaneous Recurrence of Methamphetamine Psychosis," *Drug and Alcohol Depend.*, 44: 183-187 (1997).

Yui, K. and Miura, T., "Behavioral Responses Induced by Repeated Treatment with Methamphetamine Alone and in Combination with Scopolamine in Rats," *Neuropsychobiology*, 33:21-27 (1996).

Zink, W. E., et al., "Model Systems for Assessing Cognitive Function: Implications for HIV-1 Infection and Drugs of Abuse," *Neuroimmune Circuits, Drugs of Abuse, and Infectious Diseases*, 7-27 (2001).

Birks, J. and Flicker, L., "Selegiline for Alzheimer's Disease," (Cochrane Review). In: *The Cochrane Library, Issue 4*; pp. 1-35 (2002). Oxford: Update Software.

Bishop, J., et al., "Toxicology and Carcinogenesis Studies of *dl*-Amphetamine Sulfate in F344/N Rats and B6C3F$_1$ Mice," (Technical Report Series No. 387). Research Triangle Park, NC: National Toxicology Program, U. S. Department of Health and Human Services; pp. 3-185 (1991).

Brady, et al., "Stroke Risk Predicts Verbal Fluency Decline in Heathy Older Men," *J Gerontol B Psychol Sci Soc Sci*, 56:P340-P346 (2001).

Caldarusa-Dalton, "Parkinson's Disease: Current and Future Treatments," http://sulcus.berkeley.edu/mcb/165_001/papers/manuscripts/_519.html; pp. 1-9 (1999).

Hill, "What is Neuroprotection?" *Medical News Today*, www.medicalnewstoday.com (Oct. 9, 2006).

Iudicello, et al., "Verbal Fluency in HIV Infection: A Meta-Analytic Review," *J Int Neuropsychol Soc*, 13: 183-189 (2007).

The Kenneth T. and Eileen L. Norris Laboratory for Neuroscience Research, "Alzheimer's Disease," *University of Southern California School of Pharmacy*, pp. 1-3 (2007).

Khan, "Can Clinical Outcomes be used to Detect Neuroprotection in Multiple Sclerosis?" *Neurology*, 68:S64-S71, (2007).

Piérard, et al., "Declarative Memory Impairments following a Military Combat Course: Parallel Neuropsychological and Biochemical Investigations," *Neuropsychobiology*, 49:210-17 (2004).

Rajan, "Senior Moments: The Neurobiology of Memory and Aging," *Serendip*, pp. 1-4 (2002).

Goodman, et al., *Goodman and Gilmans' The Pharmacological Basis of Therapeutics*, $9^{th}$ Ed. pp. 202 and 221 (1996).

Rohatagi, etal., "Pharmacokinetic Evaluation of a Selegiline Pulsatile Oral Delivery System," *Biopharmaceutics & Drug Diposition*, 18(8):665-680 (1997).

Van Kammen D.P., et al., "Attenuation of the Euphoriant and Activating Effects of *d*- and *l*-Amphetamine by Lithium Carbonate Treatment," *Psychopharmacologia 44*, pp. 215-224 (Aug. 1975).

Buchsbaum M.S., et al., "Individual Differences in Average Evoked Responses to *d*-and *l*-Amphetamine With and Without Lithium Carbonate in Depressed Patients," *Psychopharmacology 51*, pp. 129-135 (1977).

Cooper, J.A., et al., "Cognitive Impairment in Early, Untreated Parkinson's Disease and its Relationship to Motor Disability," *Brain 114*(5): pp. 2095-122 (Jan. 1991).

Tom, T., et al., "Depression in Parkinson's Disease, Pharmacological Characteristics and Treatment," *Drugs and Aging 12*(1): pp. 55-74 (Jan. 1998).

Angrist, and Gershon, "Relationship Between Symptoms and Urinary Levels of Amphetamine," *Some Recent Studies of Amphetamine Psychosis—Unresolved Issues*, 197-199 and 203.

Axelrod, J., et al., "Effect of Psychotropic Drugs on the Uptake of $H^{3}$-Norepinephrine by Tissues," *Science*, 133:383-384 (1961).

Batterman, R.C., "Studies with Levo-Desoxyephedrine," Combination Report to the Vicks Chemical Company, Mar. 4, 1965, pp. i and 1-5.

Beckett, A. H. and Rowland, M., "Urinary Excretion Kinetics of Amphetamine in Man," *J. Pharm. Pharmacol. 17*:628-639 (1965).

Birks, J. and Flicker, L., "Selegiline For Alzheimer's Disease," (Cochrane Review). In: *The Cochrane Library, Issue 2* (2002). Oxford: Update Software, pp. 1-25.

Bishop, J., et al., "Toxicology and Carcinogenesis Studies of *dl*-Amphetamine Sulfate in F344/N Rats and B6C3F$_1$ Mice," (Technical Report Series No. 387). Research Triangle Park, NC: National Toxicology Program, U. S. Department of Health and Human Services (1991), pp. 1-188.

CA Index Name: "Benzeneethanamine, ÿ- methyl-, (ÿS)-(9Cl)", *SciFinder Scholar*, Registry No. 51-64-9 (2001), p. 2.

Lehmann, H. E. and Ban, T. A., "Effects of Psychoactive Drugs on Conflict Avoidance Behavior in Human Subjects," *Activitas nervosa superior*, 13(2):82-85 (1971).

Lin, J. S., et al., "Effects of Amphetamine and Modafinil on the Sleep/Wake Cycle During Experimental Hypersomnia Induced by Sleep Deprivation in the Cat," *J. Sleep Res.*, March 9(1):89-96 (2000).

Melega, W. P., et al., "Effects of Deprenyl Metabolite, L-Methamphetamine on Striatal Dopamine Efflux," *Neurotransmission, Neuromodulation* 8(4): Abstract No. 2177 (1994).

Colpaert, F.C., et al., "Discriminative Stimulus Properties of a Low *dl*-Amphetamine Dose," *Arch. Int. Pharmacodyn 223*, pp. 34-42 (1976).

\* cited by examiner

METHODS FOR TREATING COGNITIVE IMPAIRMENT IN HUMANS WITH MULTIPLE SCLEROSIS

RELATED APPLICATIONS

This application is a continuation-in-part application of International Application PCT/US2004/015974, filed May 21, 2004, which designates the United States and was published in English, which is a continuation-in-part of U.S. application Ser. No. 10/791,223, filed Mar. 2, 2004, which is a continuation-in-part of U.S. application Ser. No. 10/444,970, filed May 23, 2003 now abandoned, which is a continuation-in-part of U.S. application Ser. No. 10/139,606, filed May 2, 2002, now abandoned which is a continuation-in-part of U.S. application Ser. No. 10/003,740 filed Oct. 31, 2001, now U.S. Pat. No. 6,828,351, issued Dec. 7, 2004, which claims the benefit of U.S. Provisional Application No. 60/245,323, filed on Nov. 1, 2000, and claims priority to International Application PCT/US01/45793, filed Oct. 31, 2001, which designates the United States and was published in English. This application also claims the benefit of U.S. Provisional Application No. 60/473,168, filed May 23, 2003. The teachings of the above applications are incorporated herein by reference in their entirety.

BACKGROUND OF THE INVENTION

The term "memory" subsumes many different processes and requires the function of many different brain areas. Overall, human memory provides declarative recall, e.g., for facts and events accessible to conscious recollection, and non-declarative recall, e.g., procedural memory of skills and operations not stored regarding time and place. Research in recent years has provided information necessary to understand many of the various components of memory and has identified associated brain regions. A newly acquired experience initially is susceptible to various forms of disruption. With time, however, the new experience becomes resistant to disruption. This observation has been interpreted to indicate that a labile, working, short-term memory is consolidated into a more stable, long-term memory.

Behavioral research has found that the human mind consolidates memory at certain key time intervals. The initial phase of memory consolidation occurs in the first few minutes after an exposure to a new idea or learning experience. The next phase occurs over a longer period of time, such as during sleep. If a learning experience has on-going meaning to us, the next week or so serves as a further period of memory consolidation. In effect, in this phase, the memory moves from short-term to long-term storage.

Moreover, various mechanisms have been proposed to account for the formation of long-term memory. A wide range of observations suggest an evolutionarily conserved molecular mechanism involved with the formation of long-term memory. These include increased release of synaptic transmitter, increased number of synaptic receptors, decreased $K_D$ of receptors, synthesis of new memory factors either in the presynaptic or postsynaptic element, sprouting of new synaptic connections, increase of the active area in the presynaptic membrane and many others. Synaptic plasticity, the change in the strength of neuronal connections in the brain, is thought to underlie long-term memory storage.

Memory consolidation, the process of storing new information in long-term memory is also believed to play a crucial role in a variety of neurological and mental disorders, including mental retardation, Alzheimer's disease and depression. Indeed, loss or impairment of long-term memory is a significant feature of such diseases, and no effective therapy for that effect has emerged. Short-term memory and working memory, are generally not significantly impaired in such patients.

Accordingly, methods and compositions that enhance long-term memory function and/or performance, or prophylactically (e.g., as a neuroprotective treatment) prevent or slow degradation of long-term memory function and/or performance would be desirable. Similarly, methods and compositions for restoring long-term memory function and/or performance are needed.

Impairments in cognitive and memory processes in a human can occur in a number of conditions or diseases, such as age-related memory loss, Mild Cognitive Impairment, Alzheimer's disease, Multiple Sclerosis, brain injury, brain aneurysm, stroke, schizophrenia, epilepsy, chronic fatigue syndrome, fibromyalgia syndrome, chemotherapy (e.g., cancer chemotherapy), traumatic brain injury, and Parkinson's disease. Following exposure to a muscarinic cholinergic receptor antagonist, such as atropine or scopolamine, humans can experience impairment of cognitive and memory processes. Clinical management strategies currently provide minimal, if any, improvement in memory and cognitive function. Thus, there is a need to develop new, improved and effective methods for the treatment of a human suffering with an impairment in cognitive and memory processes.

SUMMARY OF THE INVENTION

The present invention relates to methods of treating a human having an impairment in memory and/or cognitive function.

The human can have an impairment in memory consolidation (the process of storing new information in long term memory), an impairment in short term memory processes, an impairment in working memory, an impairment in long-term memory, an impairment in declarative memory or an impairment in procedural memory. The humans are treated with the amphetamine class of compounds (collectively referred to herein as "amphetamine compounds") to enhance, prevent and/or restore long-term memory function and performance, e.g., to improve the process of storing new information in long term memory in humans (memory consolidation) or to improve short term memory or to improve working memory. The human can have an impairment in memory and/or a cognition function as a consequence of exposure to a muscarinic cholinergic receptor antagonist. More particularly, the invention relates to the discovery that a particular enantiomer of amphetamine compounds (R)-(−)-amphetamine (l-amphetamine, levo-amphetamine) or (R)-(−)-methamphetamine (l-methamphetamine, levo-methamphetamine) is effective for treating humans having an impairment in memory and an impairment in cognitive function.

In one embodiment, the invention includes a method of improving memory consolidation in a human, comprising the step of administering at least one member selected from the group consisting of l-amphetamine and l-methamphetamine to a human having an impairment in memory consolidation.

In another embodiment, the invention includes a method of improving memory consolidation in a human, comprising the step of administering at least one member selected from the group consisting of l-amphetamine and l-methamphetamine to a human having an impairment in memory consolidation, wherein the l-amphetamine is at least about 80 mole percent l-amphetamine relative to d-amphetamine and the l-methamphetamine is at least about 80 mole percent l-methamphetamine relative to d-methamphetamine.

In yet another embodiment, the invention includes a method of improving memory consolidation in a human, comprising the step of administering at least one member selected from the group consisting of l-amphetamine and l-methamphetamine to a human having an impairment in memory consolidation, wherein the l-amphetamine is at least about 90 mole percent l-amphetamine relative to d-amphetamine and the l-methamphetamine is at least about 90 mole percent l-methamphetamine relative to d-methamphetamine.

An additional embodiment of the invention includes a method of improving memory consolidation in a human, comprising the steps of assessing the degree of an impairment in memory consolidation in a human; administering at least one member selected from the group consisting of l-amphetamine and l-methamphetamine to the human; and determining the improvement in memory consolidation after administering the l-amphetamine and l-methamphetamine to the human.

In still another embodiment, the invention includes a method of improving memory consolidation in a human, comprising the step of administering an amphetamine to a human having an impairment in memory consolidation in an amount effective to improve memory consolidation in the human, wherein the amphetamine is at least about 85 mole percent l-amphetamine.

In another embodiment, the invention includes a method of improving memory consolidation in a human, comprising the step of administering an amphetamine to a human having an impairment in memory consolidation in an amount effective to improve memory consolidation in the human, wherein the amphetamine is at least about 80 mole percent l-amphetamine.

Another embodiment of the invention includes a method of improving memory consolidation in a human, comprising the step of administering an amphetamine to a human having an impairment in memory consolidation in an amount effective to improve memory consolidation in the human, wherein the amphetamine is at least about 99 mole percent l-amphetamine and the l-amphetamine is administered to the human in a dose of at least about a 0.01 mg dose.

In yet another embodiment, the invention includes a method of improving memory consolidation in a human, comprising the step of administering an amphetamine to a human having an impairment in memory consolidation in an amount effective to improve memory consolidation in the human, wherein the amphetamine is at least about 90 mole percent l-amphetamine and the l-amphetamine is administered to the human in a dose between about a 0.01 mg dose to about a 125 mg dose.

In an additional embodiment, the invention includes a method of improving memory consolidation in a human, comprising the step of administering an amphetamine to a human having an impairment in memory consolidation in an amount effective to improve memory consolidation in the human, wherein the amphetamine is at least about 80 mole percent l-amphetamine and the l-amphetamine is administered to the human in a dose at lease about a 0.01 mg dose.

In a further embodiment, the invention includes a method of improving memory consolidation in a human, comprising the step of administering an amphetamine to a human having an impairment in memory consolidation in an amount effective to improve memory consolidation in the human, wherein the amphetamine is between about 80 mole percent l-amphetamine to about 99 mole percent l-amphetamine.

In still another embodiment, the invention includes a method of improving memory consolidation in a human, comprising the step of administering an amphetamine to a human having an impairment in memory consolidation in an amount effective to improve memory consolidation in the human, wherein the amphetamine is between about 80 mole percent l-amphetamine to about 99 mole percent l-amphetamine and the l-amphetamine is administered to the human in a dose at least about a 0.01 mg dose.

Another embodiment of the invention includes a method of improving memory consolidation in a human comprising assessing the degree of impairment in memory consolidation in a human having an impairment in memory consolidation and administering an amphetamine to the human in an amount effective to improve memory consolidation in the human, wherein the amphetamine is at least about 80 mole percent l-amphetamine. The improvement in memory consolidation after administering the amphetamine to the human is determined.

In an additional embodiment, the invention includes a method of improving memory consolidation in a human, comprising the step of administering an amphetamine to a human having an impairment in memory consolidation in an amount effective to improve memory consolidation in the human, wherein the amphetamine is at least about 90 mole percent l-amphetamine and has the structural formula:

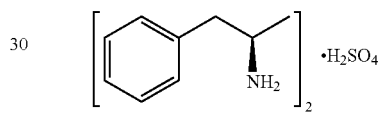

In still another embodiment, the invention includes a method of improving memory consolidation in a human, comprising the step of administering an amphetamine to a human having an impairment in memory consolidation in an amount effective to improve memory consolidation in the human, wherein the amphetamine is at least about 90 mole percent l-methamphetamine.

In a further embodiment, the invention includes a method of improving memory consolidation in a human, comprising the step of administering an amphetamine to a human having an impairment in memory consolidation in an amount effective to improve memory consolidation in the human, wherein the amphetamine is at least about 85 mole percent l-methamphetamine.

An additional embodiment of the invention includes a method of improving memory consolidation in a human, comprising the step of administering an amphetamine to a human having an impairment in memory consolidation in an amount effective to improve memory consolidation in the human, wherein the amphetamine is at least about 80 mole percent l-methamphetamine.

In yet another embodiment, the invention includes a method of improving memory consolidation in a human, comprising the step of administering an amphetamine to a human having an impairment in memory consolidation in an amount effective to improve memory consolidation in the human, wherein the amphetamine is at least about 99 mole percent l-methamphetamine and the dose of l-methamphetamine administered to the human is at least about a 0.01 mg dose.

Another embodiment of the invention includes a method of improving memory consolidation in a human, comprising the step of administering an amphetamine to a human having an impairment in memory consolidation in an amount effective to improve memory consolidation in the human, wherein the amphetamine is at least about 90 mole percent l-methamphetamine and the l-methamphetamine is administered to the human in a dose at least about a 0.01 mg dose.

In yet another embodiment, the invention includes a method of improving memory consolidation in a human, comprising the step of administering an amphetamine to a human having an impairment in memory consolidation in an amount effective to improve memory consolidation in the human, wherein the amphetamine is at least about 80 mole percent l-methamphetamine and the dose of l-methamphetamine administered to the human is at least about a 0.01 mg dose.

In a further embodiment, the invention includes a method of improving memory consolidation in a human, comprising the step of administering an amphetamine to a human having an impairment in memory consolidation in an amount effective to improve memory consolidation in the human, wherein the amphetamine is between about 80 mole percent l-methamphetamine to about 99 mole percent l-methamphetamine.

An additional embodiment of the invention includes a method of improving memory consolidation in a human, comprising the step of administering an amphetamine to a human having an impairment in memory consolidation in an amount effective to improve memory consolidation in the human, wherein the amphetamine is between about 80 mole percent l-methamphetamine to about 99 mole percent l-methamphetamine and the l-methamphetamine is administered to the human in a dose at least about a 0.01 mg dose.

Another embodiment of the invention includes a method of improving memory consolidation in a human, comprising assessing the degree of impairment in memory consolidation in a human having an impairment in memory consolidation and administering an amphetamine to the human in an amount effective to improve memory consolidation in the human, wherein the amphetamine is at least about 80 mole percent l-methamphetamine. The improvement in memory consolidation after administering the amphetamine to the human is determined.

In an additional embodiment, the invention includes a method of improving memory consolidation in a human, comprising the step of administering an amphetamine to a human having an impairment in memory consolidation in an amount effective to improve memory consolidation in the human, wherein the amphetamine is at least about 90 mole percent l-methamphetamine and has the structural formula:

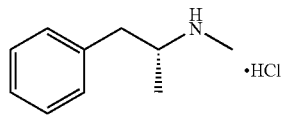

In one embodiment, the invention is a pharmaceutical kit comprising one or more amphetamine compound(s) in an amount sufficient to enhance long-term memory in a patient, a pharmaceutically acceptable carrier, and instructions (written and/or pictorial) describing the use of the formulation for enhancing memory.

In another embodiment, the invention is a pharmaceutical preparation comprising one or more amphetamine compounds provided as a single oral dosage formulation in an amount sufficient to enhance long-term memory in a patient but resulting in a concentration in the patient lower than its $EC_{50}$ as a CNS stimulant.

In still another embodiment, the invention is a pharmaceutical preparation comprising one or more amphetamine compounds provided in the form of a transdermal patch and formulated for sustained release of the amphetamine(s) in order to administer an amount sufficient to enhance long-term memory in a patient but resulting in a concentration in the patient lower than its $EC_{50}$ as a CNS stimulant.

In particular embodiments, the pharmaceutical kits and preparations of the invention comprise at least one of the amphetamine compounds represented by Formula I, or a pharmaceutically acceptable salt, solvate, metabolite or prodrug thereof:

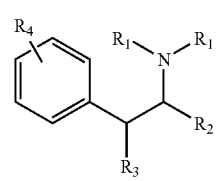

(I)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulfhydryl, cyano, nitro, lower alkyl, and sulfate.

In certain embodiments, $R_4$ represents hydrogen and at least one of $R_1$, $R_2$, and $R_3$ represents hydrogen. In certain embodiments, $R_4$ represents hydrogen and at least two of $R_1$, $R_2$, and $R_3$ represents hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

In certain embodiments, one $R_1$ represents hydrogen, one $R_1$ represents lower alkyl, such as methyl, ethyl, propyl, isopropyl, n-butyl, isobutyl, t-butyl, etc., $R_2$ represents lower alkyl, such as methyl, ethyl, propyl, isopropyl, n-butyl, isobutyl, t-butyl, etc., $R_3$ and $R_4$ represent hydrogen.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 3 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In other preferred embodiments the pharmaceutical kits and preparations of this invention comprise at least one of the amphetamine compounds as a pharmaceutically acceptable salt represented by Formula II:

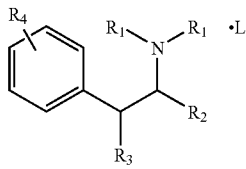

(II)

wherein, as valence and stability permit,
$R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;
$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;
$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;
$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido; and
L is a non-toxic organic or inorganic acid.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulfhydryl, cyano, nitro, lower alkyl, and sulfate.

In certain embodiments, $R_4$ represents hydrogen and at least one of $R_1$, $R_2$, and $R_3$ represents hydrogen. In certain embodiments, $R_4$ represents hydrogen and at least two of $R_1$, $R_2$, and $R_3$ represents hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

In certain embodiments, one $R_1$ represents hydrogen, one $R_1$ represent lower alkyl, such as methyl, ethyl, propyl, isopropyl, n-butyl, isobutyl, t-butyl, etc., $R_2$ represents lower alkyl, such as methyl, ethyl, propyl, isopropyl, butyl, isobutyl, t-butyl, etc., $R_3$ and $R_4$ represent hydrogen.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In other preferred embodiments the pharmaceutical kits and preparations of this invention comprise at least one of the amphetamine compounds as an amphetamine metabolite represented by Formula III:

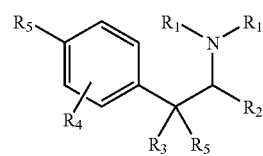

(III)

wherein, as valence and stability permit,
$R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
$R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido;

$R_5$ independently for each occurrence, represents hydrogen or hydroxy.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulfhydryl, cyano, nitro, lower alkyl, and sulfate.

In certain embodiments, $R_4$ represents hydrogen and at least one of $R_1$, $R_2$, and $R_3$ represents hydrogen. In certain embodiments, $R_4$ represents hydrogen and at least two of $R_1$, $R_2$, and $R_3$ represent hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

In certain embodiments, one $R_1$ represents hydrogen, one $R_1$ represent lower alkyl, such as methyl, ethyl, propyl, isopropyl, n-butyl, isobutyl, t-butyl, etc., $R_2$ represents lower alkyl, such as methyl, ethyl, propyl, isopropyl, n-butyl, isobutyl, t-butyl, etc., $R_3$ and $R_4$ represent hydrogen.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In one embodiment, $R_1$, independently and for each occurrence, represents hydrogen, $R_2$ represents methyl, and $R_3$ and $R_4$ independently and for each occurrence represent hydrogen.

In another embodiment, a metabolite of an amphetamine compound is selected from p-hydroxyamphetamine, benzyl methyl ketone, 1-phenylpropan-2-ol, benzoic acid, glycine, hippuric acid, p-hydroxynorephedrine, and N-hydroxylamphetamine.

In particular embodiments of the kits, preparations, compositions and methods, the invention features a pharmaceutical kit or preparation comprising a mixture of at least a single species of amphetamine compounds or at least two different species of amphetamine compounds. The different species of amphetamine compounds can be present in equal or in differing amounts with respect to one another.

In another embodiment of the kits, preparations, compositions and methods, the invention features a composition comprising at least about 51 percent (w/w (weight/weight) or mole percent), about 60 percent (w/w or mole percent), about 75 percent (w/w or mole percent), about 80 percent (w/w or mole percent), about 85 percent (w/w or mole percent), about 95 percent (w/w or mole percent) or about 99 percent (w/w or mole percent) of one amphetamine enantiomer relative to another amphetamine enantiomer (e.g., l-amphetamine relative to d-amphetamine or l-methamphetamine relative to d-methamphetamine). For example, an amphetamine composition employed in the methods can be about 80 percent (w/w or mole percent) l-amphetamine or l-methamphetamine relative to d-amphetamine or d-methamphetamine, where d-amphetamine or d-methamphetamine is about 20 percent (i.e., the remainder) (w/w or mole percent) of the amphetamine.

In another embodiment, the methods of the invention employ an amphetamine that is about 100 percent (w/w or mole percent) l-amphetamine or l-methamphetamine, wherein the l-amphetamine is a composition that includes at least about 100 mole percent l-amphetamine relative to a total amphetamine content of the composition or wherein the l-methamphetamine is administered as a composition that includes at least about 100 mole percent l-amphetamine relative to a total amphetamine content of the composition. An amphetamine that is "about 100 percent" l-amphetamine or l-methamphetamine can contain insignificant trace amounts of d-amphetamine or d-methamphetamine.

In certain preferred embodiments, particularly for those which use (R)-(−)-amphetamine (l-amphetamine) or l-methamphetamine, the kits, preparations, compositions and methods preferably use compositions of (R)-(−)-amphetamine which contain less than 10 percent (w/w or mole percent) (S)-(+)-amphetamine, and even more preferably less than less than 5 percent (w/w or mole percent), 1 percent (w/w or mole percent) or even less than 0.5 percent (w/w or mole percent) (S)-(+)-amphetamine.

In another embodiment, the amphetamine employed in the methods can be a percent of the total composition administered to the human. The amphetamine component of the composition can be about 50 percent (w/w), about 60 percent (w/w), about 75 percent (w/w), about 80 percent (w/w), about 85 percent (w/w), about 90 percent (w/w), about 95 percent (w/w) and about 100 percent (w/w) of the total composition administered to the human. For example, the human can be administered a composition which comprises about 80 weight or volume percent amphetamine and about 20 weight or volume percent, respectively, inert excipient. The amphetamine component of the composition includes at least one member selected from the group consisting of l-amphetamine, l-methamphetamine, d-amphetamine and d-methamphetamine.

In still another embodiment of the kits, preparations, compositions and methods, the invention features one or more amphetamine compound(s) provided in an amount sufficient to enhance long-term memory in a patient by a statistically significant amount when assessed by a standardized performance test.

In certain embodiments of the kits, preparations, compositions and methods, the invention features one or more amphetamine compound(s) comprising at least 2-fold less, or at least 4-fold less of the distomer(s) as compared to an equally effective long term memory enhancing dose of the distomer(s) of the amphetamine compound(s).

In certain embodiments of the kits, preparations, compositions and methods, the invention features amphetamine comprising at least 2-fold less, or at least 4-fold less of (R)-(−)-amphetamine as compared to an equally effective long term memory enhancing dose of (S)-(+)-amphetamine.

In certain embodiments of the kits, preparations, composition and methods, the invention features one or more amphetamine compound(s) provided in an amount sufficient to enhance long-term memory in a patient by a statistically significant amount when assessed by standardized performance test, such as one or more of a Rey Auditory and Verbal Learning Test (RAVLT); Cambridge Neuropsychological Test Automated Battery (CANTAB); a Children's Memory Scale (CMS); a Contextual Memory Test; a Continuous Recognition Memory Test (CMRT); a Denman Neuropsychology Memory Test; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; and a Wide Range Assessment of Memory and Learning (WRAML); First-Last Name Association (Youngjohn J. R., et al., *Archives of Clinical Neuropsychology* 6:287-300 (1991)); Name-Face Association; Wechsler Memory Scale-Revised; (Wechsler, D., Wechsler Memory Scale-Revised Manual, NY, N.Y., The Psychological Corp. (1987)); California Verbal Learning Test-Second Edition (Delis, D. C., et al., The Californian Verbal Learning Test, Second Edition, Adult Version, Manual, San Antonio, Tex.: The Psychological Corporation (2000)); Facial Recognition (delayed non-matching to sample); Cognitive Drug Research (CDR) Computerized Assessment Battery-Wesnes; Buschke's Selective Reminder Test (Buschke, H., et al., *Neurology* 24:1019-1025 (1974)); Telephone Dialing Test; and Brief Visuospatial Memory Test-Revised. In certain embodiments, the methods of the invention and pharmaceutical composition features one or more amphetamine compounds provided in an amount sufficient to enhance long-term memory (to improve memory consolidation in a human) when assessed by a word recall test such as RAVLT.

In yet another embodiment of the kits, preparations, compositions and methods, the invention features one or more amphetamine compound(s) provided in an amount sufficient to enhance long-term memory in a patient by a statistically significant amount when assessed by a Providence Recognition Memory Test.

In an additional embodiment, the invention is a method to improve a memory impairment in a human having multiple sclerosis by administration of the amphetamine compounds of the invention. The memory impairment and improvement in memory can be assessed using established criteria (for example, Thornton, A. E., et al. *Neuropsychology* 11:357-366 (1997)). These techniques include the Brown-Peterson task (Brown, J., *Quarterly J. of Exp. Psychology* 10:12-21 (1958)); the Paced Auditory Serial Addition Test (PASAT) (Gronwall, D. M. A., *Perceptual and Motor Skills* 44:367-373 (1977)); and tasks described, for example, by DeLuca, J., et al., *J. Clinical and Exp. Neuropsychology* (2004).

In another embodiment of the kits, preparations, compositions and methods, the invention features one or more amphetamine compound(s) provided in the form of a saccharate, a sulfate or an aspartate.

In certain embodiments, the subject pharmaceutical preparations are formulated for variable dosing, and preferably to deliver a sustained and increasing dose, e.g., over at least 4 hours, and more preferably over at least 8 or even 16 hours. For instance, the amphetamine compound is contained within a nonabsorbable shell that releases the drug at a controlled rate.

In certain escalating dose formulations, the amphetamine compound(s) are formulated in a delivery system including a multiplicity of layers each including the same or different polymers, a dose of the amphetamine compound(s) in an increasing dose in the multiplicity of layers, wherein in operation the preparation delivers an increasing dose of the amphetamine compound(s) over time.

In other embodiments of escalating dose formulations, the amphetamine compound(s) are formulated in a delivery system including a bioerodible polymer, a dose of the amphetamine compound(s) present in an initial dose and a final dose, whereby the preparation delivers an initial dose then a final dose over time.

In still other embodiments of escalating dose formulations, the amphetamine compound(s) are formulated in a delivery system including a plurality of beads, each bead including a amphetamine compound and having a dissolution profile, which plurality of beads is a variegated population with respect to dose and/or dissolution profile so as to deliver, upon administration, said sustained and increasing dose over at least 4 hours.

In certain escalating dose formulations, the amphetamine compound(s) are formulated in a delivery system wherein the amphetamine compound is (i) contained within a nonabsorbable shell that releases the drug at a controlled rate, and (ii) formulated in at least two different dissolution profiles.

In another embodiment of the kits, preparations, compositions and methods, the invention further features a neuronal growth factor, a neuronal survival factor, a neuronal trophic factor, a cholinergic modulator, an adrenergic modulator, a nonadrenergic modulator, a dopaminergic modulator, a glutaminergic modulator or an agent that modulates PKC, PKA, GABA, NMDA, cannabinoid, AMPA, kainate, phosphodiesterase (PDE), CREB or nootropic pathways. In one embodiment, the modulation is a stimulation of one or more of the above-referenced pathways. In another embodiment, the modulation is an antagonism of one or more of the above-referenced pathways. In yet another embodiment of the kits, preparations, compositions and methods, the invention further features methylphenidate.

Another aspect of the invention features the use of the pharmaceutical composition of amphetamine compounds in the manufacture of a medicament for prophylaxis or treatment of an animal susceptible to or suffering from anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, Multiple Sclerosis, mental retardation, Alzheimer's disease, age, age-associated memory impairment, Mild Cognitive Impairment, attention deficit disorder, attention deficit hyperactivity disorder, Anterior Communicating Artery Syndrome, chronic fatigue syndrome, fibromyalgia syndrome (also referred to herein as "fibromyalgia"), chemotherapy, and traumatic brain injury, or AIDS-related dementia, which amphetamine compound is represented by Formula I, or a pharmaceutically acceptable salt, solvate, metabolite or pro-drug thereof:

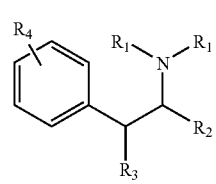

(I)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

Another aspect of the invention features the use of an amphetamine compound in the manufacture of a medicament for prophylaxis or treatment of an animal susceptible to or suffering from anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, Multiple Sclerosis, mental retardation, Alzheimer's disease, age, attention deficit disorder, attention deficit hyperactivity disorder, Anterior Communicating Artery Syndrome, age-associated memory impairment, Mild Cognitive Impairment, chronic fatigue syndrome, fibromyalgia, chemotherapy, traumatic brain injury, Parkinson's disease or AIDS-related dementia, which amphetamine compound is represented by Formula II:

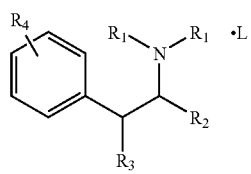

(II)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido; and L is a non-toxic organic or inorganic acid.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

Another aspect of the invention features the use of an amphetamine compound in the manufacture of a medicament for prophylaxis or treatment of an animal susceptible to or suffering from anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, age-associated memory impairment, Mild Cognitive Impairment, attention deficit disorder, attention deficit hyperactivity disorder, Multiple Sclerosis, Anterior Communicating Artery Syndrome chronic fatigue syndrome, fibromyalgia syndrome, chemotherapy, traumatic brain injury, Parkinson's disease or AIDS-related dementia, which amphetamine compound is represented by Formula III:

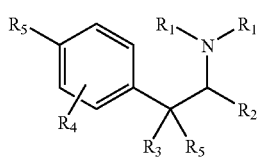

(III)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_3$ is absent or represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido;

$R_5$ independently for each occurrence, represents hydrogen or hydroxy.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

Levo-amphetamine, l-amphetamine and (R)-(−)-amphetamine are used interchangeably herein. Levo-methamphetamine, l-methamphetamine and (R)-(−)-methamphetamine are used interchangeably herein.

In one embodiment, the (R)-(−)-amphetamine employed in the methods of the invention has the structural formula:

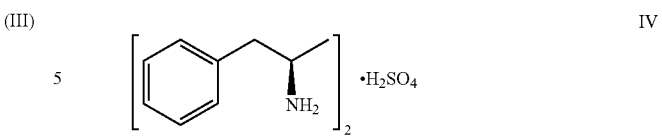

IV

Formula IV is also referred to herein as C105, levo-amphetamine sulfate or l-amphetamine sulfate. Formula IV has the molecular formula $C_{18}H_{28}N_2O_4S$ and a molecular weight of 368.50. The UPAC chemical name of Formula IV is (−)-1-methyl-2-phenylethylamine sulfate (2:1) and the CAS chemical name (−)-α-methylphenethylamine sulfate (2:1).

In another embodiment, the (R)-(−)-amphetamine employed in the methods of the invention has the structural formula:

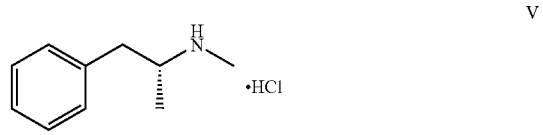

V

Formula V is also referred to herein as SN522-HCl (hydrochloride), levo-methamphetamine HCl or l-methamphetamine HCl. Formula V has the molecular formula $C_{10}H_{16}NCl$.

In still another embodiment, the (R)-(−)-amphetamine employed in the methods of the invention has the structural formula:

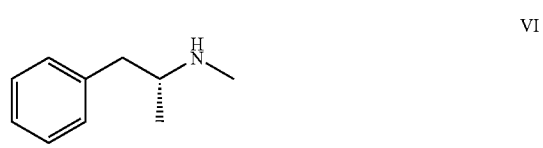

VI

Formula VI is also referred to herein as SN522, the free base of SN522, levo-methamphetamine, levo-desoxyephedrine, l-desoxyephedrine or levmetamfetamine. Formula VI has the molecular formula $C_{10}H_{15}N$ and a molecular weight of 149.24.

In still another embodiment, the amphetamine compounds employed in the methods of the invention can be a combination of the amphetamine compounds described herein, e.g., Formulas IV, V and/or VI can be employed in any combination. For example, a human having mild cognitive impairment, Alzheimer's disease and an impairment in a cognitive function (e.g., attention, executive function, reaction time, learning, information processing, conceptualization, problem solving, verbal fluency) or memory (e.g., memory consolidation, short-term memory, working memory, long-term memory, declarative memory or procedural memory) can be treated, with l-amphetamine (e.g., C105) and l-methamphetamine (e.g., SN522, SN522-HCl), either in combination or sequentially.

The amphetamine compounds employed in the methods of the invention (e.g., l-amphetamine and/or l-methamphetamine) can be administered as a component of a composition that includes at least about 99 mole %, at least about 95 mole %, at least about 90 mole %, at least about 85 mole %, at least about 80 mole %, at least about 75 mole %, at least about 70 mole %, at least about 65 mole %, or at least about 60 mole %, of l-amphetamine relative to the total amphetamine content in the composition; or at least about 99 mole %, at least about 95 mole %, at least about 90 mole %, at least about 85 mole %, at least about 80 mole %, at least about 75 mole %, at least about 70 mole %, at least about 65 mole %, or at least about 60 mole %, of l-methamphetamine relative to the total amount of amphetamine content in the composition.

In certain embodiments, the animal to be treated is a mammal. In certain preferred embodiments the animal to be treated is a human, dog, cat, cattle, horse, sheep, hog or goat.

In certain embodiments, the pharmaceutical composition is for oral administration.

In certain other embodiments the pharmaceutical composition is a transdermal patch. In certain embodiments the transdermal patch includes one or more penetration enhancers.

In certain embodiments, the pharmaceutical composition features an amphetamine compound provided as at least about 51 percent (w/w or mole percent), about 60 percent (w/w or mole percent), about 75 percent (w/w or mole percent), about 80 percent (w/w or mole percent), about 85 percent (w/w or mole percent) about 95 percent (w/w or mole percent), or 99 percent (w/w or mole percent) of the eutomers relative to the distomers of the amphetamine compound (e.g., l-amphetamine relative to d-amphetamine). In another embodiment, the amphetamine employed to treat a human is about 100% l-amphetamine (w/w or mole percent).

In certain embodiments, the pharmaceutical compositions are formulated for variable dosing, preferably to deliver a sustained dose, e.g., over at least 4 hours and more preferably over at least 8 or even 16 hours. For instance, the amphetamine compound(s) are contained within a nonabsorbable shell that releases the drug at a controlled rate.

In certain embodiments, the pharmaceutical composition features an amphetamine compound (e.g., l-amphetamine, l-methamphetamine) provided in an amount sufficient to treat Mild Cognitive Impairment, Alzheimer's disease, enhance long-term memory, short-term memory, working memory, declarative memory, procedural memory or cognitive processes such as attention, executive function, reaction time or learning in a patient by a statistically significant amount when assessed by a standardized performance test.

In certain embodiments, the pharmaceutical composition features one or more amphetamine compound(s) provided in an amount sufficient to enhance long-term memory in a patient by a statistically significant amount when assessed by one or more of a Rey Auditory and Verbal learning Test (RAVLT), Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; and a Wide Range Assessment of Memory and Learning (WRAML); First-Last Name Association (Youngjohn J. R., et al., *Archives of Clinical Neuropsychology* 6:287-300 (1991)); Name-Face Association; Wechsler Memory Scale-Revised; (Wechsler, D., Wechsler Memory Scale-Revised Manual, NY, N.Y., The Psychological Corp. (1987)); California Verbal Learning Test—Second Edition (Delis, D. C., et al., The Californian Verbal Learning Test, Second Edition, Adult Version, Manual, San Antonio, Tex.: The Psychological Corporation (2000)); Facial Recognition (delayed non-matching to sample); Cognitive Drug Research (CDR) Computerized Assessment Battery-Wesnes; Buschke's Selective Reminder Test (Buschke, H., et al., *Neurology* 24:1019-1025 (1974)); Telephone Dialing Test; and Brief Visuospatial Memory Test-Revised.

In certain embodiments, the pharmaceutical composition features one or more amphetamine compound(s) provided in an amount sufficient to enhance long-term memory in a patient by a statistically significant amount when assessed by a word recall test such as the Rey Auditory and Verbal Learning Test (RAVLT).

In certain embodiments, the pharmaceutical composition features one or more amphetamine compound(s) provided in the form of a saccharate, a sulfate or an aspartate.

In other embodiments of the kits, preparations, compositions and methods, the invention further features amphetamine compound(s) being provided as a single oral dosage formulation in an amount sufficient to enhance long-term memory in a patient but resulting in a concentration in the patient lower than its $EC_{50}$ as a CNS stimulant.

In other embodiments of the kits, preparations, compositions and methods, the invention further features amphetamine compound(s) being provided for treating and/or preventing memory impairment (impairment in memory consolidation, impairment in short term memory, impairment in working memory), wherein the memory impairment results from one or more of anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, age-associated memory impairment, Mild Cognitive Impairment, attention deficit disorder, attention deficit hyperactivity disorder, Multiple Sclerosis, Anterior Communicating Artery Syndrome or AIDS-related dementia, chronic fatigue syndrome, fibromyalgia syndrome, traumatic brain injury, or chemotherapy.

In yet another embodiment, the invention is a method of treating a perimenopausal, menopausal or postmenopausal woman having an impairment in memory (impairment in memory consolidation, impairment in short term memory, impairment in working memory) with an amphetamine compound of the invention (l-amphetamine, C105, l-methamphetamine, SN522, SN522-HCl). The amphetamine compound of the invention can be administered to the perimenopausal, menopausal or postmenopausal woman simultaneously or sequentially with other compounds, drugs or agents. For example, the amphetamine compounds can be administered to a perimenopausal, menopausal or postmenopausal woman undergoing steroid hormone replacement therapy and/or treatment for depression (e.g., selective serotonin reuptake inhibitors such as citalopram (Cipramil®), fluoxetine (Prozac®), fluvoxamine (Faverin®), paroxetine (Seroxat®), and sertraline (Lustral®).

In other embodiments of the kits, preparations, compositions and methods, the invention further features amphetamine compound(s) being provided for enhancing memory in normal individuals.

In certain preferred embodiments of the kits, preparations, compositions and methods, the invention features one or more amphetamine compound(s), wherein the amphetamine compound is (R)-(−)-amphetamine.

In certain preferred embodiments of the kits, preparations, compositions and methods, the invention features one or more amphetamine compound(s), wherein the amphetamine compound is (R)-(−)-methamphetamine.

In one embodiment of the kits, preparations, compositions and methods, the invention features a single oral dosage formulation of at least about 2.5 mg to about 25 mg, about 50 mg, about 75 mg, about 100 mg or about 125 mg of an amphetamine compound (e.g., l-amphetamine, C105, l-methamphetamine, SN522, SN522-HCl) and a pharmaceutically acceptable carrier.

In another embodiment, the single dosage formulation is at least about 0.001 mg, about 0.01 mg, about 0.1 mg, about 1 mg, about 2 mg, about 2.5 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 75 mg, about 80 mg, about 85 mg, about 90 mg, about 95 mg, about 100 mg, about 125 mg, about 150 mg, about 200 mg, about 300 mg, about 400 mg, about 500 mg, about 750 mg, or about 1000 mg of an amphetamine compound (e.g., l-amphetamine, C105, l-methamphetamine, SN522, SN522-HCl). In a particular embodiment, the dose of an amphetamine compound (e.g., l-amphetamine, C105, l-methamphetamine, SN522, SN522-HCl) is between about a 5 mg dose and about a 50 mg dose; or between about a 2 mg dose and about a 60 mg dose per day; or between about 1 mg to between about a 100 mg dose; or between about a 1 mg to about a 150 mg dose.

In still another embodiment, the methods of the invention employ multiple doses of an amphetamine compound. Each dose of the multiple dose is at least about 0.001 mg, about 0.01 mg, about 0.1 mg, about 1 mg, about 2.5 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 75 mg, about 80 mg, about 85 mg, about 90 mg, about 95 mg, about 100 mg, about 125 mg, about 150 mg, about 200 mg, about 300 mg, about 400 mg, about 500 mg, about 750 mg or about 1000 mg of an amphetamine compound (e.g., l-amphetamine, C105, l-methamphetamine, SN522, SN522-HCl). The multiple doses can be administered for a day, days, a week, weeks, a month, months or years.

The amphetamine compounds of the invention can be administered to a human acutely (briefly or short-term) or chronically (prolonged or long-term). For example, the amphetamine compounds, (e.g., l-amphetamine, C105, l-methamphetamine, SN522, SN522-HCl) of the invention can be used in methods to treat a human by administering the amphetamine to the human once a day, multiple times (e.g., 2, 3, 4) in a day, for a day, days, a week, weeks, a month, months or years.

In yet another embodiment of the kits, preparations, compositions and methods, the invention features a single oral dosage formulation of between about 0.001 mg to about 125 mg; between about 0.001 mg to about 250 mg; between 0.001 mg to 500 mg; or between about 0.01 mg to about 125 mg; or between about 0.1 mg to about 125 mg; or between about 1 mg to about 125 mg; or between about 1 mg to about 250 mg; or between about 1 mg to about 500 mg; or between about 1 mg to about 1000 mg; or between about 2.5 mg to about 25 mg, about 50 mg, about 75 mg, about 100 mg or about 125 mg of the eutomer(s) of amphetamine compound(s) (l-amphetamine, C105, l-methamphetamine, SN522) and, optionally, a pharmaceutically acceptable carrier.

In a further embodiment, the methods of the invention employ multiple doses between about 0.001 mg to about 500 mg of the amphetamine compound (e.g., l-amphetamine, C105, l-methamphetamine, SN522, SN522-HCl), wherein each of the multiple doses of the amphetamine compound is between about 0.001 mg to about 125 mg; or between about 0.001 mg to about 250 mg; or between about 0.001 mg to about 500 mg; or between about 0.01 mg to about 125 mg; or between about 0.01 mg to about 500 mg; or between about 0.1 mg to about 125 mg; or between about 1 mg to about 125 mg; or between about 1 mg and about 100 mg; or between about a 1 mg to about a 150 mg dose; or between about 1 mg and about 500 mg; between about 5 mg and about 50 mg; between about 2 mg and 60 mg between about 2.5 mg to about 25 mg, about 50 mg, about 75 mg, about 100 mg, about 125 mg, about 250 mg, about 500 mg, about 750 mg, about 1000 mg of the eutomer(s) of amphetamine compound(s) (l-amphetamine, C105, l-methamphetamine, SN522, SN522-HCl) and, optionally, a pharmaceutically acceptable carrier.

In a further embodiment, the methods of the invention employ a single dose of the amphetamine compound (l-amphetamine, C105, l-methamphetamine, SN522, SN522-HCl) between about 0.0015 mg/kg to about 2 mg/kg; between about 0.015 mg/kg to about 2 mg/kg; or about 0.07 mg to about 0.7 mg or between about 0.14 mg to about 0.7 mg; or about 0.03 mg to about 1.0 mg per day.

In yet another embodiment, the methods of the invention employ a single dose about 0.04 mg/kg, about 0.07 mg/kg, about 0.15 mg/kg, about 0.20 mg/kg, about 0.40 mg/kg, about 0.65 mg/kg, about 1 mg/kg, about 1.50 mg/kg, about 1.80 mg/kg or about 3.5 mg/kg of l-amphetamine, C105, l-methamphetamine, SN522, SN522-HCl.

In an additional embodiment, the methods of the invention employ multiple doses of the amphetamine compound (l-amphetamine, C105, l-methamphetamine, SN522, SN522-HCl), wherein each dose of the multiple dose is between about 0.0015 mg/kg to about 2 mg/kg; or between about 0.015 mg/kg to about 2 mg/kg.

In still another embodiment, the methods of the invention employ multiple doses, wherein each does of the multiple dose is about 0.04 mg/kg, about 0.07 mg/kg, about 0.15 mg/kg, about 0.20 mg/kg, about 0.40 mg/kg, about 0.65 mg/kg, about 1 mg/kg, about 1.50 mg/kg, about 1.80 mg/kg or about 3.5 mg/kg of l-amphetamine, C105, l-methamphetamine, SN522, SN522-HCl.

The cumulative dose of the amphetamine compound (l-amphetamine, C105, l-methamphetamine, SN522, SN522-HCl) employed in the methods of the invention, regardless of whether the amphetamine is administered in a single dose or in multiple doses is between about 0.2 mg to about 250 mg; or between about 1 mg to about 1250 mg of the amphetamine compound. In a particular embodiment, the cumulative dose is about 2 mg, about 10 mg, about 20 mg, about 30 mg, about 50 mg, about 60 mg, about 90 mg, about 100 mg, about 150 mg, about 200 mg, about 250 mg, about 450 mg, about 750 mg, about 1000 mg, about 1250 mg, about 2500 mg or about 5000 mg.

In certain embodiments, the invention features a method for enhancing memory in an animal, a method of treating a human with an impairment in memory consolidation or an impairment in short term memory or an impairment in working memory comprising administering to the animal a composition of an amphetamine compound in an amount sufficient to enhance long-term memory or improve memory consolidation in the animal (human), wherein the composition includes at least about 51 percent (w/w or mole percent), about 60 percent (w/w or mole percent), about 75 percent (w/w or mole percent), about 80 percent (w/w or mole percent), about 85 percent (w/w or mole percent), about 95 percent (w/w or mole percent), about 99 percent (w/w or mole percent) of the eutomers relative to the distomers of the amphetamine or about 100% (w/w or mole percent) of compound represented by Formula I, or pharmaceutically acceptable salt, solvate, metabolite or pro-drug thereof, relative to the distomer of that amphetamine compound:

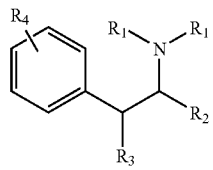
(I)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In certain embodiments, the invention features a method for enhancing memory in an animal or a method for treating a human with an impairment in memory consolidation, comprising administering to the animal a composition of an amphetamine compound in an amount sufficient to enhance long-term memory or improve memory consolidation in the animal (human), wherein the composition includes at least about 51 percent (w/w or mole percent), about 60 percent (w/w or mole percent), about 75 percent (w/w or mole percent), about 80 percent (w/w or mole percent), about 85 percent (w/w or mole percent, about 95 percent (w/w or mole percent), or about 99 percent (w/w or mole percent) of the eutomers relative to the distomers of the amphetamine compound, wherein the amphetamine compound is a pharmaceutically acceptable salt represented by Formula II:

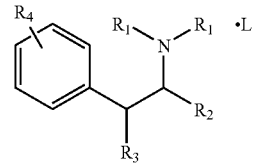
(II)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido; and L is a non-toxic organic or inorganic acid.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In certain embodiments, the invention features a method for enhancing memory in an animal or a method of treating a human with an impairment in memory consolidation, comprising administering to the animal a composition of an amphetamine compound in an amount sufficient to enhance long-term memory or improve memory consolidation in the animal (human), wherein the composition includes at least about 51 percent (w/w or mole percent), about 60 percent (w/w or mole percent), about 75 percent (w/w or mole percent), about 80 percent (w/w or mole percent), about 85 percent (w/w or mole percent), about 95 percent (w/w or mole percent), or about 99 percent (w/w or mole percent) of the eutomers relative to the distomers of the amphetamine compound, wherein the amphetamine compound is an amphetamine metabolite represented by Formula III, or pharmaceutically acceptable salt, solvate, or pro-drug thereof:

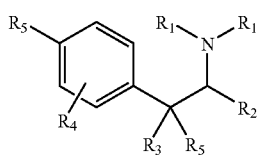

(III)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido;

$R_5$ independently for each occurrence, represents hydrogen or hydroxy.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In certain embodiments, the invention features a kit comprising an amphetamine compound formulation, e.g., as described herein and preferably provided in single oral dosage form or as a transdermal patch for enhancing memory in a patient (preferably a human), and in association with instructions (written and/or pictorial) describing the use of the formulation for enhancing memory, and optionally, warnings of possible side effects and drug-drug or drug-food interactions.

Another aspect of the invention relates to a method for conducting a pharmaceutical business, which includes: (a) manufacturing the kits, preparations, and compositions of the present invention; and (b) marketing to healthcare providers the benefits of using the kits, preparations, and compositions of the present invention to enhance memory of treated patients.

Another aspect of the invention relates to a method for conducting a pharmaceutical business, comprising: (a) providing a distribution network for selling the kits, preparations, and compositions of the present invention; and (b) providing instruction material to patients or physicians for using the kits, preparations, and compositions of the present invention to enhance memory of treated patients.

Yet another aspect of the invention relates to a method for conducting a pharmaceutical business, comprising: (a) determining an appropriate dosage of an amphetamine compound to enhance memory function in a class of patients; (b) conducting therapeutic profiling of one or more formulations of the amphetamine compound identified in step (a), for efficacy and toxicity in animals; and (c) providing a distribution network for selling the formulations identified in step (b) as having an acceptable therapeutic profile.

For instance, the subject business method can include an additional step of providing a sales group for marketing the preparation to healthcare providers.

Another aspect of the invention relates to a method for conducting a pharmaceutical business, comprising: (a) determining an appropriate dosage of an amphetamine compound to enhance memory function in a class of patients; and (b) licensing, to a third party, the rights for further development and sale of the amphetamine compound for enhancing memory.

In certain embodiments of the method, the class of patients suffer from memory impairment. In preferred embodiments of the method, the memory impairment results from one or more of anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, age-associated memory impairment, Mild Cognitive Impairment, attention deficit disorder, attention deficit hyperactivity disorder, Multiple Sclerosis, Anterior Communicating Artery Syndrome, AIDS-related dementia, chronic fatigue syndrome, fibromyalgia syndrome, traumatic brain injury, chemotherapy. In other preferred embodiments of the method, the class of patients are normal individuals.

Another aspect of the invention features solid dosage form comprising a eutomer of an amphetamine compound represented by Formula I, or a pharmaceutically acceptable salt, solvate, metabolite or pro-drug thereof, in an amount of 25 mg or less:

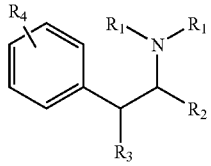

(I)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido.

Another aspect of the invention features solid dosage form comprising a pharmaceutically acceptable salt of a eutomer of an amphetamine compound employed in the methods of the invention, for example, represented by Formula II, solvate, metabolite or pro-drug thereof, in an amount of 25 mg or less:

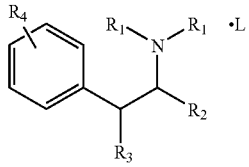

(II)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, ester, amidino, sulfonyl, sulfoxido, sulfamoyl, and sulfonamido; and L is a non-toxic organic or inorganic acid.

Another aspect of the invention features solid dosage form comprising a eutomer of an amphetamine metabolite represented by Formula III, solvate or pro-drug thereof, in an amount of about 25 mg or less:

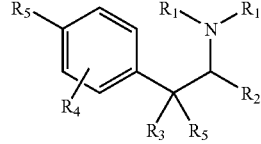

(III)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, sulfonamido;

$R_5$ independently for each occurrence, represents hydrogen or hydroxy.

In another embodiment, the invention is a method of treating mild cognitive impairment in a human, comprising the step of administering an effective amount of an amphetamine to the human, wherein the amphetamine is administered as a component of a composition that includes amphetamine and, optionally, a methamphetamine, wherein at least about 85 mole percent of the total amphetamine and methamphetamine content of the composition is l-amphetamine.

In an additional embodiment, the invention is a method of treating mild cognitive impairment in a human, comprising the step of administering an effective amount of a methamphetamine to the human, wherein the methamphetamine is administered as a component of a composition that includes methamphetamine and, optionally, an amphetamine, wherein at least about 85 mole percent of the total methamphetamine and amphetamine content of the composition is l-methamphetamine.

In a further embodiment, the invention is a method of treating mild cognitive impairment in a human, comprising the step of administering an effective amount of an amphetamine to the human, wherein the amphetamine is administered as a component of a composition that includes amphetamine and, optionally, a methamphetamine, wherein at least about 85 mole percent of the total amphetamine and methamphetamine content of the composition is l-amphetamine and wherein the amphetamine is administered at a dose of between about a 2 mg dose and about a 60 mg dose per day.

In still another embodiment, the invention is a method of treating mild cognitive impairment in a human, comprising the step of orally administering an effective amount of an amphetamine to the human, wherein the amphetamine is administered as a component of a composition that includes amphetamine and, optionally, a methamphetamine, wherein at least about 95 mole percent of the total amphetamine and methamphetamine content of the composition is l-amphetamine and wherein the amphetamine is administered at a dose of between about a 2 mg dose and about a 60 mg dose per day.

Another embodiment of the invention is a method of treating mild cognitive impairment in a human, comprising the step of administering an effective amount of a methamphetamine to the human, wherein the methamphetamine is administered as a component of a composition that includes methamphetamine and, optionally, an amphetamine, wherein at least about 85 mole percent of the total methamphetamine and amphetamine content of the composition is l-methamphetamine and wherein the methamphetamine is administered at a dose of between about a 2 mg dose and about a 60 mg dose per day.

An additional embodiment of the invention is a method of treating mild cognitive impairment in a human, comprising the step of orally administering an effective amount of a methamphetamine to the human, wherein the methamphetamine is administered as a component of a composition that includes methamphetamine and, optionally, an amphetamine, wherein at least about 95 mole percent of the total methamphetamine and amphetamine content of the composition is l-methamphetamine and wherein the methamphetamine is administered at a dose of between about a 2 mg dose and about a 60 mg dose per day.

In yet another embodiment, the invention is a method of treating Alzheimer's disease in a human, comprising the step of administering an effective amount of an amphetamine to the human, wherein the amphetamine is administered as a component of a composition that includes amphetamine and, optionally, a methamphetamine, wherein at least about 85 mole percent of the total amphetamine and methamphetamine content of the composition is l-amphetamine.

In still another embodiment, the invention is a method of treating Alzheimer's disease in a human, comprising the step of administering an effective amount of a methamphetamine to the human, wherein the methamphetamine is administered as a component of a composition that includes methamphetamine and, optionally, an amphetamine, wherein at least about 85 mole percent of the total methamphetamine and amphetamine content of the composition is l-methamphetamine.

A further embodiment of the invention is a method of treating Alzheimer's disease in a human, comprising the step of administering an effective amount of an amphetamine to the human, wherein the amphetamine is administered as a component of a composition that includes amphetamine and, optionally, a methamphetamine, wherein at least about 85 mole percent of the total amphetamine and methamphetamine content of the composition is l-amphetamine and wherein the amphetamine is administered at a dose of at least about a 2 mg and about a 60 mg dose per day.

Another embodiment of the invention is a method of treating Alzheimer's disease in a human, comprising the step of orally administering an effective amount of an amphetamine to the human, wherein the amphetamine is administered as a component of a composition that includes amphetamine and, optionally, a methamphetamine, wherein at least about 95 mole percent of the total amphetamine and methamphetamine content of the composition is l-amphetamine and wherein the amphetamine is administered at a dose of at least about a 2 mg and about a 60 mg dose per day.

In still another embodiment, the invention is a method of treating Alzheimer's disease in a human, comprising the step of administering an effective amount of a methamphetamine to the human, wherein the methamphetamine is administered as a component of a composition that includes methamphetamine and, optionally, an amphetamine, wherein at least about 85 mole percent of the total methamphetamine and amphetamine content of the composition is l-methamphetamine and wherein the methamphetamine is administered at a dose of at least about a 2 mg and about a 60 mg dose per day.

A yet another embodiment, the invention is a method of treating Alzheimer's disease in a human, comprising the step of orally administering an effective amount of a methamphetamine to the human, wherein the methamphetamine is administered as a component of a composition that includes methamphetamine and, optionally, an amphetamine, wherein at least about 95 mole percent of the total methamphetamine and amphetamine content of the composition is l-methamphetamine and wherein the methamphetamine is administered at a dose of at least about a 2 mg and about a 60 mg dose per day.

Another embodiment of the invention is a method of treating mild cognitive impairment in a human, comprising the step of orally administering an effective amount of amphetamine to the human, wherein the amphetamine is at least about 95 mole percent l-amphetamine relative to the total amphetamine content of the composition.

In yet an additional embodiment, the invention is a method of treating mild cognitive impairment in the human, comprising the step of orally administering an effective amount of methamphetamine to the human, wherein the methamphetamine is at least about 95 mole percent l-methamphetamine relative to the total methamphetamine content of the composition.

In a further embodiment, the invention is a method of treating Alzheimer's disease in a human, comprising the step of orally administering an effective amount of amphetamine to the human, wherein the amphetamine is at least about 95 mole percent l-amphetamine relative to the total amphetamine content of the composition.

In an additional embodiment, the invention is a method of treating Alzheimer's disease in the human, comprising the step of orally administering an effective amount of methamphetamine to the human, wherein the methamphetamine is at least about 95 mole percent l-methamphetamine relative to the total methamphetamine content of the composition.

In yet another embodiment, the invention is a method of treating a human for a memory impairment, comprising the step of administering an amphetamine composition selected from the group consisting of l-amphetamine, l-methamphetamine or a combination of both to a human having an impairment in memory associated with multiple sclerosis.

In still another embodiment, the invention is a method of treating a human for an impairment in a cognitive function, comprising the step of administering an amphetamine composition selected from the group consisting of l-amphetamine, l-methamphetamine or a combination of both to a human having impairment in a cognitive function associated with multiple sclerosis.

In an additional embodiment, the invention is a method of treating a human for an impairment in a cognitive function, comprising the step of administering an amphetamine composition selected from the group consisting of l-amphetamine, l-methamphetamine or a combination of both to a human having an impairment in a cognitive function associated with a brain aneurysm.

In still another embodiment, the invention is a method of treating a human for an impairment in a cognitive function, comprising the step of administering an amphetamine composition selected from the group consisting of l-amphetamine, l-methamphetamine or a combination of both to a human having an impairment in a cognitive function associated with mental retardation.

In another embodiment, the invention includes a method of treating a human for an impairment in a cognitive function, comprising the step of administering an effective amount of an amphetamine to a human having an impairment in a cognitive function associated with Mild Cognitive Impairment, wherein the amphetamine is administered as a component of a composition that includes amphetamine and, optionally, a methamphetamine, wherein at least about 85 mole percent of the total amphetamine and methamphetamine content of the composition is l-amphetamine and wherein the human does not have an impairment in memory, attention and learning.

In yet another embodiment, the invention is a method of treating a human for an impairment in a cognitive function, comprising the step of administering an effective amount of a methamphetamine to a human having an impairment in a cognitive function associated with Mild Cognitive Impairment, wherein the methamphetamine is administered as a component of a composition that includes methamphetamine and, optionally, an amphetamine, wherein at least about 85 mole percent of the total methamphetamine and amphetamine content of the composition is l-methamphetamine and wherein the human does not have an impairment in memory, attention and learning.

In still another embodiment, the invention includes a method of treating a human for an impairment in a cognitive function, comprising the step of administering an effective amount of an amphetamine to a human having an impairment in a cognitive function associated with Mild Cognitive Impairment, wherein the amphetamine is administered as a component of a composition that includes amphetamine and, optionally, a methamphetamine, wherein at least about 85 mole percent of the total amphetamine and methamphetamine content of the composition is l-amphetamine and wherein the amphetamine is administered at a dose of between about a 1 mg dose and about a 150 mg dose per day and wherein the human does not have an impairment in memory, attention and learning.

In an additional embodiment, the invention is a method of treating a human for an impairment in a cognitive function, comprising the step of orally administering an effective amount of an amphetamine to a human having an impairment in a cognitive function associated with Mild Cognitive Impairment, wherein the amphetamine is administered as a component of a composition that includes amphetamine and, optionally, a methamphetamine, wherein at least about 85 mole percent of the total amphetamine and methamphetamine content of the composition is l-amphetamine and wherein the amphetamine is administered at a dose of between about a 1 mg dose and about a 150 mg dose per day and wherein the human does not have an impairment in memory, attention and learning.

In a further embodiment, the invention is a method of treating a human for an impairment in a cognitive function, comprising the step of orally administering an effective amount of a methamphetamine to a human having an impairment in a cognitive function associated with Mild Cognitive Impairment, wherein the methamphetamine is administered as a component of a composition that includes methamphetamine and, optionally, an amphetamine, wherein at least about 85 mole percent of the total methamphetamine and amphetamine content of the composition is l-methamphetamine and wherein the methamphetamine is administered at a dose of between about a 1 mg dose and about a 150 mg dose per day and wherein the human does not have an impairment in memory, attention and learning.

In still another embodiment, the invention is a method of treating a human for an impairment in a cognitive function, comprising the step of administering an effective amount of a methamphetamine to a human having an impairment in a cognitive function associated with Alzheimer's disease, wherein the methamphetamine is administered as a component of a composition that includes methamphetamine and, optionally, an amphetamine, wherein at least about 85 mole percent of the total methamphetamine and amphetamine content of the composition is l-methamphetamine and wherein the human does not have an impairment in memory, attention and learning.

In another embodiment, the invention is a method of treating a human for an impairment in a cognitive function, comprising the step of administering an effective amount of an amphetamine to a human having an impairment in a cognitive function associated with Alzheimer's disease, wherein the amphetamine is administered as a component of a composition that includes amphetamine and, optionally, a methamphetamine, wherein at least about 85 mole percent of the total amphetamine and methamphetamine content of the composition is l-amphetamine and wherein the human does not have an impairment in memory, attention and learning.

In another embodiment, the invention is a method of treating a human for an impairment in a cognitive function, comprising the step of orally administering an effective amount of an amphetamine to a human having an impairment in a cognitive function associated with Alzheimer's disease, wherein the amphetamine is administered as a component of a composition that includes amphetamine and, optionally, a methamphetamine, wherein at least about 95 mole percent of the total amphetamine and methamphetamine content of the composition is l-amphetamine and wherein the amphetamine is administered at a dose of at least about a 1 mg and about a 150 mg dose per day and wherein the human does not have an impairment in memory, attention and learning.

In an additional embodiment, the invention is a method of treating a human for an impairment in a cognitive function, comprising the step of orally administering an effective amount of a methamphetamine to a human having an impairment in a cognitive function associated with Alzheimer's disease, wherein the methamphetamine is administered as a component of a composition that includes methamphetamine and, optionally, an amphetamine, wherein at least about 95 mole percent of the total methamphetamine and amphetamine content of the composition is l-methamphetamine and wherein the methamphetamine is administered at a dose of at least about a 1 mg and about a 150 mg dose per day and wherein the human does not have an impairment in memory, attention and learning.

In yet another embodiment, the invention is a method of treating a human for an impairment in a cognitive function, comprising the step of orally administering an effective amount of amphetamine to a human having an impairment in a cognitive function associated with Mild Cognitive Impairment, wherein the amphetamine is at least about 95 mole percent l-amphetamine relative to the total amphetamine content of the composition and wherein the human does not have an impairment in memory, attention and learning.

In still another embodiment, the invention is a method of treating a human for an impairment in a cognitive function, comprising the step of orally administering an effective amount of methamphetamine to a human having an impairment in a cognitive function associated with Mild Cognitive Impairment, wherein the methamphetamine is at least about 95 mole percent l-methamphetamine relative to the total methamphetamine content of the composition and wherein the human does not have an impairment in memory, attention and learning.

In a further embodiment, the invention is a method of treating a human for an impairment in a cognitive function, comprising the step of orally administering an effective amount of amphetamine to a human having an impairment in a cognitive function associated with Alzheimer's disease, wherein the amphetamine is at least about 95 mole percent l-amphetamine relative to the total amphetamine content of the composition and wherein the human does not have an impairment in memory, attention and learning.

In still another embodiment, the invention is a method of treating a human for an impairment in a cognitive function, comprising the step of orally administering an effective amount of methamphetamine to a human having an impairment in a cognitive function associated with Alzheimer's disease, wherein the methamphetamine is at least about 95 mole percent l-methamphetamine relative to the total methamphetamine content of the composition and wherein the human does not have an impairment in memory, attention and learning.

In still another embodiment, the invention is a method of treating a human for a memory impairment, comprising the step of administering an amphetamine composition selected from the group consisting of l-amphetamine, l-methamphetamine or a combination of both to a human having an impairment in memory associated with multiple sclerosis.

In another embodiment, the invention is a method of treating a human for an impairment in a cognitive function, comprising the step of administering an amphetamine composition selected from the group consisting of l-amphetamine, l-methamphetamine or a combination of both to a human having an impairment in a cognitive function associated with multiple sclerosis.

In a further embodiment, the invention is a method of treating a human for an impairment in a cognitive function, comprising the step of administering an amphetamine composition selected from the group consisting of l-amphetamine, l-methamphetamine or a combination of both to a human having an impairment in a cognitive function associated with a brain aneurysm and wherein the human does not have an impairment in memory, attention and learning.

In yet another embodiment, the invention is a method of treating an impairment in a cognitive function in a human, comprising the step of administering an amphetamine composition selected from the group consisting of l-amphetamine, l-methamphetamine or a combination of both to a human having an impairment in a cognitive function associated with mental retardation and wherein the impairment is not an impairment in memory, attention and learning.

In another embodiment, the invention is a method of treating a human for an impairment in a cognitive function, comprising the step of administering an effective amount of an amphetamine to a human having an impairment in a cognitive function associated with Parkinson's disease, wherein the amphetamine is administered as a component of a composition that includes amphetamine and, optionally, a methamphetamine, wherein at least about 85 mole percent of the total amphetamine and methamphetamine content of the composition is l-amphetamine and wherein the human does not have an impairment in memory, attention and learning.

In still another embodiment, the invention is a method of treating a human for an impairment in a cognitive function, comprising the step of administering an effective amount of a methamphetamine to a human having an impairment in a cognitive function associated with Parkinson's disease, wherein the methamphetamine is administered as a component of a composition that includes methamphetamine and, optionally, an amphetamine wherein at least about 85 mole percent of the total methamphetamine in amphetamine content of the composition is l-methamphetamine and wherein the human does not have an impairment in memory, attention and learning.

In still another embodiment, the invention is a method of treating a human for a memory impairment, comprising the step of administering an amphetamine composition selected from the group consisting of l-amphetamine, l-methamphetamine or a combination of both to a human having an impairment in memory associated with chronic fatigue syndrome.

In another embodiment, the invention is a method of treating a human for an impairment in a cognitive function, comprising the step of administering an amphetamine composition selected from the group consisting of l-amphetamine, l-methamphetamine or a combination of both to human having an impairment in a cognitive function associated with chronic fatigue syndrome.

In still another embodiment, the invention is a method of treating a human for a memory impairment, comprising the step of administering an amphetamine composition selected from the group consisting of l-amphetamine, l-methamphetamine or a combination of both to a human having an impairment in memory associated with fibromyalgia syndrome.

An additional embodiment of the invention is a method of treating a human for an impairment in a cognitive function, comprising the step of administering an amphetamine composition selected from the group consisting of l-amphetamine, l-methamphetamine or a combination of both to human having impairment in a cognitive function associated with fibromyalgia syndrome.

In still another embodiment, the invention is a method of treating a human for a memory impairment, comprising the step of administering an amphetamine composition selected from the group consisting of l-amphetamine, l-methamphetamine or a combination of both to a human having an impairment in memory associated with chemotherapy treatment.

In a further embodiment, the invention is a method of treating a human for an impairment in a cognitive function, comprising the step of administering an amphetamine composition selected from the group consisting of l-amphetamine, l-methamphetamine or a combination of both to a human having an impairment in a cognitive function associated with a brain injury and wherein the human does not have an impairment in memory, attention and learning.

In still another embodiment, the invention is a method of treating a human for an impairment in a cognitive function, comprising the step of administering an amphetamine composition selected from the group consisting of l-amphetamine, l-methamphetamine or a combination of both to a human having an impairment in a cognitive function associated with a stroke and wherein the human does not have an impairment in memory, attention and learning.

In another embodiment, the invention includes a method of treating a human for memory impairment, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to a muscarinic cholinergic receptor antagonist, whereby the memory impairment consequent to the exposure to the muscarinic cholinergic receptor antagonist is at least partially attenuated.

In yet another embodiment, the invention includes a method of treating a human for cognitive impairment, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to a muscarinic cholinergic receptor antagonist, whereby the cognitive impairment consequent to the exposure to the muscarinic cholinergic receptor antagonist is at least partially attenuated.

In an additional embodiment, the invention includes a method of treating a human for memory impairment, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to atropine, whereby the memory impairment consequent to the exposure to atropine is at least partially attenuated.

In yet another embodiment, the invention includes a method of treating a human for memory impairment, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to scopolamine, whereby the memory impairment consequent to the exposure to scopolamine is at least partially attenuated.

In still another embodiment, the invention includes a method of treating a human for cognitive impairment, comprising administering to the human at least one member selected the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to atropine, whereby the cognitive impairment consequent to the exposure to atropine is at least partially attenuated.

In a further embodiment, the invention includes a method of treating a human for cognitive impairment, comprising administering to the human at least one member selected the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to scopolamine, whereby the cognitive impairment consequent to the exposure to scopolamine is at least partially attenuated.

In another embodiment, the invention includes a method of treating a human, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to a memory impairment that is a consequence of exposure of the human to a muscarinic cholinergic receptor antagonist, whereby the memory impairment is at least partially attenuated.

An additional embodiment of the invention includes a method of treating a human, comprising administering to the human at least one member selected from the group consisting of l-amphetamine, l-methamphetamine, l-threo-methylphenidate, d-threo-methylphenidate, methylphenidate, atomoxetine and modafinil before, concomitantly with, or subsequent to a cognitive impairment that is a consequence of exposure of the human to a muscarinic cholinergic receptor antagonist, whereby the cognitive impairment is at least partially attenuated.

In still another embodiment, the invention includes a method of treating a human, comprising administering to the human at least one member selected from the group consisting of l-amphetamine, l-methamphetamine, l-threo-methylphenidate, d-threo-methylphenidate, methylphenidate, atomoxetine and modafinil before, concomitantly with, or subsequent to a memory impairment is a consequence of exposure of the human to atropine, whereby the memory impairment is at least partially attenuated.

In yet another embodiment, the invention includes a method of treating a human, comprising administering to the human at least one member selected from the group consisting of l-amphetamine, l-methamphetamine, l-threo-methylphenidate, d-threo-methylphenidate, methylphenidate, atomoxetine and modafinil before, concomitantly with, or subsequent to a memory impairment is a consequence of exposure of the human to scopolamine, whereby the memory impairment is at least partially attenuated.

The practice of the present invention will employ, unless otherwise indicated, conventional techniques of synthetic chemistry, organic chemistry, inorganic chemistry, organometallic chemistry, pharmaceutical chemistry, and behavioral science, which are within the skill of the art. Such techniques are described in the literature. See, for example, *Advanced Organic Chemistry: Reactions, Mechanisms, And Structure* by J. March (John Wiley and Sons, N.Y., 1992); *The Chemist's Companion: A Handbook Of Practical Data, Techniques, And References* by A. J. Gordon and R. A. Ford (Wiley, NY, 1972); *Synthetic Methods Of Organometallic And Inorganic Chemistry* by W. A. Herrmann and Brauer (Georg Thieme Verlag, N.Y., 1996); *Experimental Organic Chemistry* by D. Todd (Prentice-Hall, N.J., 1979); *Experimental Organic Chemistry: Standard And Microscale* by L. M. Harwood (Blackwell Science, M.A., 1999); *Experimental Analysis Of Behavior* by I. H. Iversen and K. A. Lattal (Elsevier, N.Y., 1991); *A Practical Guide To Behavioral Research: Tools And Techniques* by R. Sommer and B. Sommer (Oxford University Press, N.Y., 2002); *Advances In Drug Discovery Techniques* by A. L. Harvey (Chichester, N.Y., 1998); *Quantitative Calculations In Pharmaceutical Practice And Research* by T. P. Hadjiioannou (VCH, N.Y., 1993); *Drug Fate And Metabolism: Methods And Techniques* by E. R. Garrett and J. L. Hirtz (M. Dekker, N.Y., 1977); *Behavioral*

*Science Techniques: An Annotated Bibliography For Health Professionals* by M. K. Tichy (Praeger Publishers, N.Y., 1975).

The invention described herein provides methods of treating a human having an impairments in a cognitive function (e.g., attention, executive function, reaction time, learning information processing, conceptualization, problem solving, verbal fluency) and memory (e.g., memory consolidation, short term memory, working memory, long term memory, declarative memory or procedural memory). Advantages of the claimed invention include, for example, the treatment of humans suffering an impairment in a cognitive function or memory in a cost effective manner and without significant side affects, especially in individuals who have had a condition or disease for an extended period of time and where clinical management strategies are difficult to implement. Of particular importance, are conditions which require long-term treatment where addictive and potent side effects would be considerably undesirable. The claimed methods provide an efficient way to treat and reduce the severity of an impairment in a cognitive function (also referred to herein as "cognition") and memory in humans.

The invention described herein also provides a method for treating an individual, in particular a human individual, having an impairment in a cognitive function (e.g., an impairment in attention, an impairment in alertness, an impairment in wakefulness, and impairment in arousal, an impairment in executive function, an impairment in reaction time, an impairment in vigilance, an impairment in information processing, an impairment in conceptualization, an impairment in problem solving, an impairment in verbal fluency) and/or a memory process (e.g., impairment in memory consolidation, impairment in short-term memory, an impairment in working memory, an impairment in declarative memory, an impairment in procedural memory). The individual can have an impairment in a cognitive or memory processes as a consequence of exposure to a muscarinic cholinergic receptor antagonist. The claimed methods provide an efficient way to treat a human by preventing, reducing, diminishing, attenuating, minimizing or reversing the onset or severity of impairments in cognitive and memory processes in humans as, for example, a consequence of exposure to muscarinic cholinergic receptor antagonists or as associated with mild cognitive impairment, Alzheimer's disease, multiple sclerosis, mental retardation, brain aneurysm, chronic fatigue syndrome, fibromyalgia syndrome, chemotherapy, traumatic brain injury, stroke or Parkinson's disease.

In addition, the invention described herein provides methods for improving memory and cognition in subjects who do not have an impairment in memory or a cognitive function (also referred to herein as "normal" subjects).

Thus, treatment with l-amphetamine (e.g., C105) or l-methamphetamine (e.g., SN522, SN522-HCl) can halt, reverse or diminish the progression of the impairment in cognition and memory, thereby increasing the quality of life without adverse side affects, such as addiction, alterations in blood pressure and heart rate. In addition, treatment with at least one member selected from the group consisting of l-amphetamine, l-methamphetamine, l-threo-methylphenidate, d-threo-methylphenidate, methylphenidate, atomoxetine and modafinil can potentially prevent, halt, reverse, diminish, attenuate or minimize the initiation or progression of an impairment in cognitive and memory processes as a consequence of exposure to muscarinic cholinergic receptor antagonists, thereby increasing the ability to execute, form or maintain cognitive and memory processes, which can improve the quality of life.

Optionally, methods, kits, compositions or other subject matter disclosed and/or claimed in co-pending U.S. application Ser. Nos. 10/003,740 (publication no.: 20020115725) and/or 10/139,606 (publication no.: 20030119884), and/or Patent Co-operation Treaty (PCT) Application No.: PCT/US01/45793 (publication no.: WO02/39998) and/or any national or regional patent filing derived therefrom are excluded from the scope of the claims of the present invention. For example, methods of treating memory consolidation, short-term memory, long-term memory, attention, learning and anxiety for conditions or diseases as disclosed and claimed in U.S. application Ser. Nos. 10/003,740, and/or 10/139,606, and/or PCT/US01/45793, are optionally excluded from the scope of method claims in the present invention. Methods, kits, compositions or other subject matter not disclosed and/or not claimed in U.S. application Ser. Nos. 10/003,740 and/or 10/139,606, and/or PCT/US01/45793 and/or any national or regional patent filing derived therefrom are not excluded from the scope of the claims of the present invention.

DETAILED DESCRIPTION OF THE INVENTION

Figure 1:
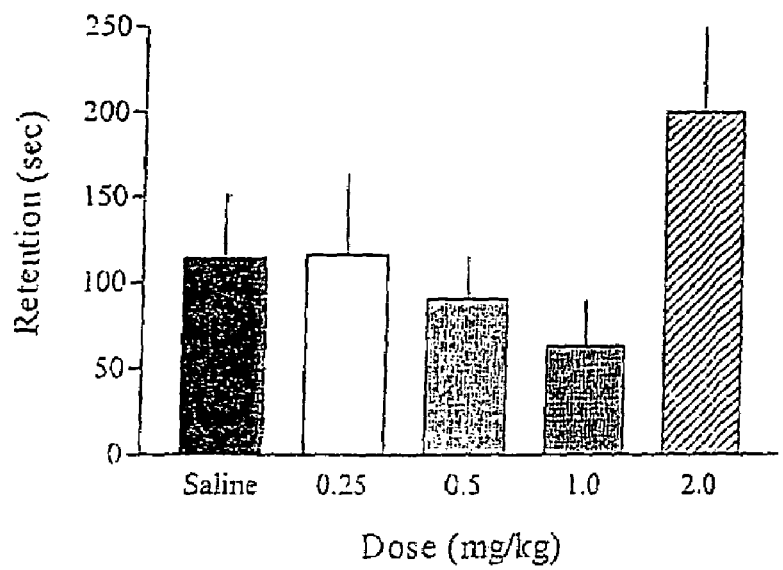
FIG. 1 presents the effectiveness of various doses of S-(+)-amphetamine on Performance in the Inhibitory Avoidance Task.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principal features of this invention can be employed in various embodiments without departing from the scope of the invention.

The present invention relates to the discovery that the amphetamine class of compounds (collectively referred to herein as "amphetamine compounds") can be used to enhance and/or restore cognitive or memory function and performance, e.g., to improve attention, executive function, reactive time, learning, short-term memory, working memory, long-term memory, declarative memory, or procedural memory in animal subjects. More particularly, the invention relates to the discovery that particular stereoisomers of amphetamine compounds are the most effective for therapeutic use. The amphetamine compounds of the invention (e.g., R-(−)-amphetamine and R-(−)-methamphetamine) improve cognitive processes and memory (e.g., memory consolidation or the process of storing new information in long-term memory) in a human.

Furthermore, the present invention relates to the discovery that the amphetamine compounds can be used to enhance and/or restore cognitive processes such as attention span, focus, executive function, reaction time or learning in animal subjects. The compounds can be useful in improving the attention span of normal individuals, as well as improving the attention span of individuals characterized by a deficit in attention span and/or focus (e.g., individuals diagnosed with an attention deficit disorder). Lack of attentiveness may lead to a failure to process new information and accordingly commit such new information to memory. Lack of focus may also lead to difficulties in later recalling previously processed information. Thus, deficits in attentiveness and/or focus may affect learning and memory. In addition to memory and learning difficulties, lack of attentiveness has many other negative social and behavioral consequences. Accordingly, the subject amphetamine compounds may be used to enhance and/or restore at least one of memory, learning, attentiveness, or focus.

In a particular embodiment, compositions of l-amphetamine or l-methamphetamine are employed to treat impairments in cognitive and memory processes in a human having Alzheimer's disease or mild cognitive impairment.

Amphetamine is a nervous system stimulant that may mildly increase blood pressure and decreases appetite. Abuse of amphetamine has been shown to cause severe side effects including dependence and possibly induced psychosis. Amphetamine is synonymous with actedron; actemin; adderall; adipan; akedron; allodene; alpha-methyl-(±)-benzeneethanamine; alpha-methylbenzeneethanamine; alpha-methylphenethylamine; amfetamine; amphate; anorexine; benzebar; benzedrine; benzyl methyl carbinamine; benzolone; beta-amino propylbenzene; beta-phenylisopropylamine; biphetamine; desoxynorephedrine; dietamine; DL-amphetamine; elastonon; fenopromin; finam; isoamyne; isomyn; mecodrin; monophos; mydrial; norephedrane; novydrine; obesin; obesine; obetrol; octedrine; oktedrin; phenamine; phenedrine; phenethylamine, alpha-methyl-; percomon; profamina; profetamine; propisamine; racephen; raphetamine; rhinalator; sympamine; simpatedrin; simpatina; sympatedrine; and weckamine.

The present invention contemplates, in part, the use of an amphetamine composition which is enriched for eutomers of amphetamine compounds. In particular, the use of pharmaceutical preparations for improving memory consolidation in humans, include (R)-(−)-amphetamine or a derivative thereof. (R)-(−)-amphetamine (l-amphetamine, levo-amphetamine, C105) is effective at a dose one-fourth (¼) the dose of the (S)-(+) enantiomer (d-amphetamine, dexo-amphetamine) of amphetamine. In addition, unlike (S)-(+)-amphetamine, the ®)-(−) enantiomer has not been shown to be addictive and does not produce undesirable side effects such as increased activity, increased blood pressure or increased heart rate.

In certain embodiments, a mixture of enantiomers of the subject compounds may be employed, e.g., a racemic mixture containing both enantiomers of a chosen compound, e.g., with each enantiomer being present in equal amounts, or in differing amounts. In certain embodiments, the therapeutic preparation may be enriched to provide predominantly one enantiomer of a subject compound. In one embodiment, an enantiomerically enriched mixture can comprise an amphetamine compound that is at least about 51 w/w or mole percent, about 60 w/w or mole percent, about 75 w/w or mole percent, about 80 w/w or mole percent, about 85 w/w or mole percent, about 90 w/w or mole percent, about 95 w/w or mole percent or about 99 w/w or mole percent l-amphetamine relative to d-amphetamine. In another embodiment, the amphetamine compound employed in the methods is about 100 w/w or mole percent l-amphetamine. In preferred embodiments, the amphetamine compound provided in the formulation is at least about 60 percent (w/w or mole percent) of the eutomer relative to the distomer of the amphetamine compound, and more preferably at least about 75 w/w or mole percent, about 80 w/w or mole percent, about 85 w/w or mole percent, about 90 w/w or mole percent, about 95 w/w or mole percent or about 99 w/w or mole percent. Furthermore, the present invention is based on using the subject compounds for enhancing or restoring attention span and/or focus. The effects of the subject compounds on attention span may have secondary consequences on the ability to process and/or recall information, and therefore may also enhance memory and/or learning.

The amphetamine compounds can also be provided in the form of pharmaceutical salts and as prodrugs.

In certain embodiments, the method includes administering, conjointly with the pharmaceutical preparation, one or more of a neuronal growth factor, a neuronal survival factor, and a neuronal trophic factor. Additionally or alternatively, a subject compound may be administered in conjunction with a cholinergic, adrenergic, nonadrenergic, dopaminergic, or glutaminergic modulator. Other agents directed at modulating GABA, NMDA, cannabinoid, AMPA, kainate, phosphodiesterase (PDE), PKA, PKC, CREB or nootropic systems may be important to the improvement of cognitive function and may be administered in conjunction with a subject compound. An agent to be administered conjointly with a subject compound may be formulated together with a subject compound as a single pharmaceutical preparation, e.g., as a pill or other medicament including both agents, or may be administered as a separate pharmaceutical preparation.

In another aspect, the present invention provides pharmaceutical preparations comprising, as an active ingredient, an enantiomerically enriched preparation of R-(−) amphetamine or a derivative thereof. The amphetamine compound is formulated in an amount sufficient to improve memory consolidation in an animal. The preparations and methods can be treatments using amphetamine compounds effective for human and/or animal subjects. In addition to humans, other animal to which the invention is applicable extend to both domestic animals and livestock, raised either as pets or for commercial purposes. Examples are dogs, cats, cattle, horses, sheep, hogs, and goats.

Still another aspect of the invention relates to the use of enantiomerically enriched preparations of amphetamine compounds for lessening the severity or prophylactically preventing the occurrence of learning and/or memory defects in an animal, and thus, altering the learning ability and/or memory capacity of the animal. As a result, the compounds of the present invention may be useful for treating and/or preventing memory impairment, e.g., due to toxicant exposure, brain injury, brain aneurysm, age-associated memory impairment, mild cognitive impairment, epilepsy, mental retardation in children, and dementia resulting from a disease, such as Parkinson's disease, Alzheimer's disease, AIDS, head trauma, Huntington's disease, Pick's disease, Creutzfeldt-Jakob disease, age-associated memory impairment, Mild Cognitive Impairment, Multiple Sclerosis, Anterior Communicating Artery Syndrome, chronic fatigue syndrome, fibromyalgia syndrome, chemotherapy, traumatic brain injury, stroke or Parkinson's disease. In addition, the compounds of the invention may be useful in enhancing memory in normal individuals.

The invention also relates to the conjoint use of an amphetamine compound with agents that mimic or stimulate PKC and/or PKA pathways.

In another embodiment, the invention is a method of treating an impairment in cognitive processes. Cognition is also referred to herein as a cognitive process or a cognitive function. Using standard cognition testing criteria, one of skill in the art would be capable of determining whether a person has an impairment in a cognitive process, the degree of cognitive impairment and an improvement in cognition following treatments by the methods described herein.

The impairment in a cognitive process can be in a human having mild cognitive impairment, Alzheimer's disease, multiple sclerosis, chronic fatigue syndrome, fibromyalgia syndrome, chemotherapy, traumatic brain injury, stroke or Parkinson's disease. In another embodiment, methods of the invention are employed to improve a cognitive function in a human having an impairment in a cognitive function associated with a brain aneurysm (e.g., anterior communicating artery brain aneurysm) or a human having an impairment in a cognitive function associated with mental retardation.

Impairment in a cognitive function treated by the methods described herein can be an impairment in attention, which is the capacity or process of selecting out of the totality of available sensory or affective stimuli, those stimuli that are most appropriate or desirable for focus at a given time (Kinchla, R. A., et al., *Annu. Rev. Psychol.* 43:711-742 (1992)). The impairment in a cognitive process can be an impairment in executive function, which are neuropsychological functions such as decision making, planning, initiative, assigning priority, sequencing, motor control, emotional regulation, inhibition, problem solving, planning, impulse control, establishing goals, monitoring results of action and self-correcting (Elliott, R., *Br. Med. Bull.* 65:49-59 (2003)). The cognitive impairment can be an impairment in alertness, wakefulness, arousal, vigilance, and reaction time information processing, conceptualization, problem solving and/or verbal fluency. One of skill in the art would be capable of identifying and evaluating the impairment in a cognitive function in the individual.

In a particular embodiment, impairments in cognitive processes are treated by the methods described herein in humans having a mild cognitive impairment or Alzheimer's disease.

DEFINITIONS

For convenience, certain terms employed in the specification, examples, and appended claims are collected here.

As used herein, the term "amphetamine compounds" is meant to include amphetamine, analogs of amphetamine, enantiomerically or isomerically enriched amphetamine, and enantiomerically or isomerically enriched analogs of amphetamine, as well as pharmaceutically acceptable salts of such compounds and prodrugs. In particular, amphetamine compounds of the invention, or analogs thereof which are administered to the human having an impairment in memory (impairment in memory consolidation, impairment in short-term memory, an impairment in working memory), include compounds having the structure as given in Formulas I, II, III, IV, V and VI above.

The term "amphetamine," such as is used when referring to "l-amphetamine" and "d-amphetamine," means a compound having Formula VII, including its salts, acids, esters, amides, carbamates, Schiff bases, prodrugs and other structural and functional derivatives thereof. "An amphetamine" can be in the form of the free base, salt, acid, ester, amide, carbamate, Schiff base, prodrug and other structural and functional derivatives of amphetamine or any combination thereof. In a preferred embodiment, the amphetamine is the compound represented by Formula VII including salts, acids, esters, amides, carbamates and Schiff bases. In another preferred embodiment, the amphetamine is the compound represented by Formula VII, including its salts and acids. In still another preferred embodiment, the amphetamine is the compound of Formula VII:

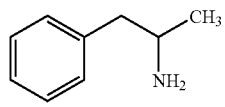

VII

The term "methamphetamine," such as is used when referring to "l-methamphetamine" and "d-methamphetamine," means a compound having Formula VIII, including its salts, acids, esters, amides, carbamates, Schiff bases, prodrugs and other structural and functional derivatives thereof. "A methamphetamine" can be in the form of the free base, salt, acid, ester, amide, carbamate, Schiff base, prodrug and other structural and functional derivatives of methamphetamine or any combination thereof. In a preferred embodiment, the methamphetamine is the compound represented by Formula VIII including salts, acids, esters, amides, carbamates and Schiff bases. In another preferred embodiment, the methamphetamine is the compound represented by Formula VIII, including its salts and acids. In still another preferred embodiment, the methamphetamine is the compound represented by Formula VIII:

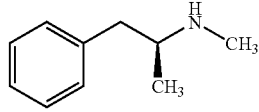

VIII

The dextro enantiomer of amphetamine is referred to in the art as the d, (+), D or S isomer and is represented by the general formula:

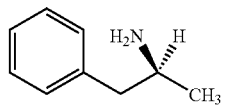

The levo enantiomer of amphetamine is referred to in the art as the l, (−), L or R isomer and is represented by the general formula:

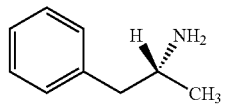

The racemic mixtures may be referred to as d,l or (+,−) or (±) or DL or (R)(S).

The term "$ED_{50}$" means the dose of a drug which produces 50% of its maximum response or effect.

An "effective amount" of, e.g., an amphetamine compound, with respect to the subject method of treatment, refers to an amount of the activator in a pharmaceutical preparation which, when applied as part of a desired dosage regimen brings about enhanced memory (memory consolidation, short term memory, working memory, declarative memory, or procedural memory) according to clinically acceptable standards.

The term "$LD_{50}$" means the dose of a drug which is lethal in 50% of test subjects.

A "patient" or "subject" to be treated by the subject method can mean either a human or non-human animal.

The term "prodrug" represents compounds which are rapidly transformed in vivo, for example, by hydrolysis in blood into the therapeutically active agents of the present invention. A common method for making a prodrug is to include selected moieties which are converted under physiologic conditions (enzymatic or nonenzymatic) to reveal the desired molecule. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "therapeutic index" refers to the therapeutic index of a drug defined as $LD_{50}/ED_{50}$.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers drug to the skin, the drug then passing through the skin into the patient's system.

The term "adrenergic" refers to neurotransmitters or neuromodulators chemically related to adrenaline (epinephrine) or to neurons which release such adrenergic mediators. Examples are dopamine, norepinephrine, epinephrine. Such agents are also referred to as catecholamines, which are derived from the amino acid tyrosine.

The term "biogenic amines" refers to a class of neurotransmitters which include catecholamines (e.g., dopamine, norepinephrine, and epinephrine) and serotonin.

The term "catecholamines" refers to neurotransmitters that have a catechol ring (e.g., a 3,4-dihydroxylated benzene ring). Examples are dopamine, norepinephrine, and epinephrine.

The term "cholinergic" refers to neurotransmitters or neuromodulators chemically related to choline or to neurons which release such cholinergic mediators.

The term "dopaminergic" refers to neurotransmitters or neuromodulators chemically related to dopamine or to neurons which release such dopaminergic mediators.

The term "dopamine" refers to an adrenergic neurotransmitter, as is known in the art.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxy groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where $R_8$ represents an aryl, a cycloalkyl, a cycloalkenyl, a heterocycle or a polycycle; and m is zero or an integer in the range of 1 to 8

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 8 or fewer carbon atoms in its backbone (e.g., $C_1$-$C_8$ for straight chains, $C_3$-$C_8$ for branched chains), and more preferably 5 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to eight carbons, more preferably from one to five carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein $R_8$ represents an aryl, a cycloalkyl, a cycloalkenyl, a heterocycle or a polycycle; and m is zero or an integer in the range of 1 to 8. Representative alkylthio groups include methylthio, ethylthio, and the like.

The terms "amine" and "amino" are art-recognized and refer to both unsubstituted and substituted amines, e.g., a moiety that can be represented by the general formula:

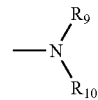

wherein $R_9$ and $R_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, $R_9$ and $R_{10}$ each independently represent a hydrogen, an alkyl, an alkenyl, or —$(CH_2)_m$—$R_8$, wherein $R_8$ represents an aryl, a cycloalkyl, a cycloalkenyl, a heterocycle or a polycycle; and m is zero or an integer in the range of 1 to 8. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

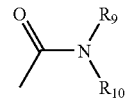

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaryls", or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle" or "cyclic alkyl", as used herein, refers to an aromatic or non-aromatic ring in which each atom of the ring is carbon.

The term "carbonyl" is art-recognized and includes such moieties as can be represented by the general formula:

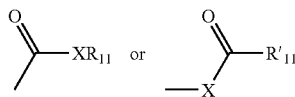

wherein X is a bond or represents an oxygen or a sulfur, and R$_1$, represents a hydrogen, an alkyl, an alkenyl, —(CH$_2$)$_m$—R$_8$ or a pharmaceutically acceptable metal or aminergic counterion, R'$_{11}$ represents a hydrogen, an alkyl, an alkenyl or —(CH$_2$)$_m$—R$_8$, wherein R$_8$ represents an aryl, a cycloalkyl, a cycloalkenyl, a heterocycle or a polycycle; and m is zero or an integer in the range of 1 to 8. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiocarbonyl" group. Where X is a sulfur and R$_{11}$ or R'$_{11}$ is not hydrogen, the formula represents a "thioester." Where X is a sulfur and R$_{11}$ is hydrogen, the formula represents a "thiocarboxylic acid." Where X is a sulfur and R$_{11}$' is hydrogen, the formula represents a "thioformate." On the other hand, where X is a bond, and R$_{11}$ is not hydrogen, the above formula represents a "ketone" group. Where X is a bond, and R$_{11}$ is hydrogen, the above formula represents an "aldehyde" group.

The term "heteroatom" as used herein means an atom of any element other than carbon or hydrogen. Preferred heteroatoms are nitrogen, oxygen and sulfur.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "metabolites" refers to active derivatives produced upon introduction of a compound into a biological milieu, such as a patient. L-amphetamine and l-methamphetamine employed in the methods of the invention are not metabolites resulting from the administration of l-deprenyl. The oral administration of l-amphetamine or l-methamphetamine means ingestion of l-amphetamine and/or l-methamphetamine by the subject (e.g., human) not a metabolite of another ingested compound such as l-deprenyl. Humans with impairments in a cognitive function or memory are treated with amphetamine and/or methamphetamine, wherein the amphetamine and/or methamphetamine is enantiomerically enriched for l-amphetamine of l-methamphetamine relative to the total content of amphetamine and/or methamphetamine in the composition, wherein the l-amphetamine and/or l-methamphetamine is not administered as l-deprenyl or a result of the metabolism of l-deprenyl in the human.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "statistically significant" as used herein means that the obtained results are not likely to be due to chance fluctuations at the specified level of probability. The two most commonly specified levels of significance are 0.05 (p=0.05) and 0.01 (p=0.01). The level of significance equal to 0.05 and 0.01 means that the probability of error is 5 out of 100 and 1 out of 100, respectively.

The term "sulfamoyl" is art-recognized and includes a moiety that can be represented by the general formula:

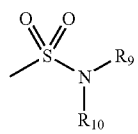

in which $R_9$ and $R_{10}$ are as defined above.

The term "sulfate" is art recognized and includes a moiety that can be represented by the general formula:

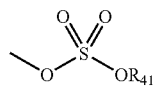

in which $R_{41}$ is an electron pair or represents a metal or aminergic counterion, hydrogen, alkyl, cycloalkyl, or aryl.

The term "sulfonamido" is art recognized and includes a moiety that can be represented by the general formula:

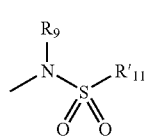

in which $R_9$ and $R'_{11}$ are as defined above.

The term "sulfonate" is art-recognized and includes a moiety that can be represented by the general formula:

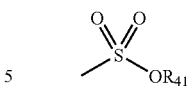

in which $R_{41}$ is an electron pair or represents a metal or aminergic counterion, hydrogen, alkyl, cycloalkyl, or aryl.

The terms "sulfoxido" or "sulfinyl", as used herein, refers to a moiety that can be represented by the general formula:

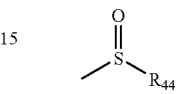

in which $R_{44}$ is selected from the group consisting of hydrogen, alkyl, alkenyl, alkynyl, cycloalkyl, heterocyclyl, aralkyl, or aryl.

The term "sulfonyl", as used herein, refers to a moiety that can be represented by the general formula:

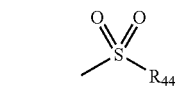

in which $R_{44}$ is selected from the group consisting of hydrogen, alkyl, alkenyl, alkynyl, cycloalkyl, heterocyclyl, aryl, or heteroaryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

Contemplated equivalents of the compounds described above include compounds which otherwise correspond thereto, and which have the same general properties thereof (e.g., the ability to effect long-term memory), wherein one or more simple variations of substituents are made which do not adversely affect the efficacy of the compound. In general, the compounds of the present invention may be prepared by the methods described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of, Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

Exemplary Compounds of the Invention

In preferred embodiments of the invention, a compound useful in the compositions and methods described herein has a structure of Formula IX:

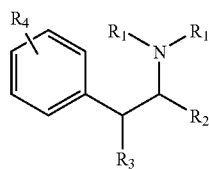

(IX)

wherein, as valence and stability permit, $R_1$, independently for each occurrence, represents H or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_2$ represents H or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_3$ represents H or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_4$ is absent, or represents from 1 to 3 substituents on the ring to which it is attached, e.g., selected from halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, sulfonamido, and phosphonate, etc.

In certain embodiments, at least one occurrence of $R_1$ represents hydrogen. In certain embodiments, both occurrences of $R_1$ represent hydrogen. In other embodiments, one occurrence of $R_1$ represents lower alkyl, such as methyl, ethyl, propyl, isopropyl, n-butyl, isobutyl, t-butyl, etc.

In certain embodiments, $R_2$ represents hydrogen, while in other embodiments, $R_2$ represents lower alkyl, such as methyl, ethyl, propyl, isopropyl, n-butyl, isobutyl, t-butyl, etc.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulfhydryl, cyano, nitro, and lower alkyl.

In certain embodiments, $R_4$ represents hydrogen and at least one of $R_1$, $R_2$, and $R_3$ represents hydrogen. In certain embodiments, $R_4$ is absent and at least two of $R_1$, $R_2$, and $R_3$ represent hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

As set out above, certain embodiments of compounds of Formula IX may contain a basic functional group, such as amino or alkylamino, and thus, can be utilized in a free base form or as pharmaceutically acceptable salt forms derived from pharmaceutically acceptable organic and inorganic acids.

The pharmaceutically acceptable salts of the subject compounds represented by Formula IX include the conventional non-toxic salts of the compounds, e.g., from non-toxic organic or inorganic acids. For example, such conventional non-toxic salts include those derived from inorganic acids such as hydrochloric, hydrobromic, sulfuric, sulfamic, phosphoric, nitric, and the like; and the salts prepared from organic acids such as acetic, 2-acetoxybenzoic, ascorbic, benzene sulfonic, benzoic, chloroacetic, citric, ethane disulfonic, ethane sulfonic, formic, fumaric, gluconic, glutamic, glycolic, hydroxymaleic, isothionic, lactic, maleic, malic, methanesulfonic, oxalic, palmitic, phenylacetic, propionic, salicyclic, stearic, succinic, sulfanilic, tartaric, toluenesulfonic, and the like.

In particular, the sulfate salt of l-amphetamine represented by Formula IV (C105) and the hydrochloride salt of l-methamphetamine represented by Formula V (SN522) are employed in the methods described herein.

In certain embodiments, such salts have a structure represented by the general Formula X:

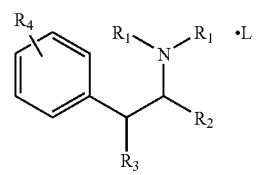

(X)

wherein, as valence and stability permit, $R_1$, $R_2$, $R_3$, and $R_4$ are defined as above;

L is a non-toxic organic or inorganic acid.

In certain embodiments, L is selected from the following inorganic acids: hydrochloric, hydrobromic, nitric, phosphoric, sulfamic, and sulfuric, or from the following organic acids: 2-acetoxybenzoic, ascorbic, benzene sulfonic, benzoic, chloroacetic, citric, ethane disulfonic, ethane sulfonic, formic, fumaric, gluconic, glutamic, glycolic, hydroxymaleic, isothionic, lactic, maleic, malic, methanesulfonic, oxalic, palmitic, phenylacetic, propionic, salicyclic, stearic, succinic, sulfanilic, tartaric, and toluenesulfonic.

The compounds of the present invention further include metabolites of the subject amphetamine compounds, included but not limited to the following: p-hydroxyamphetamine, benzyl methyl ketone, 1-phenylpropan-2-ol, benzoic acid, glycine, hippuric acid, p-hydroxynorephedrine, and N-hydroxylamphetamine.

In certain embodiments, these metabolites have a structure represented by the general Formula XI:

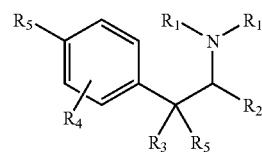

(XI)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, sulfonamido, and phosphonate, etc.;

$R_5$ independently for each occurrence, represents hydrogen or hydroxy.

In certain embodiments, the method includes administering, conjointly with the pharmaceutical preparation, one or more of a neuronal growth factor, a neuronal survival factor, and a neuronal trophic factor. Additionally or alternatively, a subject compound may be administered in conjunction with a cholinergic, adrenergic, noradrenergic, dopaminergic, glutaminergic or other modulators. Other agents directed at modulating GABA, NMDA, cannabinoid, AMPA, kainate, phosphodiesterase (PDE), PKA, PKC, CREB or nootropic systems may be important to the improvement of cognitive function and may be administered in conjunction with a subject compound.

An agent to be administered conjointly with a subject compound may be formulated together with a subject compound as a single pharmaceutical preparation, e.g., as a pill or other medicament including both agents, or may be administered as a separate pharmaceutical preparation.

In another aspect, the present invention provides pharmaceutical preparations comprising, as an active ingredient amphetamine or a derivative thereof. The subject amphetamine compound is formulated in an amount sufficient to improve LTP in an animal. The subject preparations and methods can be treatments using amphetamine compounds effective for human and/or animal subjects. In addition to humans, other animal subjects to which the invention is applicable extend to both domestic animals and livestock, raised either as pets or for commercial purposes. Examples are dogs, cats, cattle, horses, sheep, hogs, and goats.

Still another aspect of the invention relates to the use of amphetamine compounds for lessening the severity or prophylactically preventing the occurrence of cognitive, learning and/or memory defects in an animal, and thus, altering the cognitive, learning ability and/or memory capacity of the animal. As a result, the compounds of the present invention may be useful for treating and/or preventing cognitive or memory impairment, e.g., due to toxicant exposure, brain injury, brain aneurysm, age-associated memory impairment, mild cognitive impairment, epilepsy, Multiple Sclerosis, age-associated memory impairment, Mild Cognitive Impairment, mental retardation in children, and dementia resulting from a disease, such as Parkinson's disease, Alzheimer's disease, AIDS, head trauma, Huntington's disease, Pick's disease, Creutzfeldt-Jakob disease, Anterior Communicating Artery Syndrome, hypoxia, post cardiac surgery, Downs Syndrome, stroke, as a consequence of exposure to muscarinic cholinergic receptor antagonists. In addition, the compounds of the invention may be useful in enhancing cognition or memory in normal individuals.

The present invention also relates to treatment with at least one member selected from the group consisting of l-amphetamine, l-methamphetamine, l-threo-methylphenidate, d-threo-methylphenidate, methylphenidate, atomoxetine (also referred to as STRATTERA® or tomoxetine) and modafinil (also referred to as PROVIGIL®) to improve cognitive and memory processes in individuals exposed to a muscarinic cholinergic receptor antagonist.

As described herein, levo-amphetamine and levo-methamphetamine have been demonstrated to reduced impairment in memory that is a consequence of exposure to a muscarinic cholinergic receptor antagonist. Specifically, levo-amphetamine or levo-methamphetamine improves memory in rats that have an impairment in the ability to form new long term memory as a consequence of exposure to a muscarinic cholinergic receptor antagonist. The ability to form new long term memory is the process of memory consolidation ("Neuroscience: Exploring The Brain," Bear, M. F. et al., Williams & Wilkins, Baltimore, Md., Ch. 19, pp. 517-545 (1996); McGaugh, J. L. *Science* 287: 248-251 (2000)).

A human individual can have an impairment in cognitive and memory processes as a consequence of exposure to a muscarinic cholinergic receptor antagonist (agents or drugs). An embodiment of the invention includes a method of reducing a potential impairment in memory or cognition in a human who will be exposed to a muscarinic cholinergic receptor antagonist. A "potential" impairment in memory or cognition, as used herein, refers to a possible effect of the muscarinic cholinergic receptor antagonist in the human which results in a diminished capacity in memory or cognition in the human as a consequence of exposure to the muscarinic cholinergic receptor.

In one embodiment, the invention includes a method of treating a human, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to a memory and/or cognitive impairment that is a consequence of exposure of the human to a muscarinic cholinergic receptor antagonist, whereby the memory and/or cognitive impairment is at least partially attenuated.

The amphetamine (e.g., l-amphetamine, d-amphetamine, l-methamphetamine, d-methamphetamine or any combination thereof), threo-methylphenidate (e.g., d-threo-methylphenidate, l-threo-methylphenidate, or any combination therof), methylphenidate, atomoxetine and modofinil are referred to herein, with respect to the methods of treating as a consequence of exposure of a human to a muscarinic cholinergic receptor antagonist, as "compounds," "compounds of the invention," or "compounds employed in the methods."

"Before" exposure to the muscarinic cholinergic receptor antagonist, as used herein, refers to the administration of at least one member selected from the group consisting of l-amphetamine, l-methamphetamine, l-threo-methylphenidate, d-threo-methylphenidate, methylphenidate, atomoxetine and modafinil at a time (e.g., minutes, hours, days, weeks, months) preceding exposure of the individual to the muscarinic cholinergic receptor antagonist. "Prior to" is used interchangeably with "before." For example, at least one member selected from the group consisting of l-amphetamine, l-methamphetamine, l-threo-methylphenidate, d-threo-methylphenidate, methylphenidate, atomoxetine and modafinil can be administered hours (e.g., about 1, 2, 3, 4, 5, 6, 7, 8, 9, 10 or 12 hours), days (e.g., about 1, 2, 3, 4, 5, 6, 7 days) or weeks (e.g., 1, 2, 3, 4, 5, 6, 7, 8 weeks) before the individual being exposed to the muscarinic cholinergic receptor antagonist.

In another embodiment, at least one member selected from the group consisting of l-amphetamine, l-methamphetamine, l-threo-methylphenidate, d-threo-methylphenidate, methylphenidate, atomoxetine and modafinil can be administered concomitantly (also referred to herein as "at about the same point in time" or "during") with exposure of the human to a muscarinic cholinergic receptor antagonist.

"Concomitantly," as used herein, refers to the simultaneous or sequential administration of at least one member selected from the group consisting of l-amphetamine, l-methamphetamine, l-threo-methylphenidate, d-threo-methylphenidate, methylphenidate, atomoxetine and modafinil to the human and exposure of the human to the muscarinic cholinergic receptor antagonist. Concomitant administration of at least one member selected from the group consisting of l-amphetamine, l-methamphetamine, l-threo-methylphenidate, d-threo-methylphenidate, methylphenidate, atomoxetine and modafinil and exposure to the muscarinic cholinergic receptor antagonist can occur by administering a single formulation, which contains both at least one member selected from the group consisting of l-amphetamine, l-methamphetamine, l-threo-methylphenidate, d-threo-methylphenidate, methylphenidate, atomoxetine and modafinil; and the muscarinic cholinergic receptor antagonist, to the human. The single formulation results in simultaneous administration of at least one member selected from the group consisting of l-amphetamine, l-methamphetamine, l-threo-methylphenidate, d-threo-methylphenidate, methylphenidate, atomoxetine and modafinil; and exposure to the muscarinic cholinergic receptor antagonist.

Additionally, or alternatively, at least one member selected from the group consisting of l-amphetamine, l-methamphetamine, l-threo-methylphenidate, d-threo-methylphenidate, methylphenidate, atomoxetine and modafinil can be administered concomitantly to the human by sequential administration of a formulation of at least one member selected from the group consisting of l-amphetamine, l-methamphetamine, l-threo-methylphenidate, d-threo-methylphenidate, methylphenidate, atomoxetine and modafinil and a separate formulation of the muscarinic cholinergic receptor antagonist.

Both the formulation of at least one member selected from the group consisting of l-amphetamine, l-methamphetamine, l-threo-methylphenidate, d-threo-methylphenidate, methylphenidate, atomoxetine and modafinil and the separate muscarinic cholinergic receptor antagonist formulation are concomitantly administered to the human by sequential administration. The sequential administration can be the administration of at least one member selected from the group consisting of l-amphetamine, l-methamphetamine, l-threo-methylphenidate, d-threo-methylphenidate, methylphenidate, atomoxetine and modafinil followed by exposure to the muscarinic cholinergic receptor antagonist at about the same time; or exposure to the muscarinic cholinergic receptor antagonist followed by the administration of at least one member selected from the group consisting of l-amphetamine, l-methamphetamine, l-threo-methylphenidate, d-threo-methylphenidate, methylphenidate, atomoxetine and modafinil to the human at about the same time.

In yet another embodiment, at least one member selected from the group consisting of l-amphetamine, l-methamphetamine, l-threo-methylphenidate, d-threo-methylphenidate, methylphenidate, atomoxetine and modafinil is administered subsequent to a memory and/or cognitive impairment that is a consequence of exposure of the human to a muscarinic cholinergic receptor antagonist. "Subsequent to," as used herein, refers to the administration of at least one member selected from the group consisting of l-amphetamine, l-methamphetamine, l-threo-methylphenidate, d-threo-methylphenidate, methylphenidate, atomoxetine and modafinil to the human after the human is exposed to the muscarinic cholinergic receptor antagonist. For example, at least one member selected from the group consisting of l-amphetamine, l-methamphetamine, l-threo-methylphenidate, d-threo-methylphenidate, methylphenidate, atomoxetine and modafinil can be administered hours (e.g., about 1, 2, 3, 4, 5, 6, 7, 8, 9, 10 or 12 hours), days (e.g., about 1, 2, 3, 4, 5, 6, 7 days), weeks (e.g., about 1, 2, 3, 4, 5, 6, 7, 8 weeks), months (e.g., about 1, 2, 3, 4, 5, 6, 7, 8, 9, 10, 11 months) or years (e.g., about 1, 2, 3, 4, 5 years) subsequent to exposure of the individual to the muscarinic cholinergic receptor antagonist.

The amphetamine of the invention can be administered to a individual acutely (briefly or short-term) or chronically (prolonged or long-term) before, concomitantly with or subsequent to exposure of the individual to a muscarinic cholinergic receptor antagonist.

The compounds employed in the methods of the invention can be administered before, concomitantly with, subsequent to or any combination thereof (e.g., before; before and concomitantly with; concomitantly with; concomitantly with and subsequent to; before and subsequent to; subsequent to) of the human to exposure of the muscarinic cholinergic receptor antagonist.

Administration of at least one member selected from the group consisting of l-amphetamine, l-methamphetamine, l-threo-methylphenidate, d-threo-methylphenidate, methylphenidate, atomoxetine and modafinil to the human before, concomitantly with and/or subsequent to a memory and/or cognition impairment that is a consequence of exposure to the muscarinic cholinergic receptor antagonist can prevent, reduce or at least partially attenuate the impairment that can occur as a consequence of subsequent exposure to a muscarinic cholinergic receptor antagonist. "At least partially attenuated," as used herein, refers to any decrease or diminution in the severity, amount or intensity of the memory and/or cognitive impairment in the human exposed to a muscarinic cholinergic receptor antagonist, as a consequence of administration of the compounds.

Exposure to the muscarinic cholinergic receptor antagonist can be intentional exposure or unintentional exposure. Intentional exposure can be by administration (e.g., self administration) of a muscarinic cholinergic receptor antagonist to an individual. For example, intentional exposure of an individual can be administered through the application (e.g., transdermal), injection (e.g., intramuscular, intravenous) or ingestion (e.g., oral) of a muscarinic cholinergic receptor antagonist (e.g., scopolamine, atropine) to the individual. Unintentional exposure of the individual to a muscarinic cholinergic receptor antagonist can be by any route of exposure other than intentional exposure. For example, unintentional exposure of an individual can result from environmental or airborne exposure to a muscarinic cholinergic receptor antagonist.

In one embodiment, the muscarinic cholinergic receptor antagonist is an exogenous (originating or produced outside of the individual) muscarinic cholinergic receptor antagonist. In another embodiment, the muscarinic cholinergic receptor antagonist is an endogenous (originating or produced inside the individual) muscarinic cholinergic receptor antagonist.

In another embodiment, the invention includes a method of treating a human for memory impairment, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to a muscarinic cholinergic receptor antagonist, whereby the memory impairment consequent to the exposure to the muscarinic cholinergic receptor antagonist is at least partially attenuated.

In yet another embodiment, the invention includes a method of treating a human for cognitive impairment, comprising administering to the human at least one member selected from the group consisting of l-amphetamine, l-methamphetamine, l-threo-methylphenidate, d-threo-methylphenidate, methylphenidate, atomoxetine and modafinil at one or more points in time selected from the group consisting of before, concomitantly with and subsequent to exposure of the human to a muscarinic cholinergic receptor antagonist, whereby the cognitive impairment consequent to the exposure to the muscarinic cholinergic receptor antagonist is at least partially attenuated.

The cognitive and/or memory processes and impairments in cognitive and/or memory processes can be assessed or determined by established techniques. For example, memory can be assessed before, concomitantly with or after treatment of the individual with at least one member selected from the group consisting of l-amphetamine, l-methamphetamine, l-threo-methylphenidate, d-threo-methylphenidate, methylphenidate, atomoxetine and modafinil by one or more well established tests known to one of skill in the art. Such tests include the Rey Auditory Verbal Learning Test (RAVLT); Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; a Wide Range Assessment of Memory and Learning (WRAML); First-Last Name Association (Youngjohn J. R., et al., *Archives of Clinical Neuropsychology* 6:287-300 (1991)); Name-Face Association; Wechsler Memory Scale-Revised (Wechsler, D., Wechsler Memory Scale-Revised Manual, NY, N.Y., The Psychological Corp. (1987)); California Verbal Learning Test-Second Edition (Delis, D. C., et al., The Californian Verbal Learning Test, Second Edition, Adult Version, Manual, San Antonio, Tex.: The Psychological Corporation (2000)); Facial Recognition (delayed non-matching to sample); Cognitive Drug Research (CDR) Computerized Assessment Battery-Wesnes; Buschke's Selective Reminder Test (Buschke, H., et al., *Neurology* 24: 1019-1025 (1974)); Telephone Dialing Test; Brief Visuospatial Memory Test-Revised; and Test of Everyday Attention (Perry, R. J., et al., *Neuropsychologia* 38: 252-271 (2000)).

In a particular embodiment, the memory of the human before, during or after administration of at least one member selected from the group consisting of l-amphetamine, l-methamphetamine, l-threo-methylphenidate, d-threo-methylphenidate, methylphenidate, atomoxetine and modafinil is assessed or determined by a word recall test such as RAVLT.

A muscarinic cholinergic receptor antagonist includes any substance which blocks, diminishes, attenuates, inhibits, hinders, limits, decreases, reduces, restricts or interferes with the action of acetylcholine (ACh) thereby disrupting ACh-mediated cell signaling between presynaptic and postsynaptic neurons. The antagonist can, for example, oppose the action of ACh by acting in a manner which prevents ACh from binding to a muscarinic receptor on a postsynaptic neuron, from mediating post-synaptic, events following binding of ACh to a muscarinic receptor, interfere with ACh degradation by acetycholinesterase in the synaptic cleft or interfere with release of ACh from presynaptic neurons. For example, interaction of the muscarinic cholinergic receptor with an ACh receptor can prevent ACh from activating a $G_q$ protein on post-synaptic neurons which in turn can prevent activation of phospholipase C (PLC) and the subsequent generation of the second messengers diacylglycerol (DAG) and inositol 1,4,5-triphosphate ($IP_3$). Failure to generate intracellular DAG can prevent activation of protein kinase C (PKC) which can disrupt subsequent cellular events such as phosphorylation of substrates implicated in the formation of memory. Likewise, failure to generate $IP_3$ can prevent a mobilization of calcium from internal stores which can disrupt subsequent cellular events such as long-term potentiation (LTP), which may be a cellular mechanism of memory (Malenka, R. C., *Science* 285:1870-1874 (1999)).

Additionally, or alternatively, a muscarinic cholinergic receptor antagonist can prevent ACh from activating $G\alpha_{i/o}$ protein on presynaptic neurons which in turn can lead to increased levels of cAMP by preventing inhibition of adenylcyclase. Increased cAMP levels can lead to activation of cyclic-AMP-dependent protein kinase A (PKA) which can modulate subsequent cellular events such as phosphorylation of alpha-amino-3-hydroxy-5-methylisoxazoleproprionic acid (AMPA) receptors and the regulation of LTP. Phosphorylation of AMPA receptors can increase the inflow of sodium ($Na^+$) ions thereby increasing the cell depolarization and/or increasing the number of AMPA receptors at the synapse.

It is envisioned that the muscarinic cholinergic receptor antagonists can oppose the action of ACh in any one or more of the above-referenced manners. A muscarinic cholinergic receptor antagonist is also referred to as a muscarinic cholinergic antagonist.

As a consequence of exposure to a muscarinic cholinergic receptor antagonist, the individual can have deficiencies or disruptions in signaling pathways which can lead to impairments in cognitive and memory processes. "As a consequence of muscarinic cholinergic receptor antagonist" as used herein, refers to an impairment in cognition and/or memory processes that follows exposure of an individual to a muscarinic cholinergic receptor antagonist.

In one embodiment, the individual (also referred to herein as a "subject") can have an impairment in memory. The impairment in memory can be an impairment in memory consolidation, the process of storing new information in long term memory ("Neuroscience: Exploring The Brain," Bear, M. F. et al., Williams & Wilkins, Baltimore, Md., Ch. 19, pp. 517-545 (1996); McGaugh, J. L. *Science* 287: 248-251 (2000)). Alternatively, or additionally, the impairment in memory can be an impairment in short-term memory or an impairment in working memory. Short-term memory and working memory are processes whereby newly acquired information is maintained for short periods of time and the newly acquired information is made available for further information processing ("Neuroscience: Exploring The Brain," Bear, M. F. et al., Williams & Wilkins, Baltimore, Md., Ch. 19, pp. 517-545 (1996); McGaugh, J. L. *Science* 287: 248-251 (2000); Becker, J. T., et al., *Brain and Cognition* 41:1-8 (1999)).

The impairment in memory can also be an impairment in declarative memory, which is the memory of facts and events ("Neuroscience: Exploring The Brain," Bear, M. F. et al., Williams & Wilkins, Baltimore, Md., Ch. 19, pp. 517-545 (1996); McGaugh, J. L. *Science* 287: 248-251 (2000); Tulving, E., et al., *Science* 247: 301-306 (1990); Squire, L. R., et al., *Proc. Natl. Acad. Sci.* 93: 13515-13522 (1996)). The impairment in memory can also be an impairment in procedural memory (also referred to as "tacit knowledge" or "implicit knowledge"), which is the memory for skills or behavior ("Neuroscience: Exploring The Brain," Bear, M. F. et al., Williams & Wilkins, Baltimore, Md., Ch. 19, pp. 517-545 (1996); McGaugh, J. L. *Science* 287: 248-251 (2000)). The impairment can also be an impairment in attention, acquisition, retrieval or retention. One of skill in the art would be capable of identifying and evaluating the impairment in memory in the individual.

In a particular embodiment, at least one member selected from the group consisting of l-amphetamine, l-methamphetamine, l-threo-methylphenidate, d-threo-methylphenidate, methylphenidate, atomoxetine and modafinil is administered to a human having an impairment in memory consolidation as a consequence of exposure to a muscarinic cholinergic receptor antagonist.

In another embodiment, the individual can have an impairment in a cognitive process (Carlson, N. R., Physiology of Behavior, Allyn and Bacon, Boston, Mass. (1986); Cognition on Cognition, eds., Mehler, J. et al., Bradford Books (1995)). The impairment in a cognitive process can be an impairment in attention, which is the capacity or process of selecting out of the totality of available sensory or affective stimuli, those stimuli that are most appropriate or desirable for focus at a given time (Kinchla, R. A., et al., *Annu. Rev. Psychol.* 43: 711-742 (1992)). The impairment in a cognitive process can be an impairment in executive function, which are neuropsychological functions such as decision making, planning, initiative, assigning priority, sequencing, motor control, emotional regulation, inhibition, problem solving, planning, impulse control, establishing goals, monitoring results of action and self-correcting (Elliott, R., *Br. Med. Bull.* 65:49-59 (2003)). The cognitive impairment can be an impairment in alertness, wakefulness, arousal, vigilance, reaction time, attention, information processing, conceptualization, and verbal fluency. One of skill in the art would be capable of identifying and evaluating the impairment in cognition in the individual.

In an embodiment of the invention, the impairment in memory or cognition in an individual is a consequence of exposure to scopolamine (also referred to herein as hyoscine). In another embodiment, the impairment in memory or cognition can be a consequence of exposure to atropine. In yet another embodiment, the impairment in memory or cognition in an individual is a consequence of exposure to homatropine. In still another embodiment, the muscarinic cholinergic receptor antagonist is trihexyphenidyl. Muscarinic cholinergic receptor antagonism by, for example, scopolamine, atropine, homatropine and trihexyphenidyl can result in an impairment in memory (impairment in memory consolidation, impairment in short term memory, impairment in working memory) and/or cognition (e.g., alertness, executive function, arousal, wakefulness, attention, vigilance, reaction time, information processing, conceptualization, problem solving and verbal fluency) that can be ameliorated, diminished, attenuated, reversed, prevented or reduced by treatment with at least one member selected from the group consisting of l-amphetamine, l-methamphetamine, l-threo-methylphenidate, d-threo-methylphenidate, methylphenidate, atomoxetine and modafinil.

The term "threo-methylphenidate," such as is used when referring to "l-threo-methylphenidate" and "d-threo-methylphenidate," means a compound represented by Formula XII, including its salts, acids, esters, amides, carbamates, Schiff bases, prodrugs and other structural and functional derivatives thereof. In a preferred embodiment, the threo-methylphenidate is the compound represented by Formula XII including salts, acids, esters, amides, carbamates and Schiff bases. In another preferred embodiment, the threo-methylphenidate is the compound represented by Formula XII, including its salts and acids. In still another preferred embodiment, the threo-methylphenidate is the compound represented by Formula XII:

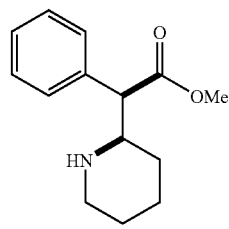

XII

The dextro enantiomer of threo-methylphenidate is referred to as the d, (+), or D enantiomer and is represented by the following structural formula:

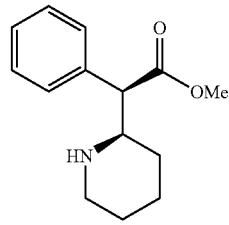

XIII

The levo enantiomer of threo-methylphenidate is referred to as the l, (−), or L enantiomer and is represented by the following structural formula:

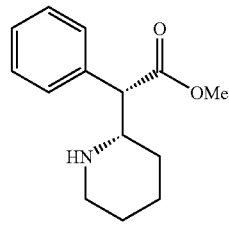

XIV

Racemic mixtures of d-threo-methylphenidate and l-threo-methylphenidate are referred to as d,l, (+,−), (±), or DL.

The term "methylphenidate," as used herein, means a compound represented by Formula XV, including its salts, acids, esters, amides, carbamates, Schiff bases, prodrugs and other structural and functional derivatives thereof. In a preferred embodiment, methylphenidate is the compound represented by Formula XV including salts, acids, esters, amides, carbamates and Schiff bases. In another preferred embodiment, methylphenidate is the compound represented by Formula XV, including its salts and acids. In still another preferred embodiment, methylphenidate is the compound represented by Formula XV:

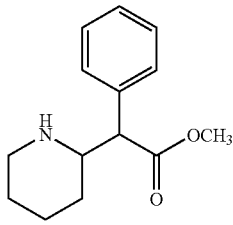

XV

The term "atomoxetine," as used herein, means a compound represented by Formula XVI, including its salts, acids, esters, amides, carbamates, Schiff bases, prodrugs and other structural and functional derivatives thereof. In a preferred embodiment, atomoxetine is the compound represented by Formula XVI including salts, acids, esters, amides, carbamates and Schiff bases. In another preferred embodiment, atomoxetine is the compound represented by Formula XVI, including its salts and acids. In still another preferred embodiment, atomoxetine is the compound represented by Formula XVI:

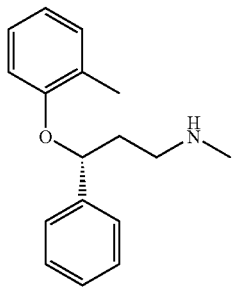

XVI

The term "modafinil," as used herein, means a compound represented by Formula XVII, including its salts, acids, esters, amides, carbamates, Schiff bases, prodrugs and other structural and functional derivatives thereof. In a preferred embodiment, modafinil is the compound represented by Formula XVII including salts, acids, esters, amides, carbamates and Schiff bases. In another preferred embodiment, modafinil is the compound represented by Formula XVII, including its salts and acids. In still another preferred embodiment, modafinil is the compound represented by Formula XVII:

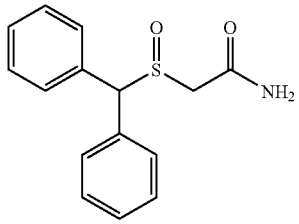

XVII

The amphetamine, threo-methylphenidate and methylphenidate, compounds employed in methods of treating a human having an impairment in memory and/or cognition as a consequence of exposure to a muscarinic cholinergic receptor antagonist can comprise at least about 51 percent (w/w (weight/weight) or mole percent), about 60 percent (w/w or mole percent), about 70 percent (w/w or mole percent), about 75 percent (w/w or mole percent), about 80 percent (w/w or mole percent), about 85 percent (w/w or mole percent), about 90 percent (w/w or mole percent), about 95 percent (w/w or mole percent), or about 99 percent (w/w or mole percent) of one enantiomer relative to another enantiomer (e.g., l-amphetamine relative to d-amphetamine; or l-threo-methylphenidate to d-threo-methylphenidate). For example, an amphetamine compound employed in the methods of the invention can be l-amphetamine, wherein the l-amphetamine is administered as a component of a composition that includes at least about 80 percent (w/w or mole percent) l-amphetamine or l-methamphetamine relative to a total amphetamine or methamphetamine, respectively, content of the composition. Likewise, a threo-methylphenidate compound employed in the methods of the invention can be l-threo-methylphenidate, wherein the l-threo-methylphenidate is administered as a component of a composition that includes at least about 80 percent (w/w or mole percent) l-threo-methylphenidate relative to a total threo-methylphenidate content of the composition.

In another embodiment, the amphetamine, threo-methylphenidate and methylphenidate compounds employed are about 100 percent (w/w or mole percent) l-amphetamine relative to d-amphetamine; or l-threo-methylphenidate relative to d-threo-methylphenidate is about 100 percent (w/w or mole percent). An amphetamine or threo-methylphenidate compound that is "about 100 percent" l-amphetamine, l-methamphetamine or l-threo-methylphenidate is a composition that includes about 100 percent (w/w or mole percent) l-amphetamine, l-methamphetamine or l-threo-methylphenidate relative to a total content of the composition. An amphetamine or threo-methylphenidate compound that is "about 100 percent" can have insignificant traces of other components, such as d-amphetamine, d-threo-methylphenidate.

Atomoxetine and modafinil can be at least about 51 percent (w/w (weight/weight) or mole percent), about 60 percent (w/w or mole percent), about 70 percent (w/w or mole percent), about 75 percent (w/w or mole percent), about 80 percent (w/w or mole percent), about 85 percent (w/w or mole percent), about 90 percent (w/w or mole percent), about 95 percent (w/w or mole percent), or about 99 percent (w/w or mole percent) of the total composition administered to the individual.

In yet another embodiment, the atomoxetine and modafinil employed in the methods of the invention are about 100 percent (w/w or mole percent) atomoxetine or about 100 percent (w/w or more percent) modafinil. An atomoxetine or modafinil that is "about 100 percent" atomoxetine or modafinil can contain insignificant trace amounts of other compounds.

The compounds employed in the methods of the invention can be the free base or can exist as salts with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid.

In another embodiment, the compounds employed in the methods can be a percent of the total composition administered to the human. The amphetamine, threo-methylphenidate, methylphenidate, atomoxetine and/or modafinil component of the composition can be about 50 percent (w/w), about 60 percent (w/w), about 75 percent (w/w), about 80 percent (w/w), about 85 percent (w/w), about 90 percent (w/w), about 95 percent (w/w) and about 100 percent (w/w) of the total composition administered to the human. For example, the human can be administered a composition which comprises about 80 weight or volume percent amphetamine and/or threo-methylphenidate and about 20 weight or volume percent, respectively, of an inert excipient. Likewise, the human can be administered a composition which comprises about 80 weight or volume percent modafinil and/or atomoxetine and about 20 weight or volume percent, respectively, of an inert excipient. Similarly, the human can be administered a composition which comprises about 80 weight or volume percent of an amphetamine, a threo-methylphenidate, a methylphenidate, atomoxetine and/or modafinil and about 20 weight or volume percent, respectively, of an inert excipient.

Another embodiment of the invention relates to assessing the degree of impairment in cognitive and/or memory processes in a human having an impairment in a cognitive and/or memory process as a consequence of exposure to a muscarinic cholinergic receptor antagonist. The improvement in cognitive or memory processes after administering at least one member selected from the group consisting of l-amphetamine, l-methamphetamine, l-threo-methylphenidate, d-threo-methylphenidate, methylphenidate, atomoxetine and modafinil to the human can be determined at one or more time points following administration of at least one member selected from the group consisting of l-amphetamine, l-methamphetamine, l-threo-methylphenidate, d-threo-methylphenidate, methylphenidate, atomoxetine and modafinil.

The method can further include comparing the impairment in memory or cognition in the human before administering at least one member selected from the group consisting of l-amphetamine, l-methamphetamine, l-threo-methylphenidate, d-threo-methylphenidate, methylphenidate, atomoxetine and modafinil to the improvement in memory in the human after administering the compound.

In a particular embodiment, memory is assessed prior to administration of the at least one member selected from the group consisting of l-amphetamine, l-methamphetamine, l-threo-methylphenidate, d-threo-methylphenidate, methylphenidate, atomoxetine and modafinil and determined after administration of at least one member selected from the group consisting of l-amphetamine, l-methamphetamine, l-threo-methylphenidate, d-threo-methylphenidate, methylphenidate, atomoxetine and modafinil by a word recall test such as RAVLT (Rey, A. (1941). L'examen psychologique dans les cas d'encéphalopathie traumatique. Archives de Psychologie, 28, 21, Lezak, M. D. (1995). Neuropsychological Assessment (3rd ed.). New York: Oxford University Press).

In yet another embodiment, the invention is a method of improving an impaired memory and/or cognition in a human. A human is exposed to a muscarinic cholinergic receptor antagonist and, as a consequence of exposure to the muscarinic cholinergic receptor antagonist, the human has an impairment in memory or cognition. The human with an impaired memory or impaired cognition is administered at least one member selected from the group consisting of l-amphetamine, l-methamphetamine, l-threo-methylphenidate, d-threo-methylphenidate, methylphenidate, atomoxetine and modafinil to improve the impairment in memory and/or cognition.

In the methods of the invention, the human can be administered at least one member selected from the group consisting of l-amphetamine, l-methamphetamine, l-threo-methylphenidate, d-threo-methylphenidate, methylphenidate, atomoxetine and modafinil concomitantly with and/or subsequent to the memory and/or cognitive impairment that is a consequence of exposure to the muscarinic cholinergic receptor antagonist. For example, a human undergoing treatment with atropine in anticipation of a nerve gas attack or to counteract the effects of nerve gas exposure can be treated with at least one member selected from the group consisting of l-amphetamine, l-methamphetamine, l-threo-methylphenidate, d-threo-methylphenidate, methylphenidate, atomoxetine and modafinil, concomitantly with or subsequent to exposure of the human to the atropine to prevent, minimize, alleviate or improve an impairment in memory or cognition as a consequence of exposure to the atropine.

The compounds employed in the methods of the invention can be administered as a single dose or as multiple doses. Additional doses of the compounds of the invention can be administered to the human, as needed, to improve cognition and/or memory or to sustain an improvement in cognition and/or memory. Cognition and/or memory can be assessed and determined before, concomitantly with or after treatment with the compounds to determine the progress of improvement in memory and the need for further doses.

In one embodiment of the methods of the invention, the compound(s) employed in the methods of the invention (e.g., l-amphetamine, l-methamphetamine, l-threo-methylphenidate, d-threo-methylphenidate, methylphenidate, atomoxetine and modafinil) is administered as a single oral dosage formulation of at least about 2.5 mg to about 25 mg, about 50 mg, about 75 mg, about 100 mg or about 125 mg of the compound (e.g., l-amphetamine, C105, l-methamphetamine, SN522, SN522-HCl, l-threo-methylphenidate, d-threo-methylphenidate, methylphenidate, atomoxetine and modafinil) and a pharmaceutically acceptable carrier.

In another embodiment, the single dosage formulation is at least about 0.001 mg, about 0.01 mg, about 0.1 mg, about 1 mg, about 2.5 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 75 mg, about 80 mg, about 85 mg, about 90 mg, about 95 mg, about 100 mg, about 125 mg, about 150 mg, about 200 mg, about 300 mg, about 400 mg, about 500 mg, about 750 mg, or about 1000 mg of the compound (e.g., l-amphetamine, C105, l-methamphetamine, SN522, SN522-HCl, l-threo-methylphenidate, d-threo-methylphenidate, methylphenidate, atomoxetine and modafinil).

In still another embodiment, the methods of the invention employ multiple doses of the compound (e.g., l-amphetamine, C105, l-methamphetamine, SN522, SN522-HCl, l-threo-methylphenidate, d-threo-methylphenidate, methylphenidate, atomoxetine and modafinil). Each dose of the multiple dose is at least about 0.001 mg, about 0.01 mg, about 0.1 mg, about 1 mg, about 2.5 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 75 mg, about 80 mg, about 85 mg, about 90 mg, about 95 mg, about 100 mg, about 125 mg, about 150 mg, about 200 mg, about 300 mg, about 400 mg, about 500 mg, about 750 mg or about 1000 mg of the compound (e.g., l-amphetamine, C105, l-methamphetamine, SN522, SN522-HCl, l-threo-methylphenidate, d-threo-methylphenidate, methylphenidate, atomoxetine and modafinil). The multiple doses can be administered for a day, days, a week, weeks, a month, months or years.

The compounds employed in the methods of the invention can be administered to a human acutely (briefly or short-term) or chronically (prolonged or long-term). For example, the compounds, (e.g., l-amphetamine, C105, l-methamphetamine, SN522, SN522-HCl, l-threo-methylphenidate, d-threo-methylphenidate, methylphenidate, atomoxetine and modafinil) of the invention can be used in methods to treat a human by administering the compound to the human once a day, multiple times (e.g., 2, 3, 4) in a day, for a day, days, a week, weeks, a month, months or years.

In yet another embodiment of the invention, the methods employ a single oral dosage formulation of between about 0.001 mg to about 125 mg; between about 0.001 mg to about 250 mg; between 0.001 mg to 500 mg; between about 0.01 mg to about 125 mg; between about 0.1 mg to about 125 mg; between about 1 mg to about 125 mg; between about 1 mg to about 250 mg; between about 1 mg to about 500 mg; or between about 1 mg to about 1000 mg of the compound employed in the methods (e.g., l-amphetamine, C105, l-methamphetamine, SN522, SN522-HCl, l-threo-methylphenidate, d-threo-methylphenidate, methylphenidate, atomoxetine and modafinil) and, optionally, a pharmaceutically acceptable carrier.

In a further embodiment, the methods of the invention employ multiple doses of the compound (e.g., l-amphetamine, C105, l-methamphetamine, SN522, SN522-HCl, l-threo-methylphenidate, d-threo-methylphenidate, methylphenidate, atomoxetine and modafinil), wherein each of the multiple doses of the compound is between about 0.001 mg to about 125 mg; or between about 0.001 mg to about 250 mg; or between about 0.001 mg to about 500 mg; or between about 0.01 mg to about 125 mg; or between about 0.1 mg to about 125 mg; or between about 0.01 mg; to about 500 mg; or between about 1 mg to about 125 mg; or between about 1 mg to about 500 mg; or between about 2.5 mg to about 25 mg, about 50 mg, about 75 mg, about 100 mg, about 125 mg, about 250 mg, about 500 mg or about 1000 mg of the compound(s) (e.g., l-amphetamine, C105, l-methamphetamine, SN522, SN522-HCl, l-threo-methylphenidate, d-threo-methylphenidate, methylphenidate, atomoxetine and modafinil) and, optionally, a pharmaceutically acceptable carrier.

In a further embodiment, the methods of the invention employ a single dose of the compound (e.g., l-amphetamine, C105, l-methamphetamine, SN522, SN522-HCl, l-threo-methylphenidate, d-threo-methylphenidate, methylphenidate, atomoxetine and modafinil) between about 0.0015 mg/kg to about 2 mg/kg; or between about 0.015 mg/kg to about 2 mg/kg.

In yet another embodiment, the methods of the invention employ a single dose about 0.04 mg/kg, about 0.07 mg/kg, about 0.15 mg/kg, about 0.20 mg/kg, about 0.40 mg/kg, about 0.65 mg/kg, about 1 mg/kg, about 1.50 mg/kg, about 1.80 mg/kg or about 3.5 mg/kg of the compound (e.g., l-amphetamine, C105, l-methamphetamine, SN522, SN522-HCl, l-threo-methylphenidate, d-threo-methylphenidate, methylphenidate, atomoxetine and modafinil).

In an additional embodiment, the methods of the invention employ multiple doses of the compound (e.g., l-amphetamine, C105, l-methamphetamine, SN522, SN522-HCl, l-threo-methylphenidate, d-threo-methylphenidate, methylphenidate, atomoxetine and modafinil), wherein each dose of the multiple dose is between about 0.0015 mg/kg to about 2 mg/kg; or between about 0.015 mg/kg to about 2 mg/kg.

In still another embodiment, the methods of the invention employ multiple doses, wherein each does of the multiple dose is about 0.04 mg/kg, about 0.07 mg/kg, about 0.15 mg/kg, about 0.20 mg/kg, about 0.40 mg/kg, about 0.65 mg/kg, about 1 mg/kg, about 1.50 mg/kg, about 1.80 mg/kg or about 3.5 mg/kg of the compound (e.g., l-amphetamine, C105, l-methamphetamine, SN522, SN522-HCl, l-threo-methylphenidate, d-threo-methylphenidate, methylphenidate, atomoxetine and modafinil).

The cumulative dose of the compounds (e.g., l-amphetamine, C105, l-methamphetamine, SN522, SN522-HCl, l-threo-methylphenidate, d-threo-methylphenidate, methylphenidate, atomoxetine and modafinil) employed in the methods of the invention, regardless of whether the compound is administered in a single dose or in multiple doses is between about 0.2 mg to about 250 mg; or between about 1 mg to about 1250 mg of the compound(s). In a particular embodiment, the cumulative dose is about 2 mg, about 10 mg, about 20 mg, about 30 mg, about 50 mg, about 60 mg, about 90 mg, about 100 mg, about 150 mg, about 200 mg, about 250 mg, about 450 mg, about 750 mg, about 1000 mg, about 1250 mg, about 2500 mg, or about 5000 mg.

The multiple doses or cumulative dose of the compound can be any combination of a compound of the invention (e.g., l-amphetamine, C105, l-methamphetamine, SN522, SN522-HCl, l-threo-methylphenidate, d-threo-methylphenidate, methylphenidate, atomoxetine and modafinil) in any combination of dose or doses.

An "effective amount" or "amount effective," when referring to the amount of the compound (e.g., l-amphetamine, C105, l-methamphetamine, SN522, SN522-HCl, l-threo-methylphenidate, d-threo-methylphenidate, methylphenidate, atomoxetine and modafinil) administered to the individual, is defined as that amount, or dose, of the compound that, when administered to an individual having an impairment in memory as a consequence of exposure to a muscarinic cholinergic receptor antagonist, is sufficient for therapeutic efficacy (e.g., an amount sufficient to improve memory in an individual having an impairment in memory; an amount sufficient to improve cognition in an individual having an impairment in cognition).

The methods of the present invention can be accomplished by the administration of the compounds (e.g., l-amphetamine, C105, l-methamphetamine, SN522, SN522-HCl, l-threo-methylphenidate, d-threo-methylphenidate, methylphenidate, atomoxetine and modafinil) of the invention by enteral or parenteral means. Specifically, the route of administration can be by oral ingestion (e.g., tablet, capsule form) or injection (e.g., intramuscular) of the compound. Other routes of administration are also encompassed by the present invention including intravenous, intraarterial, intraperitoneal, subcutaneous routes or nasal administration. Suppositories or transdermal patches can also be employed.

The compounds employed in the methods of the invention can be administered alone or can be coadministered to the human. Coadministration is meant to include simultaneous or sequential administration of one or more of the compounds (l-amphetamine, C105, l-methamphetamine, SN522, SN522-HCl, l-threo-methylphenidate, d-threo-methylphenidate, methylphenidate, atomoxetine and modafinil) individually or in combination. The simultaneous or sequential administration of compounds of the invention is conducted so that the mode of administration and the timing of administration results in a maximal improvement in memory (memory consolidation, short term memory, working memory) or cognition (e.g., attention, executive function, alertness, wakefulness, arousal, conceptualization, information processing, problem solving, verbal fluency) with minimal side effects (e.g., addiction, increases in heart rate, increases in blood pressure). It is also envisioned that multiple routes of administration (e.g., oral, transdermal, suppository, intramuscular) can be used to administer l-amphetamine, C105, l-methamphetamine, SN522, SN522-HCl, l-threo-methylphenidate, d-threo-methylphenidate, methylphenidate, atomoxetine and modafinil or any combination thereof.

The dosage and frequency (single or multiple doses) administered to an individual can vary depending upon a variety of factors, including the duration of exposure to the muscarinic cholinergic receptor antagonist and severity of the impairment in memory (e.g., impairment in memory consolidation, impairment in short-term memory, an impairment in working memory) or cognition (e.g., attention, alertness, executive function, wakefulness, arousal, vigilance, executive function, reaction time); size, age, sex, health, body weight, body mass index and diet of the human; nature and extent of symptoms of the impairment in memory or cognition, kind of concurrent treatment (e.g., atropine, scopolamine), complications from exposure to the muscarinic cholinergic receptor antagonist, or other health-related problems of the human being treated.

Other therapeutic regimens or agents can be used in conjunction with the methods and compounds employed in the methods of the invention. Adjustment and manipulation of established dosages (e.g., frequency and duration) are well within the ability of those skilled in the art.

The invention also relates to the conjoint use of a amphetamine compound with agents that mimic or stimulate PKC and/or PKA pathways.

A. Synthesis of Amphetamine Compounds

As described in further detail below, it is contemplated that the subject methods can be carried out using a stereomerically enriched preparation in a eutomer of amphetamine compound(s), particularly R-(−)-amphetamine, or a variety of different derivatives thereof. The suitability of use of a particular amphetamine compound can be readily determined, for example, by such drug screening assays as described herein.

The subject amphetamine compounds, and derivatives thereof, can be prepared readily by employing known synthetic methodology. As is well known in the art, these coupling reactions are carried out under relatively mild conditions and tolerate a wide range of "spectator" functionality. Additional compounds may be synthesized and tested in a combinatorial fashion, to facilitate the identification of additional amphetamine compounds which may be employed in the subject method.

Numerous methods for synthesizing amphetamine and for resolving the enantiomers of amphetamine have been described in the art, see for example: U.S. Pat. No. 5,075,338 to Knoll et al.; U.S. Pat. No. 2,828,343 to Tindall; U.S. Pat. No. 3,458,576 to Bryan; UK Patent No. GB 2,122,617; U.S. Pat. No. 3,996,381 to Florvall et al.; Croce et al., 1996, Gazz. Chim. Ital. 126:107-109; Mastagli et. al., 1950, Bull. Soc. Chim. Fr. 1045-1047; Smith et al., 1988, J. Med. Chem. 31:1558-1566; Bobranskii et al., 1941, J. Applied Chem. (U.S.S.R.) 14:410-414; Magidson, 1941, J. Gen. Chem. (U.S.S.R.) 11:339-343. The contents of these publications are incorporated herein by reference.

In one embodiment, a subject amphetamine compound can be synthesized according to the methods set forth in U.S. Pat. No. 5,075,338. Briefly, amphetamine compounds of the general formula:

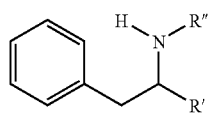

can be prepared by reacting a ketone of the formula:

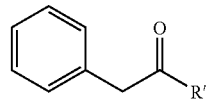

with an amine of the formula: R"NH$_2$ and reducing the ketimine intermediate formed without or after isolation. The reduction can be carried out by methods known per se, e.g., by catalytic hydrogenation (preferably in the presence of a palladium or Raney-nickel catalyst) or by using a complex metal hydride (e.g. sodium borohydride) or with the aid of a conventional reducing agent (e.g. sodium dithionite or amalgamated aluminum).

R-(−)-amphetamine and S-(+)-amphetamine may be obtained by optical resolution of racemic mixtures of R- and S-enantiomers of amphetamine. Such a resolution can be accomplished by any conventional resolution methods well known to a person skilled in the art, such as those described in J. Jacques, A. Collet and S. Wilen, "Enantiomers, Racemates and Resolutions," Wiley, N.Y. (1981). For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired R enantiomer.

In one embodiment, a subject R-(−)-amphetamine may be resolved according to the methods set forth in J. Med. Chem, 1988, 31:1558:1570. Briefly, racemic amphetamine is combined with a hot ethanol solution of D-(−)-tartaric acid. The solution is allowed to cool to room temperature and the white crystals are collected and recrystallized twice more from ethanol to give D-tartaric acid salt of R-(−)-amphetamine. To recover R-(−)-amphetamine, the D-tartaric acid salt of R-(−)-amphetamine is treated with sodium hydroxide in water and extracted with diethyl ether.

The compounds of the present invention may also be provided in the form of prodrugs, e.g., to protect a drug from being altered while passing through a hostile environment, such as the digestive tract. Prodrugs can be prepared by forming covalent linkages between the drug and a modifier. See, for example, Balant at al., Eur. J. Drug Metab. Pharmacokinetics, 1990, 15(2), 143-153. The linkage is usually designed to be broken under defined circumstances, e.g., pH changes or exposure to specific enzymes. The covalent linkage of the drug to a modifier essentially creates a new molecule with new properties such as an altered log P value and/or as well as a new spatial configuration. The new molecule can have different solubility properties and be less susceptible to enzymatic digestion. For general references on prodrug design and preparation, see: Bundraard, Design of Prodrugs, Elsevier Science Pub. Co., N.Y. (1985), and Prodrugs as Novel Drug Delivery Systems Symposium, 168.sup.th Annual Meeting, American Chemical Society, Atlantic City, N.J., Eds. T. Higuchi and V. Stella, ACS Symposium Series 14, 1975, which are herein incorporated by reference.

Prodrugs of amine-containing compounds are well known in the art and have been prepared, e.g., by reacting the amine moiety of a drug with a carboxylic acid, acid chloride, chloroformate, or sulfonyl chloride modifiers, and the like, resulting in the formation of amides, sulfonamides, carboxyamides, carbamates, Schiff bases and similar compounds. See, for example, Abuchowski et al., J. Biol. Chem. 1977, 252, 3578-358; Senter et al., J. Org. Chem., 1990, 55, 2975-2978; Amsberry et al., J. Org. Chem., 1990, 55, 5867-5877; Klotz, Clin. Pharmacokinetics, 1985, 10, 285-302, which are herein incorporated by reference. Similar and other protocols may be followed for the formation of prodrugs of the compounds of the present invention.

The compounds of the present invention, particularly libraries of amphetamine analogs having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential amphetamine analogs, as well as to refine the specificity, toxicity, and/or cytotoxic-kinetic profile of a lead compound.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject amphetamine compounds. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712, 171; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject amphetamine compounds can be synthesized and screened for particular activity or property.

In an exemplary embodiment, a library of candidate amphetamine compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with cells for which an amphetamine compound is sought. The diversomers can be released from the bead, e.g., by hydrolysis.

Many variations on the above and related pathways permit the synthesis of widely diverse libraries of compounds which may be tested as amphetamine compounds.

B. Generation of Animal Models to Test Agents

Applicants have previously described an animal model for studying fornix-mediated memory consolidation. See, for example, Taubenfield et al., supra. The fornix-lesioned animals can be used for drug screening, e.g., to identify dosages of the subject compositions which enhance memory consolidation. The lesioned mammal can have a lesion of the fornix or a related brain structure that disrupts memory consolidation (e.g., perirhinal cortex, amygdala, medial septal nucleus, locus coeruleus, hippocampus, mammallary bodies). Lesions in the mammal can be produced by mechanical or chemical disruption. For example, the fornix lesion can be caused by surgical ablation, electrolytic, neurotoxic and other chemical ablation techniques, or reversible inactivation such as by injection of an anesthetic, e.g., tetrodotoxin or lidocaine, to temporarily arrest activity in the fornix.

To further illustrate, fimbrio-fornix (rodents) and fornix (primates) lesions can be created by stereotactic ablation. In particular, neurons of the fornix structure are axotomized, e.g., by transection or aspiration (suction) ablation. A complete transection of the fornix disrupts adrenergic, cholinergic and GABAergic function and electrical activity, and induces morphological reorganization in the hippocampal formation. In general, the fornix transection utilized in the subject method will not disconnect the parahippocampal region from the neocortex. In those embodiments, the fornix transection will not disrupt functions that can be carried out by the parahippocampal region independent of processing by the hippocampal formation, and hence would not be expected to produce the full-blown amnesia seen following more complete hippocampal system damage.

In one embodiment, the animal can be a rat. Briefly, the animals are anesthetized, e.g., with intraperitoneal injections of a ketamine-xylazine mixture and positioned in a Kopf® stereotaxic instrument. A sagittal incision is made in the scalp and a craniotomy is performed extending 2.0 mm posterior and 3.0 mm lateral from Bregma. An aspirative device, e.g., with a 20 gauge tip, is mounted to a stereotaxic frame (Kopf® Instruments) and fimbria-fornix is aspirated by placing the suction tip at the correct sterotaxic location in the animal's brain. Unilateral aspirative lesions are made by suction through the cingulate cortex, completely transecting the fimbria fornix unilaterally, and (optionally) removing the dorsal tip of the hippocampus as well as the overlying cingulate cortex to inflict a partial denervation on the hippocampus target. See also, Gage et al., (1983) Brain Res. 268:27 and Gage et al. (1986) Neuroscience 19:241.

In another exemplary embodiment, the animal can be a monkey. The animal can be anesthetized, e.g., with isoflurane (1.5-2.0%). Following pretreatment with mannitol (0.25 g/kg, iv), unilateral transections of the left fornix can be performed, such as described by Kordower et al. (1990) J. Comp. Neurol., 298:443. Briefly, a surgical drill is used to create a parasagittal bone flap which exposes the frontal superior sagittal sinus. The dura is retracted and a self-retaining retractor is used to expose the interhemispheric fissure. The corpus callosum is longitudinally incised. At the level of the foramen of Monro, the fornix is easily visualized as a discrete 2-3 mm wide white fiber bundle. The fornix can be initially transected using a ball dissector. The cut ends of the fornix can then be suctioned to ensure completeness of the lesion.

In still other illustrative embodiments, the fornix lesion can be created by excitotoxicity, or by other chemical means, inhibiting or ablating fornix neurons, or the cells of the hippocampus which are innervated by fornix neurons. In certain preferred embodiments, the fornix lesion is generated by selective disruption of particular neuronal types, such as fornix cholinergic and adrenergic neurons.

For instance, the afferant fornix signals to the hippocampus due to cholinergic neurons can be ablated by atropine blockade. Another means for ablation of the cholinergic neurons is the use of 192IgG-saporin (192IgG-sap), e.g., intraventricularly injection into the fornix and hippocampus. The agents such as 6-OHDA and ibotenic acid can be used to selectively destroy fornix dopamine neurons as part of the ablative regimen.

In one embodiment, the animal is a non-human mammal, such as a dog, cat, horse, cow, pig, sheep, goat, chicken, monkey, ape, rat, rabbit, etc. In another embodiment, the animal is a non-human primate. In still another embodiment, the subject is a human.

There are a variety of tests for cognitive function, especially learning and memory testing, which can be carried our using the lesioned and normal animals. Learning and/or memory tests include, for example, Inhibitory Avoidance Test (also referred to herein as "Passive Avoidance Test"), contextual fear conditioning, visual delay non-match to sample, spatial delay non-match to sample, visual discrimination, Barnes circular maze, Morris water maze, radial arm maze tests, Ray Auditory-Visual Learning Test, the Wechsler Logical Memory Test, and the Providence Recognition Memory Test.

An exemplary Inhibitory Avoidance Test utilizes an apparatus that consists of a lit chamber that can be separated from a dark chamber by a sliding door. At training, the animal is placed in the lit chamber for some period of time, and the door is opened. The animal moves to the dark chamber after a short delay—the step-through latency—which is recorded. Upon entry into the dark chamber, the door is shut closed and a foot shock is delivered. Retention of the experience is determined after various time intervals, e.g., 24 or 48 hours, by repeating the test and recording the latency. The protocol is one of many variants of the passive avoidance procedures (for review, see Rush (1988) Behav. Neural. Biol. 50:255).

An exemplary maze testing embodiment is the water maze working memory test. In general, the method utilizes an apparatus which consists of a circular water tank. The water in the tank is made cloudy by the addition of milk powder. A clear plexiglass platform, supported by a movable stand rest on the bottom of the tank, is submerged just below the water surface. Normally, a swimming rat cannot perceive the location of the platform but it may recall it from a previous experience and training, unless it suffers from some memory impairment. The time taken to locate the platform is measured and referred to as the latency. During the experiment, all orientational cues such as ceiling lights, etc., remain unchanged. Longer latencies are generally observed with rats with some impairment to their memory.

Another memory test includes the eyeblink conditioning test, which involves the administration of white noise or steady tone that precedes a mild air puff which stimulates the subject's eyeblink.

Still another memory test which can be used is fear conditioning, e.g., either "cued" and "contextual" fear conditioning. In one embodiment, a freeze monitor administers a sequence of stimuli (sounds, shock) and then records a series of latencies measuring the recovery from shock induced freezing of the animal.

Another memory test for the lesioned animals is a holeboard test, which utilizes a rotating holeboard apparatus containing (four) open holes arranged in a 4-corner configuration in the floor of the test enclosure. A mouse is trained to poke its head into a hole and retrieve a food reward from a "baited" hole which contains a reward on every trial. There is a food reward (e.g., a Fruit Loop) in every exposed hole which is made inaccessible by being placed under a screen. The screen allows the odor of the reward to emanate from the hole, but does not allow access to the reinforcer. When an individual hole is baited, a reward is placed on top of the screen, where it is accessible. The entire apparatus rests on a turntable so that it may be rotated easily to eliminate reliance on proximal (e.g., olfactory) cues. A start tube is placed in the center of the apparatus. The subject is released from the tube and allowed to explore for the baited ("correct") hole.

As set out above, one use for the fornix-lesioned animals is for testing amphetamine compounds for ability to modulate memory consolidation, as well as for side effects and toxicity. In general, the subject method utilizes an animal which has been manipulated to create at least partial disruption of fornix-mediated signalling to the hippocampus, the disruption affecting memory consolidation and learned behavior in the animal. The animal is conditioned with a learning or memory regimen which results in learned behavior in the mammal in the absence of the fornix lesion. Amphetamine compounds are administered to the animal in order to assess their effects on memory consolidation. An increase in learned behavior, relative to the absence of the test agents, indicates that the administered combination enhances memory consolidation.

Another memory test especially developed for use in pharmaceutical studies is the Providence Recognition Memory Test. This test consists of one pictorial and one verbal assessment of long-term declarative memory. In each of the two modes, the patient views stimuli on a computer screen and is later asked to recognize those stimuli in a two-alternative forced-choice format. The pictorial assessment mode consists of two parts: a study phase and a recognition phase. In the study phase, patients view a series of 120 pictures, for 3 seconds each. They are told to look at the pictures and remember them, so that they can recognize them later. In the recognition phase, patients view pictures two at a time and are asked to indicate by button press which of the two pictures they saw in a study phase. Recognition memory testing occurs at ten minutes, one hour, and 24 hours after the end of the study phase. The verbal assessment mode consists of two parts: a study phase and a recognition phase. In the study phase, patients view a series of 60 sentences one at a time. They are asked to read the sentences aloud and remember them, so that they can recognize them later. Each sentence remains on the computer screen until the patient has finished reading it aloud. If patients read words incorrectly, the examiner supplies the correct word or words. In the recognition phase, patients view sentences two at a time and are asked to indicate by button press which of the two sentences they saw in the study phase. Recognition memory testing occurs at ten minutes, one hour, and 24 hours after the end of the study phase.

In the methods of the present invention, retention of the learned behavior can be determined, for example, after at least about 12-24 hours, 14-22 hours, 16-20 hours and or 18-19 hours after completion of the learning phase to determine whether the agents promote memory consolidation. In a particular embodiment, retention of the learned behavior can be determined 24 hours after completion of the learning phase.

In addition to models for studying memory consolidation, models to assess side effects of amphetamine compounds on behavior have been utilized including locomotor activity models. An exemplary locomotor activity test utilizes an apparatus that consists of photocell activity cages with a grid of photocell beams placed around the cage. The animals are placed in individual activity cages some period of time prior to administration of agents. Locomotor activity is measured by the number of interruptions of the photoelectric beam during a given period of time.

As used herein, a "control mammal" can be an untreated lesion mammal (i.e., a lesion animal receiving no agents or not the same combinations to be assessed), a trained control mammal (i.e., a mammal that undergoes training to demonstrate a learned behavior without any lesion) and/or an untrained control mammal (i.e., a mammal with or without a lesion, that receives no training to demonstrate a learned behavior).

C. Pharmaceutical Preparations of Amphetamine Compounds

In another aspect, the present invention provides pharmaceutical preparations comprising the subject amphetamine compounds. The amphetamine compounds for use in the subject method may be conveniently formulated for administration with a biologically acceptable, non-pyrogenic, and/or sterile medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to behavioral scientists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the amphetamine compounds, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the amphetamine compounds suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, can be used to form an implant for the sustained release of a amphetamine compound at a particular target site. In accordance with the practice of this invention, it has been found that a dosage form and a method can be provided that administers a amphetamine compound in a program that substantially lessens or completely compensates for tolerance in a patient. Tolerance, as defined in Pharmacology in Medicine, by Brill, p. 227 (1965) McGraw-Hill, is characterized as a decrease in effect followed by administering a drug. When tolerance develops following a single dose or a few doses over a very short time, it is referred to as acute tolerance. When the drug is administered over a more protracted period of time to show a demonstrable degree of tolerance, it is referred to as chronic tolerance. The medical literature, as exemplified in, The Pharmacological Bases of Therapeutics, by Goodman and Gilman, 8th Ed., p. 72 (1990) Pergamon Press, reported tolerance may be acquired to the effects of many drugs and this literature classifies tolerance as acute or chronic based on when it is acquired. That is, acute tolerance develops during a dosing phase of one dose or on one day, and chronic tolerance is acquired due to chronic administration typically weeks, months, and years.

In certain embodiments, particularly where the selected amphetamine compound is one which may produce tolerance, e.g., acute tolerance, in the patient, it may desirable to formulate the compound for variable dosing, and preferably for use in a dose-escalation regimen. In preferred embodiments, the subject amphetamine compounds are formulated to deliver a sustained and increasing dose, e.g., over at least 4 hours, and more preferably over at least 8 or even 16 hours.

In certain embodiments, representative dosage forms include hydrogel matrix containing a plurality of tiny pills. The hydrogel matrix comprises a hydrophilic polymer, such as selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin and a hydrophilic colloid. The hydrogel matrix comprises a plurality of tiny pills (such as 4 to 50), each tiny pill comprising an increasing dose population of from 100 ng ascending in dose such as 0.5 mg, 1 mg, 1.2 mg, 1.4 mg, 1.6 mg, 1.8 mg, etc. The tiny pills comprise a release rate controlling wall of 0.0 mm to 10 mm thickness to provide for the timed ascending release of drug. Representative of wall-forming materials include a triglyceryl ester selected from the group consisting of glyceryl tristearate, glyceryl monostearate, glyceryl dipalmitate, glyceryl laureate, glyceryl didecenoate and glyceryl tridecenoate. Other wall forming materials comprise polyvinyl acetate phthalate, methylcellulose phthalate, and microporous vinyl olefins. Procedures for manufacturing tiny pills are disclosed in U.S. Pat. Nos. 4,434,153; 4,721,613; 4,853,229; 2,996,431; 3,139,383 and 4,752,470, which are incorporated by reference herein.

In certain embodiments, the drug releasing beads are characterized by a dissolution profile wherein 0 to 20% of the beads undergo dissolution and release the drug in 0 to 2 hours, 20 to 40% undergo dissolution and release the drug in 2 to 4 hours, 40 to 60% exhibit dissolution and release in 4 to 6 hours, 60 to 80% in 6 to 8 hours, and 80 to 100% in 8 to 10 hours. The drug releasing beads can include a central composition or core comprising a drug and pharmaceutically acceptable composition forming ingredients including a lubricant, antioxidant, and buffer. The beads comprise increasing doses of drug, for example, 1 mg, 2 mg, 5 mg, and so forth to a high dose, in certain preferred embodiments, of 15 to 100 mg. The beads are coated with a release rate controlling polymer that can be selected utilizing the dissolution profile disclosed above. The manufacture of the beads can be adapted from, for example, Liu et al. (1994) Inter. J. of Pharm., 112:105-116; Liu et al. (1994) Inter. J. of Pharm., 112:117-124; Pharm. Sci., by Remington, 14th Ed. pp. 1626-1628 (1970); Fincher et al. (1968) J. Pharm. Sci., 57:1825-1835; and U.S. Pat. No. 4,083,949.

Another exemplary dosage form provided by the invention comprises a concentration gradient of amphetamine compound from 1 mg to 15-600 mg coated from the former low dose to the latter high dose on a polymer substrate. The polymer can be erodible or a nonerodible polymer. The coated substrate is rolled about itself from the latter high dose at the center of the dosage form, to the former low dose at the exposed outer end of the substrate. The coated substrate is rolled from the high dose to the low dose to provide for the release of from low to high dose as the substrate unrolls or erodes. For example, 1 mg to 600 mg of amphetamine is coated onto an erodible polymer such as an polypeptide, collagen, gelatin, or polyvinyl alcohol, and the substrate rolled concentrically from the high dose rolled over and inward to adapt a center position, and then outward towards the low dose to form an outer position. In operation, the dosage form erodes dispensing an ascending dose of amphetamine that is released over time.

Another dosage form provided by the invention comprises a multiplicity of layers, wherein each layer is characterized by an increasing dose of drug. The phrase "multiplicity of layers" denotes 2 to 6 layers in contacting lamination. The multiplicity of layers are positioned consecutively, that is, one layer after another in order, with a first exposed layer, the sixth layer in contact with the fifth layer and its exposed surface coated with a drug impermeable polymer. The sixth layer is coated with a drug impermeable polymer to insure release of the amphetamine compound from the first layer to the sixth layer. The first layer comprises, for example, 1 to 50 mg of drug and each successive layer comprises an additional 1 to 50 mg of drug. The biodegradable polymers undergo chemical decomposition to form soluble monomers or soluble polymer units. The biodegradation of polymers usually involves chemically or enzymatically catalyzed hydrolysis. Representative of biodegradable polymers acceptable for an increase drug loading in each layer of from 5 to 50 wt % over the first and successive layers wherein the first layer comprises 100 ng. Representative biodegradable polymers comprise a member selected from the group consisting of biodegradable poly (amides), poly(amino acids), poly(esters), poly(lactic acid), poly(glycolic acid), poly(orthoesters), poly(anhydrides), biodegradable poly(dehydropyrans), and poly(dioxinones). The polymers are known to the art in Controlled Release of Drugs, by Rosoff, Ch. 2, pp. 53-95 (1989); and in U.S. Pat. Nos. 3,811,444; 3,962,414; 4,066,747; 4,070,347; 4,079,038; and 4,093,709.

In still other embodiments, the invention employs a dosage form comprising a polymer that releases a drug by diffusion, flux through pores, or by rupture of a polymer matrix. The drug delivery polymeric system comprises a concentration gradient, wherein the gradient is an ascent in concentration from a beginning or initial concentration to a final, or higher concentration. The dosage form comprises an exposed surface at the beginning dose and a distant nonexposed surface at the final dose. The nonexposed surface is coated with a pharmaceutically acceptable material impermeable to the passage of drug. The dosage form structure provides for a flux increase delivery of drug ascending from the beginning to the final delivered dose.

Figure 17:
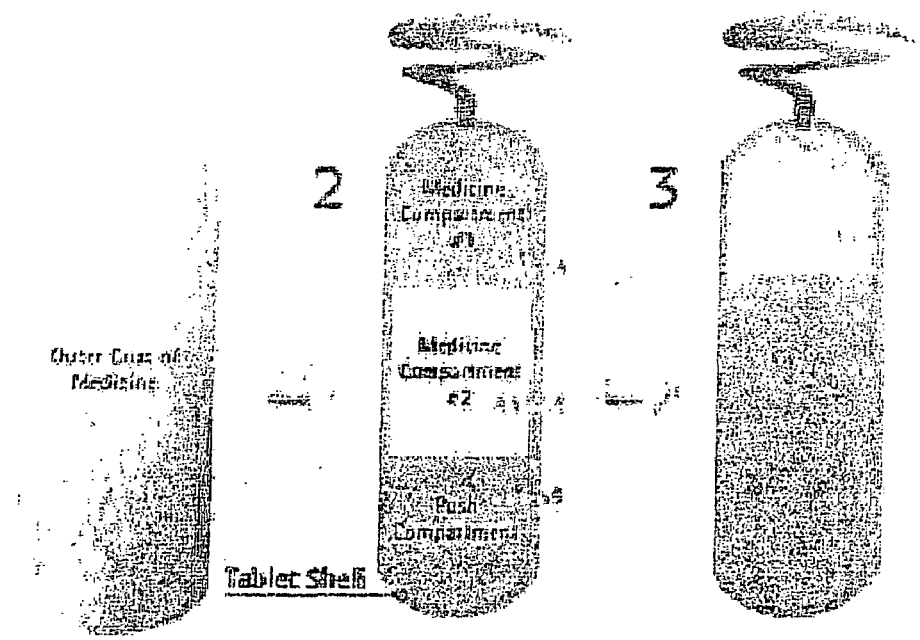
FIG. 17 shows an exemplary sustained release device.

FIG. 17 illustrates such an embodiment, where the amphetamine compound is contained within a nonabsorbable shell that releases the drug at a controlled rate.

The dosage form matrix can be made by procedures known to the polymer art. In one manufacture, 3 to 5 or more casting compositions are independently prepared wherein each casting composition comprises an increasing dose of drug with each composition overlayered from a low to the high dose. This provides a series of layers that come together to provide a unit polymer matrix with a concentration gradient. In another manufacture, the higher does is cast first followed by laminating with layers of decreasing dose to provide a polymer matrix with a drug concentration gradient. An example of providing a dosage form comprises blending a pharmaceutically acceptable carrier, like polyethylene glycol, with a known dose of a amphetamine compound and adding it to a silastic medical grade elastomer with a cross-linking agent, like stannous octanoate, followed by casting in a mold. The step is repeated for each successive layer. The system is allowed to set, for 1 hour, to provide the dosage form. Representative polymers for manufacturing the dosage form comprise a member selected from the group consisting of olefin and vinyl polymers, condensation polymers, carbohydrate polymers, and silicon polymers as represented by poly (ethylene), poly(propylene), poly(vinyl acetate), poly(methyl acrylate), poly(isobutyl methacrylate), poly(alginate), poly (amide), and poly(silicone). The polymers and manufacturing procedures are known in Polymers, by Coleman et al., Vol. 31, pp. 1187-1230 (1990); Drug Carrier Systems, by Roerdink et al., Vol. 9, pp. 57-109 (1989); Adv. Drug Delivery Rev., by Leong et al., Vol. 1, pp. 199-233 (1987); Handbook of Common Polymers, Compiled by Roff et al., (1971) published by CRC Press; and U.S. Pat. No. 3,992,518.

In still other embodiments, the subject formulations can be a mixture of different prodrug forms of one or more different amphetamine compounds, each prodrug form having a different hydrolysis rate, and therefore activation rate, to provide an increasing serum concentration of the active amphetamine compounds.

In other embodiments, the subject formulations can be a mixture different amphetamine compounds, each compound having a different rate of adsorption (such as across the gut or epithelia) and/or serum half-life.

The dose-escalation regimen of the present invention can be used to compensate for the loss of a therapeutic effect of a amphetamine compound, if any, by providing a method of delivery that continually compensates for the development of acute tolerance, by considering the clinical effect (E) of a drug at time (t) as a function of the drug concentration (C) according to Equation 1:

$$\text{Effect} = f(t, C)$$

In addition, the rate of drug delivered (A), in mg per hour is inversely proportional to the concentration times the clearance of the drug. As the effect varies with time and the functionality is expressed, then according to this invention (A) can be governed to ensure the therapeutic effect is maintained at a clinical value. If the effect from a drug is found clinically to decrease with time, this decline could be linear as expressed by Equation 2:

$$\text{Effect}_{(t)} = \text{Effect}_{(ini)} - k_{effect} * t$$

wherein, $\text{Effect}_{(ini)}$ is the clinical effect observed initially at the start of drug administration and Effect (t) is the effect observed at time (t) hours, keffect is a proportionality constant ascertained by measuring the clinical effect (E1) at time (t1) hours and (E2) at time (t2) hours while maintaining a constant plasma concentration followed by dividing (E1) minus (E2) by (t1) minus (t2). In order to maintain a constant effect, (A) must be adjusted with the same functionality according to Equation 3:

$$A_{(t)} = A_{(ini)} + k_{effect} * t$$

wherein $A_{(ini)}$ is the initial drug input in mg per hour at the start of the therapy and $A_{(t)}$ is the drug input at time (t) hours, and keffect is the proportionality constant presented above. If the therapeutic effect is found to decline exponentially with time, this relationship is expressed by Equation 4:

$$\text{Effect}_{(t)} = \text{Effect}_{(ini)} * \exp^{(-keffect*t)}$$

wherein $\text{Effect}_{(ini)}$ and $\text{Effect}_{(t)}$ are as defined before, keffect (or keffect) is a rate constant (h−1), a unit of reciprocal hours, ascertained by measuring the clinical effect (E1) at time (t1) hours and (E2) at time (t2) hours while maintaining a constant plasma concentration followed by dividing natural log of (E1) minus natural log of (E2) by (t1) minus (t2). To maintain a constant effect, (A) must be adjusted according to Equation 5:

$$A_{(t)} = A_{(ini)} * \exp^{(keffect*t)}$$

wherein $A_{(ini)}$ and $A_{(t)}$ are as defined before, keffect is the rate constant (h−1) presented above. The equations are presented in Holford et al. (1982) Pharmac. Ther., 16:143-166.

The preparations of the present invention may be given orally, parenterally, topically, or rectally. They are of course given by forms suitable for each administration route. For example, they are administered in tablets or capsule form, by injection, infusion, inhalation, rectal suppository, or controlled release patch. Oral and controlled release patch administrations are preferred. In a particular embodiment, l-amphetamine and/or l-methamphetamine are orally administered to a human. The oral administration of the l-amphetamine and/or l-methamphetamine means that the l-amphetamine and/or l-methamphetamines is ingested by the human and is not a metabolite of another ingested compound such as l-deprenyl.

In certain preferred embodiments, the subject therapeutic is delivered by way of a transdermal patch. A patch is generally a flat hollow device with a permeable membrane on one side and also some form of adhesive to maintain the patch in place on the patient's skin, with the membrane in contact with the skin so that the medication can permeate out of the patch reservoir and into and through the skin. The outer side the patch is formed of an impermeable layer of material, and the membrane side and the outer side are joined around the perimeter of the patch, forming a reservoir for the medication and carrier between the two layers.

Patch technology is based on the ability to hold an active ingredient in constant contact with the epidermis. Over substantial periods of time, drug molecules, held in such a state, will eventually find their way into the bloodstream. Thus, patch technology relies on the ability of the human body to pick up drug molecules through the skin. Transdermal drug delivery using patch technology has recently been applied for delivery of nicotine, in an effort to assist smokers in quitting, the delivery of nitroglycerine to angina sufferers, the delivery of replacement hormones in post menopausal women, etc. These conventional drug delivery systems comprise a patch with an active ingredient such as a drug incorporated therein, the patch also including an adhesive for attachment to the skin so as to place the active ingredient in close proximity to the skin. Exemplary patch technologies are available from Ciba-Geigy Corporation and Alza Corporation. Such transdermal delivery devices can be readily adapted for use with the subject amphetamine compounds.

The flux of the subject amphetamines across the skin can be modulated by changing either (a) the resistance (the diffusion coefficient), or (b) the driving force (the solubility of the drug in the stratum corneum and consequently the gradient for diffusion). Various methods can be used to increase skin permeation by the subject amphetamines, including penetration enhancers, use of pro-drug versions, superfluous vehicles, iontophoresis, phonophoresis and thermophoresis. Many enhancer compositions have been developed to change one or both of these factors. See, for example, U.S. Pat. Nos. 4,006,218; 3,551,154; and 3,472,931, for example, respectively describe the use of dimethylsulfoxide (DMSO), dimethyl formamide (DMF), and N,N-dimethylacetamide (DMA) for enhancing the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of C2 to C4 alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a C2 or C3 alkanol; and an inert diluent such as water. Other examples are included in the teachings of U.S. Pat. No. 4,933,184 which discloses the use of menthol as a penetration enhancer; U.S. Pat. No. 5,229,130 discloses the use of vegetable oil (soybean and/or coconut oil) as a penetration enhancer; and U.S. Pat. No. 4,440,777 discloses the use of eucalyptol as a penetration enhancer.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular amphetamine compounds employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 mg to about 100 mg per kilogram (kg) of body weight per day; about 0.0001 mg/kg to about 500 mg/kg; or 0.0001 mg/kg to about 1000 mg/kg.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other psychoactive drugs such as stimulants, antidepressants, modulators of neurotransmitters and anticonvulsants. Conjunctive therapy thus includes sequential, simultaneous and separate administration of the active compound in a way that the therapeutic effects of the first administered one is not entirely disappeared when the subsequent is administered.

While it is possible for a compound of the present invention to be administered alone, it is preferable to administer the compound as a pharmaceutical formulation (composition). The amphetamine compounds according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "pharmaceutically acceptable carrier" as used herein means a pharmaceutically acceptable material, composition or vehicle, such as a liquid or solid filter, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present amphetamine compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include but are not limited to following: 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, fumarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphate/diphosphate, picrate, pivalate, polygalacturonate, propionate, p-toluenesulfonate, salicylate, stearate, subacetate, succinate, sulfate, sulfosaliculate, suramate, tannate, tartrate, teoclate, thiocyanate, tosylate, triethiodide, undecanoate, and valerate salts, and the like. (See, for example, Berge et al. (1977) "Pharmaceutical Salts", *J. Pharm. Sci.* 66:1-19)

In certain embodiments, the pharmaceutically acceptable salts of the subject compounds include the conventional non-toxic salts of the compounds, e.g., from non-toxic organic or inorganic acids. Particularly suitable are salts of weak acids. For example, such conventional non-toxic salts include those derived from inorganic acids such as hydrochloric, hydrobromic, hydriodic, cinnamic, gluconic, sulfuric, sulfamic, phosphoric, nitric, and the like; and the salts prepared from organic acids such as acetic, propionic, succinic, glycolic, stearic, lactic, maleic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active amphetamine compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In certain embodiments, the subject compound(s) are formulated as part of a transdermal patch. Transdermal patches have the added advantage of providing controlled delivery of a compound of the present invention to the body. Such dosage forms can be made by dissolving or dispersing the amphetamine compounds in the proper medium. Absorption enhancers can also be used to increase the flux of the amphetamine compounds across the skin. The rate of such flux can be controlled by either providing a rate-controlling membrane or dispersing the compound in a polymer matrix or gel.

The "free base form" of amphetamine relates to a form in which amphetamine is not complexed with an acid, e.g., is not an ammonium salt. Such forms may be incorporated into a patch. It will be appreciated that the amphetamine compounds may be complexed, for example, with elements of the drug-retaining matrix of the patch and, as such, the amphetamine compounds may not necessarily be in the form of the free base, when actually retained by the patch.

The patch preferably comprises a drug-impermeable backing layer. Suitable examples of drug-impermeable backing layers which may be used for transdermal or medicated patches include films or sheets of polyolefins, polyesters, polyurethanes, polyvinyl alcohols, polyvinyl chlorides, polyvinylidene chloride, polyamides, ethylene-vinyl acetate copolymer (EVA), ethylene-ethylacrylate copolymer (EEA), vinyl acetate-vinyl chloride copolymer, cellulose acetate, ethyl cellulose, metal vapour deposited films or sheets thereof, rubber sheets or films, expanded synthetic resin sheets or films, non-woven fabrics, fabrics, knitted fabrics, paper and foils. Preferred drug-impermeable, elastic backing materials are selected from polyethylene tereplithalate (PET), polyurethane, ethylene-vinyl acetate copolymer (EVA), plasticized polyvinylchloride, woven and non-woven fabric. Especially preferred is non-woven polyethylene-tereplithalate (PET). Other backings will be readily apparent to those skilled in the art.

The term 'block copolymer', in the preferred adhesives of the invention, refers to a macromolecule comprised of two or more chemically dissimilar polymer structures, tenninally connected together (Block Copolymers: Overview and Critical Survey, Noshay and McGrath, 1977). These dissimilar polymer structures, sections or segments, represent the 'blocks' of the block copolymer. The blocks may generally be arranged in an A-B structure, an A-B-A structure, or a multi-block-$(A-B)_n$-system, wherein A and B are the chemically distinct polymer segments of the block copolymer.

It is generally preferred that the block copolymer is of an A-B-A structure, especially wherein one of A and B is an acrylic-type polymeric unit. It will be appreciated that the present invention is also applicable using block copolymers which possess three or more different blocks, such as an A-B-C block copolymer. However, for convenience, reference hereinafter to block copolymers will assume that there are only A and B sub-units, but it will be appreciated that such reference also encompasses block copolymers having more than two different sub-units, unless otherwise specified.

It will be appreciated that the properties of block copolymers are very largely determined by the nature of the A and B blocks. Block copolymers commonly possess both 'hard' and 'soft' segments. A 'hard' segment is a polymer that has a glass transition temperature (Tg) and/or a melting temperature (Tm) that is above room temperature, while a 'soft' segment is a polymer that has a Tg (and possibly a Tm) below room temperature. The different segments are thought to impart different properties to the block copolymer. Without being constrained by theory, it is thought that association of the hard segments of separate block copolymer units result in physical cross-links within the block copolymer, thereby promoting cohesive properties of the block copolymer. It is particularly preferred that the hard segments of the block copolymers form such physical close associations.

The block copolymers useful in the present invention preferably are acrylic block copolymers. In acrylic block copolymers, at least one of the blocks of the block copolymer is an acrylic acid polymer, or a polymer of an acrylic acid derivative. The polymer may be composed of just one repeated monomer species. However, it will be appreciated that a mixture of monomeric species may be used to form each of the blocks, so that a block may, in itself, be a copolymer. The use of a combination of different monomers can affect various properties of the resulting block copolymer. In particular, variation in the ratio or nature of the monomers used allows properties such as adhesion, tack and cohesion to be modulated, so that it is generally advantageous for the soft segments of the block copolymer to be composed of more than one monomer species.

It is preferred that alkyl acrylates and alkyl methacrylates are polymerized to form the soft portion of the block copolymer. Alkyl acrylates and alkyl methacrylates are thought to provide properties of tack and adhesion. Suitable alkyl acrylates and alkyl methacrylates include n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecylacrylate and tridecyl methacrylate, although other suitable acrylates and methacrylates will be readily apparent to those skilled in the art. It is preferred that the acrylic block copolymer comprises at least 50% by weight of alkyl acrylate or alkyl methacrylate(co)polymer.

Variation in the components of the soft segment affects the overall properties of the block copolymer, although the essential feature remains the cross-linking of the soft segments. For example, soft segments essentially consisting of diacetone acrylamide with either butyl acrylate and/or 2-ethylhexyl acrylate, in approximately equal proportions, work well, and a ratio by weight of about 3:4:4 provides good results. It is preferred that diacetone acrylamide, or other polar monomer, such as hydroxyethylmethacrylate or vinyl acetate, be present in no more than 50% w/w of the monomeric mix of the soft segment, as this can lead to reduced adhesion, for example. The acrylate component may generally be varied more freely, with good results observed with both 2-ethylhexyl acrylate and butyl acrylate together or individually.

As noted above, ratios of the various monomers are generally preferred to be approximately equal. For adhesives, this is preferred to be with a polar component of 50% or less of the soft segment, with the apolar portion forming up to about 85% w/w, but preferably between about 50 and 70% w/w. In the example above, this is about 72% (4+4) apolar to about 18% (3) polar.

In general, it is particularly preferred that any apolar monomer used does not confer acidity on the adhesive. Adhesives of the invention are preferably essentially neutral, and this avoids any unnecessary degeneration of the amphetamine compounds.

Limiting active functionalities, especially those with active hydrogen, is generally preferred, in order to permit wide use of any given formulation of adhesive without having to take into account how it is likely to interact, chemically, with its environment. Thus, a generally chemically inert adhesive is preferred, in the absence of requirements to the contrary.

As discussed above, polymers suitable for use as the hard portion of the block copolymer possess glass transition temperatures above room temperature. Suitable monomers for use in forming the hard segment polymer include styrene, (x-methylstyrene, methyl methacrylate and vinyl pyrrolidone, although other suitable monomers will be readily apparent to those skilled in the art. Styrene and polymethylmethacrylate have been found to be suitable for use in the formation of the hard segment of the block copolymers. It is preferred that the hard portion of the block copolymer forms from 3-30% w/w of the total block copolymer, particularly preferably from 5-15% w/w.

The block copolymer is further characterized in that the soft portions contain a degree of chemical cross-linking. Such cross-linking may be effected by any suitable cross-linking agent. It is particularly preferable that the cross-linking agent be in the form of a monomer suitable for incorporation into the soft segment during polymerization. Preferably the cross-linking agent has two, or more, radically polymerizable groups, such as a vinyl group, per molecule of the monomer, at least one tending to remain unchanged during the initial polymerization, thereby to permit cross-linking of the resulting block copolymer.

Suitable cross-linking agents for use in the present invention include divinylbenzene, methylene bis-acrylamide, ethylene glycol di(meth)acrylate, ethyleneglycol tetra(meth) acrylate, propylene glycol di(meth)acrylate, butylene glycoldi(meth)acrylate, or trimethylolpropane tri(meth)acrylate, although other suitable cross-linking agents will be readily apparent to those skilled in the art. A preferred cross-linking agent is tetraethylene glycol dimethacrylate. It is preferred that the cross-linking agent comprises between about 0.01 to about 0.6% by weight of the block copolymer, with between about 0.1 to about 0.4% by weight being particularly preferred.

Methods for the production of block copolymers from their monomeric constituents are well known. The block copolymer portions of the present invention may be produced by any suitable method, such as step growth, anionic, cationic and free radical methods (Block Copolymers, supra). Free radical methods are generally preferred over other methods, such as anionic polymerization, as the solvent and the monomer do not have to be purified.

Suitable initiators for polymerization include polymeric peroxides with more than one peroxide moiety per molecule. An appropriate choice of reaction conditions is well within the skill of one in the art, once a suitable initiator has been chosen.

The initiator is preferably used in an amount of about 0.005 to about 0.1% by weight of the block copolymer, with about 0.01 to about 0.05% by weight being particularly preferred, although it will be appreciated that the amount chosen is, again, well within the skill of one in the art. In particular, it is preferred that the amount should not be so much as to cause instant gelling of the mix, nor so low as to slow down polymerization and to leave excess residual monomers. A preferred level of residual monomers is below about 2000 ppm.

It will also be appreciated that the amount of initiator will vary substantially, depending on such considerations as the initiator itself and the nature of the monomers.

The block copolymers are adhesives, and preferably are pressure sensitive adhesives. Pressure sensitive adhesives can be applied to a surface by hand pressure and require no activation by heat, water or solvent. As such, they are particularly suitable for use in accordance with the present invention.

The block copolymers may be used without tackifiers and, as such, are particularly advantageous. However, it will be appreciated that the block copolymers may also be used in combination with a tackifier, to provide improved tack, should one be required or desired. Suitable tackifiers are well known and will be readily apparent to those skilled in the art.

Without being constrained by theory, it is thought that the combination of chemical cross-links between the soft segments of the copolymer combined with the, generally, hydrophobic interaction, or physical cross-linking, between the hard portions results in a "matrix-like" structure. Copolymers having only physical cross-linking of the hard segments are less able to form such a matrix. It is believed that the combination of both forms of cross-linking of the block copolymers provides good internal strength (cohesion) and also high drug storage capacity.

More particularly, it is believed that the hard segments associate to form "islands", or nodes, with the soft segments radiating from and between these nodes.

There is a defined physical structure in the "sea" between the islands, where the soft segments are cross-linked, so that there is no necessity for extensive intermingling of the soft segments. This results in a greater cohesion of the whole block copolymer while, at the same time, allowing shortened soft segment length and still having as great, or greater, distances between the islands, thereby permitting good drug storage capacity.

The block copolymer preferably cross-links as the solvent is removed, so that cross-linking can be timed to occur after coating, this being the preferred method.

Accordingly, not only can the block copolymer easily be coated onto a surface, but the complete solution can also be stored for a period before coating. Accordingly, in the manufacturing process of the patches, the process preferably comprises polymerizing the monomeric constituents of each soft segment in solution, then adding the constituents of the hard segment to each resulting solution and polymerizing the resulting mix, followed by cross-linking by removal of any solvent or solvent system, such as by evaporation. If the solution is to be stored for any length of time, it may be necessary to keep the polymer from precipitating out, and this may be achieved by known means, such as by suspending agents or shaking. It may also be necessary to select the type of polymers that will be subject to substantially no cross-linking until the solvent is evaporated.

In general, it is preferred that the adhesive possesses a minimum number of functionalities having active hydrogen, in order to avoid undesirable reactions/interactions, such as with any drug that it is desired to incorporate into the adhesive material. It will be appreciated that this is only a preferred restriction, and that any adhesive may be tailored by one skilled in the art to suit individual requirements.

Suitable monomers for use in forming the hard segment include styrene, a-methylstyrene, methyl methacrylate and vinyl pyrrolidone, with the preferred proportion of the hard segment being between about 5 to about 15 percent (w/w). In particular, it is advantageous to use the compounds of WO 99/02141, as it is possible to load over about 30 percent of drug into such a system.

Thus, in the patches of the present invention, it is generally possible to calculate the amount of drug required and determine the appropriate patch size with a given drug loading in accordance with a patient's body weight, and this can be readily calculated by those skilled in the art.

In certain embodiments, small amounts of plasticizer, such as isopropyl myristate (IPM), are incorporated. This has the advantage of helping to solubilize the amphetamine as well as rendering the adhesive less rough on the skin. Levels of between about 2 to about 25%, by weight, are generally useful, with levels of between about 3 to about 20% being more preferred and levels of about 5 to about 15%, especially about 10%, being most preferred. Other plasticizers may also be used, and suitable plasticizers will be readily apparent to those skilled in the art.

Plasticizers generally take the form of oily substances introduced into the adhesive polymer. The effect of the introduction of such oily substances is to soften the physical structure of the adhesive whilst, at the same time, acting at the interface between the adhesive and the skin, thereby helping to somewhat weaken the adhesive, and to reduce exfoliation.

The free base oil may be obtained by basifying amphetamine salts, or any other suitable salt, with a suitable base, in the presence of a hydrophilic solvent, especially water, and an organic solvent. For instance, water and ethyl acetate, in approximately equal proportions, work well, with ammonia serving as the basifying agent. The water may then be removed and the preparation washed with further water, or other aqueous preparation, after which the preparation may be suitably extracted with ether, for example, after having removed the ethyl acetate. It is preferred to keep the preparation under an inert atmosphere, especially after completion.

Whilst it will be appreciated that patches of the present invention may be removed from the patient at any time, once it is desired to terminate a given dose, this can have the disadvantage of providing an opportunity for potential drug abuse of the partially discharged patch. Abuse of amphetamines is highly undesirable.

In certain embodiments, it may be advantage to use a patch tailored to have delivered the majority of the amphetamine that it is capable of delivering, in a 24 hour period, by about 8 hours after application, so that a patch can be left in place, and levels of drug still diminish appreciably. It is advantageous that the drug delivery profile has first order kinetics, so that the majority of the drug is delivered during the main part of the day and, even if the patient omits to remove the patch, the drug is moving towards exhaustion by the end of the day, and the amount of drug is dropping rapidly.

It will be appreciated that patches of the invention may be constructed in any suitable manner known in the art for the manufacture of transdermal patches. The patches may simply comprise adhesive, drug and backing, or may be more complex, such as having edging to prevent seepage of drug out of the sides of the patch. Patches may also be multi-layered.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form.

Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, about 0.1 to about 99.5% (more preferably, about 0.5 to about 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and Co., San Francisco, U.S.A., 1969 or "Livestock Feeds and Feeding" O and B books, Corvallis, Oreg., U.S.A., 1977).

Exemplary Uses of the Compounds of the Invention.

In various embodiments, the present invention contemplates modes of treatment and prophylaxis which utilize one or more of the amphetamine compounds. These agents may be useful for increasing the occurrence of memory consolidation or decreasing or preventing the effects of defects in an animal which mitigate memory consolidation. In other embodiments, the preparations of the present invention can be used simply to enhance normal memory function.

In various other embodiments, the present invention contemplates modes of treatment and prophylaxis which utilize one or more of the subject amphetamine compounds to alter defects in attention span and/or focus in an organism. The enhancement and/or restoration of attention span in an organism has positive behavioral, social, and psychological consequences. Additionally, enhancement of attention span can improve memory and learning.

In certain embodiments, the subject method can be used to treat patients who have been diagnosed as having or at risk of developing disorders in which diminished declarative memory is a symptom, e.g., as opposed to procedural memory. The subject method can also be used to treat normal individuals for whom improved declarative memory is desired.

Memory disorders which can be treated according to the present invention may have a number of origins: a functional mechanism (anxiety, depression), physiological aging (age-associated memory impairment, mild cognitive impairment, etc.), drugs, or anatomical lesions (dementia), associated with multiple sclerosis, chronic fatigue syndrome, fibromyalgia syndrome, chemotherapy, traumatic brain injury, stroke or Parkinson's disease. Indications for which such preparations may be useful include learning disabilities, memory impairment, e.g., due to toxicant exposure, brain injury, brain aneurysm, age, schizophrenia, epilepsy, mental retardation in children, and senile dementia, including Alzheimer's disease.

In certain embodiments, the invention contemplates the treatment of amnesia. Amnesias are described as specific defects in declarative memory. Faithful encoding of memory requires a registration, rehearsal, and retention of information. The first two elements appear to involve the hippocampus and medial temporal lobe structures. The retention or storage appears to involve the heteromodal association areas. Amnesia can be experienced as a loss of stored memory or an inability to form new memories. The loss of stored memories is known as retrograde amnesia. The inability to form new memories is known as anterograde amnesia.

Complaints of memory problems are common. Poor concentration, poor arousal and poor attention all may disrupt the memory process to a degree. The subjective complaint of memory problems therefore must be distinguished from true amnesias. This is usually done at the bedside in a more gross evaluation and through specific neuropsychological tests. Defects in visual and verbal memory can be separated through such tests. In amnesias there is by definition a preservation of other mental capacities such as logic. The neurobiologic theory of memory described above would predict that amnesias would have relatively few pathobiologic variations. Clinically the problem of amnesias often appears as a result of a sudden illness in an otherwise healthy person.

Exemplary forms of amnesias which may be treated by the subject method include amnesias of short duration, alcoholic blackouts, Wernicke-Korsakoff's (early), partial complex seizures, transient global amnesia, those which are related to medication, such as triazolam (Halcion), and basilar artery migraines. The subject method may also be used to treat amnesias of longer duration, such as post concussive or as the result of Herpes simplex encephalitis.

In certain embodiments, this invention contemplates the treatment of the Anterior Communicating Artery Syndrome. This syndrome is prevalent among survivors of Anterior Communicating artery aneurysms and often includes anterograde amnesia, a specific deficit in new memory formation, with relative sparing of older memories as well as intelligence and attention. The Anterior Communicating Artery Syndrome may also include some personality changes and confabulation. There is a considerable anatomic and clinical evidence that the Anterior Communicating Artery Syndrome in man is a result of a focal lesion in the basal forebrain area (particularly the medial septal area), secondary to combined damage from the aneurysm and the surgical or endovascular treatment of the aneurysm.

In addition, the compounds of the invention enhance memory in normal individuals, in particular, memory consolidation in humans.

The present invention is further illustrated by the following examples, which are not intended to be limiting in any way.

EXEMPLIFICATION

The invention now being generally described, it will be more readily understood by reference to the following examples which are included merely for purposes of illustration of certain aspects and embodiments of the present invention, and are not intended to limit the invention.

The Inhibitory Avoidance (IA) task (also referred to herein as "Passive Avoidance") (Bammer, G., *Neurosci & Biobev. Rev.* 6:247-296 (1982)) and the Spontaneous Object Recognition (SOR) task (Ennaceur, A., et al., *Psychopharmacol.* 109:321-330 (1992); Ennaceur, A., et al., *Behav. Brain Res.* 33:197-207 (1989)) are well-studied behavioral paradigms which can provide the researcher with a consistent and long lasting measure of memory. The paradigms consists of one training trial and one retention trial. Test substances may be administered to the rats either before or after training. Improved memory, as a result of test substance administration, is evident on the retention trial. The objective of the following experiments was to investigate the effects of amphetamine on IA and SOR memory in the rat.

General Experimental Procedures

Inhibitory Avoidance

The Inhibitory Avoidance apparatus (Coulbourn Instruments) consisted of a light chamber and a dark chamber, which were joined by means of a sliding guillotine door. The floor of the dark compartment consisted of 2.4 mm diameter steel rods, through which a foot-shock could be administered to the animal by a constant current 18-pole shock scrambler. The test apparatus was enclosed in a ventilated, sound-attenuating cabinet, and was controlled by Graphic State™ Notation Software (Version 1.013) and a Hewlett Packard Pavilion Computer. Training involved the rat being placed in the light chamber for a ten second period, after which time the sliding door was opened, allowing the rat access to the dark chamber. Two seconds after entering the dark chamber, a continuous 0.46 mA foot-shock was delivered through the floor grid for two seconds. The animal was then removed from the apparatus and returned to the home cage. The animals received a retention test 24 hours following training. The retention test was identical to training except that no foot-shock was delivered. Latency to enter the dark chamber was recorded, and the animals were then returned to their home cages. Data was collected by the Graphic State™ Notation software, and was recorded onto an appropriate data sheet.

Spontaneous Object Recognition

Apparatus for Object Recognition testing consisted of a plexiglass open field activity chamber, measuring 30 by 30 cm. A video camera was mounted on the wall above the chamber. Three plastic objects served as stimuli for the experiment. Two of the objects were identical to one another, and the third was different. Rats were individually habituated to the open-field box for three consecutive days. Habituation sessions were six minutes in duration. Twenty-four hours after the last day of habituation, a training session was conducted, in which two identical objects were placed in the open-field box, 10 cm from the back wall. The animal was placed into the box and was allowed to explore freely for a period of four minutes. Twenty-four hours after the training session, retention testing was conducted. During retention testing, the rat was placed back into the same activity box with one of the familiar objects used during the training session and a novel object that the rat had not seen before. The rat was allowed to explore the box and objects for a period of four minutes. Testing was conducted at the same time each day, and was videotaped for off-line analysis. Two discrimination indices, D1 and D2 were calculated in order to measure the strength of recognition memory. D1 reflects the amount of time spent exploring the novel object minus the amount of time spent exploring the familiar object, and D2 reflects D1 divided by total exploration time.

Activity Monitoring

Activity monitoring was conducted in a Plexiblas open-field box. Activity levels were measured by a grid of infrared light beams that traversed the cage from left to right and back to front. The location of the animal was detected by breaks in the infrared light beams. General behavior and activity levels were recorded by a computerized monitoring system for a period of ten minutes. The analyzed behaviors included but were not limited to; horizontal activity, total distance moved, movement time, number of movements, number of rears, number of stereotyped movements, and time spent resting. Data was collected on-line using Versa Max (Version 1.83) computer software and a Hewlett Packard Pavilion computer.

Tail Flick

For Tail-Flick Analgesia Testing, the animal was placed on top of the Tail-Flick monitor and gently held in place with a cotton towel. The tail of the animal was placed in a shallow groove lying between two sensors and over the top of a radiant heat wire. The Tail Flick monitor was activated, and the latency for the animal to flick its tail out of the groove and away from the heat source was recorded. The animal was returned to its home cage immediately following testing.

Fornix Lesions

Rats were anesthetized with Nembutal (55 mg/kg) and prepared for surgery. The rat was placed in the stereotaxic apparatus, a midline incision made, and the scalp retracted to expose the skull. The skull was cleaned and dried using sterile saline and cotton swabs, and four stereotaxically determined holes were drilled in the skull at the following coordinates: 0.3 and 0.8 mm posterior to Bregma, and 0.5 and 0.7 mm lateral to the midline. An electrode (Teflon-coated wire, 125 µm in diameter) was lowered into the brain to a depth of 4.6 mm, and DC current at 1.0 mA was passed through the electrodes for a duration of 10 seconds. The electrodes were then removed, and the wound was sutured. Animals were removed from the stereotaxic apparatus and received postoperative care and monitoring until fully conscious. The rats were left to recover for a period of seven days prior to behavioral testing. The health status of the animals was checked on a daily basis during the recovery period.

Example 1

Dose Response Testing

Effects of (S)-(+)-amphetamine on Inhibitory Avoidance

Figure 2:
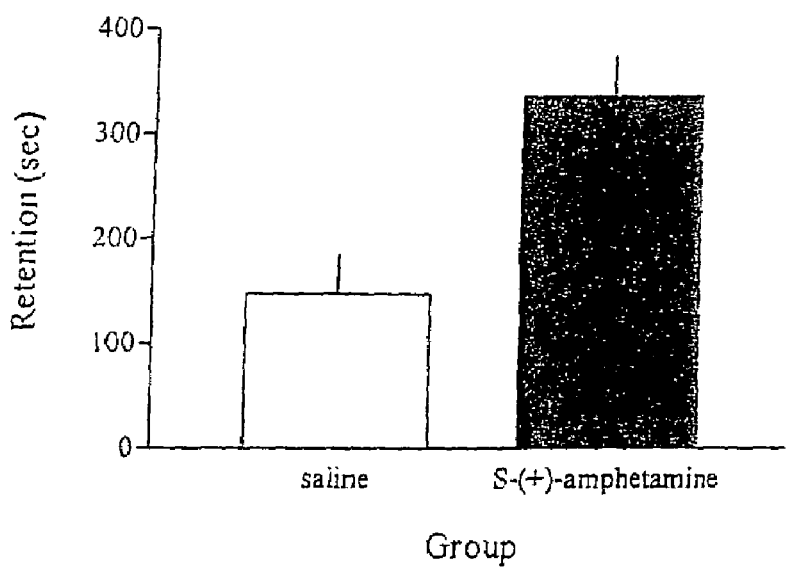
FIG. 2 demonstrates the effect of 2 mg/kg of S-(+)-amphetamine on Performance in the Inhibitory Avoidance Task.

In this experiment, rats were injected with three different doses of (S)-(+) amphetamine thirty minutes prior to being trained on the IA task. As can be seen from FIG. 1, a dose of about 2 mg/kg of amphetamine improved retention of the task, while doses of about 0.25, about 0.50 and about 1.0 mg/kg had no effect. In order to verify this result, a second experiment was conducted. Rats were injected with about 2.0 mg/kg of amphetamine and trained on the IA task. As can be seen from FIG. 2, this dose of (S)-(+)-amphetamine significantly improved retention of the task. An unpaired t-test demonstrated that this enhancement was statistically significant ($p<0.01$).

Effects of (R)-(−)-Amphetamine (C105) on Inhibitory Avoidance

The first experiment to be conducted using C105 was a dose response experiment, in which different doses of C105 (about 0.4, about 0.5, about 0.75, 1.0 and about 2.0 mg/kg) were administered to the rats one hour prior to training on the Inhibitory Avoidance task. Retention for the task was tested 24-hours later. A one way ANOVA was conducted on the data, and the results revealed a statistically significant difference between the dose level groups ($F(5.59)=3.368$, $p<0.01$). Subsequent post hoc analysis (Student Newman Keuls) demonstrated that the 1.0 mg/kg group performed significantly better than saline injected controls ($p<0.05$). The 0.5 mg/kg dose also appeared to be effective in enhancing the animals performance, however, this trend did not reach statistical significance. This experiment was subsequently replicated using 0.5 mg/kg as the target dose in order to verify this result (see section 9.1.4). Dose Response data is presented individually in Table 3.

Effects of (R)-(−)-Amphetamine (C105) on Inhibitory Avoidance

Figure 8:
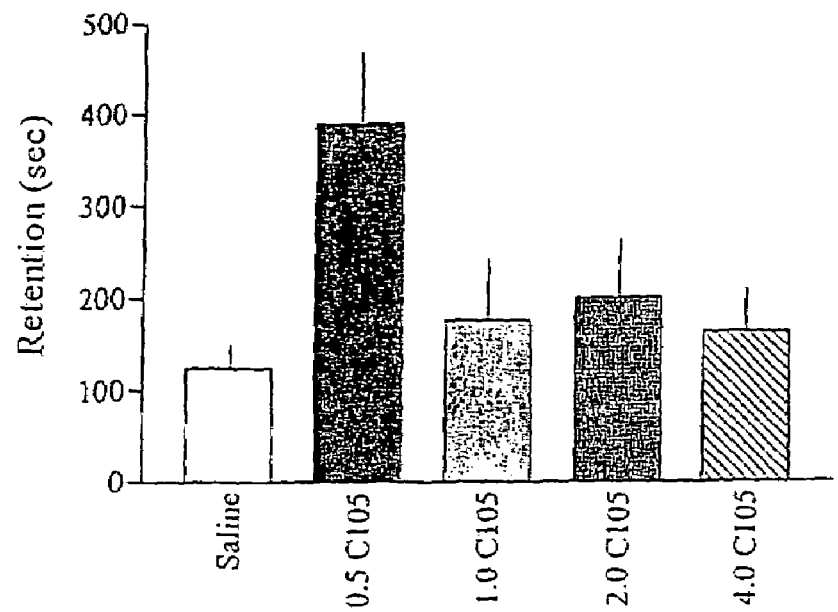
FIG. 8 shows the effectiveness of various doses of R-(−)-amphetamine on memory retention.

In this experiment, four groups of 10 rats were injected with different doses (0.5 mg/kg, 1.0 mg/kg, 2.0 mg/kg or 4.0 mg/kg) of the R-(−) enantiomer of amphetamine one hour prior to being trained on the IA task. The experiments were conducted with a 24 hour retention interval and a 0.46 mA shock intensity. As can be seen in FIG. 8, a much lower dose of (R)-(−)-amphetamine is required for the same improved retention effect as obtained with (S)-(+)-amphetamine (compare to FIG. 1). Increasing the dose above 0.5 kg/mg did not further improve the retention results obtained with this dose possibly indicating a saturation effect.

Effects of (R)-(−)-Amphetamine (C105) on Inhibitory Avoidance

In order to investigate whether doses of C105 lower than 0.5 mg/kg enhanced performance, rats were injected with 0.1, 0.25 or 0.5 mg/kg of C105 one hour prior to training. Retention was tested 24-hours later. This experiment revealed that doses of C105 lower than 0.5 mg/kg were not effective in improving the mnemonic performance of the rats. In contrast, the 0.5 mg/kg dose significantly enhanced performance on the task ($F(3.39)=67450$, $p<0.0477$). These data are presented individually in Table 4.

Example 2

Time Course of Effectiveness

Figure 3:
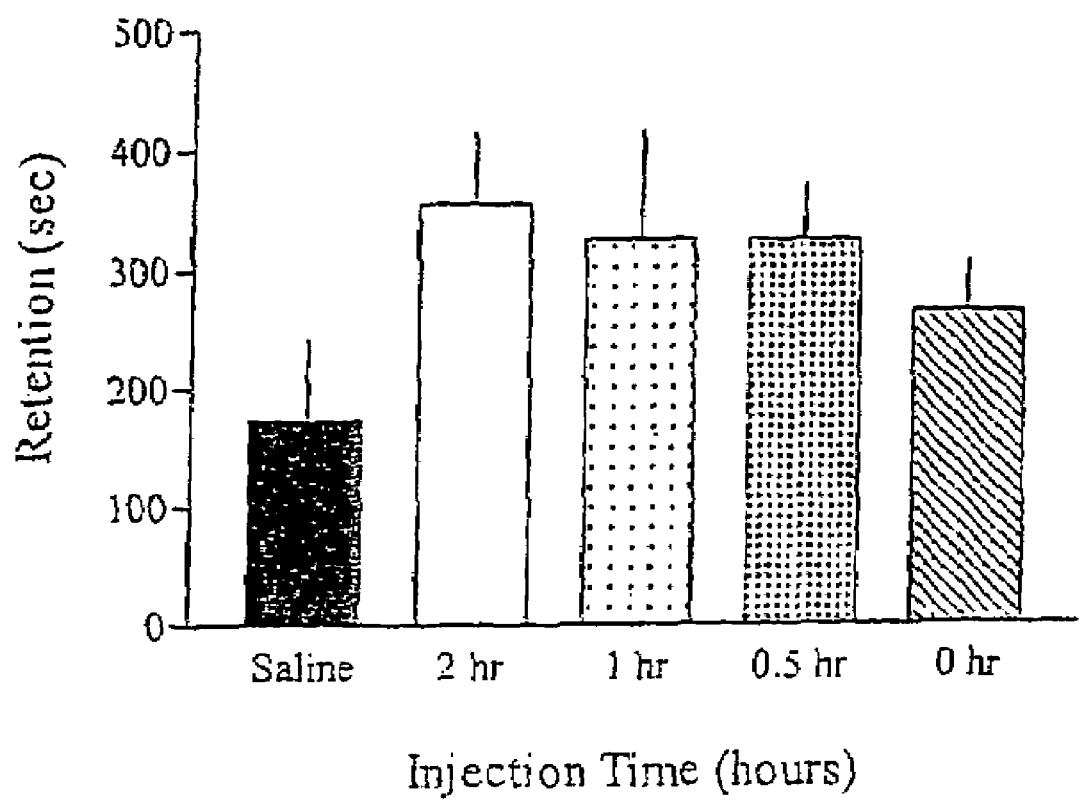
FIG. 3 shows the varying effect of S-(+)-amphetamine depending on the time between administration and inception of training.

In this experiment, the time of drug administration was varied in order to determine the optimal pre-training drug administration time. FIG. 3 shows that (S)-(+) amphetamine (2.0 mg/kg) is effective when administered to the rats between 0 and 2 hours prior to training.

Example 3

Long Term Retention

Figure 4:
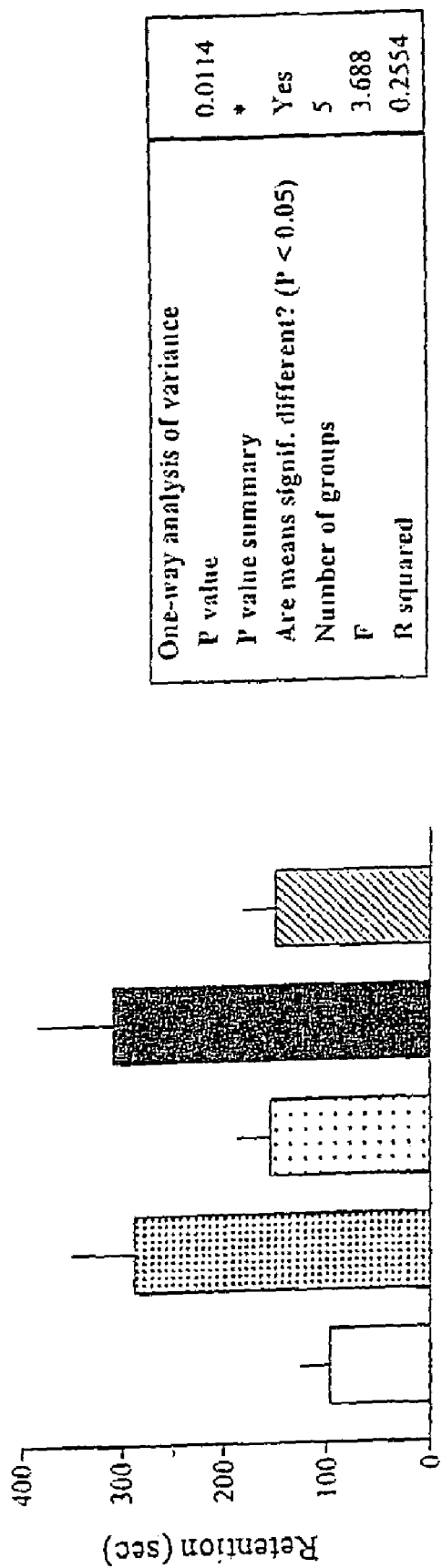
FIG. 4 illustrates the effect of S-(+)-amphetamine on memory retention one week after the initial training.

This experiment was conducted in order to determine whether the enhanced retention observed in Experiment 2 was long-lasting. Rats received a second retention test one week after the first retention test. No additional training or drug was administered to the animals in the interim period. FIG. 4 illustrates that rats that had received (S)-(+)-amphetamine the previous week performed significantly better than rats that had received control injections of vehicle solution ($F(4.47)=3.688$, $p<0.01$).

Example 4

Effects of Lesioned Animals

Effects of (−)(+)-Amphetamine on Lesioned Animals

The findings of the above experiments are important, as they identify the most effective dose and time of administration for this compound. Moreover, the results demonstrate that (S)-(+)-amphetamine improves memory in normal rats, and that this improvement is long-lasting. In the next experiment, we investigated whether the performance of amnesic rats could be improved by administration of d-amphetamine. In this experiment, control rats and rats with lesions of the fornix received injections of either saline or d-amphetamine (2.0 mg/kg), and one hour later, were tested on the IA task.

Figure 5:
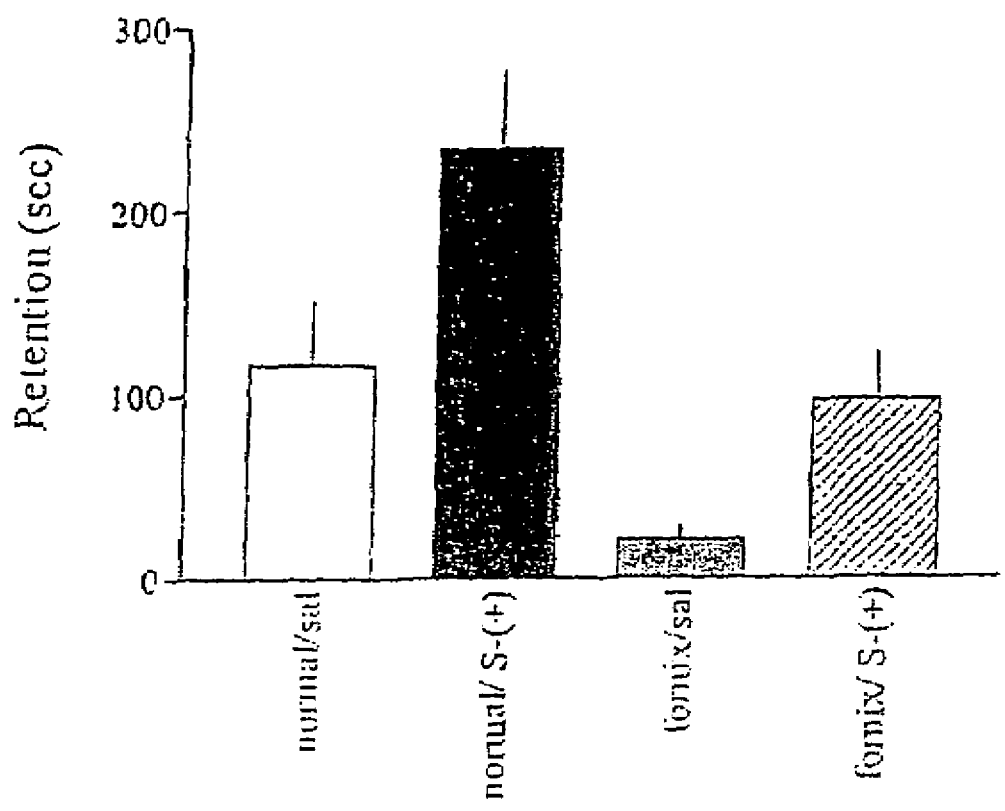
FIG. 5 depicts the effects of S-(+)-amphetamine on normal and fornix-lesioned animals.

As FIG. 5 illustrates, (S)-(+)-amphetamine dramatically enhanced the performance of normal rats and in addition, appeared to improve the performance of the fornix lesion rats. A one way ANOVA demonstrated that there was a significant difference between the performance of the four groups ($F(3.36)=8.687$, $p<0.002$). Student-Newman-Keuls post hoc tests revealed firstly that the performance of normal rats that received (S)-(+)-amphetamine was significantly enhanced relative to all other experimental groups ($p<0.05$). In addition, the performance of fornix animals that received (S)-(+)-amphetamine was not significantly different from normal, saline injected animals. These results demonstrate that amphetamine is capable of enhancing memory in normal rats and has beneficial effects in brain damaged, amnesic rats.

Effects of (R)-(−)-Amphetamine on Lesioned Animals

Figure 12:
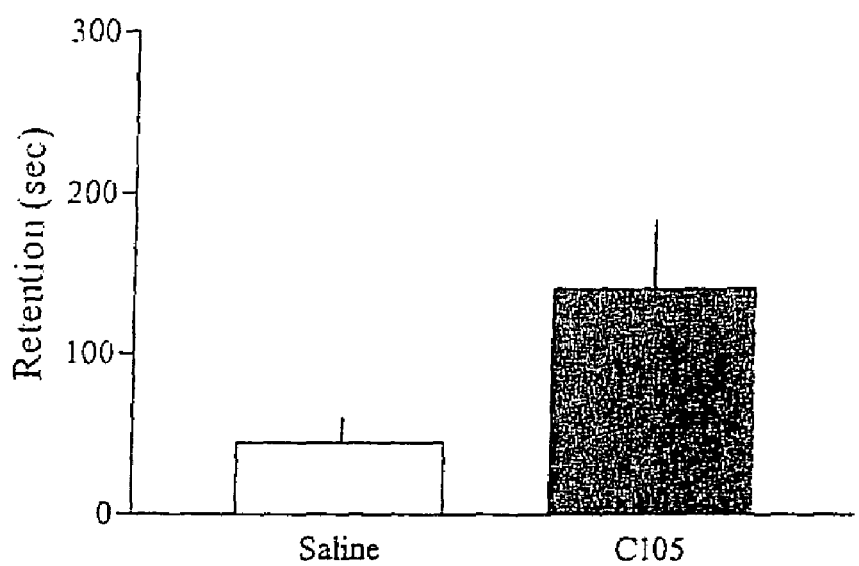
FIG. 12 shows the effect of R-(−)-amphetamine (1.0 mg/kg) on Inhibitory Avoidance Performance in Fornix Lesion Rats.
Figure 13A:
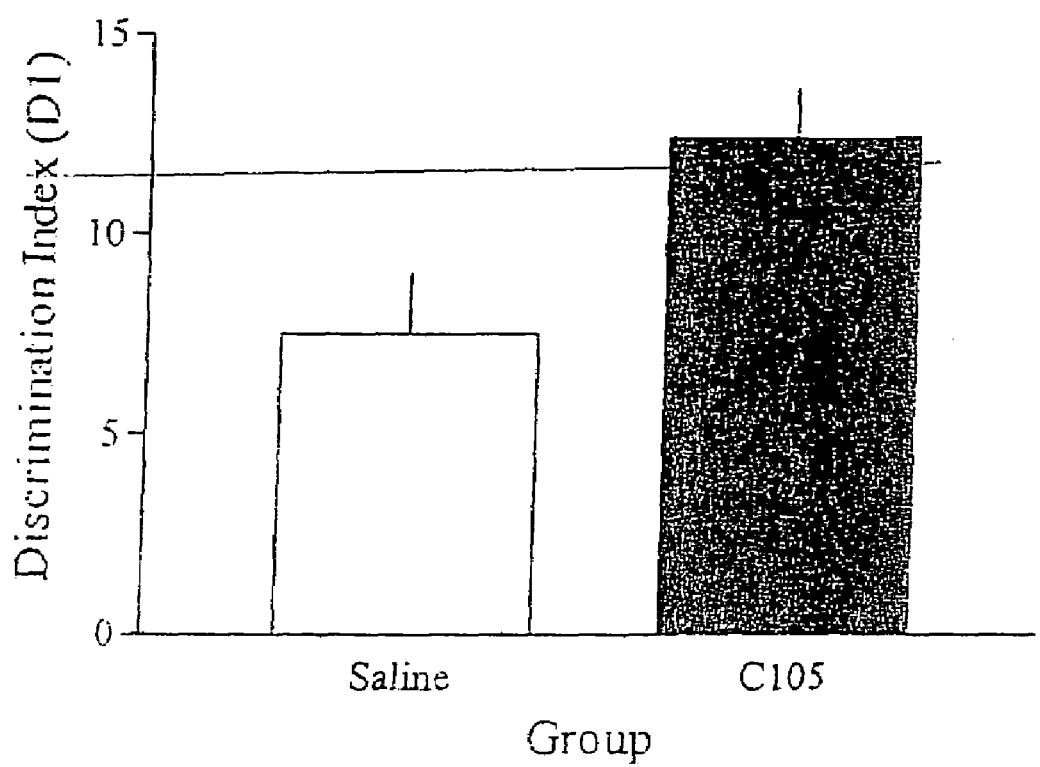
FIGS. 13A, 13B, 13C and 13D show the effect of R-(−)-amphetamine on Performance in the Object Recognition Task in Normal and Fornix Lesion Rats.
Figure 13B:
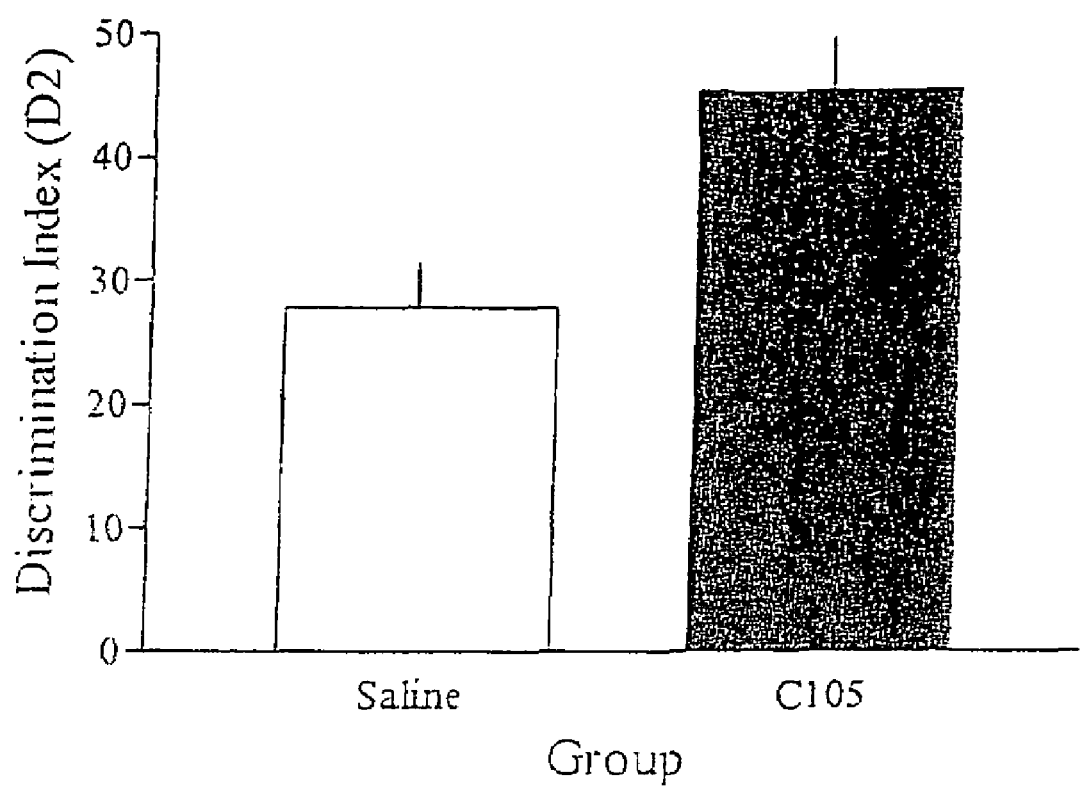
Figure 13C:
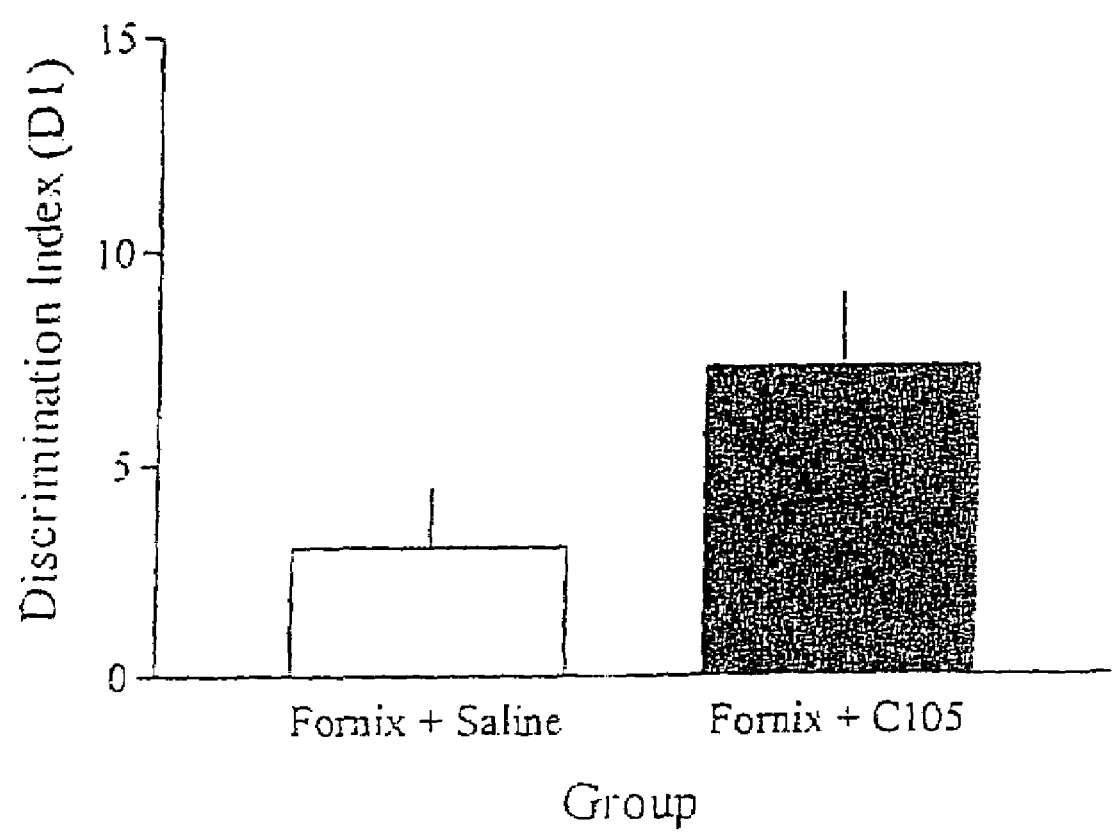
Figure 13D:
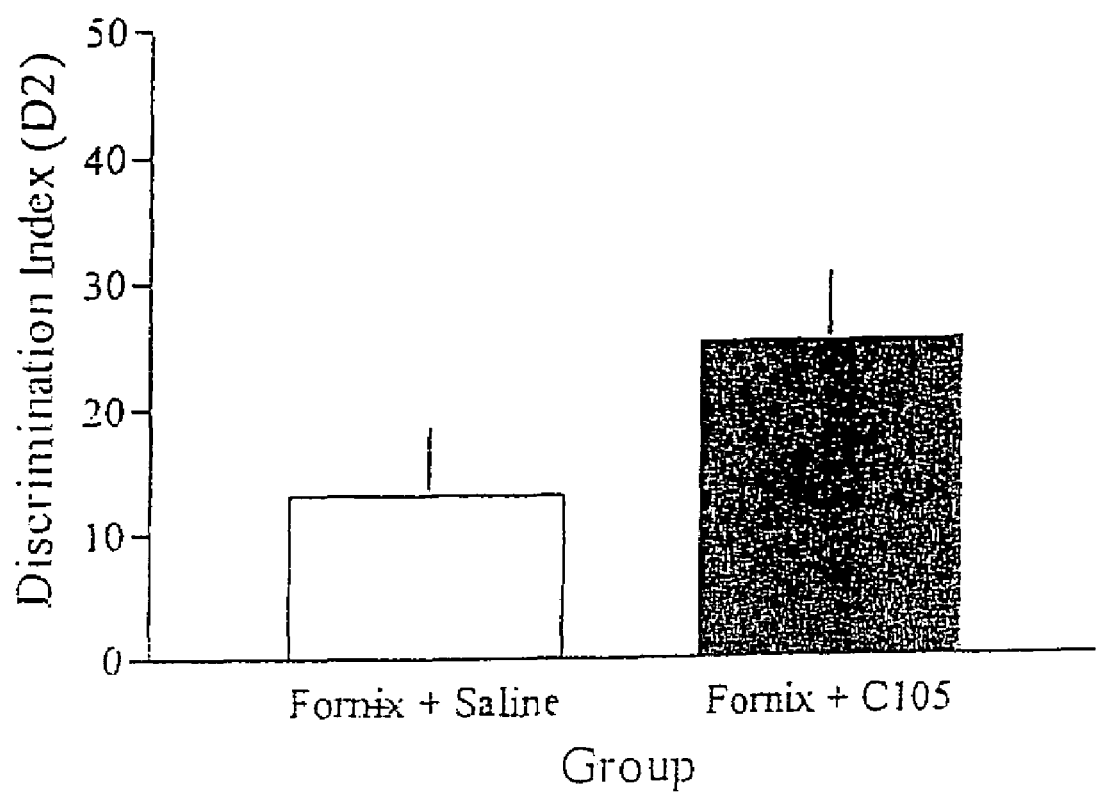
Figure 14A:
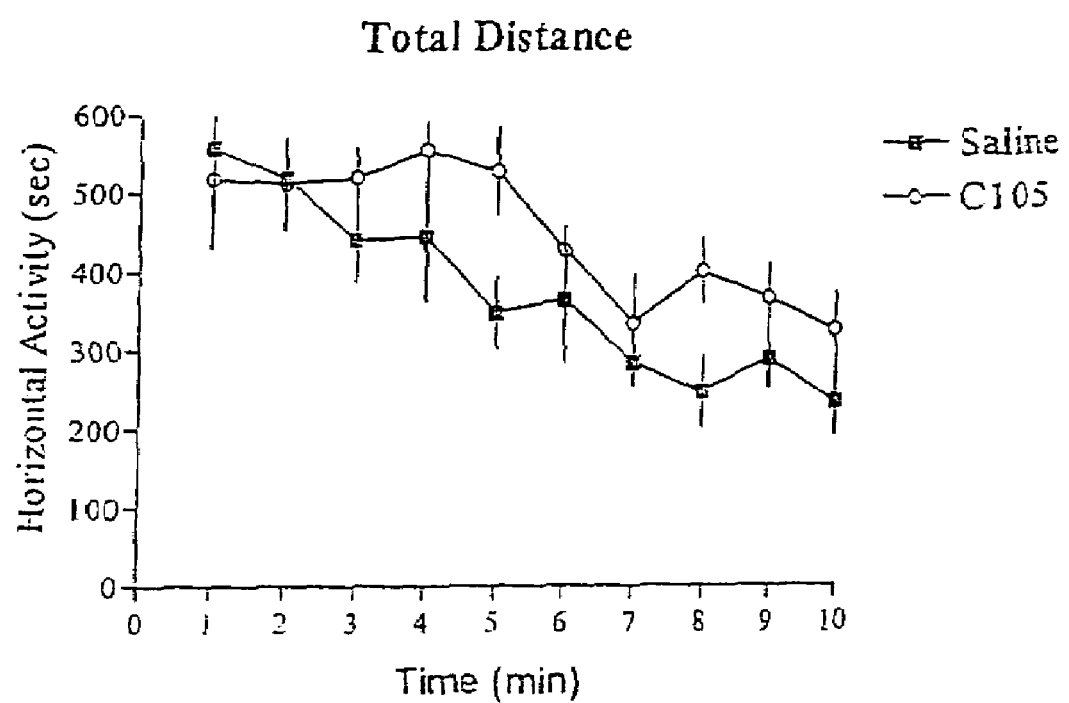
FIGS. 14A, 14B, 14C, 14D, 14E and 14F show the effect of R-(−)-amphetamine (0.5 mg/kg) on Activity Levels.
Figure 14B:
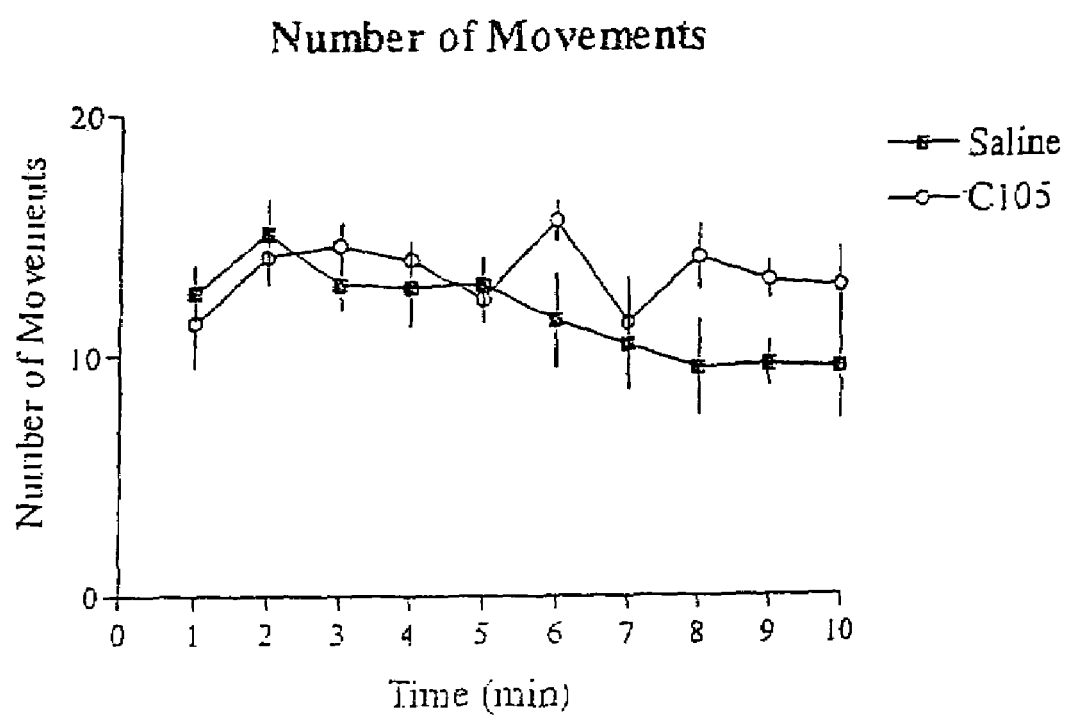
Figure 14C:
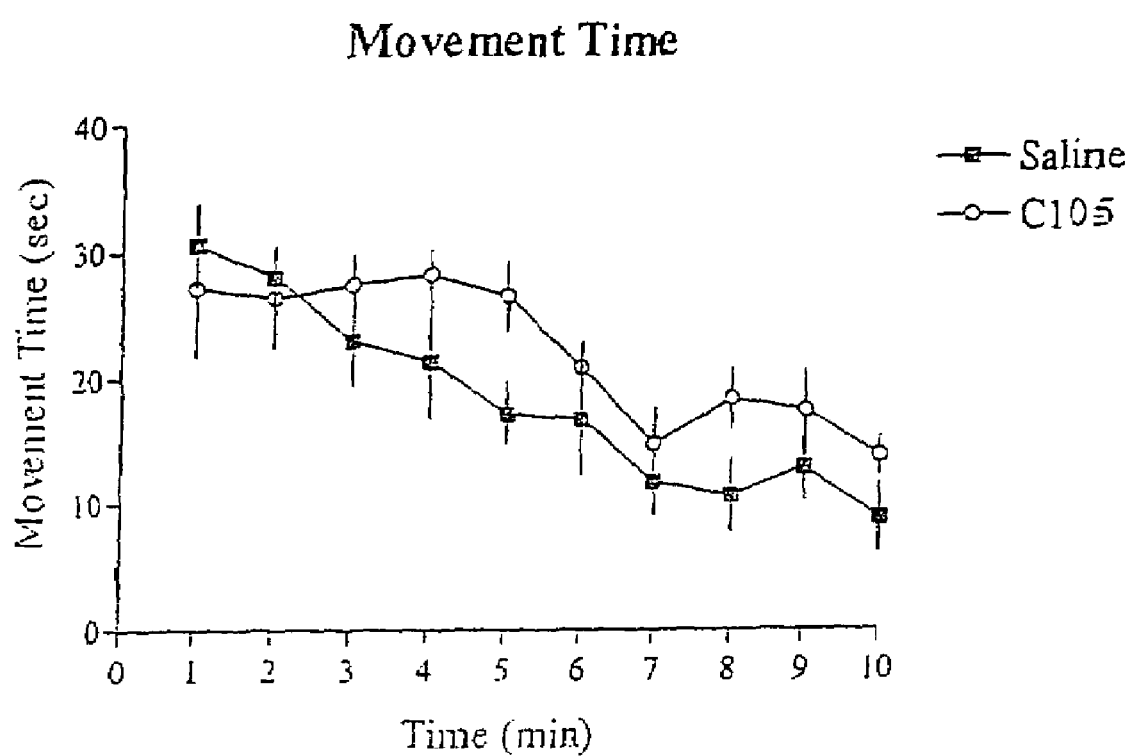
Figure 14D:
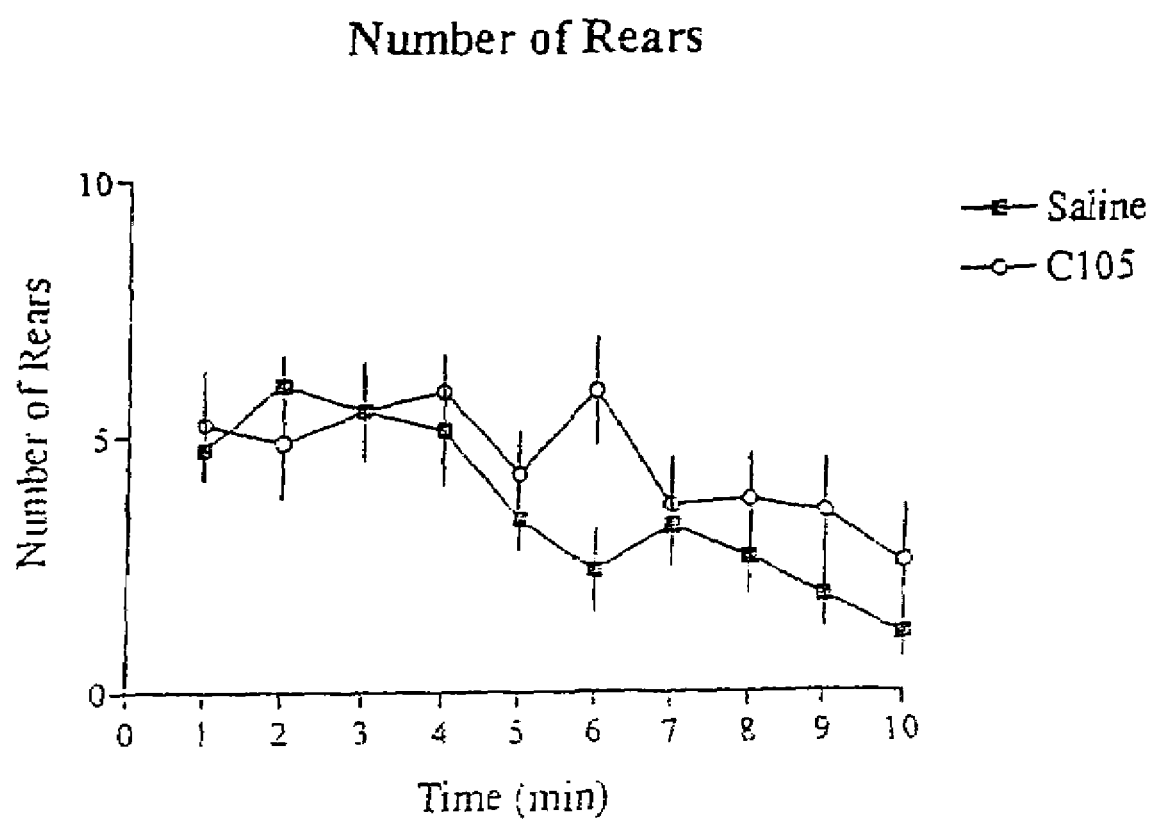
Figure 14E:
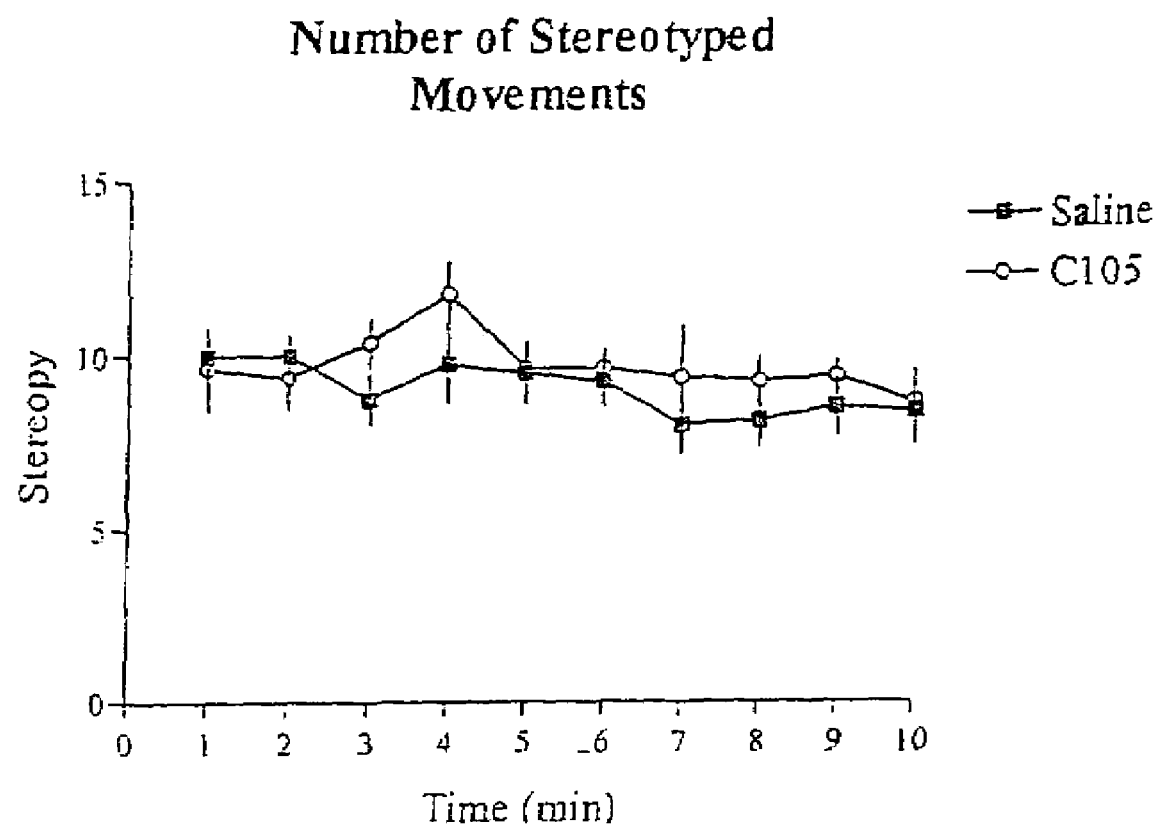
Figure 14F:
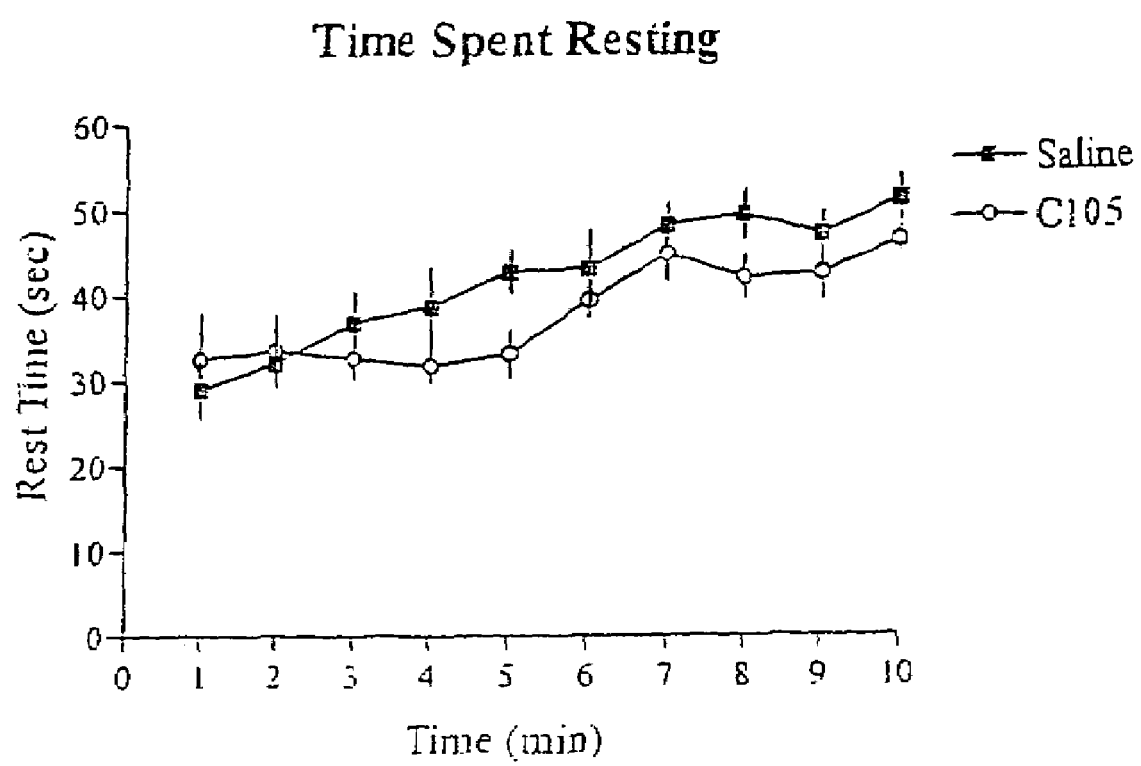
Figure 15A:
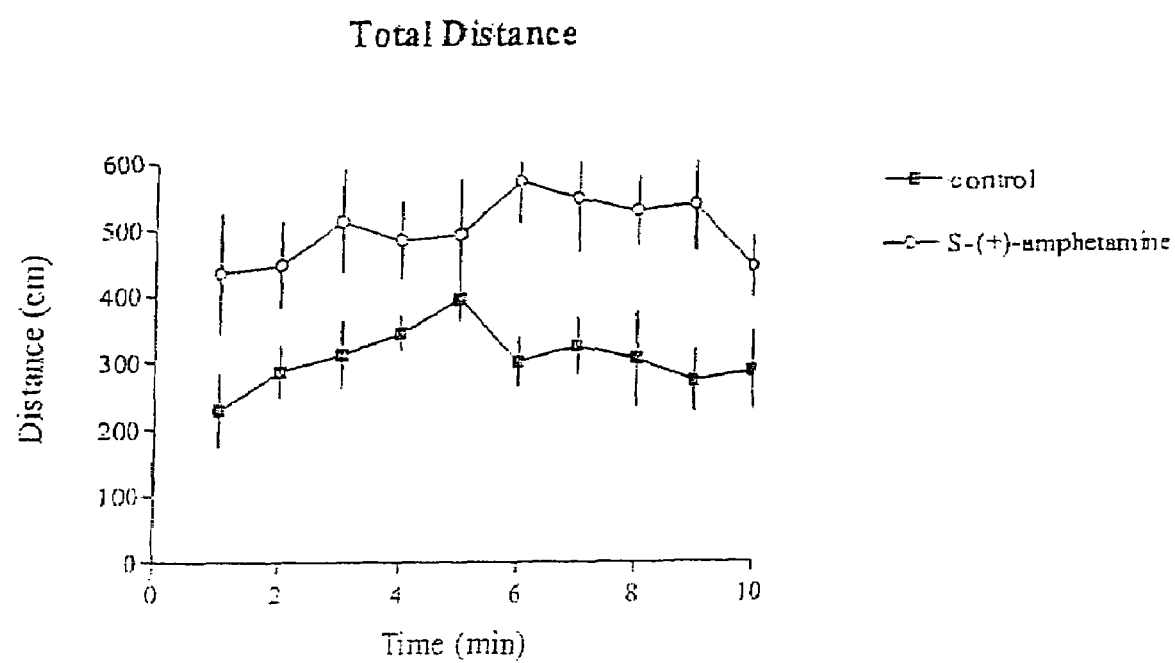
FIGS. 15A, 15B, 15C, 15D, 15E and 15F shows the effect of S-(+)-amphetamine (2 mg/kg) on Activity Levels.
Figure 15B:
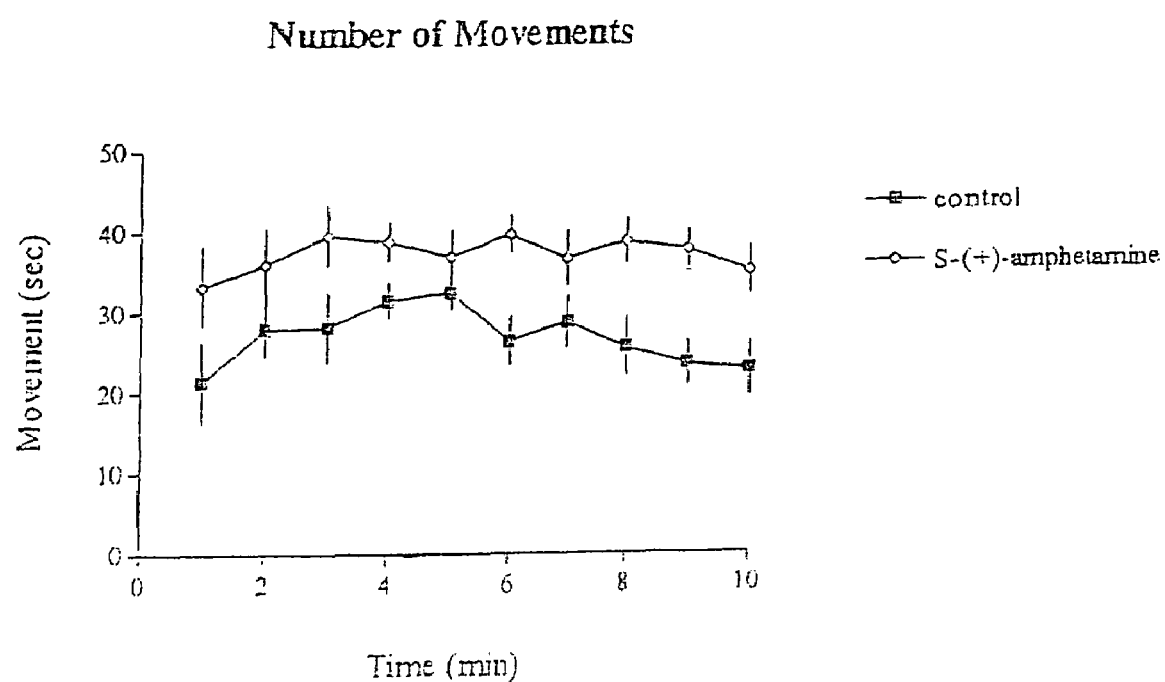
Figure 15C:
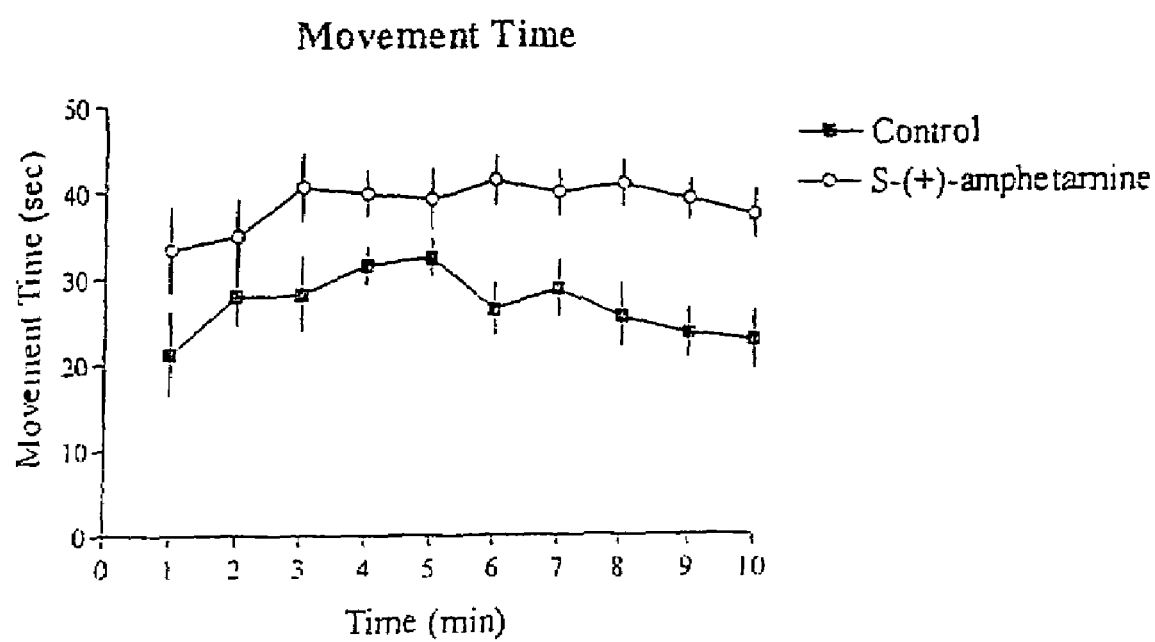
Figure 15D:
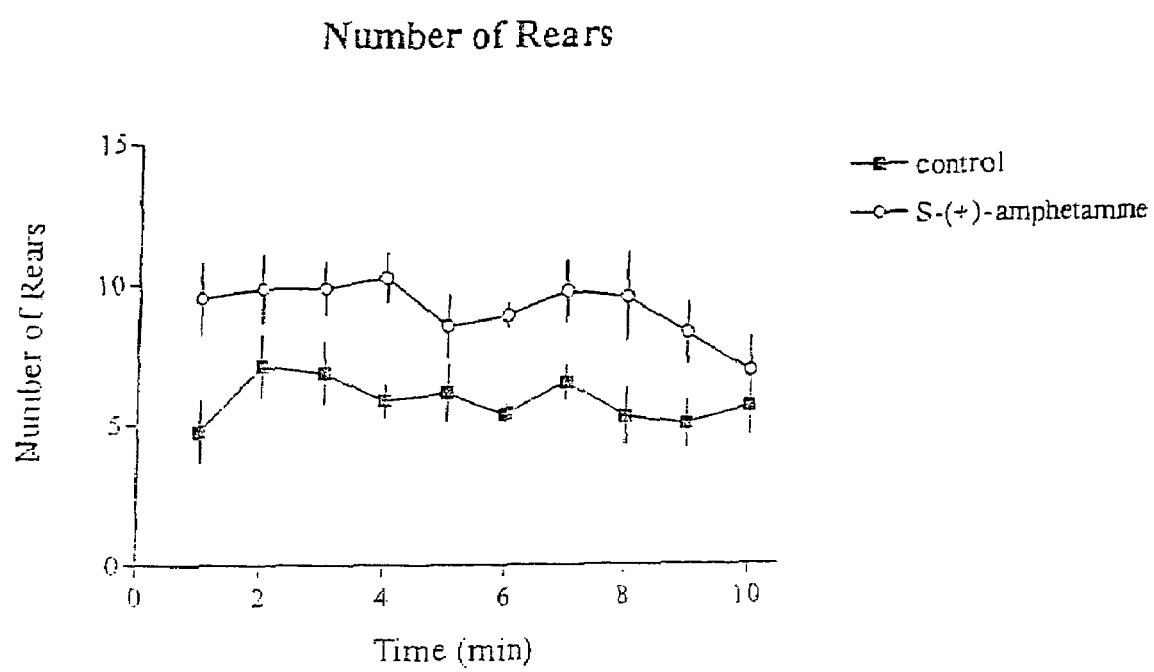
Figure 15E:
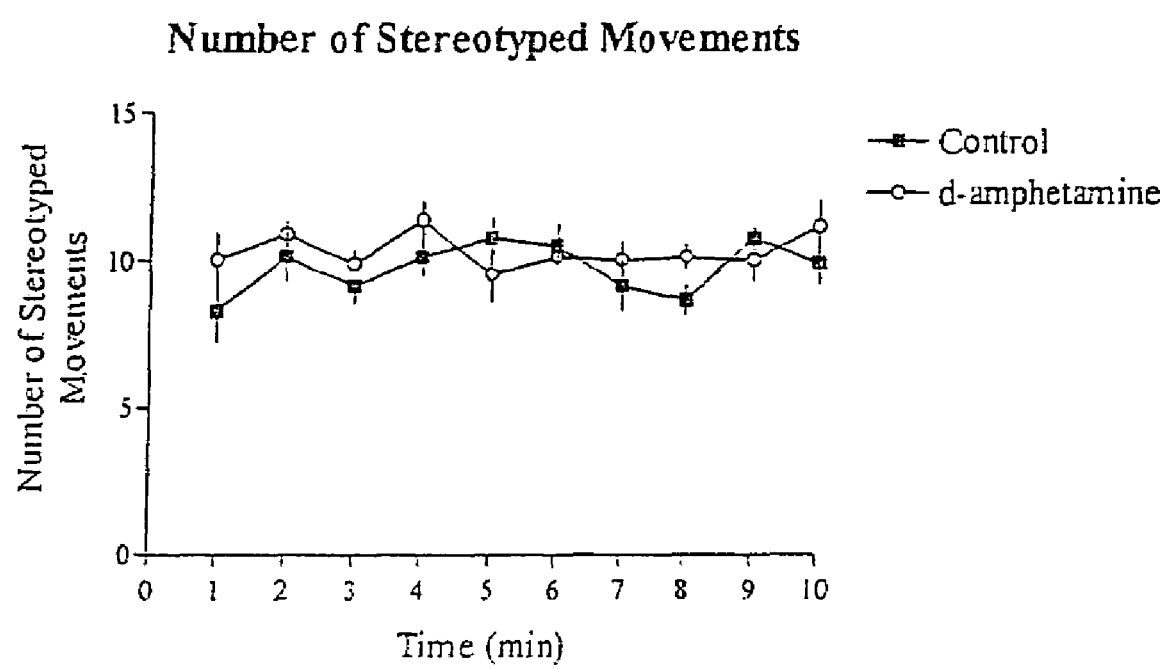
Figure 15F:
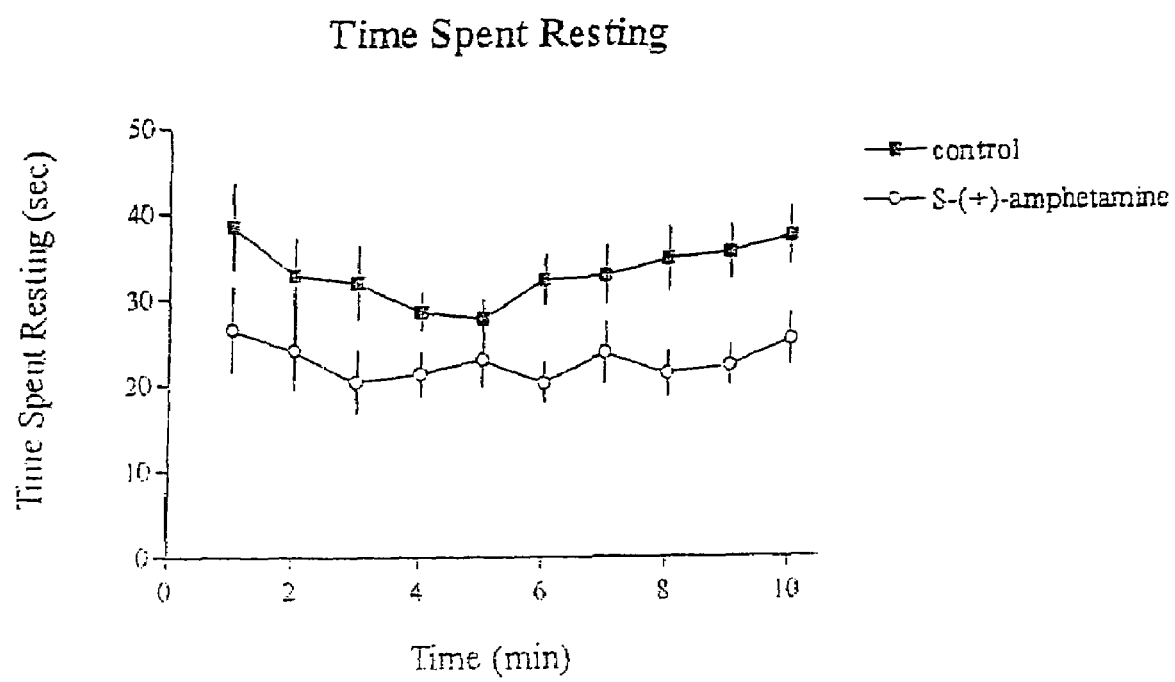

Rats with bilateral lesions of the fornix were tested on the Inhibitory Avoidance task. All rats were injected with test (0.5, 1.0, 2.0 and 4.0 mg/kg) or control article one hour prior to testing. A one-way ANOVA demonstrated that there was a significant main effect of dose ($F(4.45)=15580$, $p<0.0316$). A dose of 1.0 mg/kg of C105 appeared to be most effective in improving the performance of the fornix lesion animals. Data from this experiment are illustrated in FIG. 12 and presented individually in Table 7.

Rats with lesions of the fornix were also tested on the Object Recognition task. Rats received I.P injections of C105 (1.0 mg/kg) or saline immediately after the training session, and were tested for retention 24-hours later. As can be seen from FIG. 13, when compared with controls, lesions of the fornix had a detrimental effect on performance of this task. Administration of C105 produced a trend towards improving discrimination performance in D1 ($p=0.0685$), and slightly improved performance in D2.

Example 5

Effects of (R)-(−) vs. (S)-(+) Amphetamine Enantiomers on Stimulation of Memory Consolidation The effects of the (R)-(−)-amphetamine and the (S)-(+) amphetamine enantiomers on stimulation of memory consolidation and motor stimulation were compared. The (R)-(−) enantiomer of amphetamine is referred to as C105 in the figures.

Effects of (S)-(+)-Amphetamine on Inhibitory Avoidance

Figure 6:
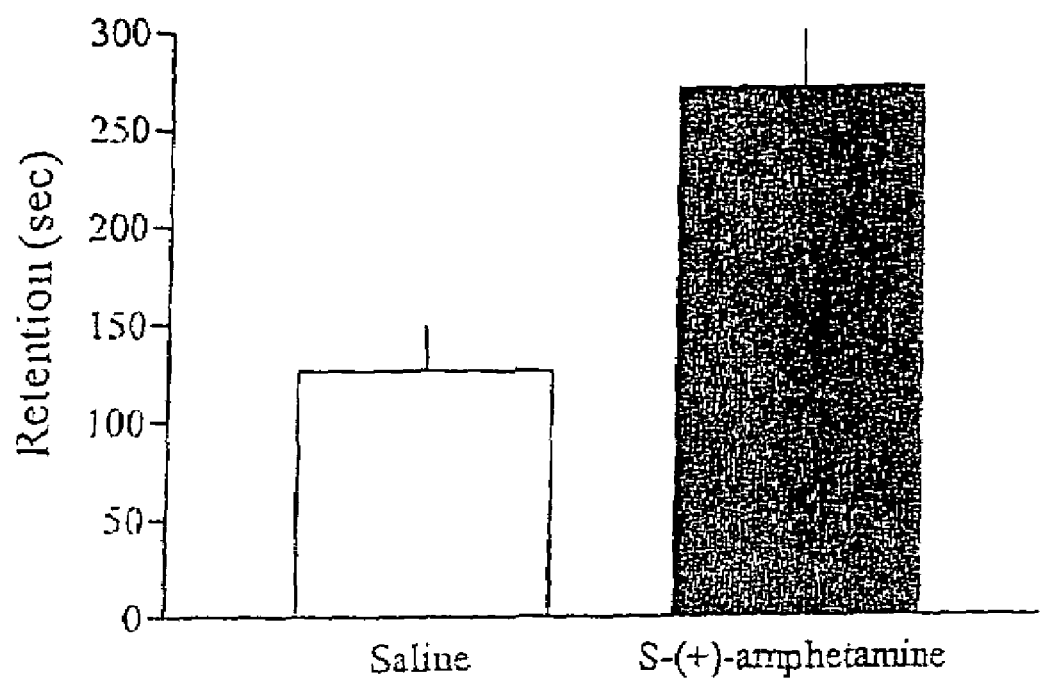
FIG. 6 shows the effect of S-(+)-amphetamine (2.0 mg/kg) on Performance in Inhibitory Avoidance.
Figure 7A:
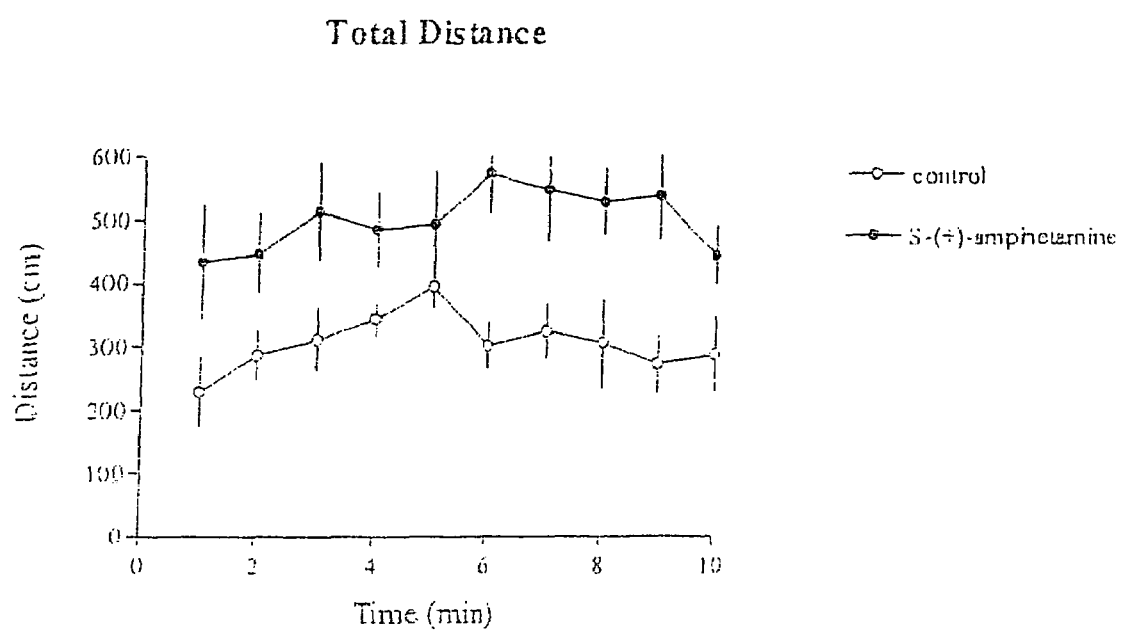
FIGS. 7A, 7B, 7C, 7D, 7E and 7F show the effect of S-(+)-amphetamine on Activity Levels.
Figure 7B:
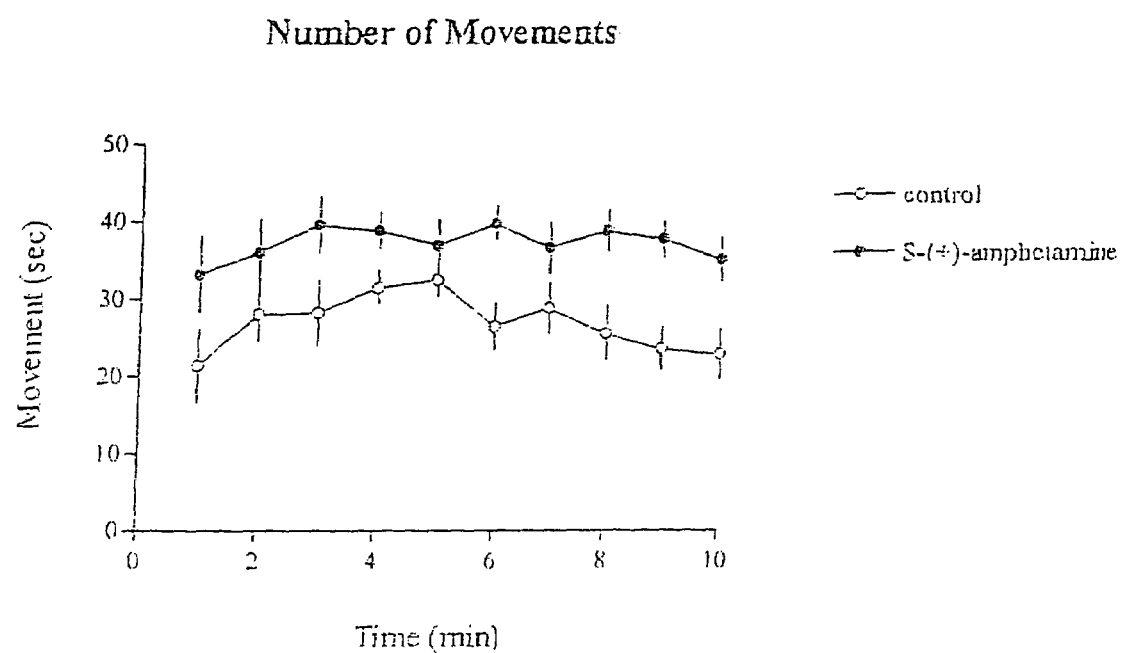
Figure 7C:
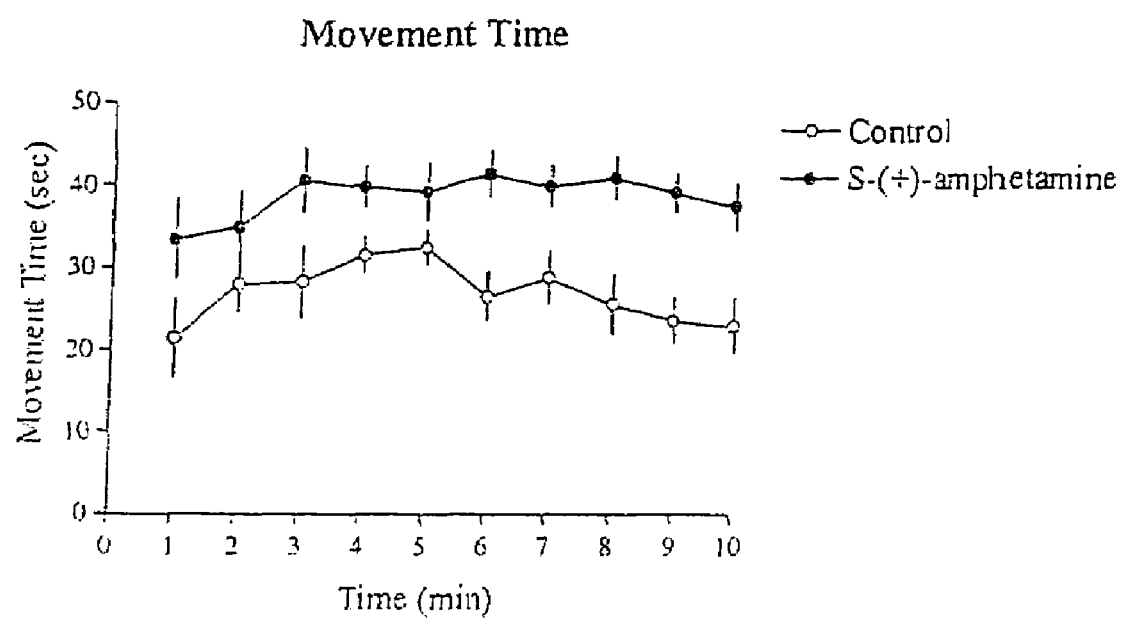
Figure 7D:
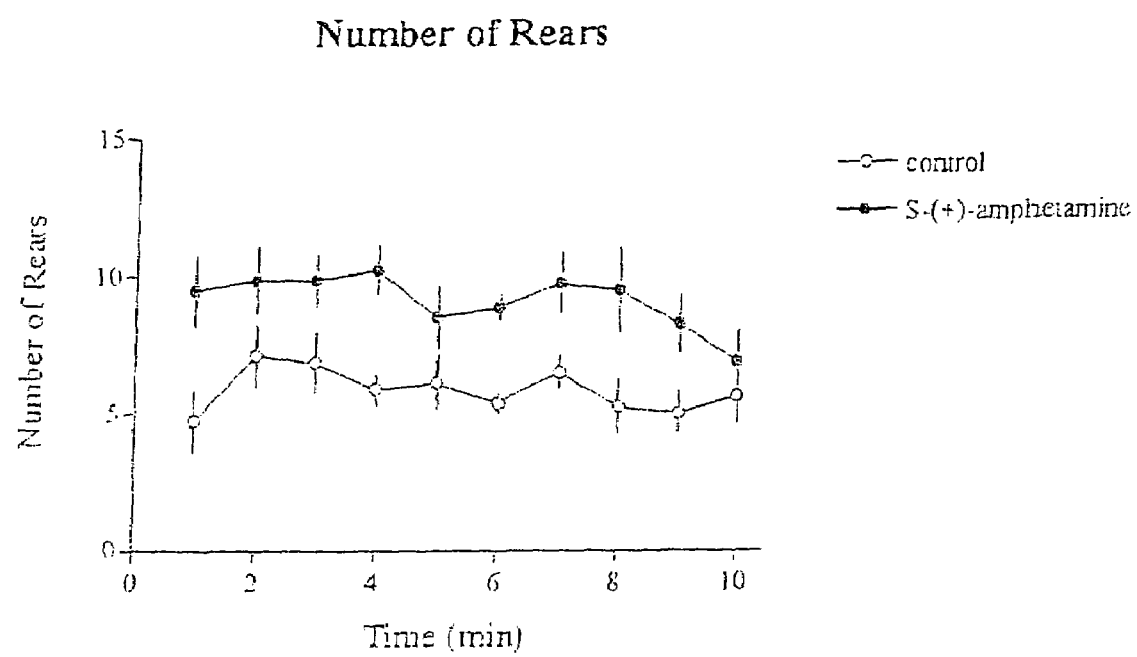
Figure 7E:
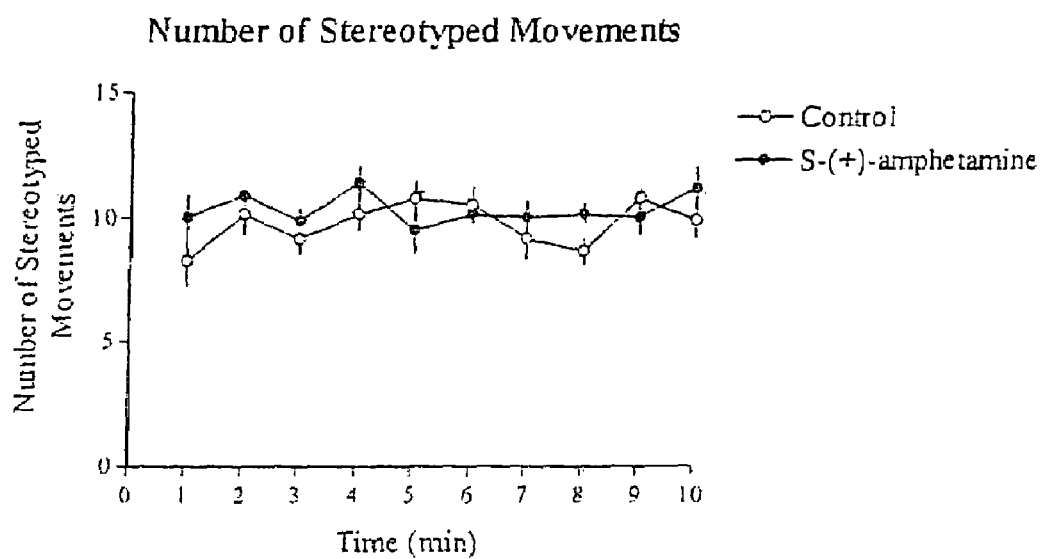
Figure 7F:
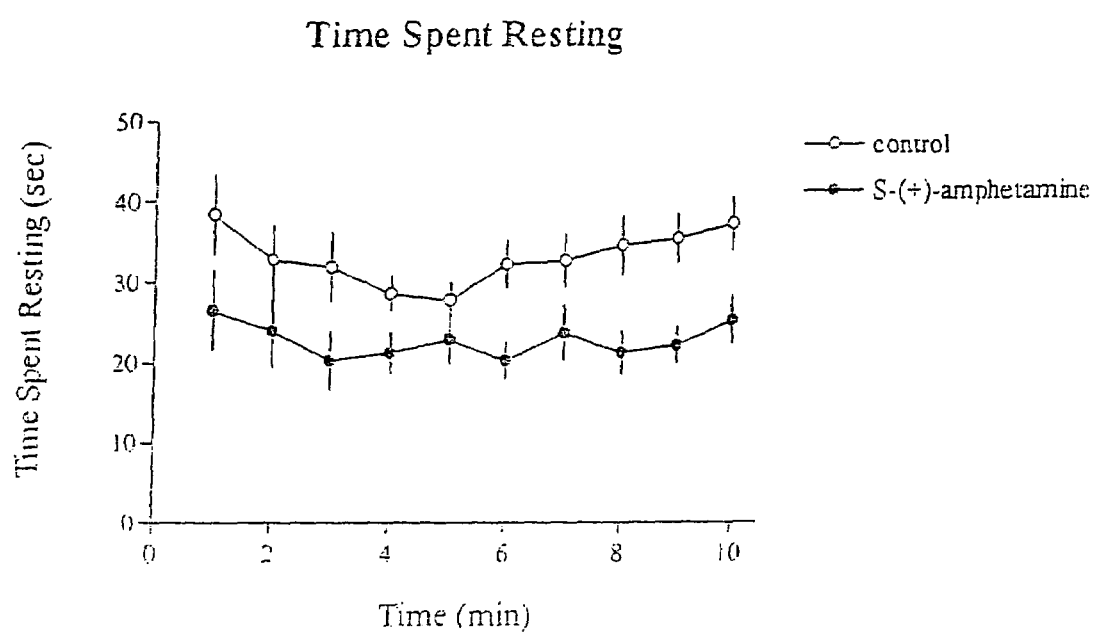

An experiment was conducted in which different doses of (S)-(+)-amphetamine were administered to rats one hour before training on the Inhibitory Avoidance task and were compared to a control group of rats injected with saline. Retention for the task was tested 24 hours later with a 0.46 mA shock intensity. Results for this experiment are presented individually in Tables 1 and 2, and demonstrated that (S)-(+)-amphetamine appeared to enhance performance when administered at a dose of 2.0 mg/kg. The experiment was subsequently replicated several times using a test-article dose of 2.0 mg/kg. Results from these experiments are represented in FIG. 6, and demonstrate that (S)-(+)-amphetamine significantly enhanced memory for the Inhibitory Avoidance task (t(76)=3.416, p<0.001). These results are in agreement with previous research and help to demonstrate the effectiveness of (S)-(+)-amphetamine as a memory-enhancing drug.

Effects of (R)-(−)-Amphetamine (C105) on Inhibitory Avoidance

Figure 9:
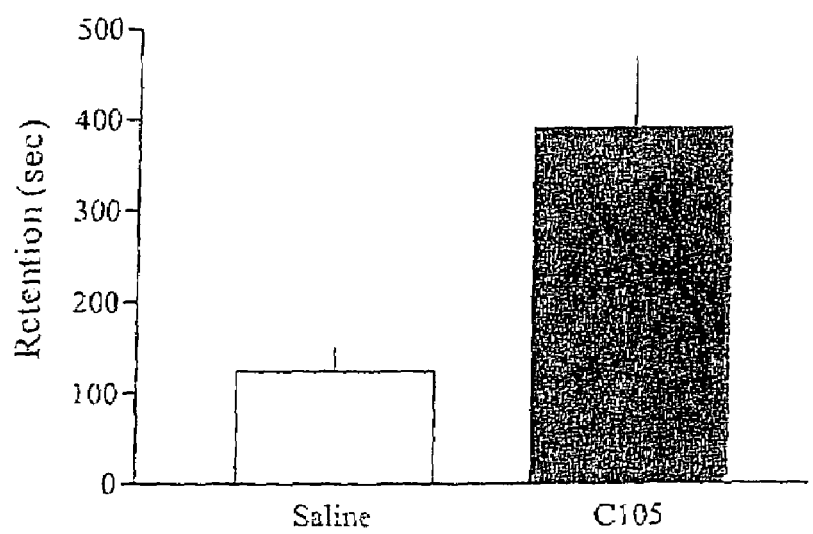
FIG. 9 shows the effectiveness of R-(−)-amphetamine on memory retention.

In order to verify the results from the dose response test, a second experiment with (R)-(−)-amphetamine was conducted. Eighteen rats were injected with a dose of 0.5 mg/kg of (R)-(−)-amphetamine one hour prior to being trained on the IA task. The (R)-(−) amphetamine treated rats were compared to control rats injected with saline. The experiments were conducted with a 24 hour retention interval and a 0.46 mA shock intensity. As can be seen in FIG. 9, this dose of (R)-(−)-amphetamine significantly improved retention of the task. An unpaired t-test demonstrated that this enhancement was statistically significant (p<0.002).

Figure 10:
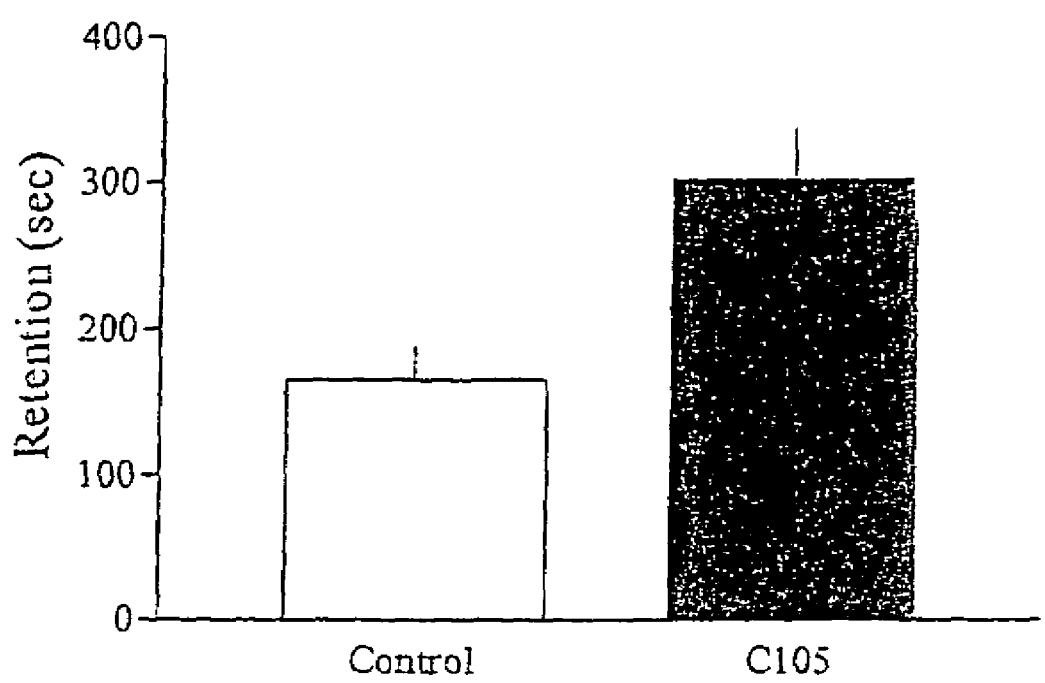
FIG. 10 shows the effect of R-(−)-amphetamine (0.5 mg/kg) on Performance in the Inhibitory Avoidance Task.

Based on the results obtained from the experiments described above, several more experiments were conducted investigating the effects of a 0.5 mg/kg dose of C105 on Inhibitory Avoidance. The data presented in FIG. 10, and individually in Table 5, represent a summary of all such experiments. The results of these experiments clearly demonstrate a memory enhancing effect as measured by the Inhibitory Avoidance task. Rats that had been injected with C105 (0.5 mg/kg) one hour prior to training performed significantly better than control animals on the 24-hour retention test (t (132)=3.438, p<0.0008).

Effects of (R)-(−)-Amphetamine (C105) on Object Recognition

In order to investigate the effects of C105 on recognition memory, rats were trained on the Spontaneous Object Recognition task. Normal rats were injected with 0.5 mg/kg C105 immediately following the training session, and were tested for retention 24-hours later. The results of the experiment indicate that C105 significantly improved recognition memory. Rats that had received injections of test article immediately after the training session, performed significantly better than their saline injected counterparts, as they spent more time exploring the novel object during retention testing. Both discrimination indices, D1 and D2, which reflect discrimination between the familiar and novel object, were significantly higher in C105 treated animals [(t(51)=2.526, p<0.0147) and (t(51)=3.197, p<0.0024) respectively]. These results are particularly interesting, as recognition memory is the process by which a subject is aware that a stimulus has previously been experienced. This process requires that incoming stimuli be identified and compared with representations of previously encountered stimuli stored in memory. Recognition memory is used during everyday life and failures of recognition memory undoubtedly contribute to the problems encountered by amnesic patients. Results from this experiment are presented in FIG. 13, and individual data are presented in Table 8.

It is interesting at this point to compare the results obtained with (R)-(−)-amphetamine (C105) to those obtained with (S)-(+)-amphetamine. (S)-(+)-Amphetamine had a memory enhancing effect at a dose of 2.0 mg/kg, while (R)-(−)-amphetamine had a memory enhancing effect on the same task at a dose of 0.5 mg/kg. Although definitive dose-response relationship experiments between these two compounds have not been conducted, it seems likely that C105 is a more potent memory enhancer for this particular task in rats. It should be noted however, that the maximal efficacy of the two compounds are the same.

Example 6

Effects of (R)-(−) vs. (S)-(+)-Amphetamine on Motor Stimulation

Effects of (S)-(+)-Amphetamine on Activity Levels

In order to provide a comparison point for the results described above, a second experiment was conducted in which rats were injected with 2 mg/kg of (S)-(+)-amphetamine prior to activity testing. Results for this experiment are presented in FIG. 7. The results demonstrated that (S)-(+)-amphetamine produced a clear and significant enhancement in locomotor activity for the entire 10 minute session. Significant main effects for the variables of total distance (F(9,70)=1514000, p<0.0001); number of movements (F(9.70)=45.89, p<0.0001); movement time (F(9.70)=53.07, p<0.0001); rears (F(9.70)=49.47, p<0.0001), stereotyped movements (F(9.70)=24.65, p<0.0001) and rest time (F(9.70)=44.34, p<0.0001) were observed. No significant effects of time or time-drug interactions were observed.

Effects of (R)-(−)-Amphetamine (C105) on Activity Levels

In this experiment, rats were injected with 0.5 mg/kg of (R)-(−)-amphetamine (C105) and compared to a control group of rats injected with saline. Rat activity was monitored for a 10 minute period one hour after (R)-(−)-amphetamine injection. As can be seen in FIG. 14, treatment with (R)-(−)-amphetamine had no significant effects on the activity levels of the rats as compared to the control group.

This data indicates that (R)-(−)-amphetamine can provide improved memory consolidation without producing the motor stimulatory effects observed in the (S)-(+)-amphetamine treated rats (compare to FIG. 7). A comparison of the results obtained for (S)-(+)- versus (R)-(−)-amphetamine indicates that (S)-(+)-amphetamine produced a larger locomotor effect than (R)-(−)-amphetamine, at doses that are equally effective in enhancing memory. This observation is consistent with previous research, which has repeatedly demonstrated that (S)-(+)-amphetamine is between 4 and 10 times more potent than (R)-(−)-amphetamine in producing elevated locomotor responses.

Example 7

Tail Flick

Figure 16:
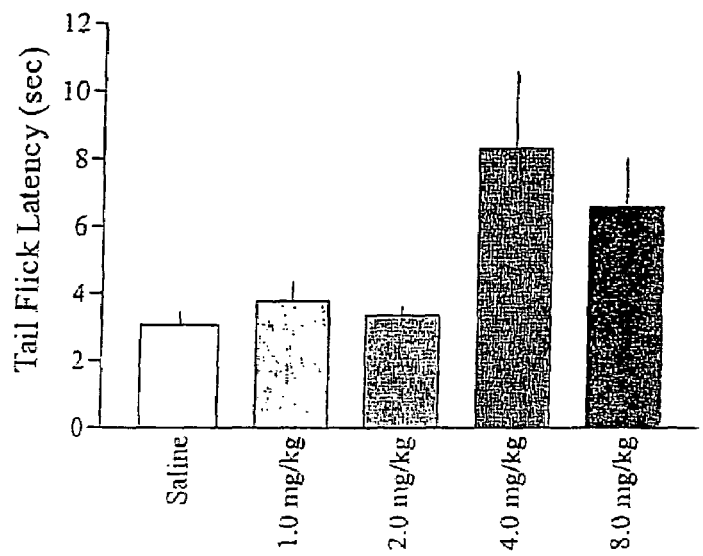
FIG. 16 shows the effect of R-(−)-amphetamine on Tail-Flick Analgesia.

Tail Flick Analgesia data is presented in FIG. 16, and individual data in Table 12. Administration of 1.0, 2.0, 4.0 or 8.0 mg/kg of C105 one hour prior to testing resulted in varying degrees of analgesia. 1.0 and 2.0 mg/kg had no analgesic properties, while 4.0 and 8.0 did. Statistical significance was observed at the 4.0 mg/kg dose (F(4.39)=43.18, p<0.0117). This experiment indicates that the therapeutic dose of (R)-(−)-amphetamine had no effect on analgesia, as measured by the tail-flick analgesiometer.

Example 8

Post Training Administration

Figure 11:
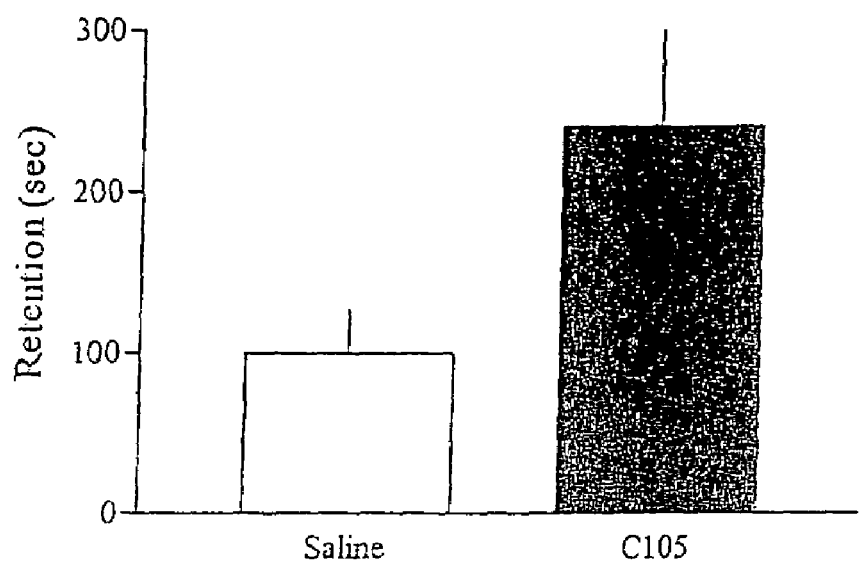
FIG. 11 shows the effect of Post Training Administration of R-(−)-amphetamine (0.5 mg/kg) on Performance in the Inhibitory Avoidance Task.

While the results described above provide evidence to suggest that C105 enhances memory, it is possible that these results are due to non-mnemonic factors. Because the drug was administered prior to training, it is possible that learning or acquisitional processes were affected by drug administration. For this reason, a post training experiment was conducted in which C105 was administered to the rats immediately after the training session. Injecting the drug after the training session affects memory consolidation rather than acquisition, primarily because the drug is not on board at the time of training. The results of this experiment are represented in FIG. 11 and presented individually in Table 6. As can be seen from FIG. 11, post training administration of 0.5 mg/kg of C105 significantly enhanced performance on the Inhibitory Avoidance task (t(26)=2.160, p<0.0402). This experiment therefore, provides strong evidence that C105 works by selectively enhancing memory consolidation.

TABLE 1

Effects of Different Doses of S-(+)-Amphetamine on Inhibitory Avoidance

| Saline | 0.25 mg/kg | 0.5 mg/kg | 1.0 mg/kg | 2.0 mg/kg |
|---|---|---|---|---|
| 22.0 | 6.0 | 2.0 | 7.0 | 33.0 |
| 25.0 | 19.0 | 26.0 | 17.0 | 63.0 |
| 26.0 | 29.0 | 38.0 | 19.0 | 82.0 |
| 33.0 | 29.0 | 39.0 | 25.0 | 84.0 |
| 41.0 | 44.0 | 63.0 | 31.0 | 101.0 |
| 71.0 | 59.0 | 65.0 | 34.0 | 190.0 |
| 121.0 | 94.0 | 110.0 | 35.0 | 230.0 |
| 216.0 | 124.0 | 153.0 | 47.0 | 245.0 |
| 234.0 | 310.0 | 207.0 | 157.0 | 457.0 |
| 358.0 | 452.0 | 207.0 | 263.0 | 517.0 |

Data are expressed as latency to enter the dark side of the apparatus in seconds for each animal (10 animals per treatment group). Data is rank-ordered.

TABLE 2

Summary of Effects of S-(+)-Amphetamine (2.0 mg/kg) on Inhibitory Avoidance

| Saline | S-(+)-Amphetamine |
|---|---|
| 3.0 | 5.0 |
| 6.0 | 15.0 |
| 11.0 | 26.0 |
| 17.0 | 32.0 |
| 19.0 | 33.0 |
| 22.0 | 60.0 |
| 25.0 | 63.0 |
| 26.0 | 82.0 |
| 30.0 | 84.0 |
| 33.0 | 100.0 |
| 33.0 | 101.0 |
| 33.0 | 127.0 |
| 36.0 | 148.0 |
| 40.0 | 167.0 |
| 41.0 | 169.0 |
| 42.0 | 188.0 |
| 44.0 | 190.0 |
| 53.0 | 201.0 |
| 53.0 | 204.0 |
| 57.0 | 222.0 |
| 63.0 | 230.0 |
| 71.0 | 237.0 |
| 80.0 | 245.0 |
| 105.0 | 248.0 |
| 110.0 | 289.0 |
| 121.0 | 296.0 |
| 148.0 | 300.0 |
| 204.0 | 300.0 |
| 214.0 | 364.0 |
| 216.0 | 365.0 |
| 234.0 | 371.0 |
| 242.0 | 457.0 |
| 262.0 | 461.0 |
| 266.0 | 517.0 |
| 286.0 | 557.0 |
| 297.0 | 636.0 |
| 349.0 | 736.0 |

TABLE 2-continued

Summary of Effects of S-(+)-Amphetamine (2.0 mg/kg) on Inhibitory Avoidance

| Saline | S-(+)-Amphetamine |
|---|---|
| 358.0 | 820.0 |
| 673.0 | 900.0 |

Data are expressed as latency to enter the dark side of the apparatus in seconds for each animal (39 animals per treatment group). Data is rank-ordered.

TABLE 3

Effects of Different Doses of C105 on Inhibitory Avoidance

| Saline | 0.4 mg/kg | 0.5 mg/kg | 0.75 mg/kg | 1.0 mg/kg | 2.0 mg/kg |
|---|---|---|---|---|---|
| 17.0 | 45.0 | 16.0 | 9.0 | 101.0 | 30.0 |
| 55.0 | 62.0 | 38.0 | 15.0 | 115.0 | 59.0 |
| 60.0 | 80.0 | 137.0 | 16.0 | 121.0 | 59.0 |
| 77.0 | 87.0 | 203.0 | 21.0 | 202.0 | 127.0 |
| 103.0 | 170.0 | 267.0 | 150.0 | 265.0 | 137.0 |
| 107.0 | 231.0 | 332.0 | 157.0 | 343.0 | 230.0 |
| 116.0 | 236.0 | 556.0 | 229.0 | 729.0 | 231.0 |
| 129.0 | 250.0 | 698.0 | 237.0 | 813.0 | 253.0 |
| 240.0 | 265.0 | 741.0 | 288.0 | 824.0 | 366.0 |
| 280.0 | 629.0 | 900.0 | 650.0 | 900.0 | 384.0 |

Data are expressed as latency to enter the dark side of the apparatus in seconds for each animal (10 animals per treatment group). Data is rank-ordered.

TABLE 4

Effects of Low Doses of C105 on Inhibitory Avoidance

| Saline | 0.1 mg/kg | 0.25 mg/kg | 0.5 mg/kg |
|---|---|---|---|
| 33.0 | 37.0 | 24.0 | 127.0 |
| 38.0 | 37.0 | 28.0 | 137.0 |
| 55.0 | 39.0 | 29.0 | 144.0 |
| 62.0 | 39.0 | 71.0 | 164.0 |
| 80.0 | 55.0 | 71.0 | 167.0 |
| 100.0 | 55.0 | 100.0 | 182.0 |
| 216.0 | 110.0 | 113.0 | 219.0 |
| 235.0 | 113.0 | 117.0 | 265.0 |
| 370.0 | 124.0 | 120.0 | 362.0 |
| 518.0 | 366.0 | 205.0 | 886.0 |

Data are expressed as latency to enter the dark side of the apparatus in seconds for each animal (10 animals per treatment group). Data is rank-ordered.

TABLE 5

Summary of the Effects of C105 (0.5 mg/kg) or Saline on Inhibitory Avoidance

| Saline | C105 |
|---|---|
| 21.0 | 21.0 |
| 21.0 | 33.0 |
| 24.0 | 40.0 |
| 26.0 | 41.0 |
| 27.0 | 43.0 |
| 27.0 | 63.0 |
| 33.0 | 65.0 |
| 38.0 | 65.0 |
| 39.0 | 66.0 |
| 39.0 | 79.0 |

TABLE 5-continued

Summary of the Effects of C105 (0.5 mg/kg) or Saline on Inhibitory Avoidance

| Saline | C105 |
|---|---|
| 55.0 | 126.0 |
| 59.0 | 127.0 |
| 59.0 | 137.0 |
| 62.0 | 154.0 |
| 75.0 | 164.0 |
| 79.0 | 167.0 |
| 80.0 | 181.0 |
| 96.0 | 182.0 |
| 100.0 | 188.0 |
| 109.0 | 219.0 |
| 109.0 | 225.0 |
| 113.0 | 225.0 |
| 113.0 | 261.0 |
| 121.0 | 265.0 |
| 121.0 | 357.0 |
| 168.0 | 362.0 |
| 179.0 | 418.0 |
| 179.0 | 444.0 |
| 193.0 | 521.0 |
| 216.0 | 540.0 |
| 235.0 | 556.0 |
| 235.0 | 595.0 |
| 248.0 | 660.0 |
| 370.0 | 880.0 |
| 431.0 | 886.0 |
| 431.0 | 900.0 |
| 518.0 | 900.0 |
| 17.0 | 16.0 |
| 23.0 | 37.0 |
| 27.0 | 38.0 |
| 33.0 | 52.0 |
| 36.0 | 137.0 |
| 40.0 | 170.0 |
| 41.0 | 184.0 |
| 46.0 | 203.0 |
| 47.0 | 209.0 |
| 48.0 | 231.0 |
| 55.0 | 267.0 |
| 55.0 | 273.0 |
| 56.0 | 293.0 |
| 60.0 | 332.0 |
| 74.0 | 426.0 |
| 77.0 | 556.0 |
| 82.0 | 582.0 |
| 92.0 | 698.0 |
| 103.0 | 741.0 |
| 105.0 | 900.0 |
| 107.0 | |
| 108.0 | |
| 114.0 | |
| 116.0 | |
| 120.0 | |
| 120.0 | |
| 129.0 | |
| 154.0 | |
| 176.0 | |
| 204.0 | |
| 218.0 | |
| 225.0 | |
| 240.0 | |
| 281.0 | |
| 334.0 | |
| 518.0 | |
| 680.0 | |
| 900.0 | |
| 900.0 | |
| 900.0 | |

Data are expressed as latency to enter the dark side of the apparatus in seconds for each animal. This table reflects data gathered from all experiments conducted using C105. The numbers of animals in the saline (n=77) and drug conditions (n=57) differ because in several experiments, extra control animals were run. Data is rank-ordered.

TABLE 6

Effects of Post-Training Administration of C105 on Inhibitory Avoidance

| Saline | C105 |
|---|---|
| 17.0 | 38.0 |
| 25.0 | 65.0 |
| 26.0 | 77.0 |
| 34.0 | 112.0 |
| 36.0 | 123.0 |
| 37.0 | 133.0 |
| 41.0 | 170.0 |
| 64.0 | 185.0 |
| 64.0 | 194.0 |
| 120.0 | 223.0 |
| 137.0 | 276.0 |
| 175.0 | 338.0 |
| 271.0 | 603.0 |
| 349.0 | 824.0 |

Data are expressed as latency to enter the dark side of the apparatus in seconds for each animal (14 animals per treatment group). Data is rank-ordered.

TABLE 7

Effects of C105 on Inhibitory Avoidance in Control and Fornix Lesion Rats

| Control Saline | Fornix Saline | Control 0.5 mg/kg | Fornix 0.5 mg/kg | Control 1.0 mg/kg | Fornix 1.0 mg/kg | Control 2.0 mg/kg | Fornix 2.0 mg/kg | Control 4.0 mg/kg | Fornix 4.0 mg/kg |
|---|---|---|---|---|---|---|---|---|---|
| 50.0 | * | 28.0 | 4.0 | 26.0 | ** | 21.0 | 4.0 | 21.0 | 2.0 |
| 72.0 | ** | 28.0 | 7.0 | 26.0 | 4.0 | 25.0 | 17.0 | 36.0 | 8.0 |
| 92.0 | 2.0 | 93.0 | 13.0 | 48.0 | 7.0 | 41.0 | 18.0 | 64.0 | 13.0 |
| 123.0 | 19.0 | 162.0 | 21.0 | 56.0 | 19.0 | 84.0 | 26.0 | 64.0 | 21.0 |
| 126.0 | 22.0 | 214.0 | 21.0 | 106.0 | 19.0 | 86.0 | 28.0 | 83.0 | 25.0 |
| 164.0 | 23.0 | 240.0 | 32.0 | 195.0 | 166.0 | 92.0 | 30.0 | 83.0 | 28.0 |
| 180.0 | 35.0 | 252.0 | 55.0 | 197.0 | 221.0 | 106.0 | 40.0 | 86.0 | 42.0 |
| 217.0 | 40.0 | 271.0 | 65.0 | 213.0 | 246.0 | 160.0 | 70.0 | 98.0 | 96.0 |

TABLE 7-continued

Effects of C105 on Inhibitory Avoidance in Control and Fornix Lesion Rats

| Control Saline | Fornix Saline | Control 0.5 mg/kg | Fornix 0.5 mg/kg | Control 1.0 mg/kg | Fornix 1.0 mg/kg | Control 2.0 mg/kg | Fornix 2.0 mg/kg | Control 4.0 mg/kg | Fornix 4.0 mg/kg |
|---|---|---|---|---|---|---|---|---|---|
| 222.0 | 72.0 | 284.0 | 72.0 | 238.0 | 274.0 | 192.0 | 84.0 | 193.0 | 140.0 |
| 228.0 | 141.0 | 577.0 | 209.0 | 317.0 | 314.0 | 581.0 | 153.0 | 208.0 | 159.0 |

Data are expressed as latency to enter the dark side of the apparatus in seconds for each animal (10 animals per treatment group). Data is rank-ordered.
* animal died during surgery - no data available
** data from these subjects excluded from analysis as they were outliers: more than two SD's away from the mean

TABLE 8

Effects of C105 on Spontaneous Object Recognition: Control Data, Discrimination Index D1

| Saline | C105 |
|---|---|
| −1.00 | * |
| −1.00 | 1.00 |
| 0.87 | 5.00 |
| 1.59 | 5.00 |
| 2.00 | 6.00 |
| 2.00 | 6.47 |
| 3.00 | 7.00 |
| 3.00 | 8.00 |
| 3.82 | 8.00 |
| 3.92 | 9.00 |
| 4.00 | 9.00 |
| 4.00 | 9.76 |
| 4.84 | 12.00 |
| 4.97 | 12.06 |
| 5.00 | 12.31 |
| 6.00 | 13.00 |
| 7.00 | 13.00 |
| 7.00 | 13.29 |
| 7.60 | 14.03 |
| 8.00 | 16.00 |
| 9.00 | 16.00 |
| 10.00 | 18.59 |
| 11.00 | 20.00 |
| 18.00 | 20.00 |
| 23.00 | 20.00 |
| 23.00 | 22.00 |
| 32.00 | 26.00 |

* data for one subject in the C105 excluded as it was an outlier - more than two SD's away from the mean. Data is rank-ordered.

TABLE 9

Effects of C105 on Spontaneous Object Recognition: Fornix Data, Discrimination Index D1

| Fornix + Saline | Fornix + C105 |
|---|---|
| * | −4.79 |
| ** | −0.12 |
| ** | 0.00 |
| −2.60 | 1.92 |
| −0.60 | 3.00 |
| −0.30 | 3.26 |
| 0.00 | 5.00 |
| 0.00 | 6.00 |
| 1.00 | 6.00 |
| 1.00 | 6.00 |
| 2.90 | 8.00 |
| 3.00 | 9.00 |
| 3.00 | 12.30 |
| 4.00 | 14.80 |
| 7.00 | 16.46 |
| 10.00 | 18.00 |
| 17.00 | 19.29 |

* animal died during surgery: no data collected
** data for these two animals not videotaped Data is rank-ordered.

TABLE 10

Effects of C105 on Spontaneous Object Recognition: Control Data, Discrimination Index D2

| Saline | C105 |
|---|---|
| −5.88 | * |
| −3.03 | 4.00 |
| 6.48 | 10.20 |
| 8.69 | 24.32 |
| 8.77 | 25.00 |
| 10.00 | 25.30 |
| 14.29 | 27.14 |
| 17.95 | 30.36 |
| 20.67 | 31.33 |
| 22.09 | 33.52 |
| 22.48 | 36.36 |
| 22.58 | 37.14 |
| 23.08 | 39.37 |
| 23.18 | 41.18 |
| 25.00 | 42.11 |
| 27.27 | 47.06 |
| 30.77 | 47.83 |
| 31.43 | 48.15 |
| 33.33 | 52.94 |
| 35.58 | 55.56 |
| 45.45 | 55.56 |
| 50.00 | 55.61 |
| 51.11 | 57.50 |
| 52.84 | 63.29 |
| 53.49 | 76.47 |
| 56.25 | 83.33 |
| 66.67 | 100.00 |

* data excluded because it was more than 2 SD's away from the mean Data is rank-ordered.

TABLE 11

Effects of C105 on Spontaneous Object Recognition: Fornix Data, Discrimination Index D2

| Fornix + Saline | Fornix + C105 |
|---|---|
| * | −26.45 |
| ** | −0.75 |
| ** | 0.00 |
| −14.29 | 9.50 |
| −8.78 | 15.55 |
| −5.23 | 17.64 |
| 0.00 | 22.22 |
| 0.00 | 27.09 |
| 2.84 | 29.41 |
| 7.69 | 30.00 |
| 9.09 | 31.25 |
| 10.59 | 36.00 |
| 20.00 | 37.50 |
| 30.28 | 40.91 |
| 33.33 | 42.86 |
| 48.57 | 55.45 |
| 50.00 | 62.34 |

* animal died during surgery: no data collected
** data for these two animals not videotaped Data is rank-ordered.

TABLE 12

Effects of C105 on Tail-Flick Analgesia

| Saline | 1.0 mg/kg | 2.0 mg/kg | 4.0 mg/kg | 8.0 mg/kg |
|---|---|---|---|---|
| 1.55 | 1.13 | 2.46 | 2.22 | * |
| 2.19 | 2.28 | 2.68 | 3.13 | 3.13 |
| 2.37 | 3.26 | 2.79 | 5.43 | 4.67 |
| 2.71 | 3.30 | 3.05 | 6.26 | 4.72 |
| 3.44 | 4.59 | 3.56 | 6.42 | 5.22 |
| 3.58 | 4.60 | 3.89 | 6.66 | 6.54 |
| 3.64 | 5.09 | 3.96 | 16.44 | 7.39 |
| 5.34 | 6.01 | 4.45 | 20.00 | 14.43 |

* no data for this subject was collected Data is rank-ordered.

Example 9

Comparison of D-Amphetamine, L-Amphetamine and L-Methamphetamine

Materials and Methods

Animals

Male, Long-Evans rats (3-5 months of age) obtained from Charles River Laboratories weighing between 250 and 350 grams at the time of arrival served as subjects in these experiments. The rats were housed two to a cage in plastic cages with corncob bedding. The rats were maintained on a 12/12 light dark cycle with ad libitum access to food and water.

Drugs

L-methamphetamine (SN522), l-amphetamine (C105) and d-amphetamine were dissolved in saline and administered to the rats via intraperitoneal (i.p.) injections, in a volume of 1 ml/kg body weight.

Experiment 1: Passive Avoidance Test

The Passive Avoidance apparatus (Coulbourn Instruments) consisted of a light chamber and a dark chamber, which were joined by means of a sliding guillotine door. The floor of the dark compartment consisted of 2.4 mm diameter steel rods, through which a foot-shock could be administered to the animal by a constant current 18-pole shock scrambler. The test apparatus was enclosed in a ventilated, sound-attenuating cabinet, and was controlled by Graphic State™ Software (Version 1.013) and a Hewlett Packard Pavilion Computer.

Training involved placing the rat inside the light chamber with its head facing away from the door. Ten seconds later, the sliding door was opened, and the latency to enter the dark chamber was recorded (100 second maximum). When the rat entered the dark chamber, it received a continuous foot-shock (0.4 mA) through the metal grid floor until it returned in the light chamber for a period of 100 consecutive seconds or until a maximum of 5 foot-shocks had been received.

Retention testing was conducted 24 hours later. The rat was placed into the light chamber with its head facing away from the door. Ten seconds later, the door was opened, allowing the rat access to the dark chamber. No foot-shock was administered during retention testing. Latency to enter the dark chamber was recorded (900 seconds maximum) and used as a measure of memory.

In this experiment, rats were injected (ip) immediately after training with saline (control/vehicle), SN522 (0.25 and 0.5 mg/kg), C105 (0.5 and 1.0 mg/kg) or d-amphetamine (1.0 and 2.0 mg/kg). Retention was tested 24 hours after training.

Figure 20:
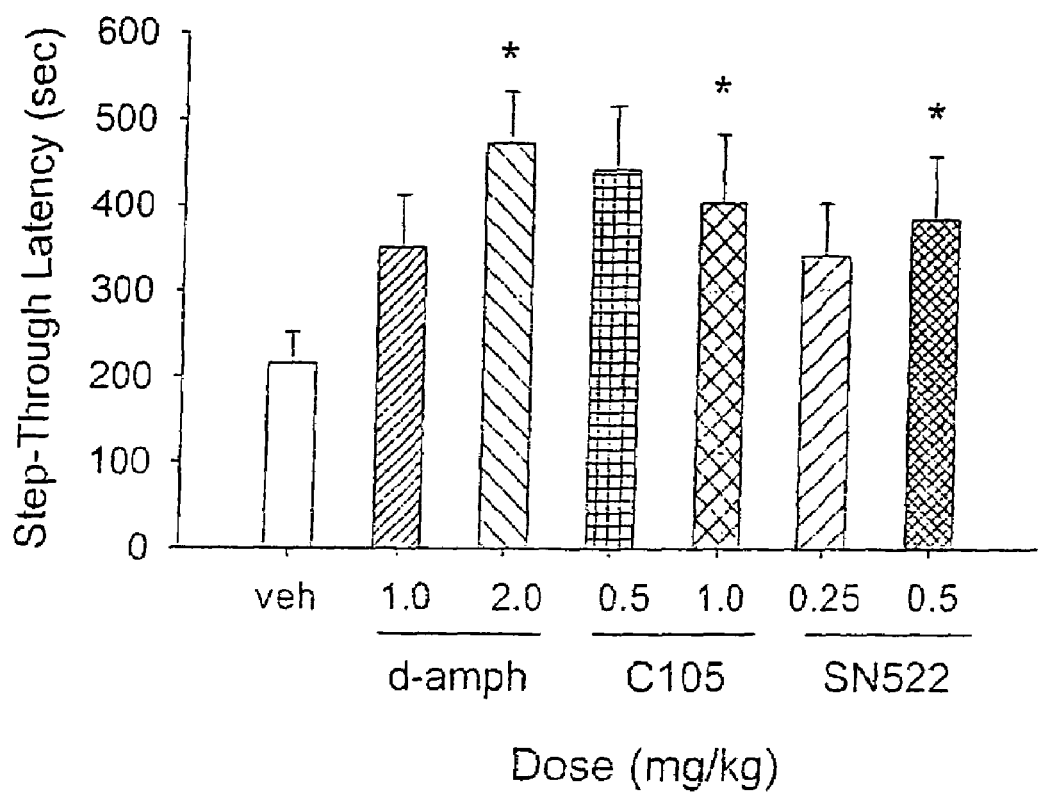
FIG. 20 depicts the Step-Through Latency (sec) for rats treated with control/vehicle (veh), d-amphetamine (d-amph), l-amphetamine (C105) or l-methamphetamine (SN522).

The results from this experiment are illustrated in FIG. 20 and demonstrate that the different doses of the three drugs differ in terms of their potency. FIG. 20 depicts a comparison of d-amphetamine, C105 and SN522 administered immediately after training in inhibitory avoidance. Data show the mean (±SEM) step-through latency (seconds) on a test 24 hours following training. Separate groups of animals (n=10 for each treatment group) were injected (ip) with vehicle (0.9% saline), d-amphetamine (1.0, or 2.0 mg/kg), C105 (0.5 or 1.0 mg/kg) or SN522 (0.25 or 0.5 mg/kg) immediately after training. Data were analyzed using Cox regression within a Kaplan-Meier survival analysis (p<0.05).

A Kaplan Meier Survival Analysis demonstrated that doses of 0.5 mg/kg of C105, 2.0 mg/kg d-amphetamine and 0.5 mg/kg SN522 significantly improved performance on this task (p values=0.007, 0.0004, and 0.03 respectively). Thus, l-methamphetamine and l-amphetamine significantly improve memory consolidation.

Example 10

L-Methamphetamine and Memory

Materials and Methods

Animals

Male, Long-Evans rats (3-5 months of age) obtained from Charles River Laboratories weighing between 250 and 350 grams at the time of arrival served as subjects in these experiments. The rats were housed two to a cage in plastic cages with corncob bedding. The rats were maintained on a 12/12 light dark cycle with ad libitum access to food and water.

Drugs

L-methamphetamine (SN522) was dissolved in saline and administered to the rats via intraperitoneal (i.p.) injections, in a volume of 1 ml/kg body weight.

Results and Discussion

Experiment 1: Passive Avoidance

The Passive Avoidance apparatus (Coulbourn Instruments) consisted of a light chamber and a dark chamber, which were joined by means of a sliding guillotine door. The floor of the dark compartment consisted of 2.4 mm diameter steel rods, through which a foot-shock could be administered to the animal by a constant current 18-pole shock scrambler. The test apparatus was enclosed in a ventilated, sound-attenuating cabinet, and was controlled by Graphic State™ Software (Version 1.013) and a Hewlett Packard Pavilion Computer.

Training involved placing the rat inside the light chamber with its head facing away from the door. Ten seconds later, the sliding door was opened, and the latency to enter the dark chamber was recorded (100 second maximum). When the rat entered the dark chamber, it received a continuous foot-shock (0.4 mA) though the metal grid floor until it returned to the light chamber. This sequence of events was continued until the rat remained in the light chamber for a period of 100 consecutive seconds or until a maximum of 5 foot-shocks had been received.

Retention testing was conducted 24 hours later. The rat was placed into the light chamber with its head facing away from the door. Ten seconds later, the door was opened, allowing the rat access to the dark chamber. No foot-shock was administered during retention testing. Latency to enter the dark chamber was recorded (900 seconds maximum) and used as a measure of memory.

In this experiment, the effects of SN522 on consolidation of the passive avoidance task were investigated. Rats were injected with saline (control, no or zero drug) or six different doses (0, 0.10, 0.25, 5.0, 0.75 or 1.0 mg/kg, i.p.) of SN522 immediately after the training session. Retention for the task was tested 24 hours later.

Figure 21:
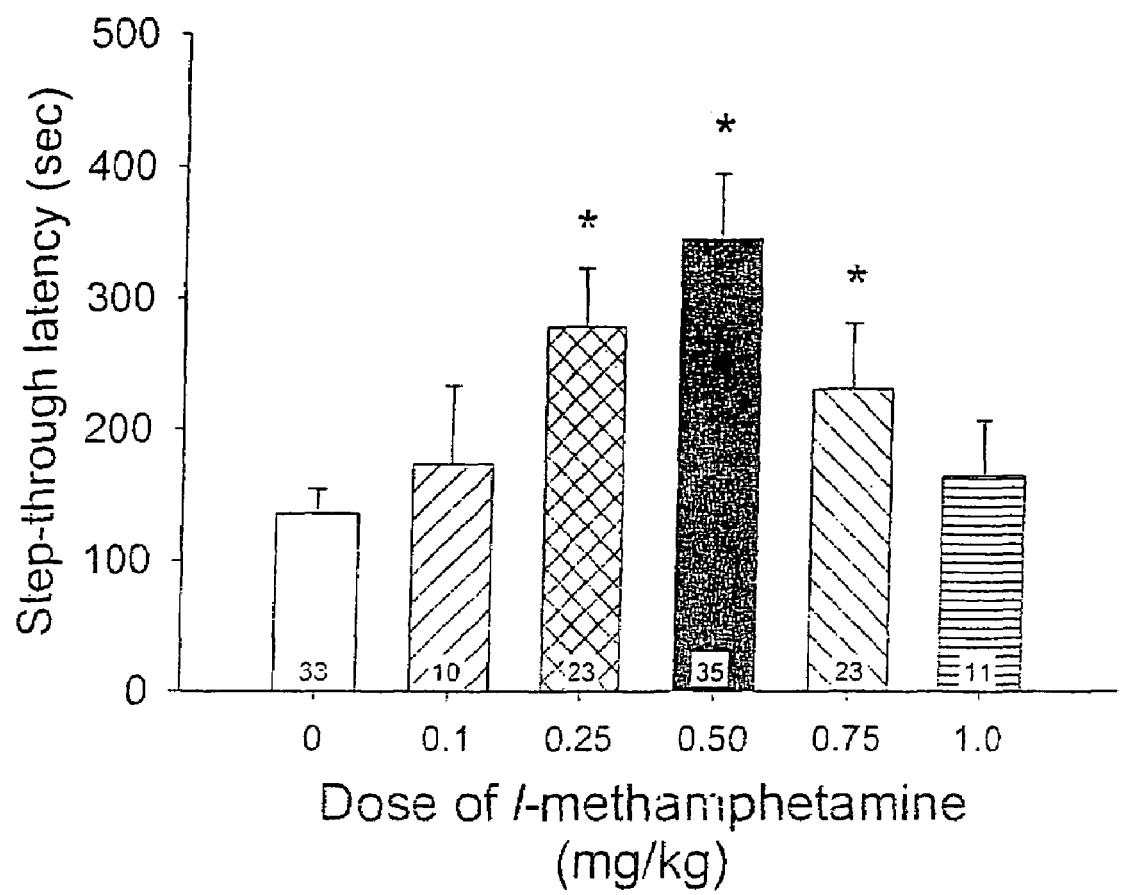
FIG. 21 depicts the Step-Through Latency (sec) for rats treated with control (0) or varying doses of l-methamphetamine (SN522). The asterisk indicates a significant difference from the control ($p<0.05$).

The results from this experiment are illustrated in FIG. 21. FIG. 21 depicts the effects of SN522 administered immediately after training in inhibitory avoidance. Data show the mean (±SEM) step-through latency (seconds) on a test 24 hours following training. Separate groups of animals (number of animals in each treatment group indicated inside bars) were injected with vehicle (0.9% saline) or one of five doses of SN522 (0.1, 0.25, 0.5, 0.75, or 1.0 mg/kg). Data were analyzed using Cox regression within a Kapaln-Meier survival analysis (p<0.05).

The step-through latency in response to SN522 is an inverted U-shaped dose response curve. A Kaplan Meier survival analysis with cox regression confirmed significant improvement in memory performance relative to the saline group at doses of 0.25, 0.5, and 0.75 mg/kg (p<0.05).

Experiment 2: Water Maze

Water Maze testing (Morris, R., *J. Neurosci Methods* 11:47-60 (1984)) was conducted in a galvanized steel pool, painted white, measuring 180 cm in diameter and 60 cm in height. The pool was equipped with a removable circular platform (10 cm in diameter) made of clear Plexiglas. The pool was filled with water (26° C.) to a level of 1 cm above the surface of the platform. Nontoxic white paint was added to the water to obscure the platform's appearance. The pool was divided conceptually into four quadrants and the platform was located in the NW quadrant 30 cm from the pool wall. Extramaze cues were provided by large geometric shapes adhered to curtains that surrounded two sides of the pool, and by shelving units, a sink, and posters on the visible walls.

The training procedure involved placing the rat into the water, with the rat's head facing the wall of the pool, at one of four different starting points. The rat was allowed 60 seconds to locate the hidden platform. If the rat did not find the platform within 60 seconds, it was gently guided to the platform. After 15 seconds spent on the platform at the end of each trial, the rat was removed from the pool and injected with saline or SN522 (0.25 and 0.5 mg/kg, i.p.). The rat was dried, and returned to its home cage. One trail was conducted each day for 10 days. The latency to reach the platform (escape latency) was recorded on each days training trial.

Figure 22:
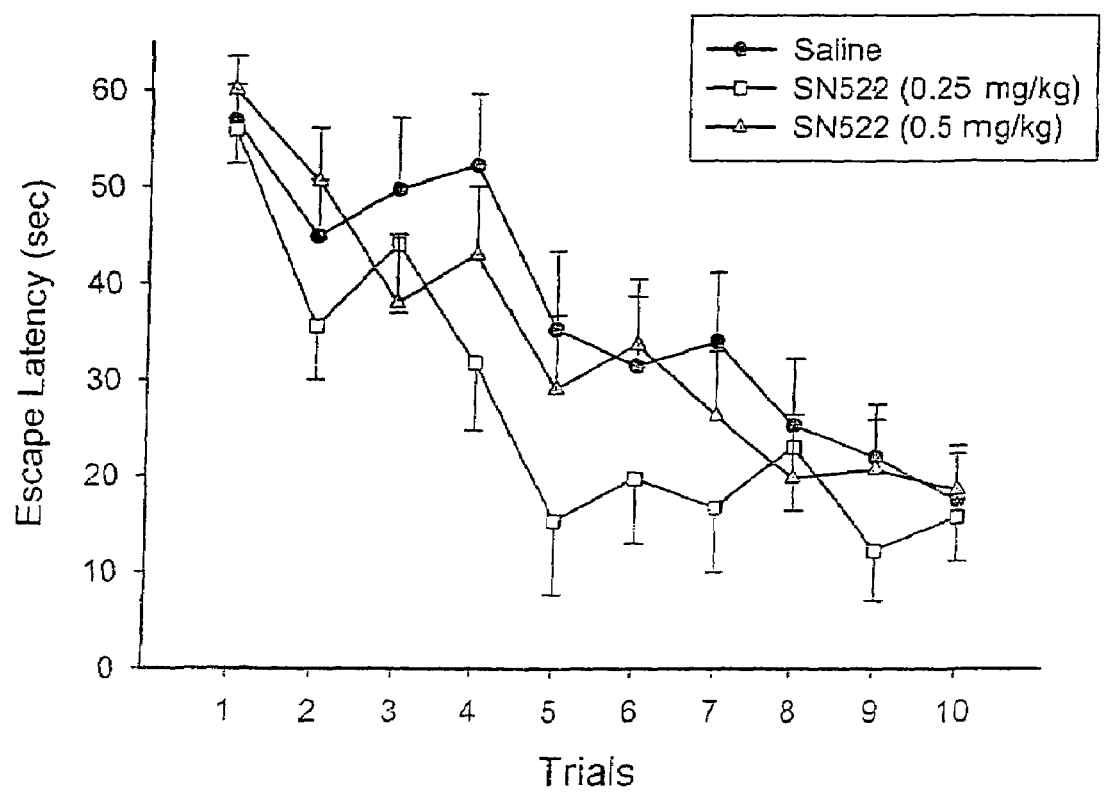
FIG. 22 depicts the Escape Latency (sec) for rats treated with saline control or l-methamphetamine (SN522).

An ANOVA show a significant enhancement in acquisition rate in animals administered 0.25 mg/kg SN522 relative to controls (See FIG. 22; $F_{1,17}$=10.245, p<0.005).

FIG. 22 depicts the effect of SN522 on acquisition of the water maze task. Data are the mean (±SEM) latency to locate a hidden platform by three separate groups of rats (n=10 for each treatment group). Animals were given a single learning trial each day. Immediately following the learning trial, vehicle (saline) or SN522 (0.25 or 0.5 mg/kg) were administered IP. The data show that while all groups learned to find the platform during the 10 training days indicated by the decrease in escape latency, animals that were treated with 0.25 mg/kg SN522 after each trial learned to find the platform more quickly than rats in the saline treated group.

The comparison between the control (saline) group and the group administered the higher dose of SN522 did not reveal any statistical differences (p>0.05). These data confirm that SN522 has potent effects on mnemonic processing.

Figure 23:
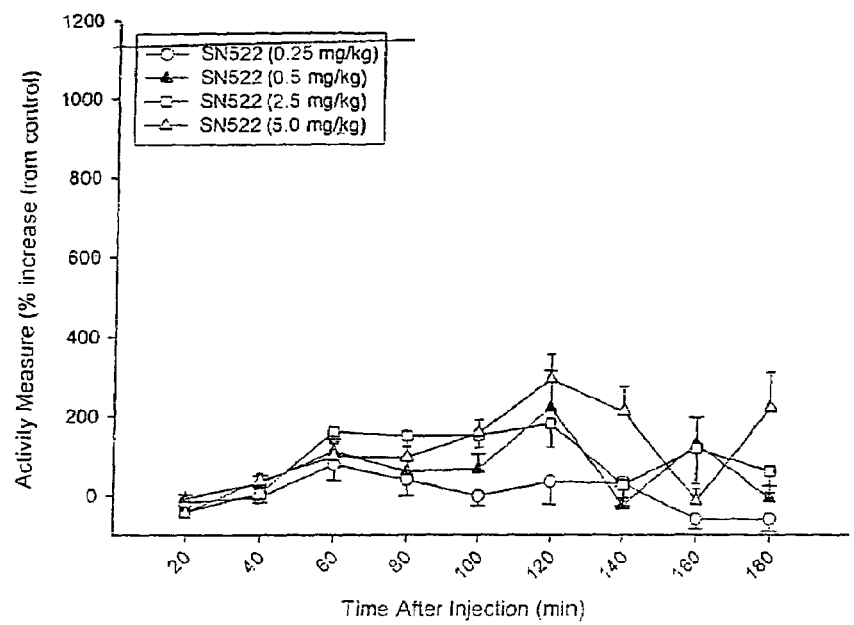
FIG. 23 depicts the Activity Measure (% increase from control) for rats treated with l-methamphetamine (SN522).

FIG. 23 depicts the effect of SN522 on activity levels measured by an automated motion detector. Data are the mean activity (±SEM) of four separate groups of rats (n=7 or 8 per group) treated with SN522 (0.25, 0.5, 2.5, and 5.0 mg/kg, ip) as measured by an activity monitor system, tracking beam breaks around an open field. Data are shown as a percent change from a control group treated with vehicle (0.9% saline). The data show that doses of l-methamphetamine (SN522) have profound effects on memory processes produce no or modest changes in motor behavior (0.25 and 0.5 mg/kg). Doses of SN522 ten times over the therapeutic doses yielded only mild increases in activity. Thus, l-methamphetamine has no or minimal side effects.

Experiment 3: Locomotor Activity

Activity monitoring was conducted in a Plexiglas open-field box measuring 30 by 30 cm. Activity levels were measured via a grid of infrared light beams that traversed the cage from left to right and back to front. The location of the animal within the cage was detected by breaks in the infrared light beams. Light beams status information was collected and rapidly analyzed by a computerized activity monitoring system (VersaMax System, Accuscan Instruments.)

In order to determine whether SN522 had any adverse effects on locomotor or exploratory activity, rats were injected with saline or 0.25, 0.5, 2.5 and 5.0 mg/kg of SN522 and immediately afterwards placed into the activity monitoring chambers for a period of three hours. Data was collected on-line using Versa Max (Version 1.83) computer software and a Hewlett Packard Pavilion computer. Analyzed behaviors included; horizontal activity, total distance moved, movement time, number of movements, number of rears, number of stereotyped movements, and time spent resting.

Figure 24:
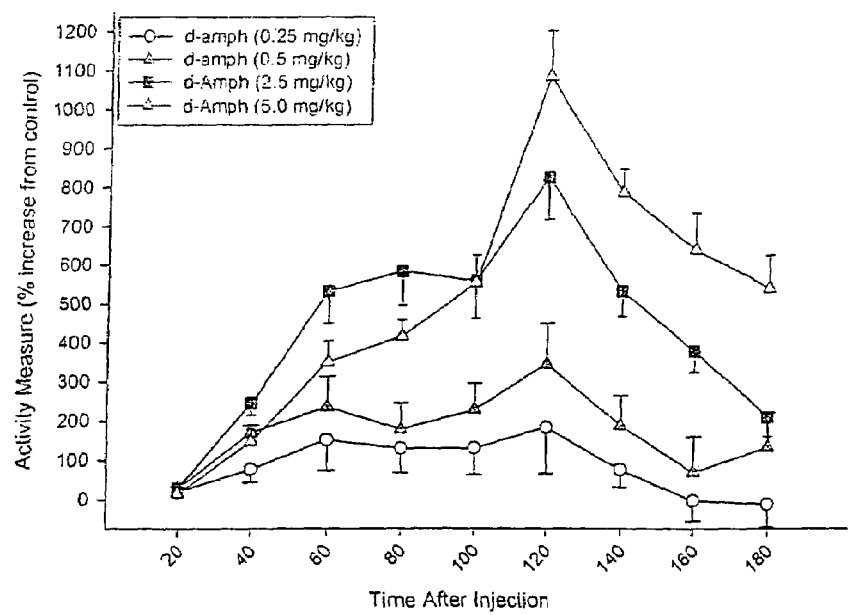
FIG. 24 depicts the Activity Measure (% increase from control) for rats treated with D-amphetamine (d-amph).

FIG. 24 depicts the effect of d-amphetamine on activity levels measured by an automated motion detector. Data are the mean activity (±SEM) of four separate groups of rats treated with SN522 Mean activity (±SEM) of four separate groups of rats (n=7 or 8 per group) treated with d-amphetamine sulfate (0.25, 0.5, 2.5, and 5.0 mg/kg, ip). Data are shown as a percent change from a control group treated with vehicle (0.9% saline). The data show that even very low doses of d-amphetamine have effects on activity. These effects are significant even at the very lowest dose tested (0.25 mg/kg), with profound increases in activity at the higher doses all p's, 0.05.

As can be seen in FIG. 24 (data are shown as a percent increase relative to the saline control), low doses SN522 resulted in no increase in activity at doses that were efficacious in the memory assays (0.25 mg/kg, p>0.05), and produced only modest increases in activity at a slightly higher dose (0.5 mg/kg; $F_{8,112}$=2.303, p=0.028). Relatively high doses of SN522 (2.5 and 5.0 mg/kg) resulted in small, but significant increases in activity relative to the saline control (0.25 mg/kg; $F_{8,112}$=10.936, p<0.001; 5.0 mg/kg; $F_{8,112}$=8.749, p<0.001). However, when compared with activity produced by similar doses of d-amphetamine, the increases in activity levels after administration of SN522 are minimal indicating minimal side effects from SN522.

Experiment 4: Tailflick Test of Analgesia

The tail-flick response was assessed using a radiant heat tail flick monitor (Accuscan Instruments model TFS) equipped with a radiant heat element and two light beam sensors to detect tail movement.

In order to determine whether SN522 has any analgesic properties, rats (n=10 per treatment group) were injected with saline or SN522 (0.25, 0.5, 2.5 and 5.0 mg/kg, i.p.) and tested at four time points: immediately prior to injection, and again 15, 30, and 60 minutes following drug administration for a tail flick response (D'Amour, F. E., et al., *J. Pharmacol. Exp. Ther.* 72:174-179 (1941)). To test the tail-flick, the animal was placed on top of the Tail-Flick monitor and gently held in place with a cotton towel. The tail of the animal was placed in a shallow groove lying between the two sensors and over the top of the radiant heat wire. The heat element was activated, and the latency for the animal to flick its tail out of the groove and away from the heat source was automatically recorded via activation of the sensors. The intensity of the heat source was adjusted so that the animal flicked its tail within 3-4 seconds. A 10 second cutoff was imposed to avoid tissue damage. The animal was returned to its home cage immediately following testing.

The results of an ANOVA over the five drug treatments and four test intervals did not reveal any differences in tail flick latency. Thus, SN522 does not alter pain sensitivity in this test.

Example 11

L-Methamphetamine Improves Memory in Subjects with a Memory Impairment

Materials and Methods

Animals

Male, Long-Evans rats (3-5 months of age), obtained from Charles River Laboratories and weighing between 250 and 350 grams, served as subjects in these experiments. The rats were housed two to a cage in plastic cages with corncob bedding and were maintained on a 12/12 light dark cycle with ad libitum access to food and water.

Drugs

L-methamphetamine (SN522) was dissolved in saline and administered to the rats via intraperitoneal (i.p.) injections, in a volume of 1 ml/kg body weight.

Passive Avoidance Testing

The Passive Avoidance apparatus (Coulbourn Instruments) consisted of a light chamber and a dark chamber, which were joined by means of a sliding guillotine door. The floor of the dark compartment consisted of 2.4 mm diameter steel rods, through which a foot-shock could be administered to the animal by a constant current 18-pole shock scrambler. The test apparatus was enclosed in a ventilated, sound-attenuating cabinet, and was controlled by Graphic State™ Software (Version 1.013) and a Hewlett Packard Pavilion Computer.

Training involved placing the rat inside the light chamber with its head facing away from the door. Ten seconds later, the sliding door was opened, and the latency to enter the dark chamber was recorded (100 second maximum). When the rat entered the dark chamber, it received a continuous foot-shock (0.4 mA) through the metal grid floor until it returned to the light chamber. This sequence of events was continued until the rat remained in the light chamber for a period of 100 consecutive seconds or until a maximum of 5 foot-shocks had been received.

Retention testing was conducted 24 hours later. The rat was placed into the light chamber with its head facing away from the door. Ten seconds later, the door was opened, allowing the rat access to the dark chamber. No foot-shock was administered during retention testing. Latency to enter the dark chamber was recorded (900 seconds maximum) and used as a measure of memory.

In order to determine whether l-methamphetamine (SN522) reverses memory deficiencies (also referred to herein as a "memory impairment"), separate groups of rats were injected with scopolamine hydrochloride (0.75 mg/kg, i.p.) 30 minutes before training. Rats were then trained on the passive avoidance task and immediately afterwards, injected with either saline or SN522 (0.12, 0.25, 0.5 and 1.0 mg/kg, i.p.). Retention was tested 24 hours after training.

Results and Discussion

Figure 32:
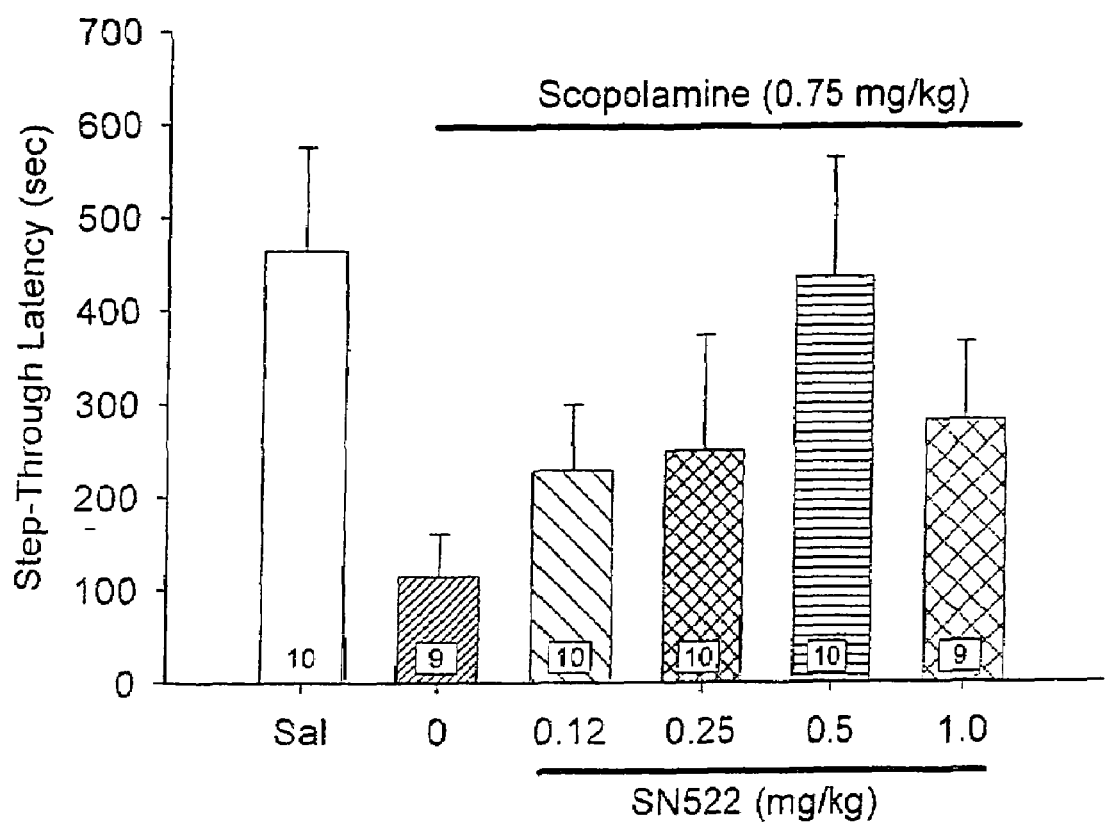
FIG. 32 depicts the Step-Through Latency (sec) for rats treated with saline control (Sal); and scopolamine rats treated with varying doses of l-methamphetamine (SN522) or no l-methamphetamine (0).

FIG. 32 depicts the effects of SN522 on memory deficiencies, in particular, as a consequence of exposure to scopolamine (the number of animals in each group are indicated inside bars). The data shown represent the mean (±SEM) step-through latency (secs) 24 hours following training. A Kaplan Meier survival analysis demonstrated that SN522 was effective at alleviating the impairment in the scopolamine-injected animals (log rank statistic c2(6)=14.73 p=0.02).

As shown in FIG. 32, scopolamine treated rats receiving 0.25, 0.5 and 1.0 mg/kg SN522 performed significantly better than animals treated with scopolamine and saline (p values=0.01, 0.04 and 0.007 respectively). There was no significant difference between control rats who received injections of saline, and scopolamine treated rats who received injections of SN522 at the 0.25, 0.5 and 1.0 mg/kg doses (p>0.05).

These results show that l-methamphetamine improves memory in subjects with a memory impairment.

Example 12

L-Amphetamine Improves Memory in Subjects with a Memory Impairment

Materials and Methods

Animals

Male, Long-Evans rats (3-5 months of age), obtained from Charles River Laboratories and weighing between 250 and 350 grams, served as subjects in these experiments. The rats were housed two to a cage in plastic cages with corncob bedding and were maintained on a 12/12 light dark cycle with ad libitum access to food and water.

Drugs

L-amphetamine (C105) was dissolved in saline and administered to the rats via intraperitoneal (i.p.) injections, in a volume of 1 ml/kg body weight.

Passive Avoidance Testing

In order to determine whether l-amphetamine (C105) reverses memory deficiencies (also referred to herein as a "memory impairment"), separate groups of animals (the number of animals in each treatment group are indicated inside bars) were injected with either vehicle (0.9% saline; SAL) or scopolamine (0.75 mg/kg) 30 min prior to training. Rats were then trained on the passive avoidance task and immediately afterwards were injected with saline (SAL) or C105 (0.12, 0.25, 0.5 and 1.0 mg/kg, i.p.) and an additional group was treated with physostigmine (0.075 mg/kg, i.p.) as a positive control. Retention was tested 24 hours after training. Data were analyzed using Cox regression within a Kaplan-Meier survival analysis.

Results and Discussion

Figure 33:
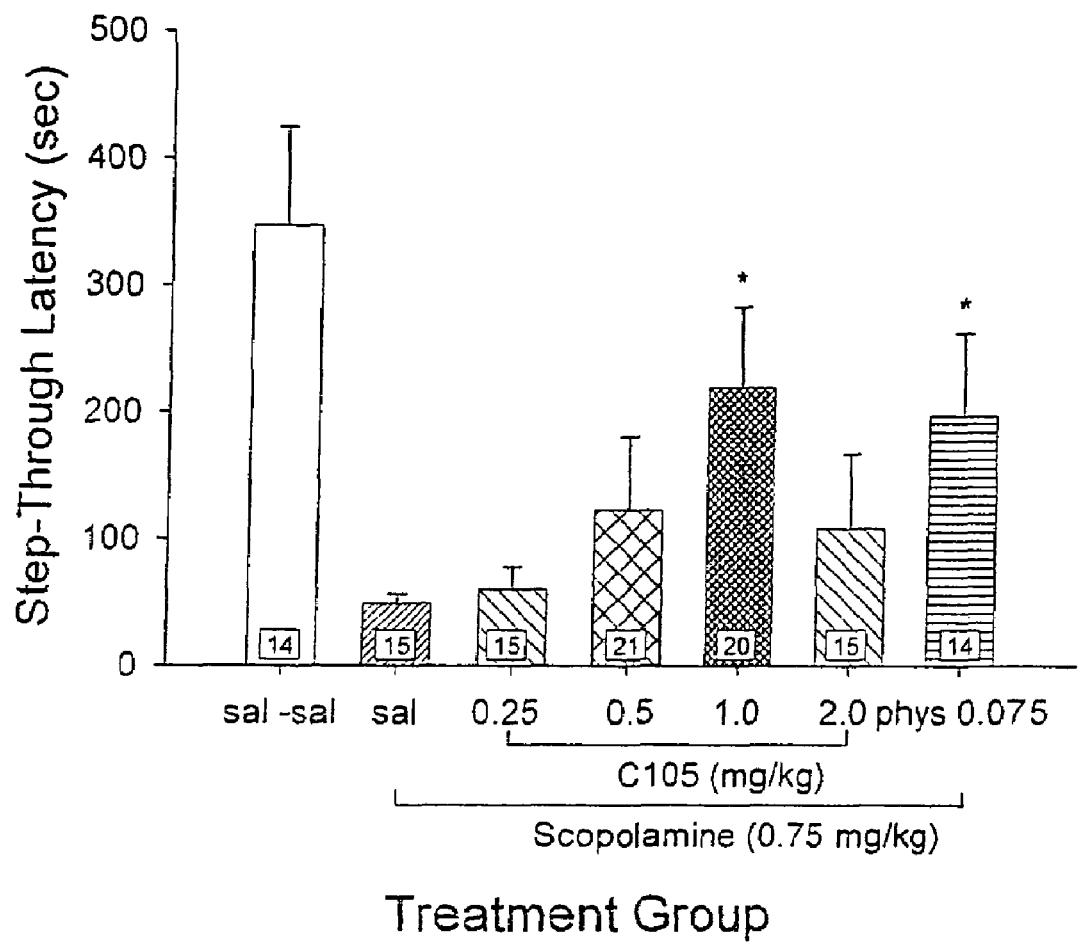
FIG. 33 depicts the Step-Through Latency (sec) for rats treated with saline alone (sal-sal); and scopolamine rats treated with varying doses of l-amphetamine (C105) or saline (sal). The asterisk indicates a significant difference between group means ($p<0.05$).

FIG. 33 depicts the effects of l-amphetamine (C105) memory deficiencies, in particular, as a consequence of exposure to scopolamine. Data shown represent the mean (±SEM) step-through latency (secs) 24 hours following training. A Kaplan Meier survival analysis demonstrated that C105 was effective at alleviating the impairment in the scopolamine-injected animals (log rank statistic c2(6)=14.73 p=0.02). As shown in FIG. 33, scopolamine treated rats receiving 1.0 mg/kg of C105 performed significantly better than animals treated with scopolamine and saline (p>0.05). There was no significant difference between saline only treated rats, and scopolamine treated rats who received 1.0 mg/kg of C105 (p>0.05).

These results show that l-amphetamine improves memory in subjects with a memory impairment.

Example 13

Study of (R)-(−)-Amphetamine in Humans

Sixteen (n=16) healthy adult male/female subjects, ages 20-72, took part in the study. Subjects were selected from a volunteer database. Study-related procedures were carried out after informed consent had been given.

Figure 18:
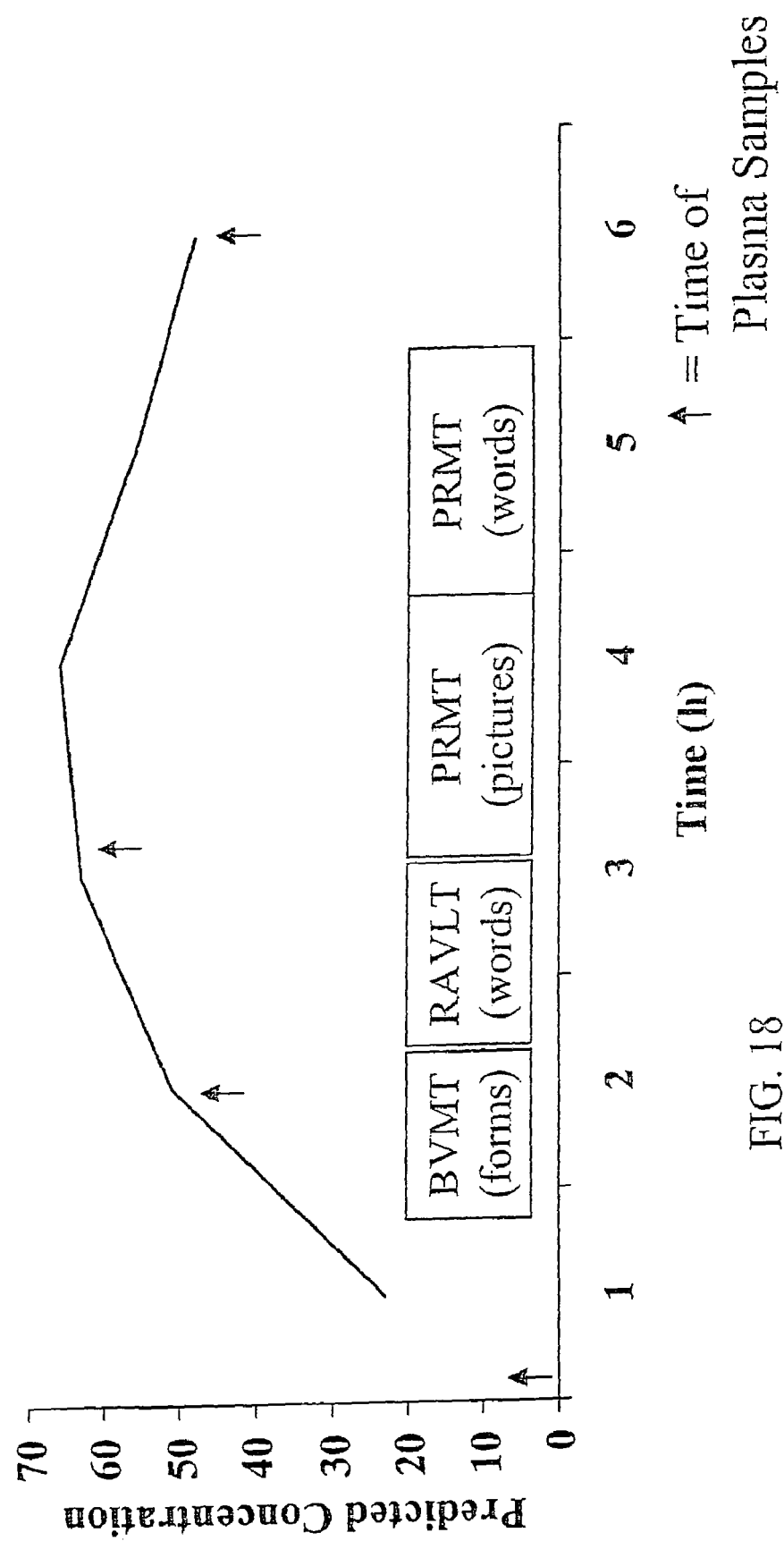
FIG. 18 depicts the pharmacokinetics of R-(−)-amphetamine and Memory Assessments and PK.

FIG. 18 shows a pharmacokinetic measure, in the form of serum levels, for (R)-(−)-amphetamine up to 6 hours after administration. In the ascending dose portion of the dose curve, the Brief Visuospatial Memory Test (BVMT) and Rey Auditory and Verbal learning Test (RAVLT) tests were performed and observed to be statistically significantly higher when compared to controls, having a $p<0.01$. Higher BVMT and RAVLT scores indicate an improvement in memory, in particular memory consolidation. On the other hand, patients were assessed using the Providence Recognition Memory Test (Pictoral) after 3 hours, e.g., after the ascending arm of the dose curve, and the PRMT scores (both for words and pictures) were both not observed to be statistically significant from controls. These experiments demonstrate that (R)-(−)-amphetamine can enhance memory in patients, and is more effective during the ascending portion of the plasma curve.

Figure 19:
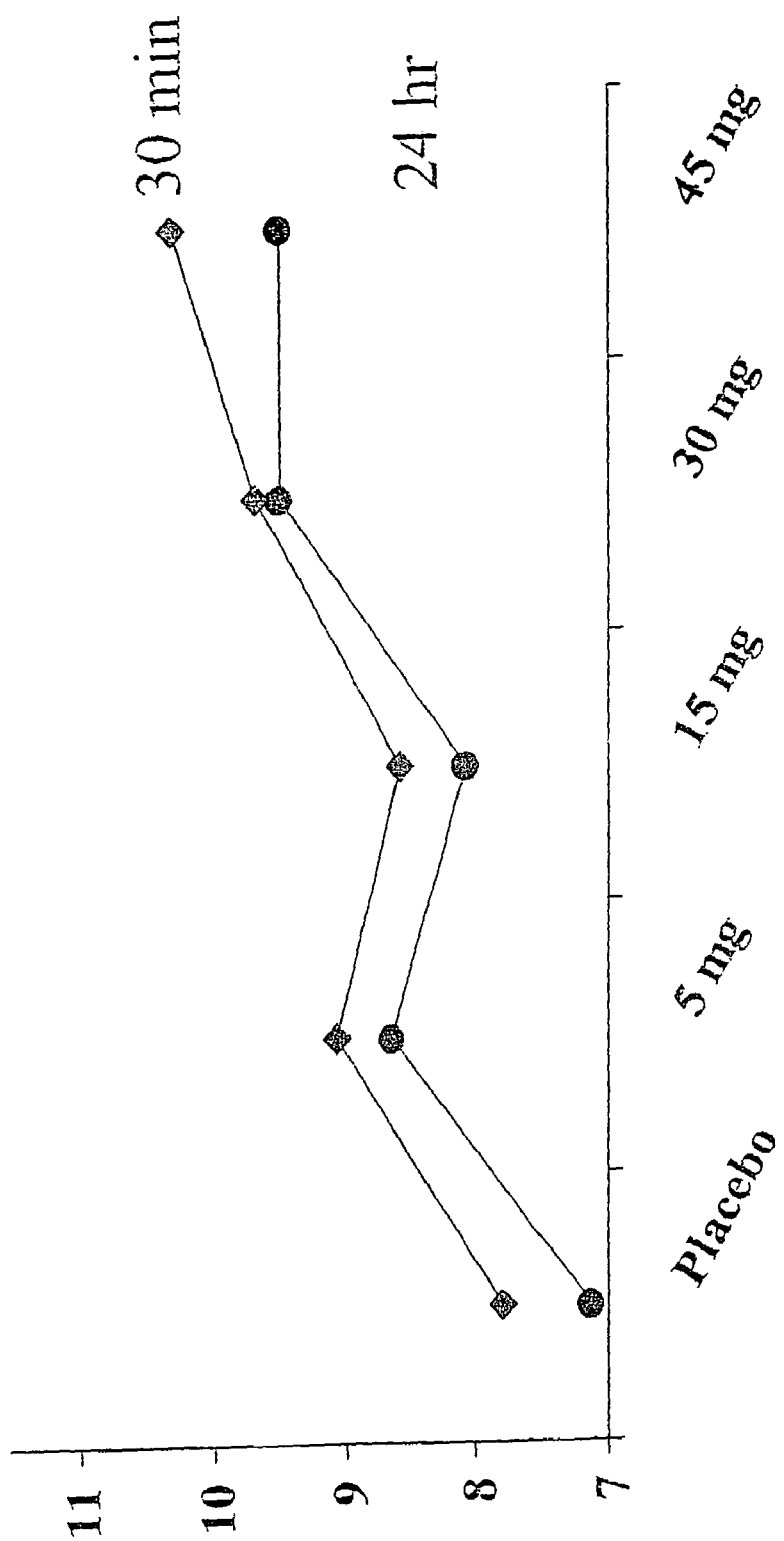
FIG. 19 shows that administration of R-(−)-amphetamine to human patients can improve verbal memory.

FIG. 19 shows a dose response curve for acute dosing with (R)-(−)-amphetamine. Statistically significant differences, e.g., as illustrated by the p values, were observed between placebo and dosages of about 30 mg and about 45 mg per day. In particular, at 30 min: $p=0.004$ for placebo vs about 30 mg, and $p=0.03$ for placebo vs. about 45 mg. At 24 hour, $p=0.002$ for placebo vs about 30 mg, and $p=0.05$ for placebo vs about 45 mg.

Example 14

Improvement in Memory in Humans with L-Amphetamine

Two (2) Phase 1 randomized, double-blind, placebo-controlled clinical studies of l-amphetamine (C105) were conducted in normal healthy adult male and female subjects. The first trial was conducted in eight (8) Caucasian subjects (3 male and 5 female) with a mean age of 35.1 years (range 21-49 years), and the second trial was conducted in eight (8) Caucasian subjects (1 male and 7 female) with a mean age of 65.4 years (range 60-72 years).

The studies were intended to identify the maximum tolerated dose (MTD) and dose-limiting side effects of C105, to assess the effects of C105 on quantitative memory scores, to assess the perceived central nervous system (CNS) effects following C105 administration, to assess the effects of C105 on the cardiovascular system, to explore the relationship between dose, tolerability, safety and pharmacological effects of C105, and to define the pharmacokinetics (PK) of C105.

There were five (5) treatment periods in each Phase 1 trial. Each treatment period was one (1) week in duration and consisted of two (2) consecutive days of treatment ("treatment period") with C105 (5 mg, 15 mg, 30 mg, 45 mg) or placebo, followed by five (5) consecutive days without C105 or placebo ("washout period"). The design is a ascending dose safety design with a placebo dose randomly inserted into the sequence. Each subject was randomly administered a single dose of one of the C105 doses (5 mg, 15 mg, 30 mg, 45 mg) or a randomly assigned dose of placebo during each treatment period on the two consecutive treatment days. Each subsequent treatment group would included whatever dose of C105 (or placebo) had not previously been administered, until the patient had received each of the four C105 doses (5 mg, 15 mg, 30 mg, 45 mg) or single placebo treatment to conclude the five week treatment period. Safety data were reviewed after each dose prior to advancement to the next dose level.

The Rey Auditory Visual Learning Test (RAVLT, Rey, A. (1941). L'examen psychologique dans les cas d'encéphalopathie traumatique. Archives de Psychologie, 28, 21, Lezak, M. D. (1995). Neuropsychological Assessment (3rd ed.). New York: Oxford University Press) was conducted during each of the two consecutive days when the patent received C105 or placebo. RAVLT was not conducted during the washout period.

The RAVLT assessment for word recall was made at two (2) different times following C105 or placebo treatment during each of the five treatment periods. The first RAVLT assessment was made on the first day of treatment in each treatment period and consisted of two parts. Fifteen (15) nouns were read aloud to the patient by an Examiner, followed by an interference or distraction trial, which is then followed by a free-recall test of the 15 nouns. After a additional 30-minute delay period, the subject was again required to recall the first set of 15 nouns and also complete a 50-word recognition test. The second RAVLT assessment was made on the second day of treatment in each treatment period and consisted of a repeat of the Recall test and the 50-word Recognition test given on the previous day. The second RAVLT assessment evaluated word recall 24 hours (±2 hours) after the first RAVLT assessment and did not consist of another exposure to nouns by an Examiner, but rather a recall of the nouns given to the subject 24 hours earlier.

Safety and tolerability assessments were changes in vital signs, ECGs, Holter monitoring, laboratory tests, physical examination and adverse events. Serial blood and urine samples were collected up to 24 hours after dosing for subsequent determination of C105 plasma concentrations and calculation of pharmacokinetic parameters.

C105 was well tolerated when administered in single oral doses ranging from 5 to 45 mg. Reported adverse events were minor. The most frequently reported adverse events were dizziness, headache, insomnia, sinus tachycardia, supraventricular tachycardia and aptyalism. Reported adverse events were generally mild in severity and resolved without requiring treatment. There were no reported serious adverse events and no subject was discontinued from the study due to an adverse event. There were no clinically meaningful findings with respect to C105 administration on physical examinations, laboratory tests, vital signs, 12-lead ECGs or Holter recordings.

For each patient, RAVLT data showed that all dose groups have mean values higher than the placebo at 30 minutes. The two highest doses (30 mg and 45 mg) exhibited the greatest improvement (highest values) compared to placebo testing. The benefit observed at 30 minutes was maintained at 24 hours, with the recalled number of words slightly lower at 24 hours for each dose compared to the corresponding results at 30 minutes. The recall scores were approximately 10 words following administration of the 45 mg dose, compared to approximately 7-8 words recalled when the placebo dose had been administered.

Figure 25:
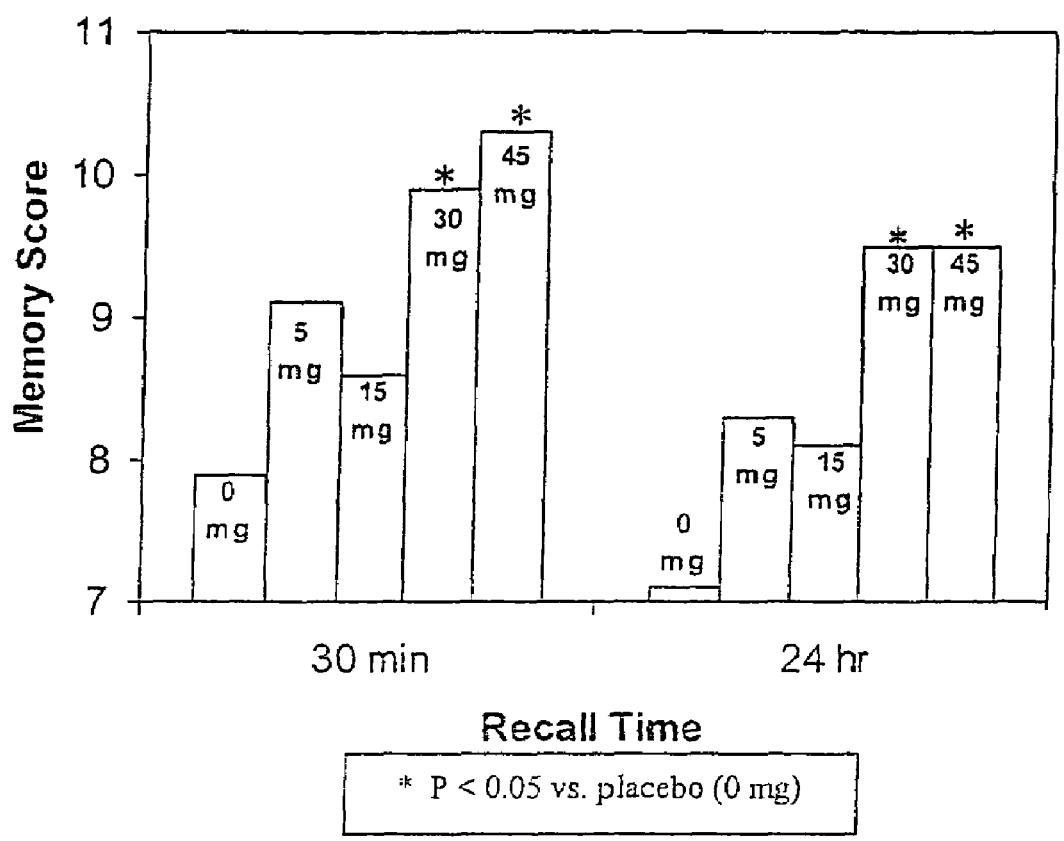
FIG. 25 depicts the Memory Score, as assessed by the Rey Auditory and Verbal Learning Test, following a 30 minute (min) and a 24 hour (hr) recall time for humans treated with l-amphetamine (C105). The asterisk depicts significant differences.
Figure 26:
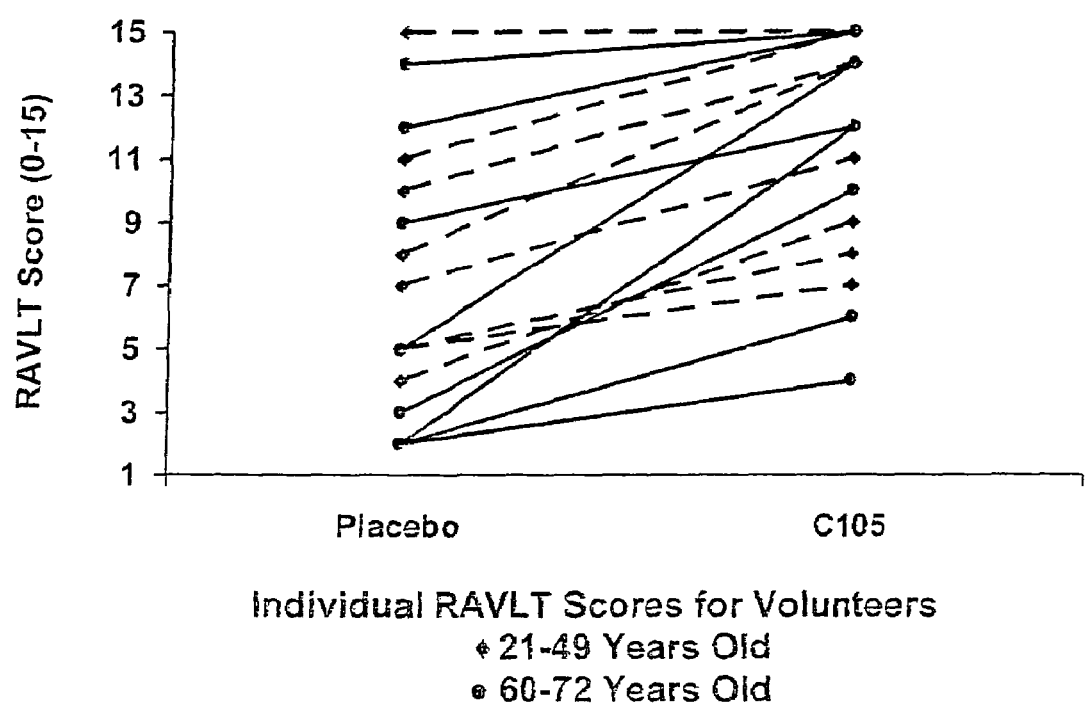
FIG. 26 compares individual subject's memory scores, as assessed by the Rey Auditory and Verbal Learning Test (RAVLT Score (0-15)), following placebo treatment to their best score following treating with l-amphetamine (C105).

FIG. 25 shows a pooled statistical analysis of the 30-minute and 24-hour RAVLT memory scores for all subjects. The scores showed an overall statistically significant ($p<0.05$) improvement in RAVLT score with respect to C105 dose at both 30 minutes and 24 hours post-treatment. In addition, improvements in RAVLT scores observed with the 30 mg and 45 mg doses of C105 were statistically significant ($p<0.05$), based on the Wilcoxon signed rank test, when compared to placebo at both 30 minutes and 24 hours post-dose. The difference is also significant ($p=0.0559$) at the 5 mg dose for the 24-hour recall scores. A comparison of each individual subject's placebo score to their best score on any dose of C105 showed that RAVLT memory performance for all subject (except for one subject who had a perfect RAVLT score under both conditions) improved following C105 treatment (see FIG. 26).

These data demonstrate that l-amphetamine (C105) enhance memory, in particular memory consolidation.

Example 15

Improvement in Cognitive Processes Following L-Amphetamine Administration

A computerized cognitive screening tool (HeadMinder, Inc. (New York, N.Y.)), was employed for the assessment and longitudinal tracking of cognitive functioning (Erlanger, D. M., et al., *J. Head Trauma Rehabil.* 17:458-476 (2002); US2003/0073885A1 (2003); WO 01/54650 (2001); WO 01/72217 (2001); WO 01/54559 (2001), the entire teachings of which are hereby incorporated by reference in their entirety).

Mild cognitive impairment in subjects was diagnosed based on conventional neuropsychiatric testing parameters—scoring below the age- and educational-adjusted cutoff on the Logical Memory II subscale from the Wechsler Memory Scale. A single test score was used to define subjects with mild cognitive impairment. In addition, the subjects used in this study did not score higher than 0.5 on the Clinical Dementia Rating scale. Some subjects with a Clinical Dementia Rating of 0.5 can have early Alzheimer's disease. Some subjects enrolled in this study scored in the Alzheimer's disease range of some cognitive assessments. Thus, some subjects classified as having mild cognitive impairment may actually have early Alzheimer's disease. In populations of humans with mild cognitive impairment and early Alzheimer's disease, neuropsychiatric tests typically measure a continuum (bell-shaped curve) and the definitions are relatively arbitrary cut points for the abnormal population—typically 1 or 1.5 standard deviations below the norm adjusted for age and education.

The battery of nine (9) tests completed by the subjects included two (2) "warm-up" tasks. The remaining seven (7) subtests were included to evaluate cognitive abilities, such as learning and memory, attention, reaction time, and executive function.

Test Factors and Subtest Descriptions

Keyboard Proficiency—Warm-Up Tasks
  Keyboard Proficiency 1
    A green ball appears on the screen. The subject presses the space bar as quickly as possible until the ball turns red.
  Keyboard Proficiency 2
    Numbers from 0-9 appear. The subject presses the number that appears on the screen on the keyboard as quickly as possible.

Figure 39:
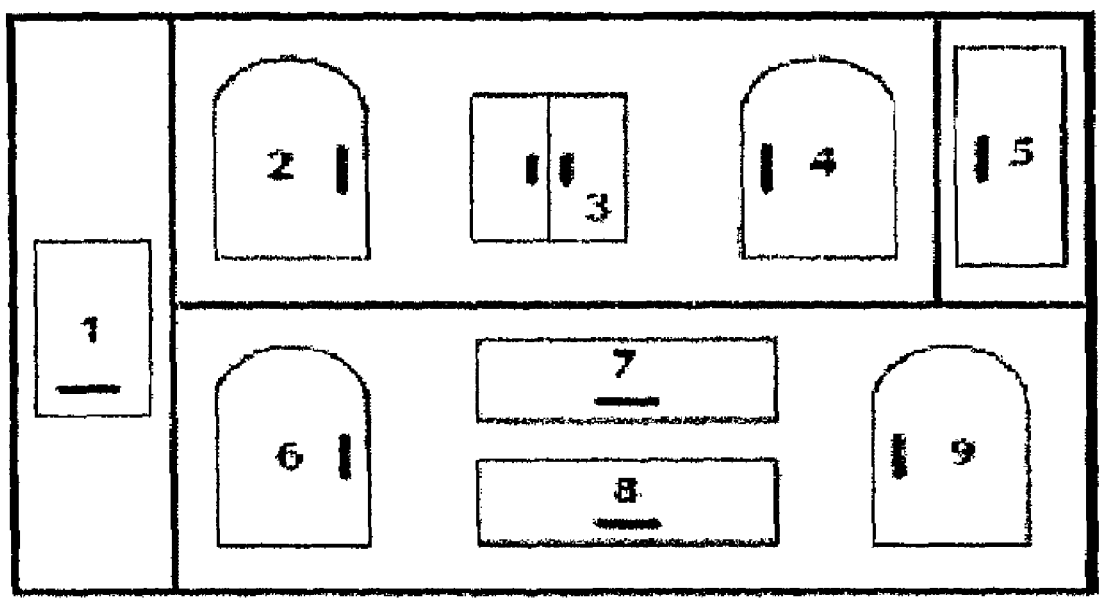
FIG. 39 depicts the memory cabinet employed in learning and memory tests.

Learning and Memory
  Memory Cabinet 1
    Subjects learn the placement of nine (9) household objects placed in a cabinet over three (3) learning trials.
  Memory Cabinet 2—Delayed Memory
    Following intervening tasks, one (1) recall trial of the Memory Cabinet is administered to the subject.
  FIG. 39 depicts the memory cabinet (Where is the key?) employed in the study.

Figure 40:
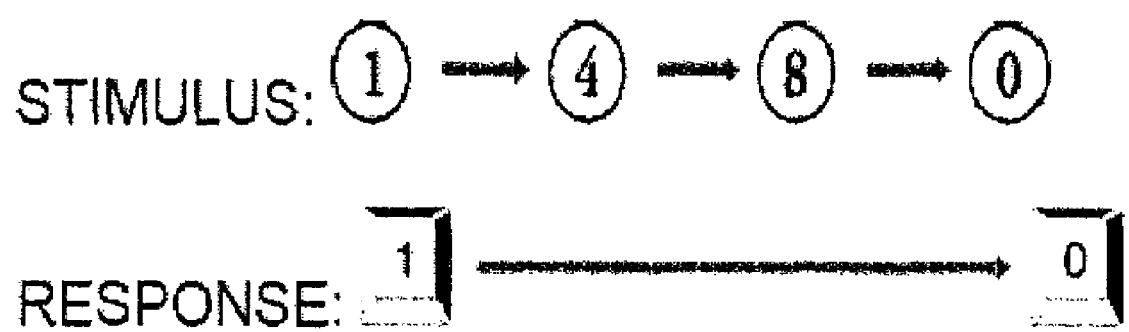
FIG. 40 depicts a key for simple attention (response direction 1) and response reversal (response direction 2) tests.

Attention and Executive Function
  Response Direction 1—Simple Attention (a low demand task) Numbers are presented. The subject presses the "1" key when a 1 is presented and presses the "0" key when a 0 is presented. FIG. 40 depicts a schematic of this task.
  Response Direction 2—Response Reversal (a High Demand Task)
    Numbers are presented one at a time. The subject presses the "1" key when a 0 is presented and presses the "0" key when a 1 is presented. FIG. 40 depicts a schematic of this task.

Figure 41A:
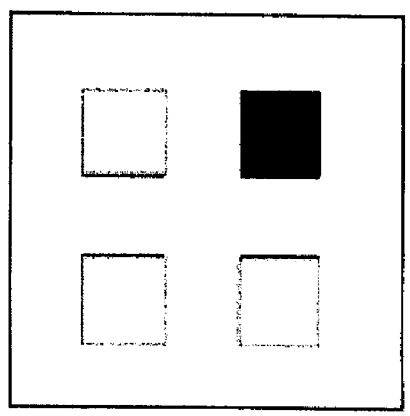
FIG. 41A-41C depict keys for visuo-motor speed tests.
Figure 41B:
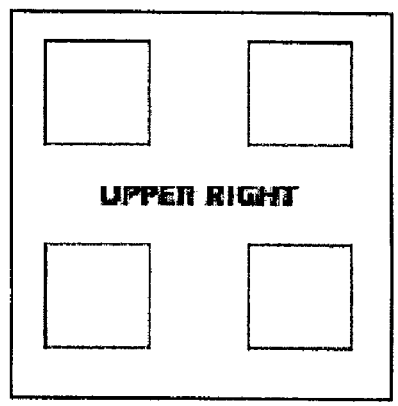
Figure 41C:
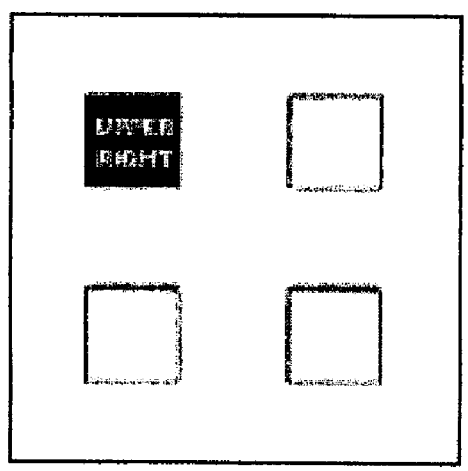

Supplemental Tests
  The subject places his or her fingers on 4 keys, each representing a box on the screen.
  Visuo-Motor Speed 1
    Boxes light up one at a time. The subject presses the corresponding key shown in FIG. 41A as quickly as possible.
  Visuo-Motor Speed 2
    Instructions appear in the center of the screen. The subject presses the corresponding key shown in FIG. 41B as quickly as possible (e.g., "UPPER RIGHT" appears in the middle)
  Visuo-Motor Speed 3
    Instructions are presented on the screen in the wrong location. The subject presses keys shown in FIG. 41C according to each instruction while ignoring the location of the instruction (e.g., "UPPER RIGHT" appears in the lower right).

Subjects
  Thirteen (13) patients (age 64-88 years old, mean age 77 years old) completed the study. One subject was not included in the analyses because he was unable to conform to the protocol. In the l-amphetamine treated group, there were 5 females and 3 males. The placebo group included 1 female and 4 males. Gender did not have an effect on cognitive performance at intake, optimal titrated dose, and washout. All participants were Caucasian. The groups differed in age ($F=4.44$, $df=1$, 11, $p=0.05$) and marginally in level of education ($F=4.2$, $df=1$, 11, $p=0.06$) at time of testing. Groups did not differ significantly on any cognitive test variable at screening for inclusion in the study or washout assessment.

| Age and Education of the two groups | | | | | | |
|---|---|---|---|---|---|---|
| | l-amphetamine (n = 8) | | | Placebo (n = 5) | | |
| | Mean | St. Dev. | Range | Mean | St. Dev. | Range |
| Age | 80.3 | 5.5 | 72.1-88.7 | 73.3 | 6.3 | 64.9-79.6 |
| Education | 12.12 | 2.4 | 9-16 | 15.4 | 3.4 | 12-20 |

Subjects were randomly assigned to receive either l-amphetamine or a placebo. Subjects treated with l-amphetamine (n=8) received 5 mg of l-amphetamine per day for the first seven (7) days of the study, following by 15 mg per day for the next seven (7) days of the study, followed by 30 mg per day for the next fourteen (14) days of the study. Subjects receiving placebo received identical dosages of placebo pills for the duration of the study. Cognitive functions were assessed at baseline (day 0) and on days 1, 8, 15 and 28 of treatment or placebo.

Results

Figure 27:
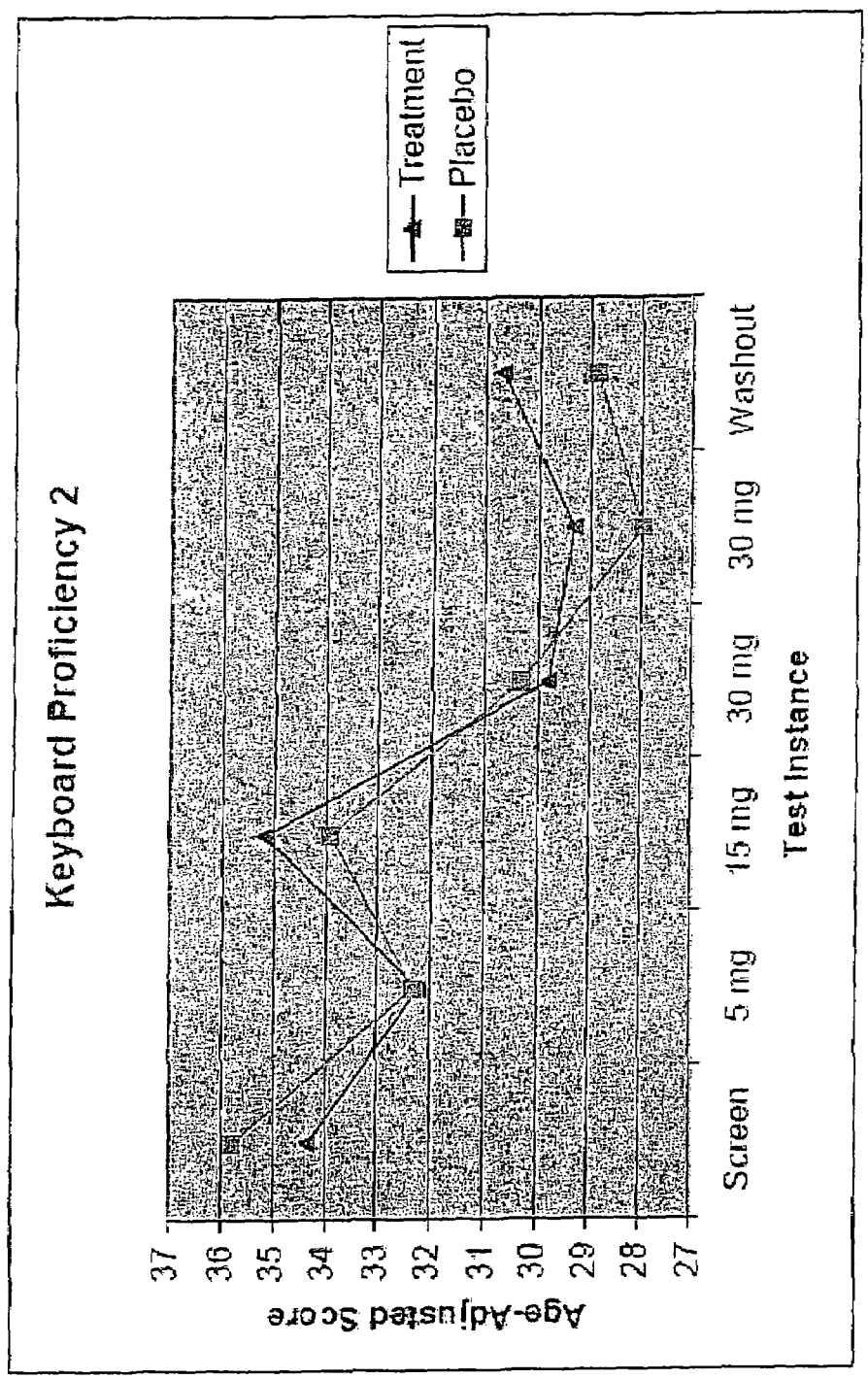
FIG. 27 illustrates the keyboard proficiency for subjects diagnosed with mild cognitive impairment treated with l-amphetamine (5 mg, 15 mg, 30 mg) and subjects diagnosed with mild cognitive impairment receiving placebo.

To demonstrate equivalent keyboard and general cognitive skills, an ANCOVA (Analysis of Co-Variance) exploring the treatment condition (treatment=l-amphetamine administration at 5 mg, 15 mg, 30 mg) was performed with Keyboard Proficiency 2 as the dependent variable and age as the covariate. As expected, l-amphetamine and placebo subjects did not differ in performance on this task at any test instance, indicating they were roughly equivalent (FIG. 27). Higher scores in the keyboard proficiency indicate slower performance.

Figure 28:
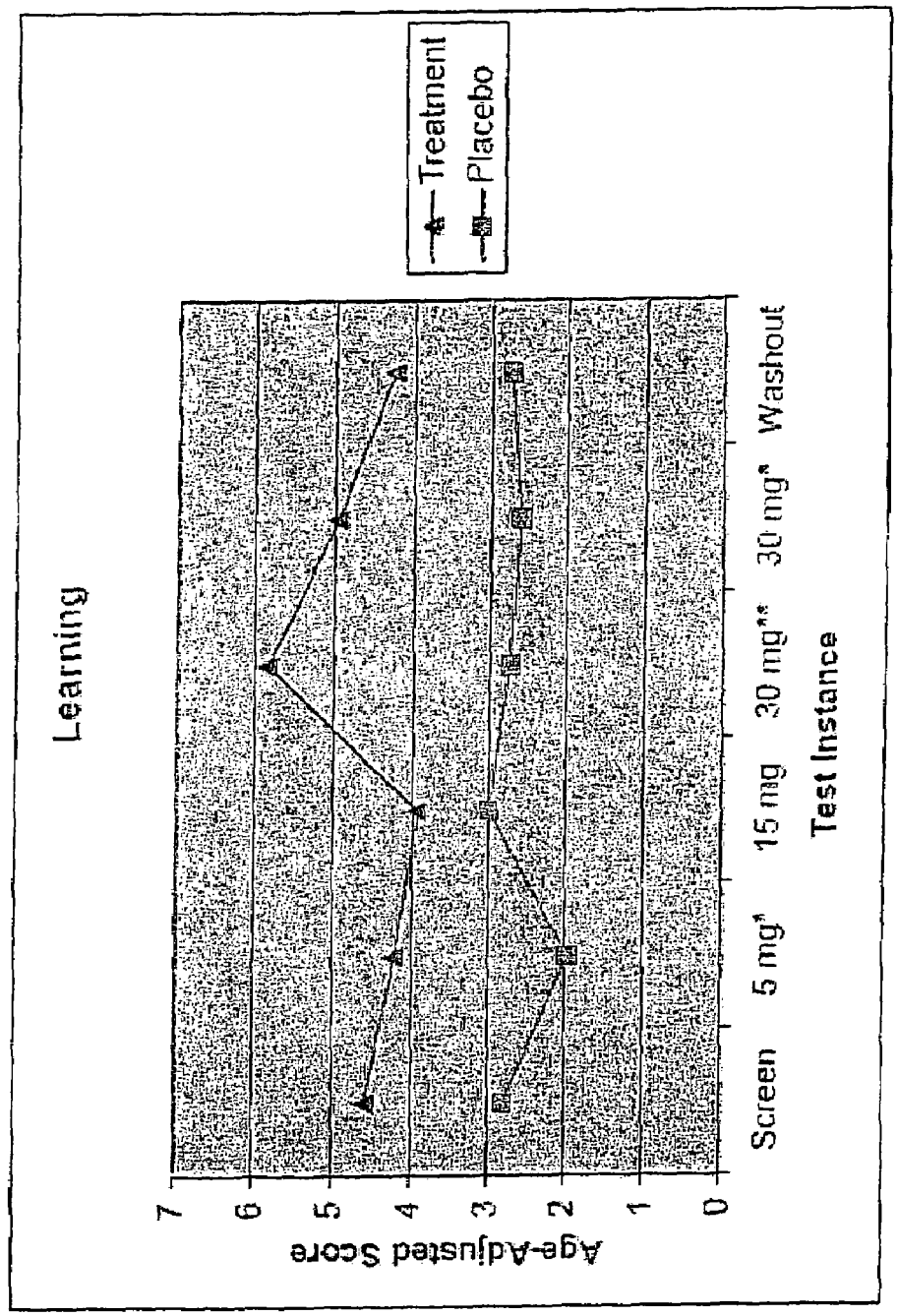
FIG. 28 illustrates improvements in learning in subjects diagnosed with mild cognitive impairment following treatment with l-amphetamine compared to placebo controls.
Figure 29:
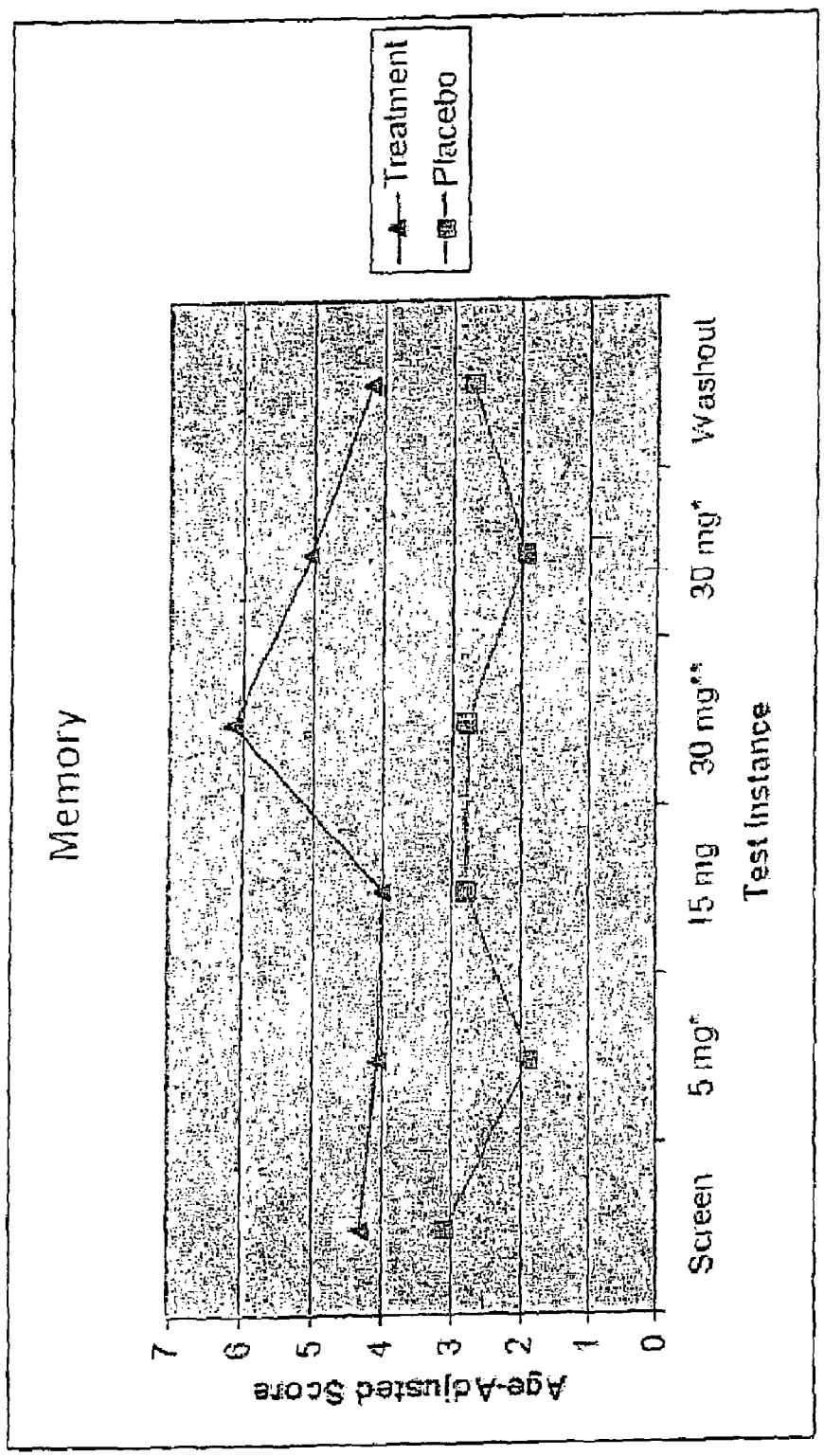
FIG. 29 illustrates improvements in memory in subjects diagnosed with mild cognitive impairments following treatment with l-amphetamine compared to placebo controls.

To determine whether the subjects receiving l-amphetamine had improved memory function, two ANCOVAS exploring the treatment condition were performed with learning and memory as the dependent variables and age as the covariate. Learning (FIGS. 28 and 31) and memory (FIGS. 29 and 31) were improved in subjects receiving l-amphetamine. Significant improvements ($p \leq 0.05$) in the learning and memory at 30 mg doses (days 15 and 29) were observed in subjects receiving l-amphetamine compared to subjects receiving placebo. Placebo treated subjects showed no improvement in learning and memory.

| Keyboard Proficiency 2: Age Scaled Scores and Contrast Statistics | | | | | | |
|---|---|---|---|---|---|---|
| | Screen | 5 mg | 15 mg | 30 mg | 30 mg | Washout |
| l-amphetamine (means/st error) | 34.3 (c.7) | 32.2 (2.2) | 35.1 (7.3) | 29.7 (1.7) | 29.3 (1.6) | 30.6 (2.6) |
| Placebo (mean/st error) | 35.8 (4.9) | 32.3 (2.9) | 33.9 (9.7) | 30.2 (2.2) | 27.9 (2.1) | 28.8 (3.4) |
| F (p) (active vs. control) | .048 (.83) | .001 (.97) | .009 (.92) | .029 (.86) | .22 (.64) | .14 (.71) |
| Adjusted $R^2$ (total model) | −.16 | −.20 | −.10 | −.11 | −.13 | −.13 |

| Learning: Age Scaled Scores and Group Contrast Statistics | | | | | | |
|---|---|---|---|---|---|---|
| | Screen | 5 mg | 15 mg | 30 mg | 30 mg | Washout |
| l-amphetamine (means/st error) | 4.5 (.66) | 4.2 (.59) | 3.9 (.62) | 5.87 (.54) | 4.9 (.54) | 4.2 (.55) |
| Placebo (mean/st error) | 2.8 (.87) | 1.9 (.78) | 3.0 (.81) | 2.7 (.72) | 2.6 (.71) | 2.7 (.72) |
| F (p) (active vs. control) | 2.21 (.16) | 4.49 (.06) | .69 (.42) | 10.01 (.01) | 5.85 (.03) | 2.34 (.15) |
| Adjusted $R^2$ (total model) | .44 | .32 | .14 | .61 | .55 | .48 |

| Memory: Age Scaled Scores and Group Contrast Statistics | | | | | | |
|---|---|---|---|---|---|---|
| | Screen | 5 mg | 15 mg | 30 mg | 30 mg | Washout |
| l-amphetamine (means/st error) | 4.3 (.68) | 4.0 (.63) | 3.9 (.82) | 6.1 (.66) | 5.0 (.78) | 4.1 (.62) |
| Placebo (mean/st error) | 3.0 (.90) | 1.8 (.83) | 2.8 (1.0) | 2.7 (.86) | 1.9 (1.0) | 2.7 (.81) |
| F (p) (active vs. control) | 1.00 (.33) | 3.74 (.08) | .66 (.43) | 8.15 (.01) | 4.97 (.05) | 1.78 (.21) |
| Adjusted $R^2$ (total model) | .43 | .27 | .05 | .50 | .41 | .37 |

Improvements in executive function following treatment with l-amphetamine or placebo were assessed by determining the difference between performance on Response Direction 1 (Low Demand Task) and Response Direction 2 (High Demand Task). Maintained learning efficiency is associated with a stable difference score across repeated assessments. Decreased learning efficiency, which is expected in a subject with mild cognitive impairment, is associated with increased differences across repeated assessments since inefficient subjects make greater improvements due to practice effects on the low demand task than on the high demand task, while efficient subjects improve on both tasks at a similar rate.

Figure 30:
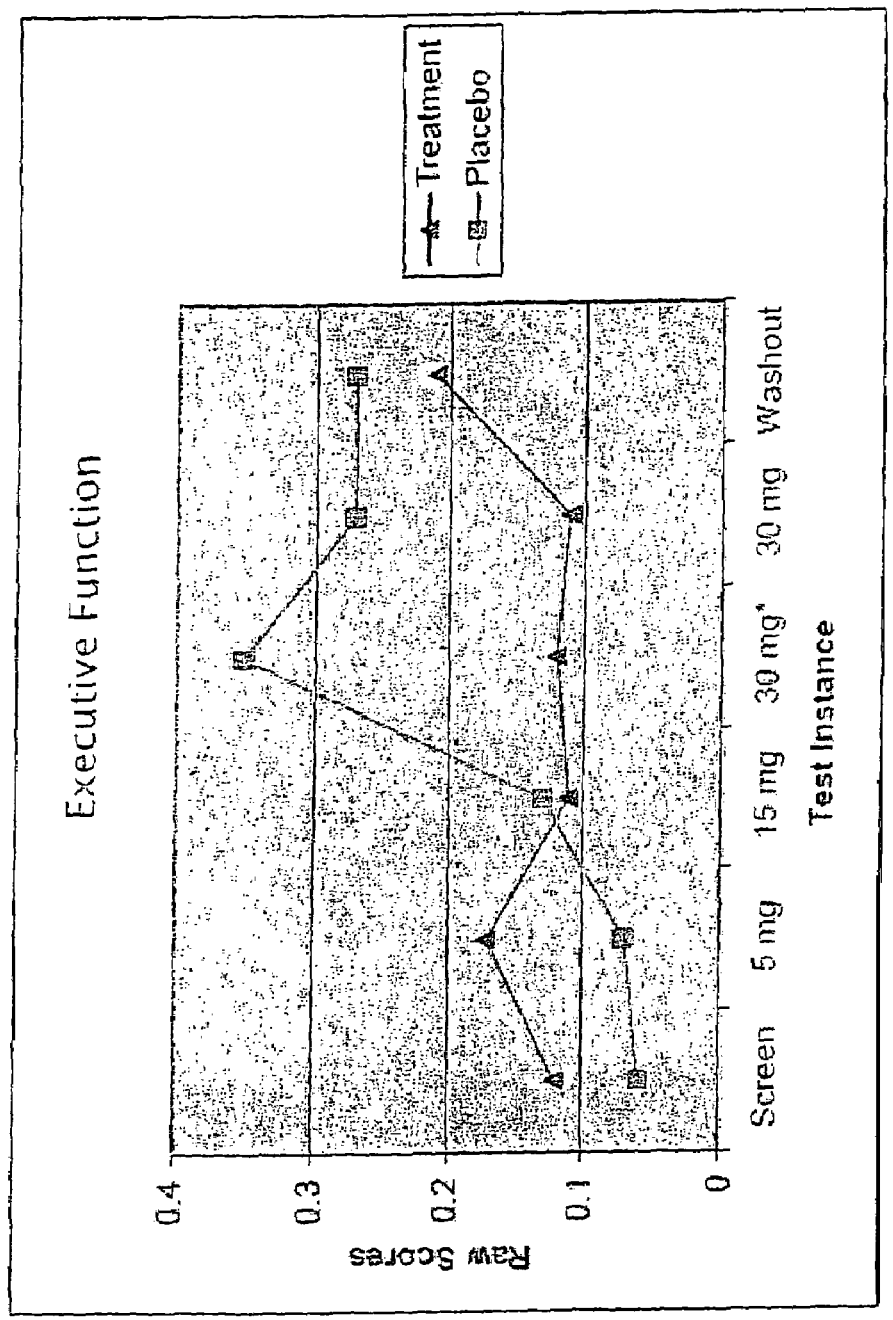
FIG. 30 illustrates improvements in executive function in subjects diagnosed with mild cognitive impairment following treatment with l-amphetamine compared to placebo controls.

An ANCOVA showed significant differences between subjects treated with l-amphetamine (30 mg, day 15) and placebo. A linear contrast of difference scores between the low and high demand tasks across repeated assessments was not significant for participants in the l-amphetamine group (F=0.20, p=0.65) and was significant for participants in the placebo group (F=2.98, p=0.05, one-tailed test). This indicated that those in the l-amphetamine group maintained learning efficiency and that those in the placebo group did not. The placebo group's performance improved on the low demand task, but not on the high demand task, causing the differences to increase in a linear manner. In contrast, the l-amphetamine group improved equally on both the low and high demand tasks, so that the differences remain roughly the same. These differences are shown in FIG. 30 and the following Table. A higher score in FIG. 30 indicates a greater inefficiency. In the l-amphetamine group, a large decrease in learning efficiency at the final assessment—when the medication is no long active—was observed.

placebos controls. A Z-score of 0 represents average performance for healthy individuals and a standard deviation equals 1.

At baseline (prior to treatment) both groups were about equivalent and scored in ranges clearly consistent with mild cognitive impairment and early Alzheimer's disease. At a peak dose of 30 mg per day of l-amphetamine, subject's scores improved by approximately 1 standard deviation to within normal limits. No change was observed in the control, placebo group.

Improvements in memory, learning and executive function by treatment with l-amphetamine can have profound implications for improvement in the clinical symptoms of mild cognitive impairment, early Alzheimer's disease and in performances of everyday tasks ranging from managing medications to grocery shopping and operating a vehicle.

Example 16

Improvement in Memory in Humans Treated with L-Methamphetamine

Two (2) Phase I randomized, double-blind, placebo-controlled clinical studies were conducted in healthy adult male and female subjects who were administered l-methamphetamine (SN522). The first clinical trial was conducted with sixteen (16) healthy subjects, who did not have memory or cognitive impairments (also referred to herein as "normal subjects"), ranging in age from 20-60 years (n=8) and 61-80 years (n=8) who were administered placebo or 1 mg, 4 mg, 16 mg or 32 mg of l-methamphetamine. A second Phase I clini- Executive Function Scores: Raw Scores and Group Contrast Statistics

|  | Screen | 5 mg | 15 mg | 30 mg | 30 mg | Washout |
|---|---|---|---|---|---|---|
| l-amphetamine (means/st error) | .12 (.34) | .17 (.16) | .11 (.16) | .12 (.19) | .11 (.23) | .21 (.08) |
| Placebo (mean/st error) | .06 (.39) | .07 (.46) | .13 (.15) | .35 (.16) | .27 (.24) | .27 (.07) |
| F (p) (active vs. control) | .09 (.76) | .33 (.57) | .07 (.78) | 4.60 (.05) | 1.25 (.28) | 1.32 (.27) |
| Adjusted $R^2$ (total model) | .08 | .06 | .08 | .223 | .02 | .02 |

CONCLUSIONS

Prior to treatment with l-amphetamine, mild cognitive impairment and early Alzheimer's disease subjects had cognitive impairments. Treatment of subjects with placebo did not improve cognitive function. In contrast, subjects treated with l-amphetamine had improved performance on tests for learning, memory and executive function to the extent (one standard deviation or more) such that subjects treated with l-amphetamine were scoring within the normal range on tests assessing learning, memory and executive function. The magnitude of improvement in learning, memory and executive function following l-amphetamine treatment is considered to be clinically significant and efficaciously statistically significant ($p<0.05$) for each of the learning, memory and executive function assessments.

Figure 31:
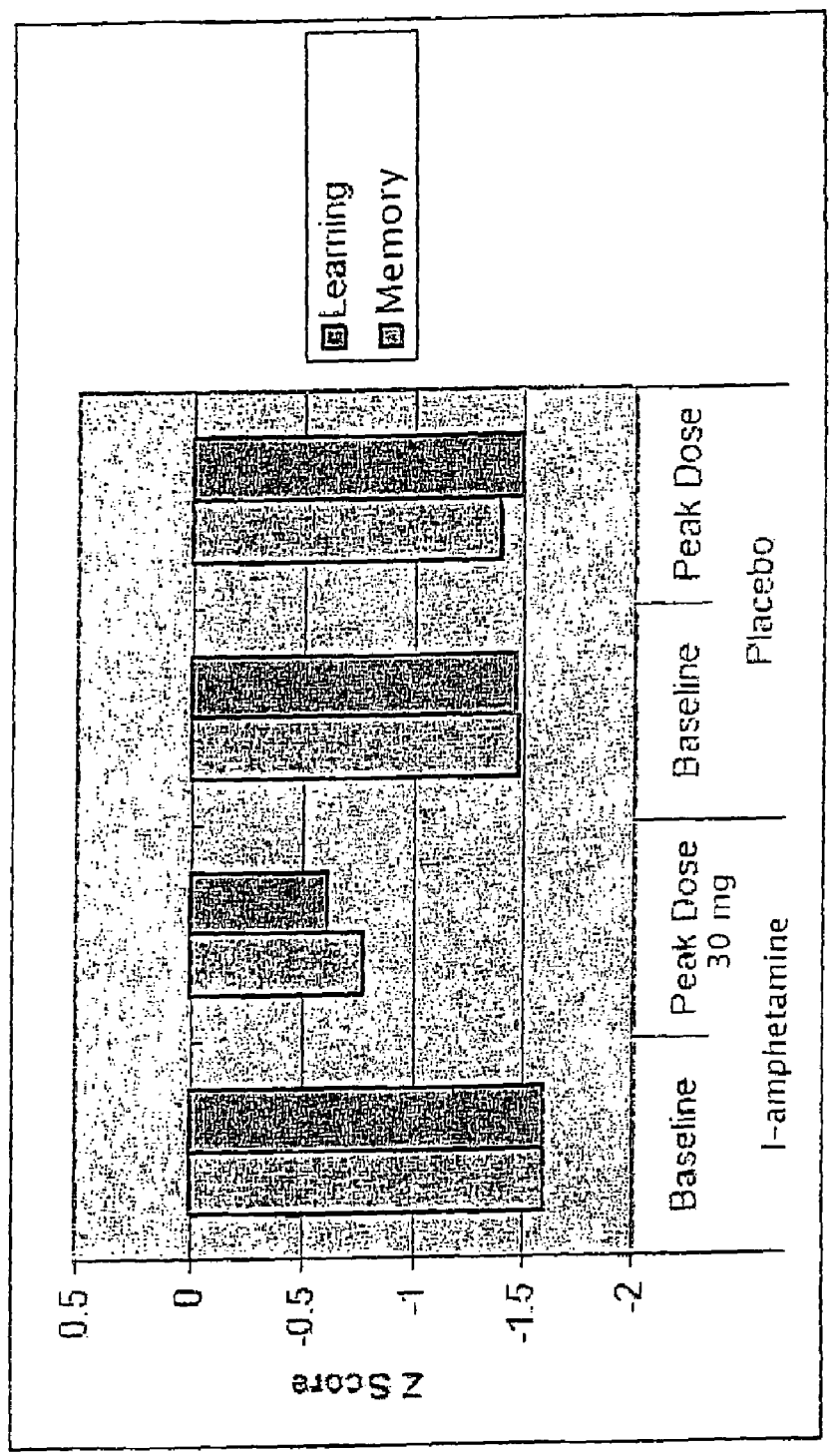
FIG. 31 illustrates improvement in memory and learning, as depicted by Z scores, in subjects diagnosed with mild cognitive impairment following treatment with l-amphetamine (30 mg) compared to placebo controls.

FIG. 31 illustrates the performance of subjects treated with l-amphetamine at a peak dose of 30 mg per day compared to cal trial was conducted with eight (8) normal subjects with an age range of 50-64 years. In the second Phase I clinical trial, the eight (8) subjects received 25 mg, 50 mg, 100 mg of l-methamphetamine; of these eight (8) subjects, five (5) subjects also received placebo (0 mg of l-methamphetamine) and three (3) subjects received 150 mg of l-methamphetamine.

The Phase I studies were designed to identify a maximum tolerated dose and dose-limiting side effects of l-methamphetamine; to assess the effects of l-methamphetamine on quantitative memory scores for example, by the California Verbal Learning Test (CVLTII) or RAVLT; to assess the perceived CNS effects following the administration of l-methamphetamine on the cardiovascular system; to explore the relationship between dose, tolerability, safety and pharmacological effects of l-methamphetamine; and to define the pharmacokinetics of l-methamphetamine.

There were six (6) treatment periods in the first Phase I clinical trial. There were four (4) treatment periods in the second Phase I clinical trial. Each treatment period was one (1) week in duration and consisted of two (2) consecutive days of treatment with l-methamphetamine (1, 4, 16 or 32 mg for the first Phase I study and 25, 50 or 100 mg for the second Phase I study) or a placebo, followed by five (5) consecutive days without l-methamphetamine or a placebo. Each subject was randomly administered a single dose of one of the l-methamphetamine doses or randomly assigned a dose of placebo during each treatment period. Each subsequent treatment group would include whatever dose of l-methamphetamine had not previously been administered, until the patient had received each of the l-methamphetamine doses or a single placebo treatment to conclude the treatment period. Safety data were reviewed after each dose prior to advancement to the next dose level. The RAVLT assessment for word recall was performed as described above and made at two different times following the administration of l-methamphetamine or a placebo during each of the treatment periods. The initial RAVLT training was conducted approximately two and a half hours after administration of the l-methamphetamine or a placebo. After a 30-minute delay period, the subject was required to recall a first set of 15 nouns. The second RAVLT assessment was made approximately 24-hours following treatment with l-methamphetamine.

Safety and tolerability assessments were as described for treatment with Phase I clinical study with l-amphetamine and consisted of assessments in vital signs, ECGs, physical examination and the noting of any adverse events.

L-methamphetamine was generally well tolerated in the first and second Phase I trials. In a few subjects in the second Phase I trial, a 150 mg dose was not well tolerated and this dose was not continued.

Figure 34:
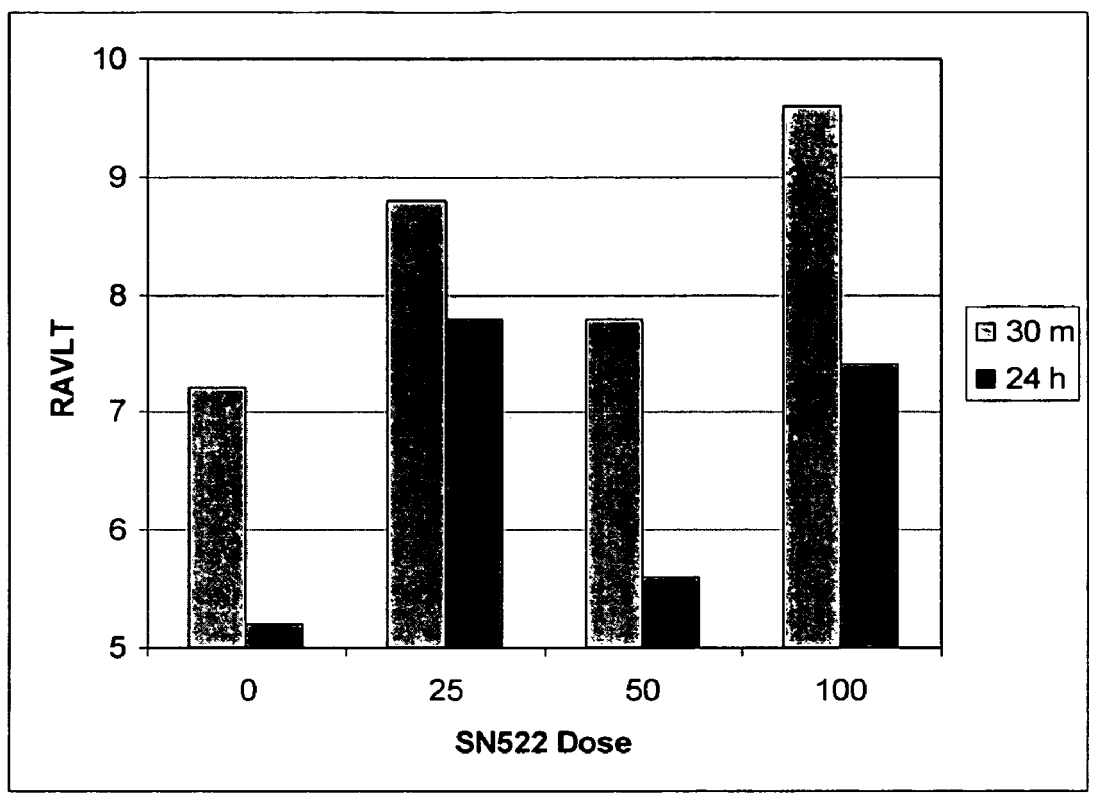
FIG. 34 depicts an improvement in memory in humans following the administration of l-methamphetamine (SN522).

As shown in FIG. 34, RAVLT data from the second Phase I study show that all dose groups have mean values greater than placebo at 30 minutes and 24 hours. Thus, the benefit in improving memory following the administration of l-methamphetamine observed at 30 minutes was maintained at 24 hours. No difference in memory scores was observed in subjects in the first Phase I study.

These data show that administration of l-methamphetamine can enhance memory in subjects who do not have any known impairment in memory or cognition.

Example 17

Improvement in Cognitive Processes Following L-Methamphetamine Administration

A randomized, double-blind, placebo-controlled, dose escalation study in human subjects, who were not suffering from an impairment in a memory or cognitive process ("normal subjects"), was conducted to assess the safety, tolerability and pharmacokinetics and improvement in cognitive processes, including memory, following the administration of l-methamphetamine (25 mg, 50 mg, 100 mg, 150 mg).

Eight (8) subjects received 25 mg, 50 mg, 100 mg of l-methamphetamine; of these eight (8) subjects, five (5) subjects also received placebo and three (3) subjects received 150 mg of l-methamphetamine. The studies were conducted employing a battery of cognitive tests developed by Cognitive Drug Research (CDR) in the United States.

A selection of tasks from the CDR computerized cognitive assessment system was administered and parallel forms of the tests were presented on each testing session. The CDR tasks are well-established assessments of cognition and known to one of skill in the art. All tasks were computer-controlled, the information was presented on high resolution screens, and the responses recorded via a response module containing two buttons, one marked 'NO' and the other 'YES'. The tracking task additionally involved the use of a joystick. The test battery takes about 20-25 minutes to perform. The tests were administered in the following order:

Picture Presentation: A series of 20 pictures was presented on the screen at the rate of 1 every 3 seconds for the subject to remember. No data were recorded from this task.

Simple Reaction Time: The subject was instructed to press the 'YES' response button as quickly as possible every time the word 'YES' is presented on the screen. Fifty stimuli were presented with a varying inter-stimulus interval.

Digit Vigilance: A target digit was randomly selected and constantly displayed to the right of the screen. A series of digits was then presented in the center of the screen at the rate of 150 per minute and the subject was required to press the 'YES' button as quickly as possible every time the digit in the series matches the target digit. There were 45 targets in the series. The task lasted for 3 minutes.

Choice Reaction Time: Either the word 'NO' or the word 'YES' was presented on the screen and the subject was instructed to press the corresponding button as quickly as possible. There were 50 trials for which each stimulus word was chosen randomly with equal probability and there was a varying inter-stimulus interval.

Rapid Visual Information Processing: A series of digits was presented on the screen at the rate of 100 per minute. The subject had to detect targets consisting of consecutive sequences of either three odd digits or three even digits, and to report them by pressing the 'YES' button as quickly as possible. There were 32 targets. The task lasted for 4 minutes.

Tracking: The subject used a joystick to track a randomly moving target on the screen for one minute. The distance off-target per second was recorded.

Spatial Working Memory: A picture of a house was presented on the screen with four of its nine windows lit. The subject had to memorize the position of the lit windows. For each of the 36 subsequent presentations of the house, the subject was required to decide whether or not the one window that was lit was also lit in the original presentation. The subject responded by pressing the 'YES' or 'NO' buttons as appropriate, as quickly as possible.

Numeric Working Memory: A series of five digits was presented for the subject to hold in memory. This was followed by a series of 30 probe digits for each of which the subject had to decide whether or not it was in the original series and press the 'YES' or 'NO' response button as appropriate, as quickly as possible. This procedure was repeated twice more, using two different series and probes.

Picture Recognition: The original pictures plus 20 distracter pictures were presented one at a time in a randomized order. For each picture the subject had to indicate whether or not the subject recognized it as being from the original series by pressing the 'YES' or 'NO' button as appropriate, as quickly as possible.

Summary statistics were calculated for the unadjusted scores, and the difference from baseline (pre-dose) data collected. Repeated measures analysis of variance (ANOVA) was conducted on the difference from baseline data fitting terms for dose, time, period and the dose-time interaction. A random effect of subjects was fitted to the model.

Figure 35:
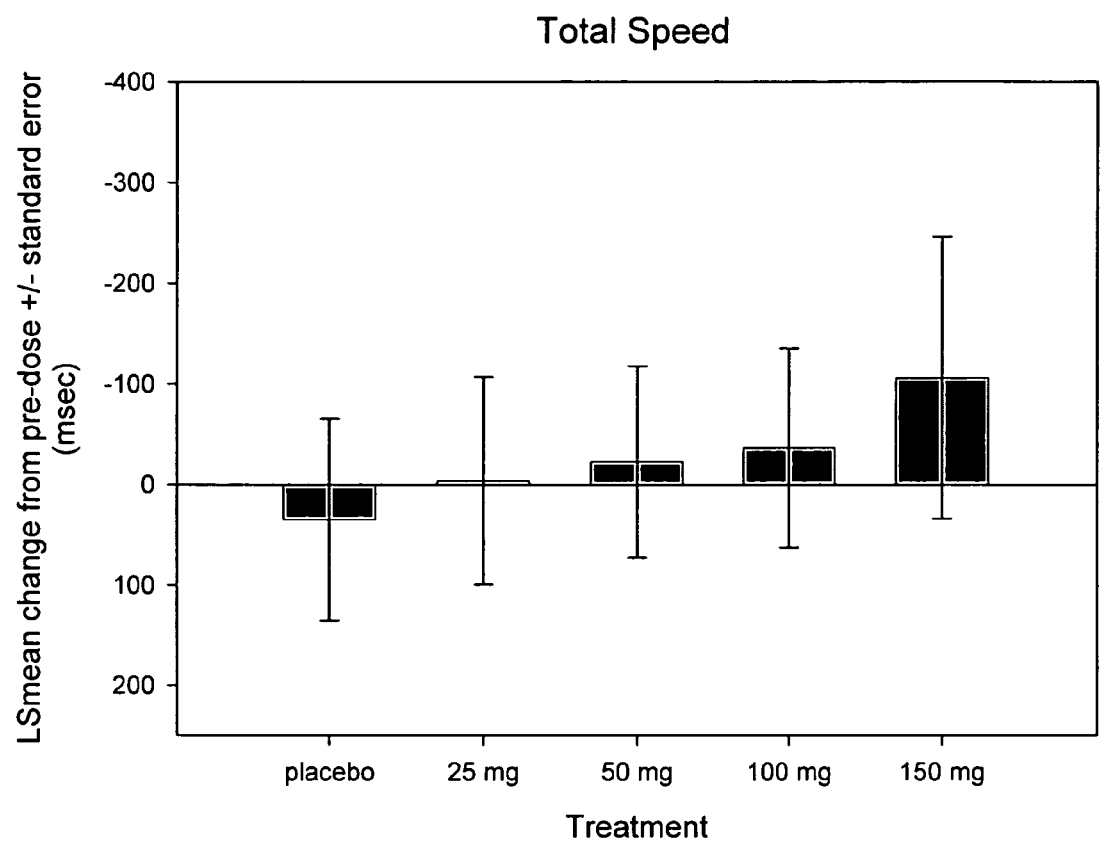
FIG. 35 depicts an improvement in total speed score from baseline following the administration of l-methamphetamine to humans.

As shown in FIG. 35, l-methamphetamine (SN522) had a dose-dependent effect on speed of response. This dose dependent pattern indicates a post-dose decline with placebo treatment, and increasing post-dose improvements in response speed with active dosing as shown using a combined Total Speed score, which combines the reaction time measures from all the CDR tasks, except the Tracking task. The data shown in FIG. 35 compares the score obtained after l-methamphetamine treatment with a pre-dose score. Subjects receiving placebo take a longer time to respond with a dose-response reduction in the total response time. A dose dependent pattern was evident in the LSmean difference from baseline, as shown in FIG. 35.

A pattern for dose dependent benefit was evident on several of the reaction time measures, as shown in FIG. 35. Total speed tasks assess cognitive functions.

Figure 36:
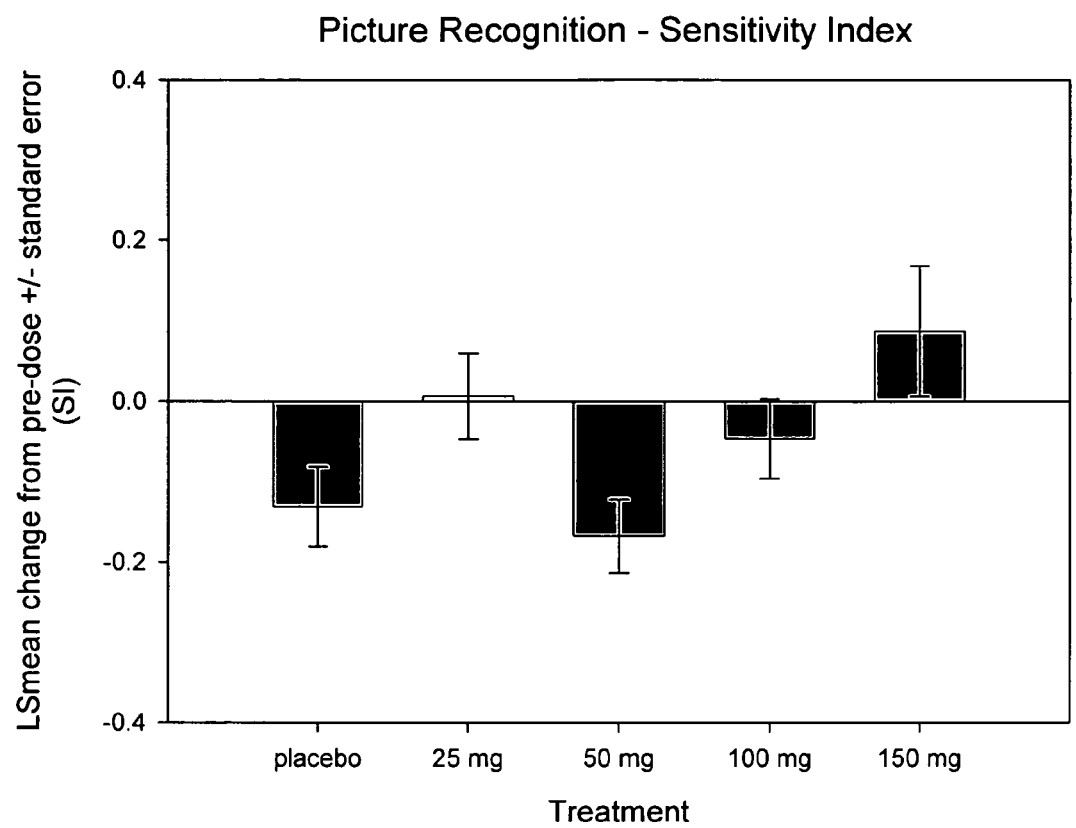
FIG. 36 depicts improvements in Picture Recognition/Sensitivity Index following the administration of l-methamphetamine to humans.

As shown in FIG. 36, administration of l-methamphetamine (25 mg, 150 mg) improved the Picture Recognition-Sensitivity Index, a task that assesses memory. A significant effect of treatment was seen from the ANOVA ($p=0.004$). The LSmean comparisons showed significant benefits for 25 mg ($p=0.0177$) and 150 mg ($p=0.0254$) over placebo. Three (3) subjects received 150 mg dose of l-methamphetamine. FIG. 36 shows a pattern for dose dependent improvement for 50 mg, 100 mg and 150 mg of l-methamphetamine. A possible explanation for the lack of fit of the 25 mg dose was that the pre-dose baseline for 25 mg was poor, leading to a post-dose improvement. Thus, the relative pre-dose performance of the dose groups should be considered.

Figure 37:
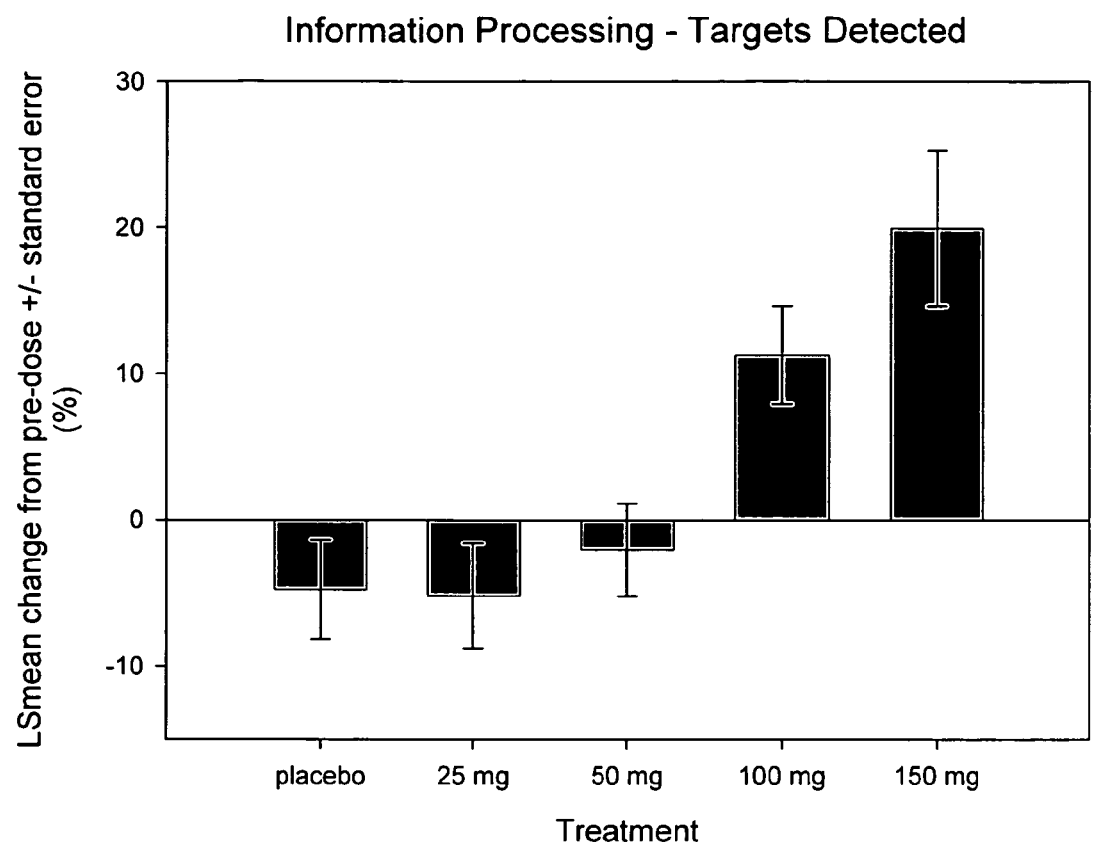
FIG. 37 depicts an improvement of l-methamphetamine in Information Processing-Targets Detected following the administration of l-methamphetamine to humans.
Figure 38:
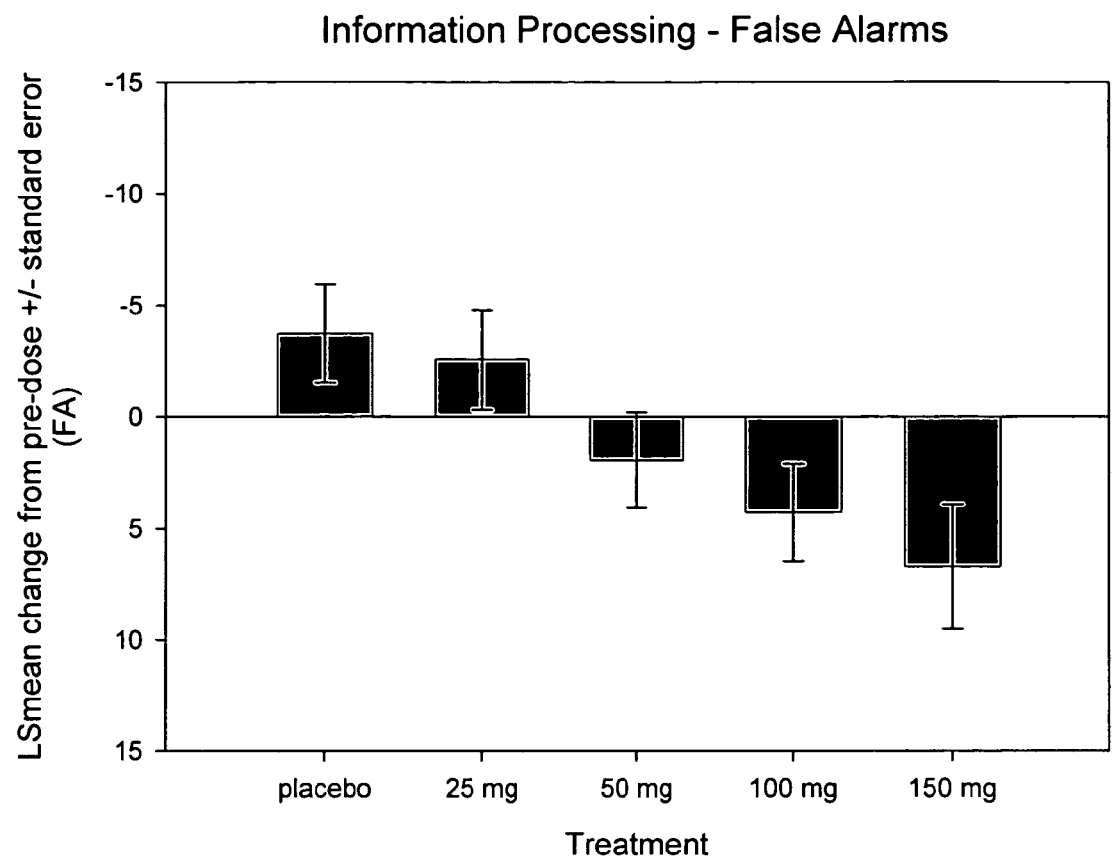
FIG. 38 depicts an improvement in Information Processing-False Alarms following the administration of l-methamphetamine to humans.

As shown in FIGS. 37 and 38, a significant effect of dose was observed for Information Processing Targets Detected ($p=0.0005$), an assessment of cognition, following administration of l-methamphetamine. The LSmean comparisons showed significant benefits for 100 mg ($p=0.0002$) and 150 mg ($p=0.0001$) over placebo (FIG. 37). This pattern was improved with a 100 and 150 mg dose and was in contrast to a pattern for a dose dependent increase in False Alarms, which also showed a significant main effect of dose ($p=0.0001$). The LSmean comparisons showed significant decrements against placebo for 50 mg ($p=0.0002$), 100 mg ($p=0.0001$) and 150 mg ($p=0.0001$) doses (FIG. 38).

In summary, these data show a dose dependent effect of l-methamphetamine on reaction time (speed of response) on the CDR task measures. A dose of 25 mg and 150 mg of l-methamphetamine improved Picture Recognition-Sensitivity Index (accuracy), an assessment of memory. A dose dependent benefit of l-methamphetamine on Information Processing Targets Detected (accuracy) was also observed, which is an assessment of cognition. This benefit was also associated with increased False Alarms on the task, which may indicate a change in response strategy (increased responding), rather than a direct benefit to accuracy. However, when the False Alarms measures was used as a covariate in the analysis of the Targets Detected (accuracy) measure, the benefits following l-methamphetamine administration remained, indicating a benefit to accuracy following l-methamphetamine administration. Therefore, l-methamphetamine has dose dependent effects benefiting response speed, and beneficial effects, on memory and information processing accuracy. These beneficial effects observed in normal healthy subjects support the beneficial effects for use of the amphetamine compounds of the invention in subjects having cognitive impairments.

Example 18

Treatment of Humans with Multiple Sclerosis

Introduction

Multiple Sclerosis (MS) is an immune mediated, relapsing, often progressive multifocal demyelinating disease of the white matter of the central nervous system resulting in the formation of plaques in multiple areas of the brain, spinal cord and frequently in the optic nerves. It is estimated that 250-350,000 patients in the US and 1.1 million worldwide suffer from the disease. MS symptoms typically present in early adulthood with 2:1 predominance in women. It is estimated that 40-65% of patients with MS have evidence of a cognitive deficit on neuropsychiatric testing.

Multiple sclerosis typically presents with sensory disturbances, optic neuritis, diplopia, limb weakness, clumsiness, ataxia, neurogenic bowel and bladder dysfunction. During MS relapses, symptoms or signs develop over a few days, stabilize and then improve over a few weeks either spontaneously or in response to corticosterids. Patients may experience either complete or partial recovery following an exacerbation. While cognitive deficits may occur in the context of an exacerbation, deficits are generally detected as the disease progresses over time. Cognitive deficits generally have a subtle presentation and are often not detected on general screening tests such as the Mini Mental Status Exam (MMSE), thus requiring more sensitive neuropsychological testing for detection. A natural history cohort study of early MS patients demonstrated that significant cognitive deficits on neuropsychiatric testing were detected after 4 years of follow-up, which did not necessarily correlate with other neurological deficits.

The nature of cognitive deficit in MS varies but primarily affects areas of memory, learning, attention, and information processing, and less commonly affect areas of executive function, conceptual reasoning, recognition memory, and auditory or visual span. Unlike the deficits in Alzheimer's disease and other dementing disorders, the cognitive deficits in MS tend to be subcortical and largely related to slowing of information processing, frontal lobe deficits, and memory retrieval problems. Once cognitive deficits appear, they are not likely to improve and may progress with the exception of deficits associated with acute attacks.

Cognitive deficits undermine the quality of life in MS patients and are a significant source of morbidity and disability. Patients may have fewer social interactions, sexual dysfunction, difficulty with household tasks and a greater degree of unemployment. Fatigue, another prominent symptom in MS is often disabling and may contribute to worsening of cognitive performance. Additionally, depression is estimated to occur in 27-54% of MS patients. Depression may impair cognitive function, but does not entirely account for cognitive deficits observed in MS patients. The depression associated with MS is generally responsive to pharmacologic treatment, with selective serotonin reuptake inhibitors (SSRIs) being the most commonly used agents.

There are currently five approved agents that have been shown to decrease new lesion formation and reduce relapse rates in comparison with placebo in MS patients: interferon beta 1-a (Avonex®, Rebif®), interferon beta 1-b (Betaseron®), glatiramer acetate (Copaxone®), and mitoxantrone (Novantrone®). Additionally, there is evidence that interferon beta 1-a (Avonex®) has a significant treatment effect in delaying the progression of deficits in cognition. The effects are seen most prominently in the areas of memory, information processing, executive function, and visuospatial ability.

There are currently no approved therapies for the management of cognitive impairment in MS. Evaluation of centrally acting cholinesterase inhibitors that have been used successfully to treat Alzheimer's dementia are currently being investigated in MS patients. Ginko Biloba is commonly used among MS patients to treat memory impairment, although there are no controlled studies of its efficacy in this patient population. A variety of agents have been used to treat fatigue including amantidine, pemoline, modafanil, although there is no evidence that treatment of fatigue improves cognitive function in MS patients.

A number of studies have shown that either pre- or post-training administration of d-amphetamine enhances performance in rats on a variety of different tasks, including inhibitory avoidance and water maze, and in humans on verbal memory consolidation.

Psychostimulant drugs such as d-amphetamine have a known propensity to increase extracellular dopamine levels in the nucleus accumbens, frontal cortex, amygdala and other limbic regions. They also elevate extracellular dopamine in these regions by inhibiting reuptake of dopamine by the dopamine transporter, depleting vesicular stores of dopamine, and by promoting the reverse transport of dopamine from the cytoplasm. Although l-amphetamine can also elevate dopamine levels, it is ½ to ¹⁄₁₀th as potent as d-amphetamine, depending on the experiment and the measure used.

Despite the difference in effect on dopamine transmission, d- and l-amphetamine appear to have a similar efficacy for increasing extracellular norepinephrine levels in the hippocampus and cortex.

This distinct pharmacologic profile of l-amphetamine, i.e. weaker effects on dopaminergic systems coupled with a strong effect on noradrenergic systems, is the likely explanation for the enhanced effects of l-amphetamine on memory, relative to the d-isomer. In addition, the weaker effect of l-amphetamine on dopaminergic systems and brain regions involved in hyperactivity and addiction suggest that stimulant effects and abuse liability potential will be greatly reduced relative to d-amphetamine.

As shown herein l-amphetamine (e.g., l-amphetamine sulfate, also referred to herein as C105) improves memory function. Data shows that l-amphetamine improves memory in rats at significantly lower doses when compared to d-amphetamine sulfate (0.5 mg/kg versus 2.0 mg/kg, respectively). The improvement in memory function observed with l-amphetamine was seen at doses that did not increase locomotor activity. In contrast, the doses of d-amphetamine required to improved memory function also significantly increased locomotor activity.

The effects of l-amphetamine in humans have been evaluated in 49 subjects in 5 Phase 1 studies, and 129 subjects have been evaluated in 3 Phase 2 studies. The overall incidence of adverse events following l-amphetamine administration was low and most events resolved without intervention. Single daily doses up to 45 mg have been well-tolerated. Repeat doses up to 30 mg daily for 28 days have also been well-tolerated. Statistically significant dose-related improvements in RAVLT scores, a measurement of memory performance, were also observed 30 minutes and 24 hours following administration of single oral doses of l-amphetamine.

Memory and other cognitive problems are among the principal complaints of MS patients, and are a well recognized source or morbidity and disability in these patients. At present, there are no approved therapies that improve memory or cognitive function in MS patients. The methods described herein show that treatment of MS patients with l-amphetamine improve cognitive deficits.

REFERENCES

1 Rao S M. 1995. Neuropsychology of multiple sclerosis. Curr Opin Neurol 8(3), 216-20.
2 Amato, M. P., G. Ponziani, et al. 1995. Cognitive Impairment in Early-Onset Multiple Sclerosis. Archives of Neurology 52, 168-72.
3 Jennekens-Schinkel A, Laboyrie P M, Lanser J B, et al. 1990. Cognition in patients with multiple sclerosis after four years. J Neurol Sci 99 (2-3), 229-47.
4 Kujala P, Portin R, Ruutiainen J. 1997. The progress of cognitive decline in multiple sclerosis: a controlled 3-year follow-up. Brain 120 (Pt 2), 289-97.
5 Foong J, Rozewicz L, Quaghebeur G, et al. 1998. Neuropsychological deficits in multiple sclerosis after acute relapse. J Neurol Neurosurg Psychiatry 64 (4), 529-32.
6 Rao, S., G. Leo, et al. 1991. Cognitive Dysfunction in Multiple Sclerosis. Neurology 41 (5), 685-91; 692-6.
7 Minden S L, Schiffer R B. 1990. Affective disorders in multiple sclerosis: review and recommendations for clinical research. Arch Neurol 47 (1), 98-104.
8 Fischer, J., R. Priore, et al. 2000. Neuropsychological Effects of Interferon B-la in Relapsing Multiple Sclerosis. Annals of Neurology 48 (6), 885-892.
9 Krupp, C. Christodoulou, et al. Interventions to Improve Memory in MS: The Aricept in MS Study (AIMS): 24 Week Data. 55th Annual Meeting. American Academy of Neurology, Honolulu, Hi. 2003
10 Geisler, M. Sliwinksi, et al. 1996. The Effects of Amantadine and Pemoline on Cognitive Functioning in Multiple Sclerosis. Arch. Neurology 53.
11 Lee, E. H. Y., Ma, Y. L. 1995. Amphetamine enhances memory retention and facilitates norepinephrine release from the hippocampus in rats. Brain Res Bull 37, 411-6.
12 Packard, M. G., McGaugh, J. L. 1994. Quinpirole and d-amphetamine administration post-training enhances memory on spatial and cued discriminations in a water maze. Psychobiol 22, 54-60.
13 Soetens, E., D'Hooge, R., Hueting, J. E. 1993. Amphetamine enhances human memory consolidation. Neurosci. Lett 161 (1), 9-12.
14 Soetens, E., Casner, S., D'Hooge, R., Hueting, J. E. 1995. Effect of amphetamine on long-term retention of verbal material. Psychopharm 119, 155-62.
15 Koob, G. F., Sanna, P. P., et al. 1998. Neuroscience of addiction. Neuron 21, 467-476.
16 Jones, S. R., Gainetdinov, R. R., et al. 1998. Mechanisms of amphetamine action revealed in mice lacking the dopamine transporter. J Neurosci 18 (6), 1979-1986.
17 Kuczenski, R., Segal, D., et al. 1995. Hippocampus Norepinephrine, Caudate Dopamine and Serotonin, and Behavioral Responses to the Stereoisomers of Amphetamine and Methamphetamine. J Neuroscience 15 (2), 1308-1317.
18 Heikkila R E, et al. 1975. Amphetamine: evaluation of d- and l-isomers as releasing agents and uptake inhibitors for 3H-dopamine and 3H-norepinephrine in slices of rat neostriatum and cerebral cortex. J Pharmacol Exp Ther 194 (1), 47-56.
19 Kanbayashi, T., Honda, K., et al. 2000. Implications of dopaminergic mechanisms in the wake-promoting effects of amphetamine: A study of D and L derivatives in canine narcolepsy. Neuroscience 99 (4), 651-659.

The teachings of all of the references cited herein are hereby incorporated by reference in their entirety.

Study Objectives
   To assess the efficacy of l-amphetamine in improving measures of cognition and fatigue, using the following secondary assessments:
      Rey Auditory Verbal Learning Test (RAVLT)—Total Learning and Delayed Recall
      Brief Visuospatial Memory Test—Revised (BVMT-R)—Total Learning and Delayed Recall
      Symbol Digit Modalities Test (SDMT)—Total # Correct
      Paced Auditory Serial Addition Test (PASAT)—Total # Correct
      Controlled Oral Word Association Test (COWAT)—total number of words across the 3 letters
      Trail Making Test Parts A and B
      Global Assessment
      9 Hole Peg Test (9 HPT)

Inclusion Criteria
   Subjects are eligible for the study if they fulfilled all the inclusion criteria specified below:
1. Males/females who were at least the minimum age of consent and were capable of understanding and complying with the protocol including speaking and writing fluent English and had at least a 9$^{th}$ grade education.
2. Have a clinically definite diagnosis per McDonald criteria of a relapsing form of Multiple Sclerosis.
3. Have stable disease and relapse-free for at least 3 months.
4. Presence of memory deficit as measured by a CVLT-II Total Learning or Delayed List A Recall score at least 1.0 SD below the age-adjusted norms within 2 years of randomization.
5. Screening EDSS score <6.5.
6. Have given written informed consent, prior to any study-related procedure not part of normal medical care, with the understanding that consent may be withdrawn by the subject at any time without prejudice to his/her future medical care.
7. Are capable of performing the requirements of a neuropsychological test battery.
8. If female, must be neither pregnant nor breast-feeding and she must
   either a) be >12 months post-menopausal or surgically sterilized;
   or b) use 2 acceptable forms of birth-control, including hormonal contraceptives, intra-uterine device, or barrier method (e.g., condoms, diaphragm, etc.) with spermicidal, for the duration of the study.

Exclusion Criteria
   Subjects were excluded from the study if any one of the following is fulfilled:
1. Subjects who had memory deficits caused by concomitant medication usage or other significant neurological/psychological disease, e.g., Parkinson's Disease, stroke, TIA, Multi-Infarct Dementia, Huntington's Disease, head trauma, or chronic CNS infection.
2. Evidence of other medical causes of dementia, e.g., untreated hypothyroidism or vitamin deficiencies such as niacin, B12 or folic acid.
3. Subjects who had evidence of Major Depressive Disorder as determined by standard interview with a trained study personnel.
4. Subjects who had previously been administered the RAVLT assessment within the past 12 months.
5. Subjects who required or were expected to require treatment with medications known to enhance or impair cognitive function.
6. History of a myocardial infarction, symptomatic Coronary Artery Disease or unstable cardiovascular disease.
7. Any clinically significant, unstable, or major concomitant disorder.

Figure 42:
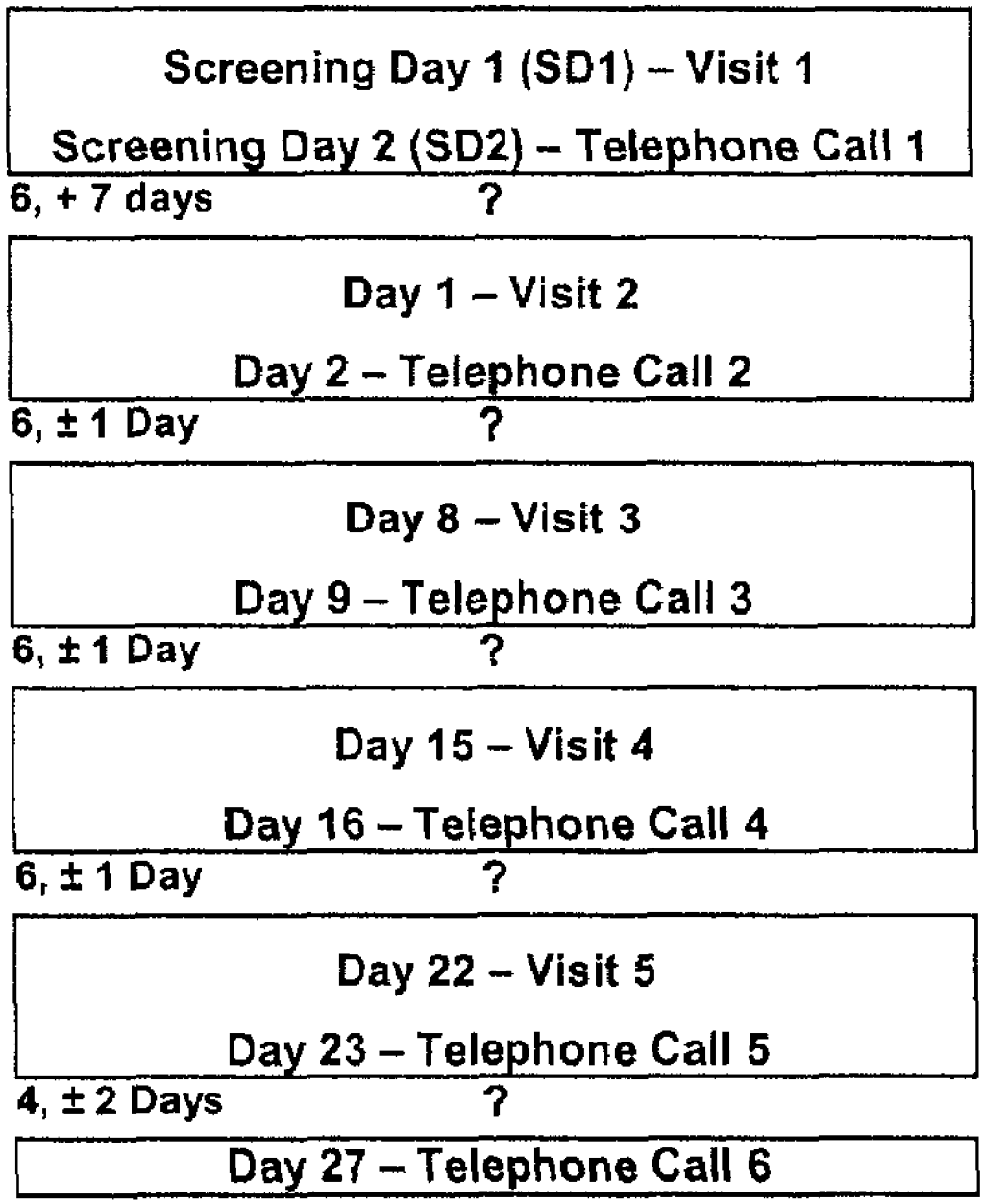
FIG. 42 depicts the study design for treatment of humans with multiple sclerosis.

Randomization Procedures
   All subjects received acute doses of 15 mg l-amphetamine, 30 mg l-amphetamine, 45 mg l-amphetamine, and Placebo during the clinic visits which occur on Days 1, 8, 15, and 22. Doses of l-amphetamine were administered in ascending order with a 6-8 day washout separating each dose.
   A schematic illustration of the study design and detailing the timing of visits is depicted in FIG. 42.

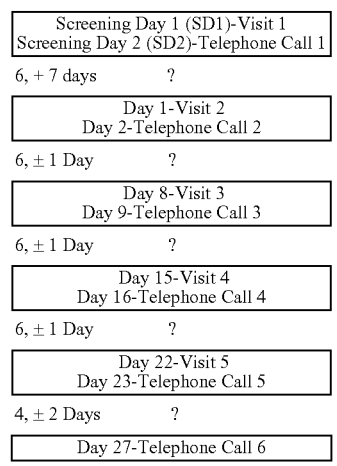

There were four possible randomization patterns that may occur in this protocol. A schematic illustration of the possible randomization patterns is shown below:

| Day 1 | Day 8 | Day 15 | Day 22 |
|---|---|---|---|
| Placebo | 15 mg L-AMPHETAMINE | 30 mg L-AMPHETAMINE | 45 mg L-AMPHETAMINE |
| 15 mg L-AMPHETAMINE | Placebo | 30 mg L-AMPHETAMINE | 45 mg L-AMPHETAMINE |
| 15 mg L-AMPHETAMINE | 30 mg L-AMPHETAMINE | Placebo | 45 mg L-AMPHETAMINE |
| 15 mg L-AMPHETAMINE | 30 mg L-AMPHETAMINE | 45 mg L-AMPHETAMINE | Placebo |

Study Methods

Screening Period
   Neuropsychological assessments were be performed on Screening Day 1 to measure baseline cognitive function and to train subjects on how to perform the tests.

Treatment Period
   At the successful completion of the Screening Period, subjects began the Treatment Period. The active treatment period phase was for 22 3 consecutive days (with study medication being provided in the clinic on Days 1, 8, 15, and 22) and consisted of the following clinic visits: Day 1—Visit 2
   Day 8—Visit 3 (±1 day)
   Day 15—Visit 4 (±1 day)
   Day 22—Visit 5 (±1 day).

In addition, the following telephone calls took place:
Day 2—Telephone Call 2 (±3 hours)
Day 9—Telephone Call 3 (±3 hours)
Day 16—Telephone Call 4 (±3 hours)
Day 23—Telephone Call 5 (±3 hours)

During the Treatment Period, clinic visit dates occurred 7 (±1 day) from the previous clinic visit. Day 1 occurred 7 (+7 days) after Screening Day 1. All Telephone calls occurred 24 hours 3 hours after the initiation of the RAVLT assessment on the preceding clinic visit date.

Various fatigue, motor, memory, and cognitive assessments were given to the subjects over the course of the Treatment Period.

Screening Period (SD1 [Visit 1] and SD2 [Telephone Call 1])

The Screening Period consisted of a clinic visit on Screening Day 1 (Visit 1), and a telephone call on Screening Day 2 (Telephone Call 1).

Screening Day 1 (Visit 1)

Screening Day 1 (Visit 1) occurred 7-14 days before administration of study medication (Day 1—Visit 2)

At this visit, potential subjects underwent the following procedures:
Provide written informed consent (subject or authorized representative)
Demographics
Review of medical history (including tobacco, alcohol, caffeine, and illicit drug use), and concomitant medication use
EDSS
CVLT
PASAT
SDMT
BVMT-R
COWAT
Practice RAVLT (Sequence EF)
Trail Making Test Parts A and B)
Standardized Depression Interview
9 HPT Screening Day 2 (Telephone Call 1)

This telephone call was placed 24 hours (±3 hours) after the initiation of the RAVLT on the previous visit day. During this telephone call, the following assessments were made:
RAVLT-II
Global Assessment Treatment Period Day 1 (Visit 2); Day 8 (Visit 3); Day 15 (Visit 4); Day 22 (Visit 5)

Subjects reported to the site at approximately 0830. Subjects were told not eat within six hours of dosing the day of study visits. They were permitted to drink non-caffeinated, clear, low-fat beverages at any time prior to study visits.

Prior to dosing, subjects underwent the following assessments:
Full vital signs (HR, BP, Respiration and Oral Temp)
Record alcohol, tobacco, caffeine use since previous visit and food and beverage intake for the past 6 hours
Concomitant medication review (evaluate from previous visit for changes or additions)

Subjects were dosed at the site at 0900. Study drug could be taken with clear juice or water, but no food or caffeine was allowed for at least 1 hour post-dose. Water could be consumed at any time.

Subjects were dosed anytime between 0800 and 1100. All possible efforts were made to keep the time of dosing consistent within each subject between study visits. If dosing occurred at an alternate time, the assessments were performed at the appropriate post-dose interval. The investigator or authorized designee, e.g., study coordinator, was responsible for calculating the appropriate time for assessments and recording the actual time of assessment on the subject's source notes.

The post-dose assessments or activities were conducted in the following order:
RAVLT
PASAT (to be performed during RAVLT delay period)
SDMT (to be performed during RAVLT delay period)
9 HPT (to be performed during RAVLT delay period)
BVMT-R
COWAT (to be performed during BVMT delay period)
Trail Making Test Parts A and B (to be performed during BVMT delay period)
Discharge to Home Day 2 (TC 2); Day 9 (TC 3); Day 16 (TC 4): Day 23 (TC 5)

All telephone calls occurred 24 hours (±3 hours) after the initiation of the RAVLT on the previous visit day. During this telephone call, the following assessments were made:
RAVLT-II
Global Assessment Special Study Assessments The following describes the motor, memory, and cognitive assessments performed for this protocol. All tests were validated and are commonly used to assess function in subjects with multiple sclerosis.[A]

To facilitate the completion of assessments, each site designated at least two individuals to perform ratings. A primary rater completed all assessments if possible. An additional rater, assigned and trained on all assessments, served as a back-up in case of non-availability or emergencies. All rating assessments were made on the basis of interviews/observations by the rater. To maintain continuity for every subject, every effort was made to ensure that a subject was rated by the same trained rater throughout the study.

9 Hole Peg Test (9 HPT)

The 9-HPT is a brief, standardized, quantitative test of upper extremity function.[K] Both the dominant and non-dominant hands are tested twice. The subject was seated at a table with a small, shallow container holding nine pegs and a wood or plastic block containing nine empty holes. The subject was prompted to start, at which point he or she picked up the nine pegs one at a time, puts them in the nine holes, and, once they were in the holes, removed them again as quickly as possible replacing them into the shallow container. The total time to complete the task was recorded. Two consecutive trials with the dominant hand were immediately followed by two consecutive trials with the non-dominant hand.

The score for the 9-HPT was an average of the four trials. The two trials for each hand were averaged, converted to the reciprocals of the mean times for each hand and then the two reciprocals were averaged.

Brief Visuospatial Memory Test-Revised (BVMT-R)

The BVMT-R Part 1 included 3 learning trials, a 25-minute delayed Recall test, and a delayed yes/no Recognition task.[B] The subject was shown a page containing 6 geometric visual designs for 10 seconds. The subject was then instructed to draw as many of the designs as possible after the stimulus were removed from view. There was no time limit for recall. The first recall test was followed by 2 additional learning trials during which the subject was again shown the same stimulus designs and encouraged to improve his/her performance. Following a 25 minute period of intervening tasks, the subject was asked to reproduce the designs from memory.

Finally, a series of 12 individual designs were presented for the Recognition test. The subject was asked to respond "yes" to those designs included in the original 6 figures and to respond "no" to those that were not.

California Verbal Learning Test II (Cvlt)

The CVLT provides a short, individually administered assessment of the strategies and processes involved in learning and remembering verbal information.[C] The CVLT not only assesses the amount of verbal material remembered, but also measures multiple aspects of how verbal learning occurs or fails to occur. The test offers a comprehensive assessment of each subject's profile of verbal learning and memory strengths and weaknesses.

The purpose of the CVLT at screening was to determine study participation eligibility.

The CVLT was similar in scope and design to the RAVLT. The CVLT assessment consists of 16 nouns read aloud for 5 consecutive trials, followed by an interference trial, which was then followed by a free-recall test of the first 16 nouns. After a 25-minute long delay period, the subject was again required to recall the first set of nouns and also completes a 50-word recognition test.

Controlled Oral Word Association (COWAT)

The COWAT consists of three one-minute word-naming trials. F In each trial, the subject was asked to say as many words as they can think of that begin with a specific letter of the alphabet (two three-letter combinations, "CFL" and "PRW," will be used for this study), excluding proper nouns, numbers and the same word with a different suffix. The assessment was scored by summing the total acceptable words produced in the three one-minute trials. Total numbers of errors and repetitions were also recorded.

Expanded Disability Status Scale (EDSS)

The EDSS is a standard way to rate the 7 functional systems (plus "other") which is based on a standard neurological examination.[I] These ratings were then used in conjunction with observations and information concerning gait and use of assistive devices to rate the EDSS. Scoring the EDSS was based on an ordinal clinical rating scale ranging from 0 (normal neurologic examination) to 10 (death due to MS) in half-point increments.

Global Assessment

In order to measure the acute effects of l-amphetamine on subjects, each subject was asked to complete a 7 point Likert scale during the telephone calls that occurred throughout the study.[L] The scale that was used asked the subject to rate their cognitive functioning over the past 24 hours.

Paced Auditory Serial Addition Test (PASAT)

The PASAT is a measure of cognitive function that assesses auditory information processing speed and flexibility, as well as calculation ability.[G,H] The PASAT was presented using audio cassette tape or compact disk to ensure standardization in the rate of stimulus presentation. Single digits were presented every 3 seconds and the subject must add each new digit to the one immediately prior to it. Two alternate forms were developed to minimize possible familiarity with the stimulus items when the PASAT was repeated over more than one occasion. The score for the PASAT was the total number correct out of 60 possible answers.

Rey Auditory Verbal Learning Test (RAVLT)

The RAVLT is a test of verbal memory that assesses learning, recall, and recognition of a word list.[D] The assessment consisted of 15 nouns read aloud for 5 consecutive trials, followed by an interference trial, which was then followed by a free-recall test of the first 15 nouns. After a 30-minute delay period, the subject was again required to recall the first set of nouns and also completed a 50-word recognition test.

Symbol Digit Modalities Test (SDMT)

The subject was given 90 seconds to pair specific numbers with given geometric figures based on a reference list.[E] This assessment was completed orally by the subject.

The SDMT primarily assessed complex scanning and visual tracking while comparing visuomotor and oral responses. Manual speed and agility contributed significantly to SDMT performance, but visual acuity was not an important factor.

The score for the SDMT was the total number of correct matches made by the subject within the 90 second time period. The total number of responses given was also be recorded.

Trail Making Test—Parts A and B

Trail—Part A required the subject to connect a series of circles labeled with numbers in order as quickly as possible.[J] It was considered a test of information processing speed. Trail—Part B required the subject to connect a series of circles labeled with numbers or letters as quickly as possible, alternating from number to letter (1-A-2-B, etc.). The test was scored as the number of seconds needed to complete the task. Errors were pointed out immediately by the examiner and contributed to the score insofar as additional time was needed for corrections. The number of errors that a subject committed and the raw time scores (in seconds) were recorded.

REFERENCES

A. Benedict R H B, Fischer J S, Archibald C J, et al. 2002. Minimal neuropsychological assessment of MS patients: a consensus approach. Clin Neuropsychol 16, 381-397.

B. Benedict R. H. B. 1997 Brief Visuospatial Memory Test— Revised: Professional Manual. Odessa, Fla.: Psychological Assessment Resources C. Delis D C, Kramer J H, Kaplan E, Kramer J H. 2001. California Verbal Learning Test manual: Second edition, Adult version. San Antonio, Tex.: Psychological Corporation.

D. Schmidt M. 1996. Rey auditory verbal learning test: a handbook. Western Psychological Services, Los Angeles E. Smith A. 1982. Symbol Digit Modalities Test: Manual. Los Angeles: Western Psychological Services.

F. Benton A L, Hamsher K. 1989. Multilingual Aphasia Examination. Iowa City: AJA Associates.

G. Gronwall D M A. 1977. Paced auditory serial addition task: A measure of recovery from concussion. Perceptual and motor skills 44:367-373

H. Rao S M, Leo G J, Bernardin L, Unverzagt F. 1991. Cognitive dysfunction in multiple sclerosis I. Frequency, patterns, and prediction. Neurology 41:685-691.

I. Kurtzke J F. 1983. Rating neurologic impairment in multiple sclerosis: an expanded disability status scale (EDSS). Ann Neurol 13:227-231

J. Reitan R M. 1958. Validity of the trail making test as a measure of organic brain damage. Percept Motor Skills 8:271-276.

K. Cutter G R, Baier M L, Rudick R A, et al. 1999. Development of a multiple sclerosis functional composite as a clinical trial outcome measure. Brain 122:871-882

L. Likert R. 1932. A technique for the measurement of attitudes. New York: McGraw-Hill.

Results

A repeated measures ANOVA was performed comparing scores obtained when subjects were receiving placebo, 15 mg, 30 mg, and 45 mg. Particular focus was placed upon the most valid and reliable measures in the battery [total learning and delayed recall from the RAVLT and BVMT-R, SDMT, PASAT, TMTA, TMTB, and the Global rating]. If the ANOVA was significant or there was a trend toward significance, then Paired T tests were performed comparing each subject against scores during screening/training, and each against each other. The most relevant differences were for comparison against placebo, because differences from baseline/training could result from training effects.

Robust efficacy for l-amphetamine was observed on measures of processing speed. The ANOVAs were significant for SDMT, PASAT, TMTA, and TMTB. Comparing SDMT placebo (52.5±9.4) and 45 mg (57.0±9.9) revealed an effect size of d=0.5, which was expected to provide clinically significant benefit for subjects with MS cognitive impairment. In addition, significant differences were observed across the dosages, so that 30 mg was better than 15, and 45 better than 30 and 15. Although the greatest and most consistent effects were observed for SDMT, similar improvements with the highest dose were observed for PASAT, TMTA and TMTB.

In addition, memory was improved following the administration of higher doses of l-amphetamine (RAVLT, d=0.3 for 45 mg l-amphetamine compared to placebo for delayed recall scores).

Cognitive test scores for subjects during screening/training, and while receiving each dose of drug or placebo are shown below:

Study 22028 MS Trial Outcomes (n = 19)

| Outcome Measure | Screening/Training | Placebo | 15 mg | 30 mg | 45 mg |
|---|---|---|---|---|---|
| RAVLT Total Learning (Sum of Trials 1-5) | 46.3 | 43.3 | 45.1 | 43.7 | 45.3 |
| RAVLT 30-Min Delay Recall | 6.6 | 6.6 | 7.0 | 7.1 | 8.0 $p = 0.12$* |
| RAVLT 24-Hr Delay Recall | 4.3 | 5.6 | 4.8 | 5.5 | 6.5 |
| RAVLT % Forgetting (Trial 5 minus Delay Recall divided by Trial 5 × 100%) | 40.4 | 42.7 | 34.8 | 36.2 | 31.2 $p = 0.08$ |
| SDMT (Total # Correct) | 48.1 | 52.5 | 52.1 | 54.7 $p = 0.11$ | 57.0 $p = 0.001$ |
| PSAT (Total # Correct) | 38.2 | 46.9 | 45.8 | 46.9 | 51.0 $p = 0.007$ |
| COWAT (Sum of admissible words) | 33.1 | 38.1 | 36.9 | 40.0 | 41.4 $p = 0.047$ |
| BVMT (Delay Recall) | 7.10 | 7.89 | 7.47 | 7.95 | 8.11 |
| Trails Part A (Sec) | 34.46 | 28.24 | 28.26 | 25.78 | 25.12 $p = 0.012$ |
| Trails Part B (Sec) | 78.88 | 60.51 | 65.50 | 62.14 | 55.10 $p = 0.177$ |
| Global (7-point Scale) (Sum of Slightly Better, Better, and Much Better) | 2/19 | 4/19 | 7/19 | 13/19 $p = 0.004$ | 10/19 $p = 0.04$ |

*All p values represent statistical comparisons of subject performance while receiving placebo versus performance while receiving l-amphetamine using a paired t-test, except for the global scale which used the Fisher's exact test.

Discussion

Administration of l-amphetamine to humans with multiple sclerosis and cognitive impairment produced significant improvement in cognitive function as measured on commonly used, and well validated, cognitive tests. These data show that l-amphetamine produced clinically relevant improvement in cognitive function in subjects with multiple sclerosis.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

All patents, publications, and other references cited above are hereby incorporated by reference in their entirety.

What is claimed is:

1. A method of treating a human for an impairment in a cognitive function, comprising the step of administering an effective amount of an amphetamine composition that includes at least one member selected from the group consisting of l-amphetamine and l-methamphetamine to a human having an impairment in a cognitive function associated with multiple sclerosis, wherein the l-amphetamine is at least 60 mole percent l-amphetamine relative to the total l-amphetamine and l-methamphetamine components of the composition or wherein the l-methamphetamine is at least 90 mole percent l-methamphetamine relative to the total l-methamphetamine and l-amphetamine components of the composition.

2. The method of claim 1, wherein l-amphetamine is administered, and wherein the l-amphetamine is administered as a component of a composition that includes at least 80 mole percent l-amphetamine relative to the total l-amphetamine and l-methamphetamine components of the composition.

3. The method of claim 1, wherein l-methamphetamine is administered, and wherein the l-methamphetamine is administered as a component of a composition that includes at least 95 mole percent l-methamphetamine relative to the total l-methamphetamine and l-amphetamine components of the composition.

4. The method of claim 1, wherein at least one member selected from the group consisting of attention, executive function, reaction time, learning, information processing, conceptualization, problem solving and verbal fluency is improved in the human following administration of the amphetamine.

5. The method of claim 1, wherein the l-amphetamine is administered at a dose of about a 1 mg dose to about a 150 mg dose per day.

6. The method of claim 1, wherein the l-methamphetamine is administered at a dose of about a 1 mg dose to about a 150 mg dose per day.

7. The method of claim 2, wherein l-amphetamine is administered, and wherein the l-amphetamine is administered as a component of a composition that includes at least 99 mole percent l-amphetamine relative to the total l-amphetamine and l-methamphetamine components of the composition.

8. The method of claim 3, wherein l-methamphetamine is administered, and wherein the l-methamphetamine is administered as a component of a composition that includes at least 99 mole percent l-methamphetamine relative to the total l-methamphetamine and l-amphetamine components of the composition.

* * * * *